(12) United States Patent
Kato

(10) Patent No.: US 8,406,838 B2
(45) Date of Patent: Mar. 26, 2013

(54) APPARATUS FOR EVALUATING BIOLOGICAL FUNCTION, A METHOD FOR EVALUATING BIOLOGICAL FUNCTION, A LIVING BODY PROBE, A LIVING BODY PROBE MOUNTING DEVICE, A LIVING BODY PROBE SUPPORT DEVICE AND A LIVING BODY PROBE MOUNTING ACCESSORY

(76) Inventor: Toshinori Kato, Tokyo (JP)

( * ) Notice: Subject to any disclaimer, the term of this patent is extended or adjusted under 35 U.S.C. 154(b) by 1656 days.

(21) Appl. No.: 11/655,998

(22) Filed: Jan. 22, 2007

(65) Prior Publication Data

US 2008/0262327 A1    Oct. 23, 2008

Related U.S. Application Data

(63) Continuation of application No. PCT/JP2005/013327, filed on Jul. 20, 2005.

(30) Foreign Application Priority Data

Jul. 20, 2004 (JP) ................................. 2004-211012

(51) Int. Cl.
*A61B 5/1455* (2006.01)

(52) U.S. Cl. ........ 600/322; 600/310; 600/323; 600/324; 600/328

(58) Field of Classification Search ................. 600/310, 600/322, 323, 326, 328, 340, 344, 476, 32; 356/39, 40

See application file for complete search history.

(56) References Cited

U.S. PATENT DOCUMENTS

| | | | |
|---|---|---|---|
| 5,803,909 A | | 9/1998 | Maki et al. |
| 5,853,370 A | * | 12/1998 | Chance et al. ................ 600/323 |
| 6,587,703 B2 | | 7/2003 | Cheng et al. |
| 6,640,130 B1 | | 10/2003 | Freeman et al. |
| 6,723,047 B1 | | 4/2004 | Yamamoto et al. |
| 6,901,284 B1 | | 5/2005 | Maki et al. |
| 7,065,392 B2 | | 6/2006 | Kato |
| 7,187,962 B2 | | 3/2007 | Shingo |
| 2004/0054271 A1 | * | 3/2004 | Maki et al. .................... 600/341 |
| 2004/0242979 A1 | * | 12/2004 | Kawasaki .................... 600/323 |

FOREIGN PATENT DOCUMENTS

| | | |
|---|---|---|
| JP | 09-135825 | 5/1997 |
| JP | 09-149903 | 6/1997 |
| JP | 09-238914 | 9/1997 |
| JP | 2000-237194 | 9/2000 |
| JP | 2002-177281 | 6/2002 |
| JP | 2003-10188 | 1/2003 |
| JP | 2003-75331 | 3/2003 |
| JP | 2003-144437 | 5/2003 |
| WO | WO 00/74572 | 12/2000 |
| WO | WO 03/068070 | 8/2003 |

\* cited by examiner

*Primary Examiner* — Eric Winakur
*Assistant Examiner* — Chu Chaun (JJ) Liu
(74) *Attorney, Agent, or Firm* — Jacobson Holman PLLC

(57) ABSTRACT

The apparatus for evaluating biological function of the present invention has living body probes 1, a behavioral information measuring part 2 and an apparatus body 3, and it utilizes near-infrared spectroscopy to evaluate biological function; apparatus body 3 has a controller 8 for calculating (based on light information from living body probes 1) a variety of parameters derived from two-dimensional diagrams showing relationships between changes in oxyhemoglobin and changes in deoxyhemoglobin and two-dimensional diagrams showing relationships between absolute amounts of oxyhemoglobin and absolute amounts of deoxyhemoglobin, a behavioral information input part for entering behavioral information measured by means of behavioral information measuring part 12, and a display part 10 for performing various types of image displays based on various parameters calculated by means of controller 8 and/or behavioral information entered in the behavioral information input part.

29 Claims, 92 Drawing Sheets

Figure 3
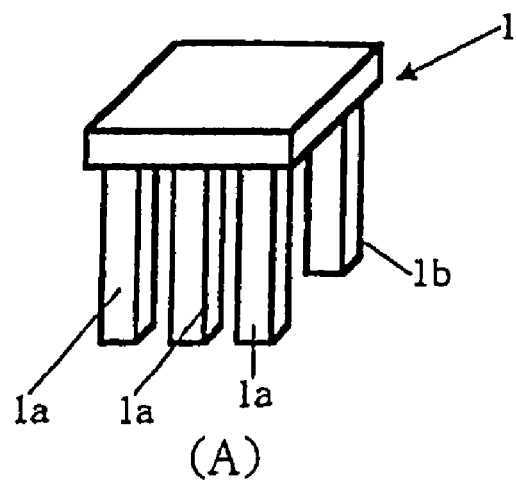
(A)
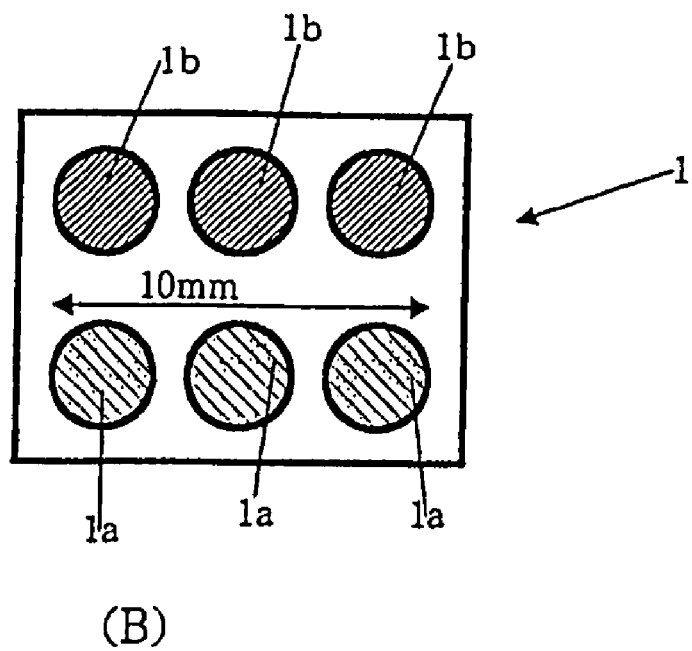
(B)

Figure 4
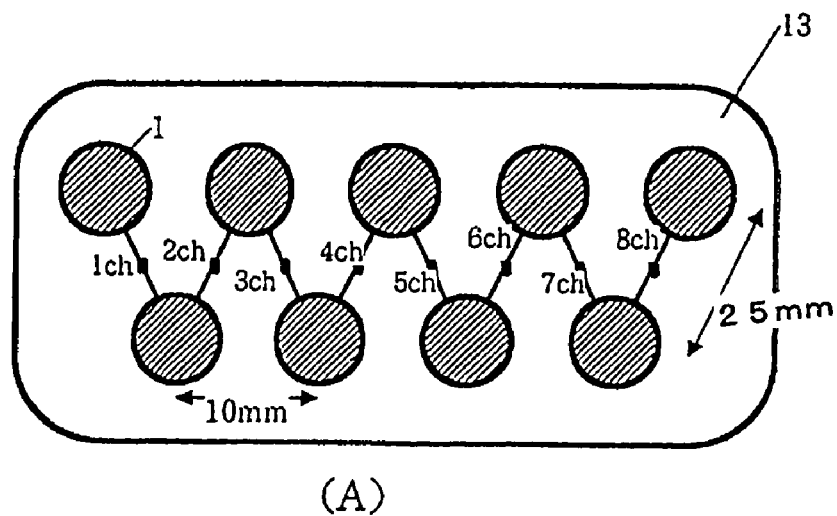
(A)
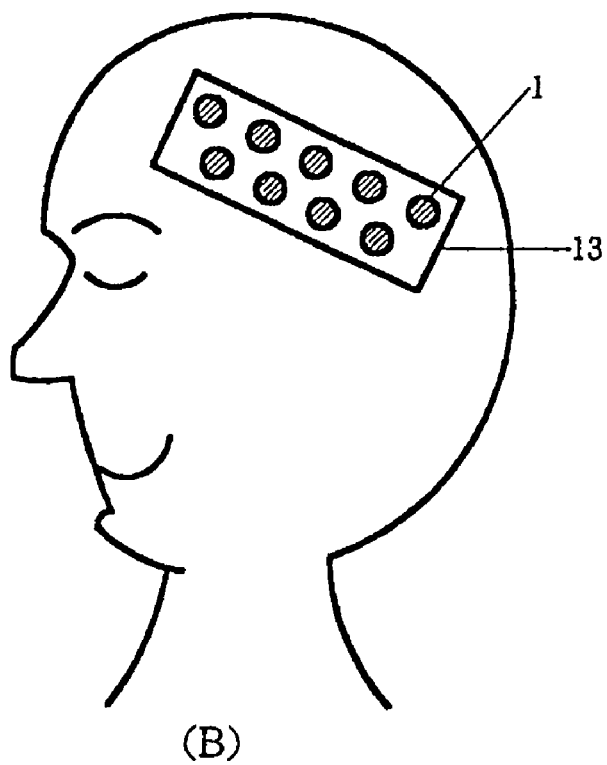
(B)

Figure 5
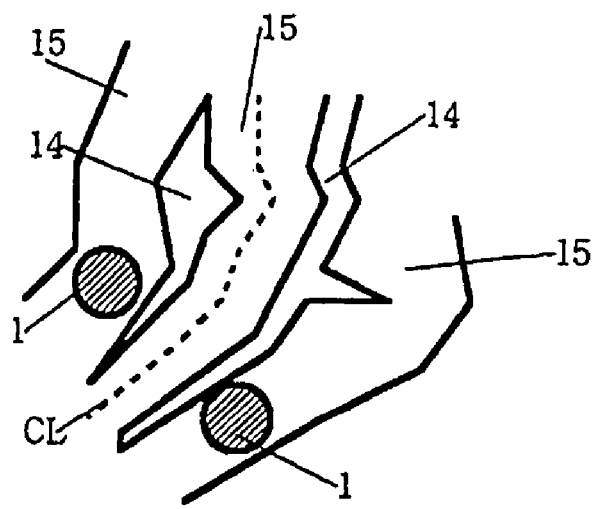
(A)
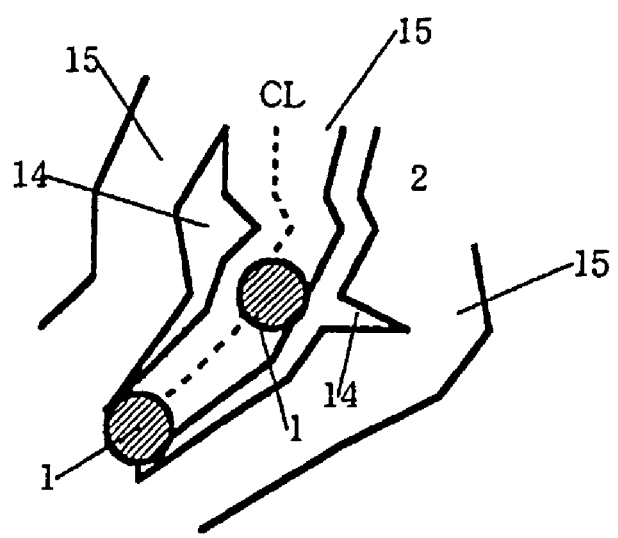
(B)

Figure 8
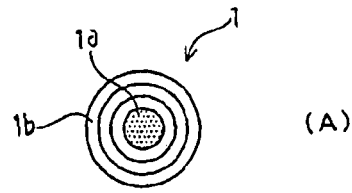
(A)
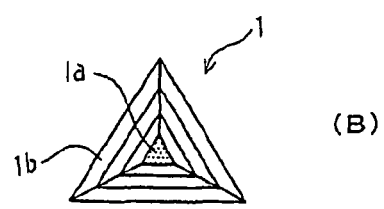
(B)
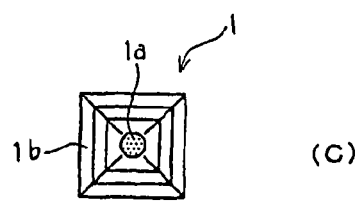
(C)
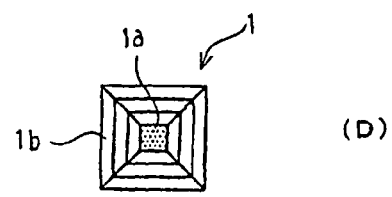
(D)
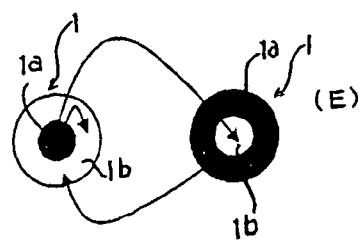
(E)

Figure 9
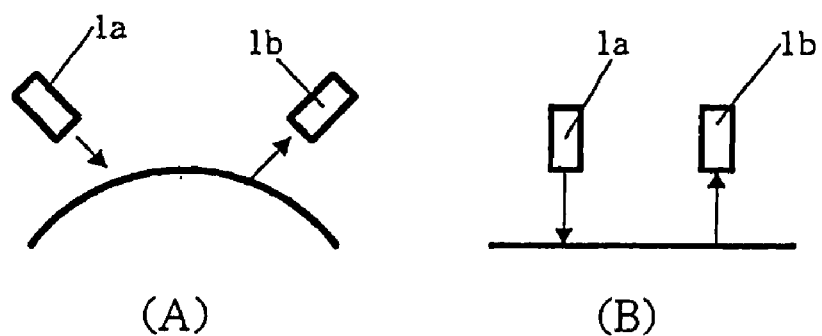
(A)                    (B)
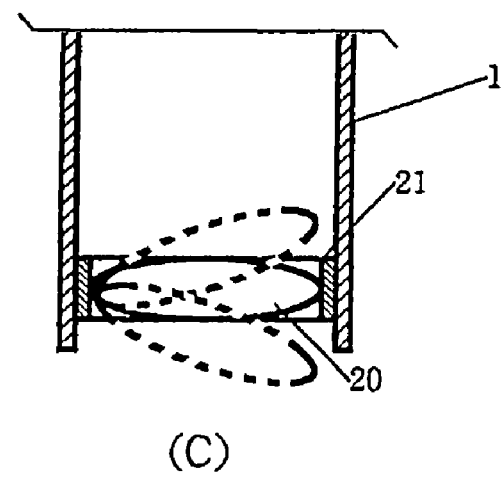
(C)

Figure 14
(A)
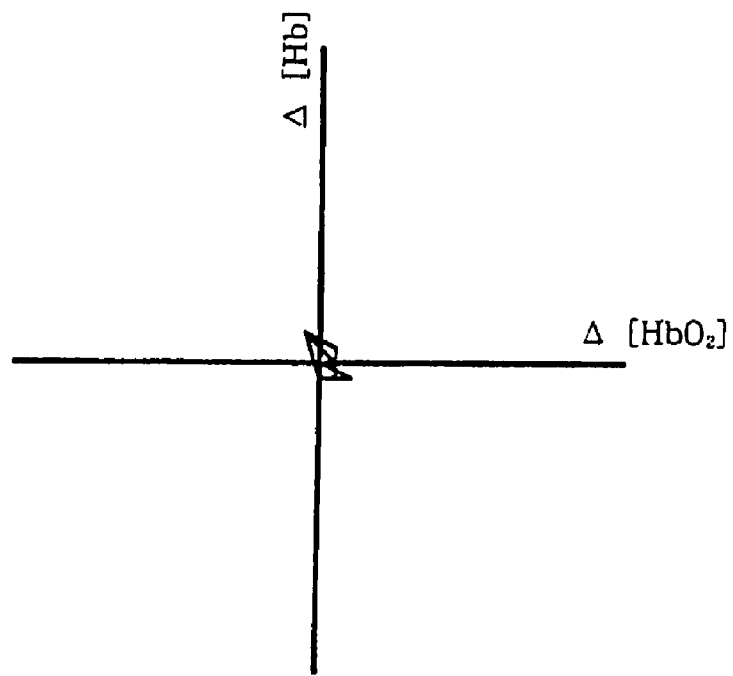
(B)
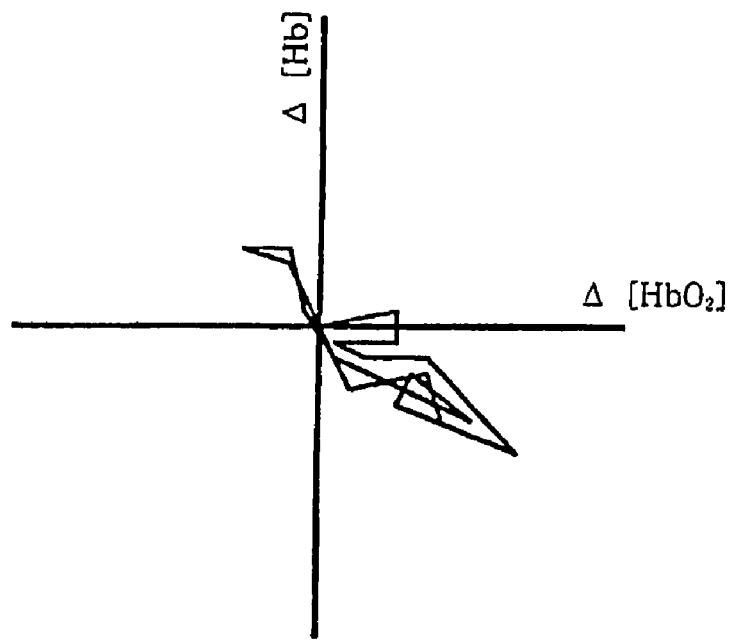

Figure 16
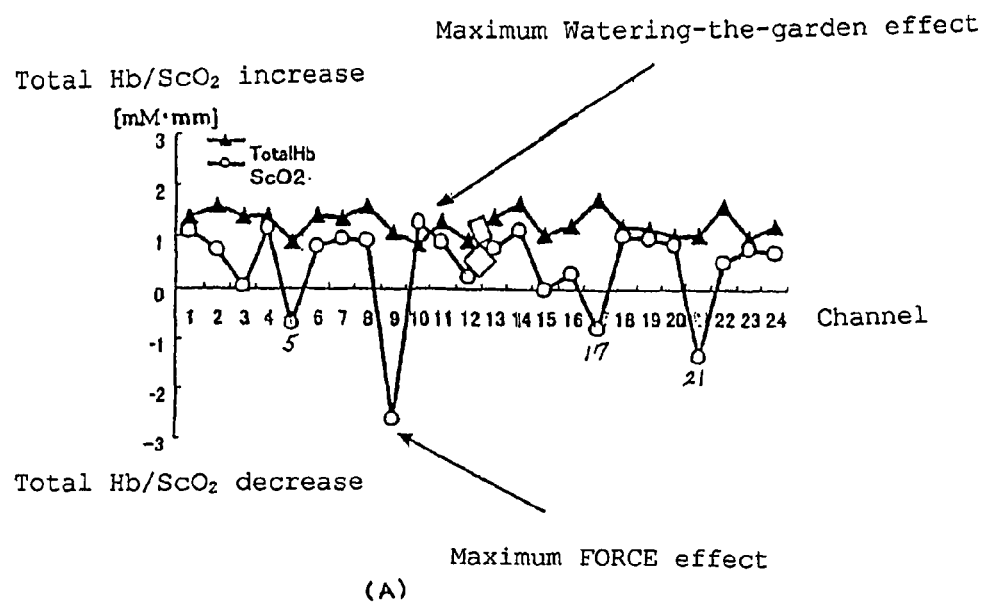
(A)
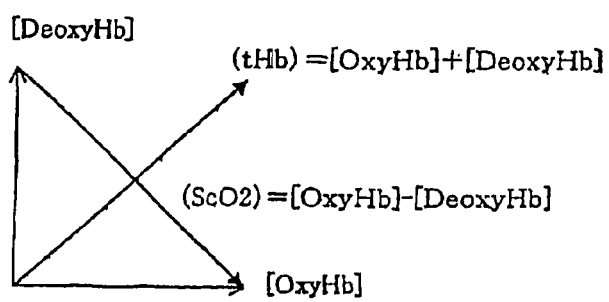
(B)

Figure 28
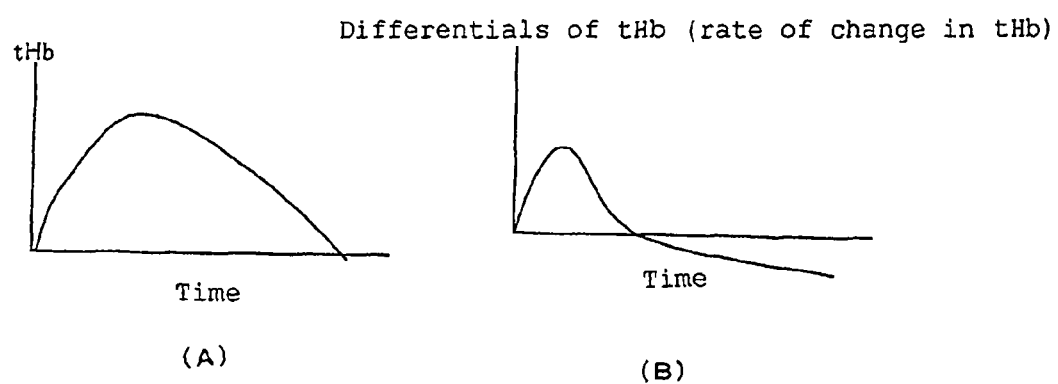
(A)            (B)
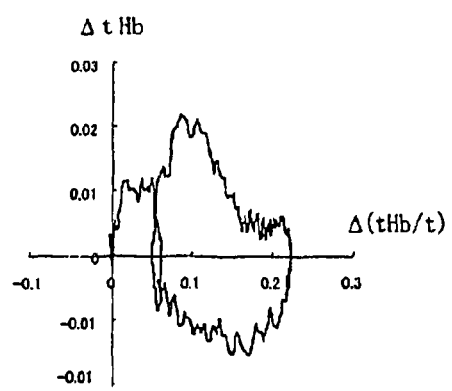
(C)

Figure 30
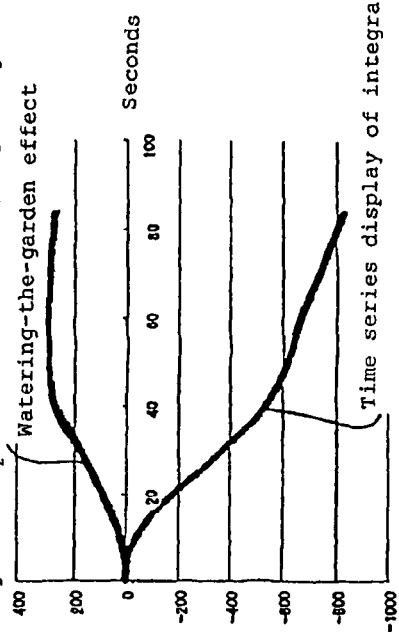
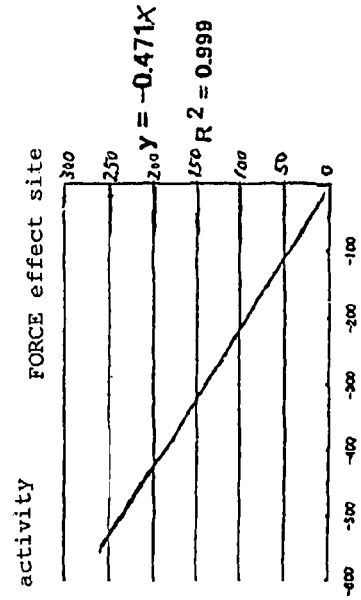
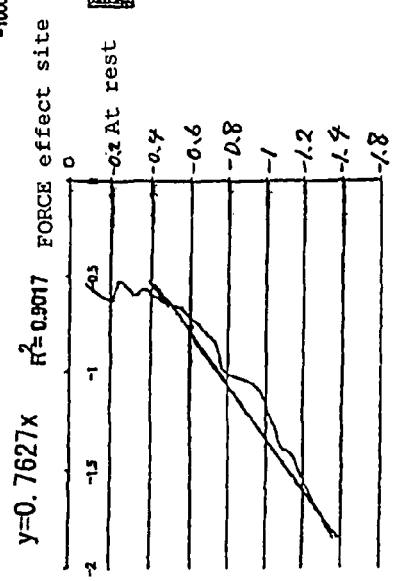

Figure 33
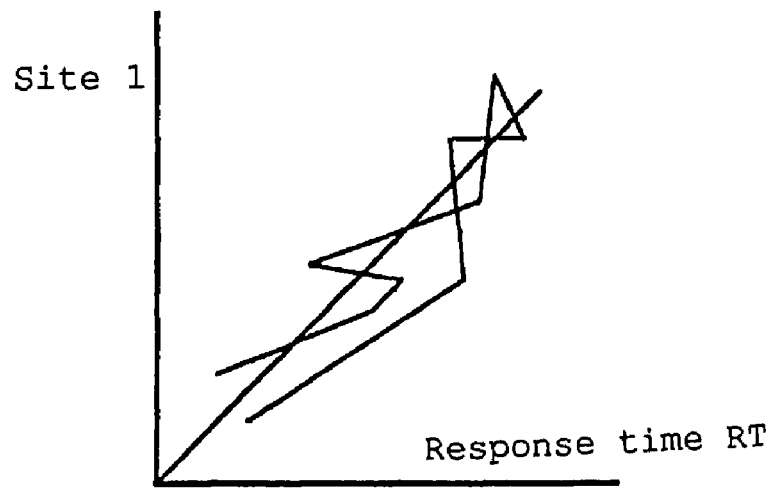
(A)
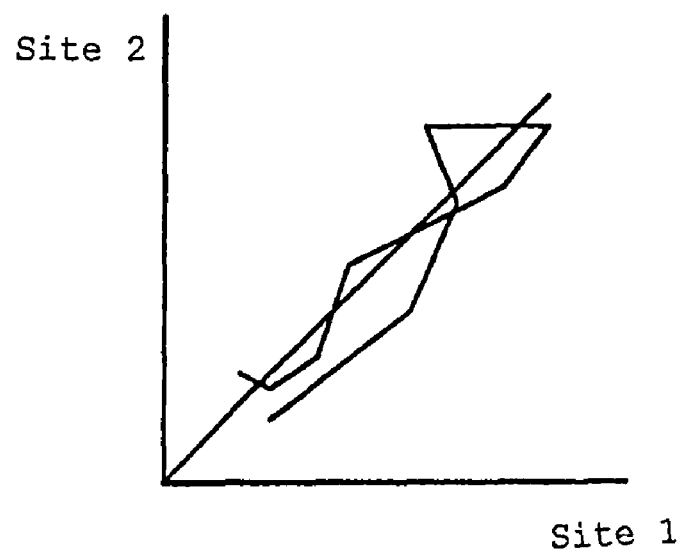
(B)

Figure 34
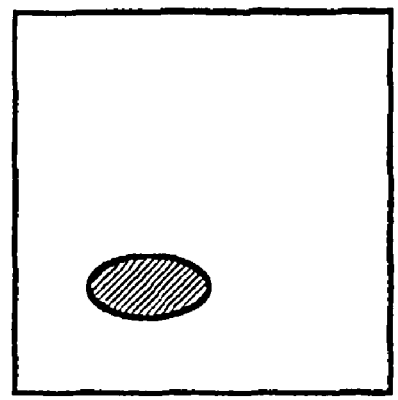
(A)
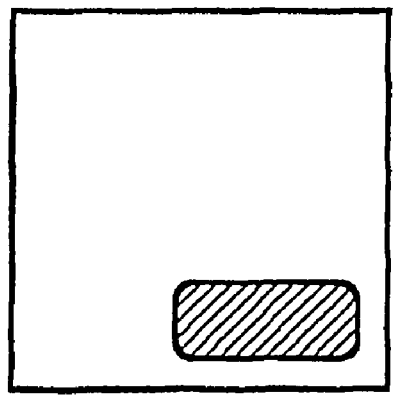
(B)
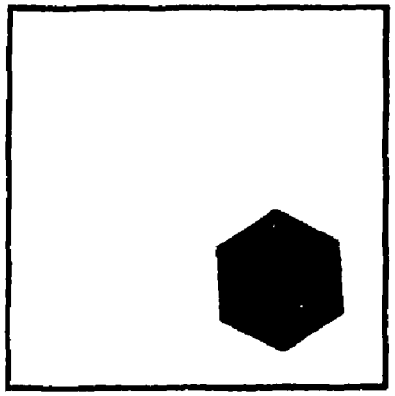
(C)

Figure 35
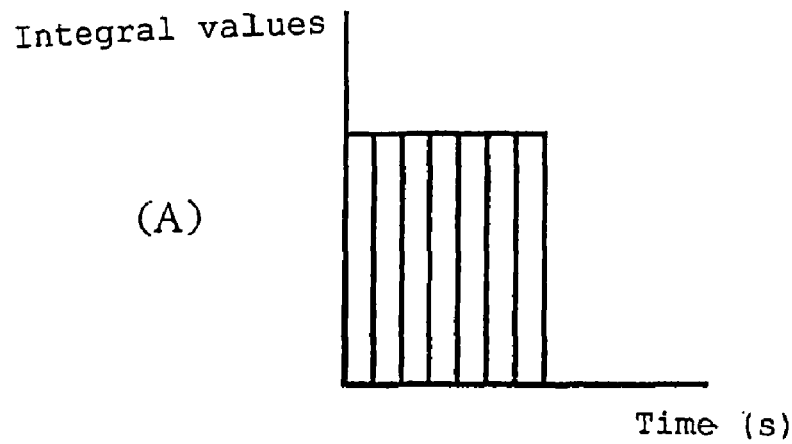
(A)
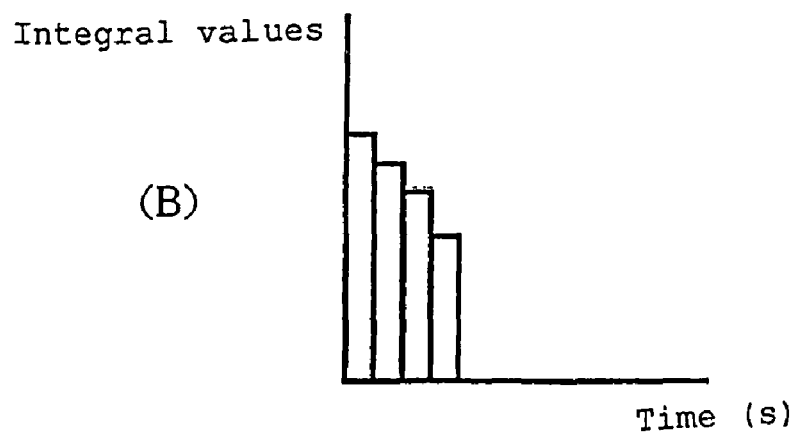
(B)
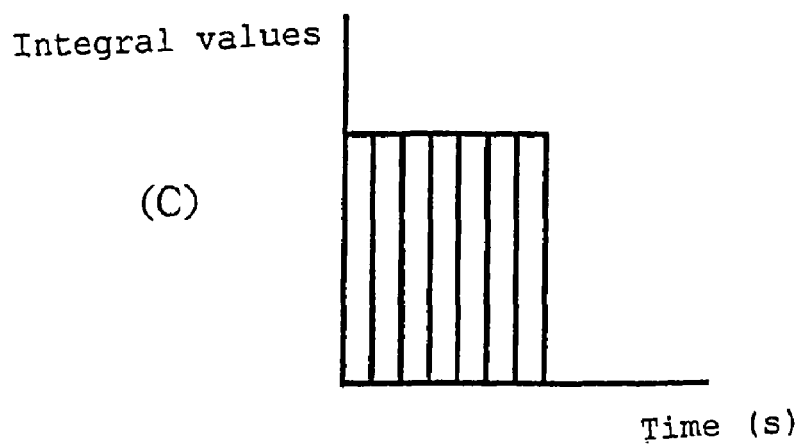
(C)

Measurement point K

Figure 47
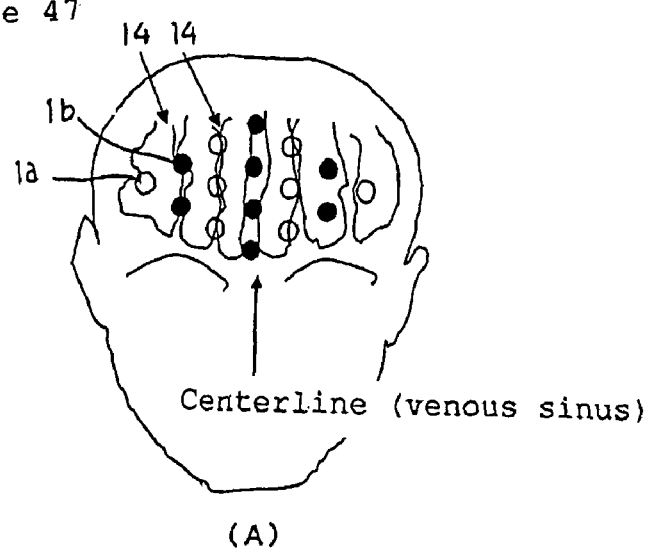
(A)
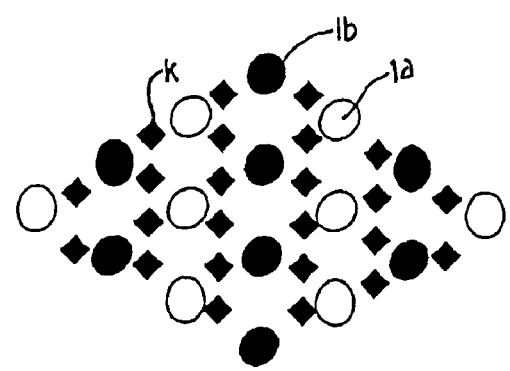
(B)
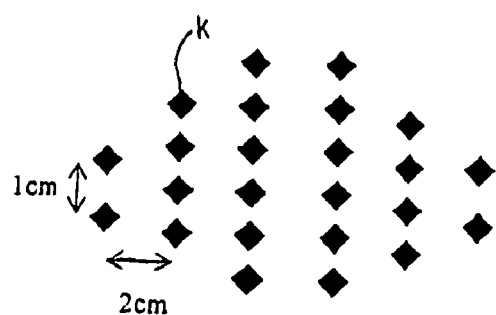
(C)

Figure 51
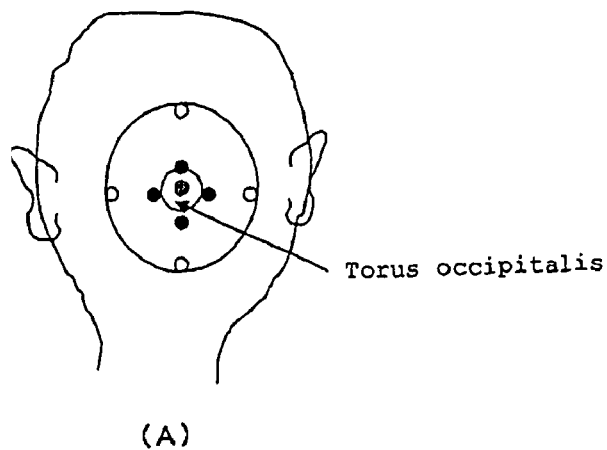
(A)
Point of intersection p of the line joining the left and right outer ear canals and the line joining the glabella and the torus occipitalis
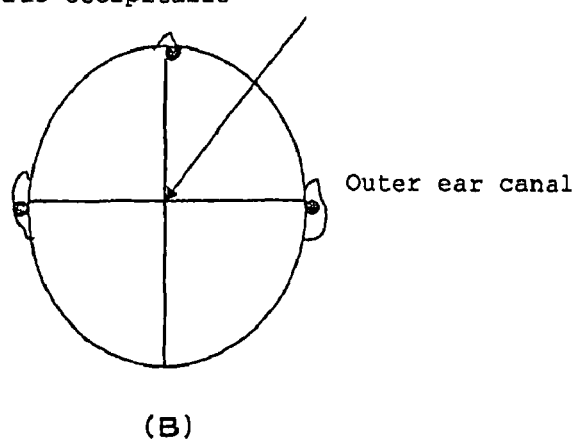
(B)

Fig.52
(A) 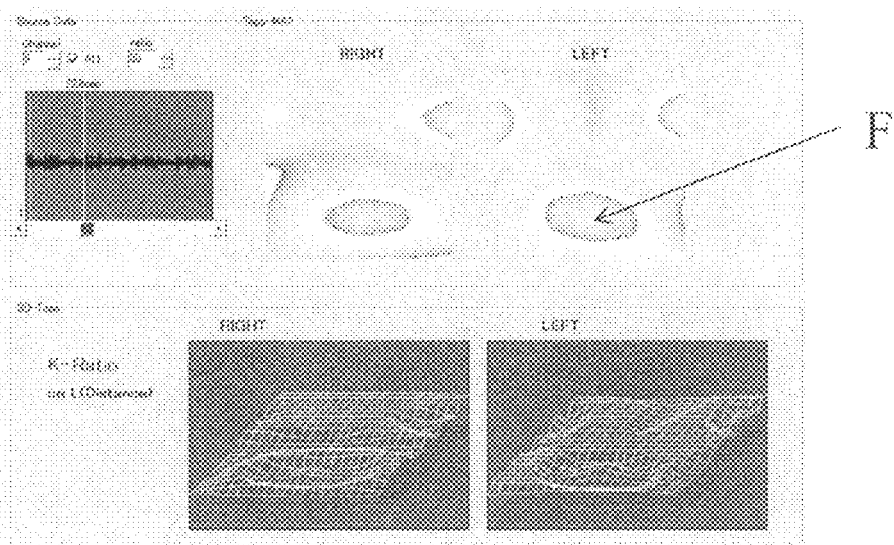
(B) 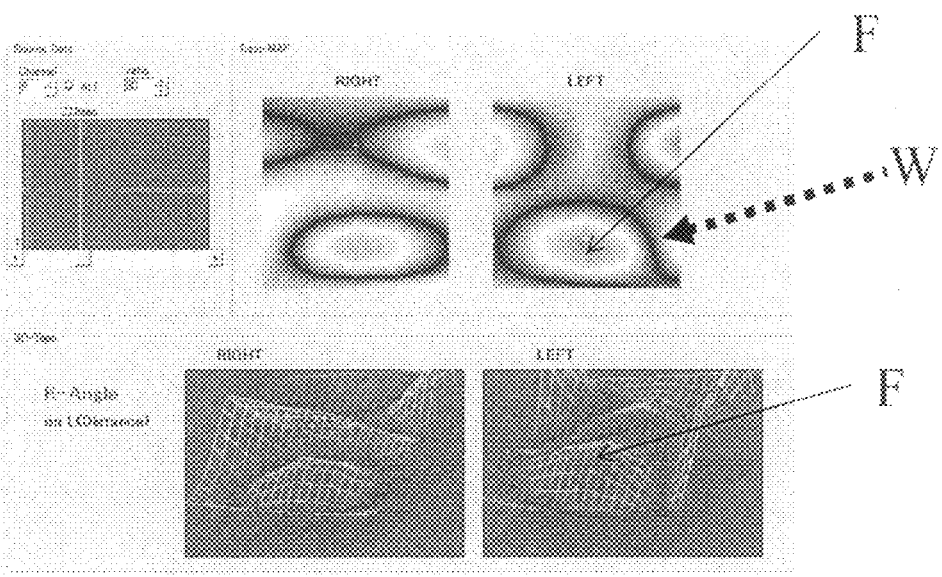

Figure 82
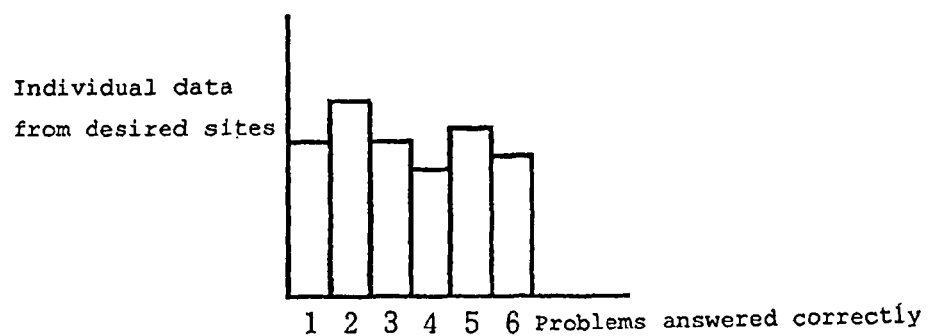
(A)
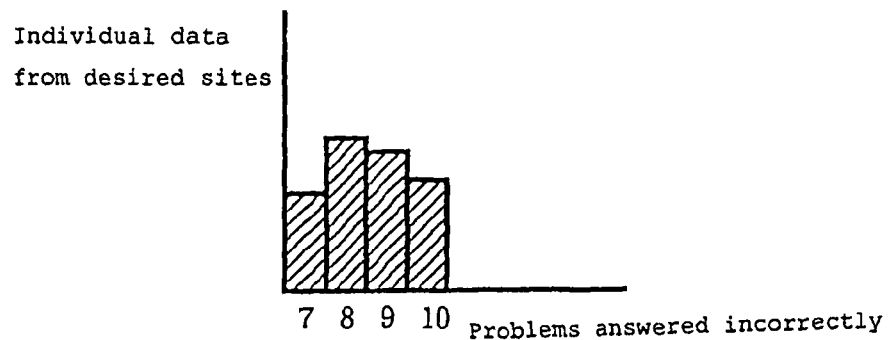
(B)

Figure 83
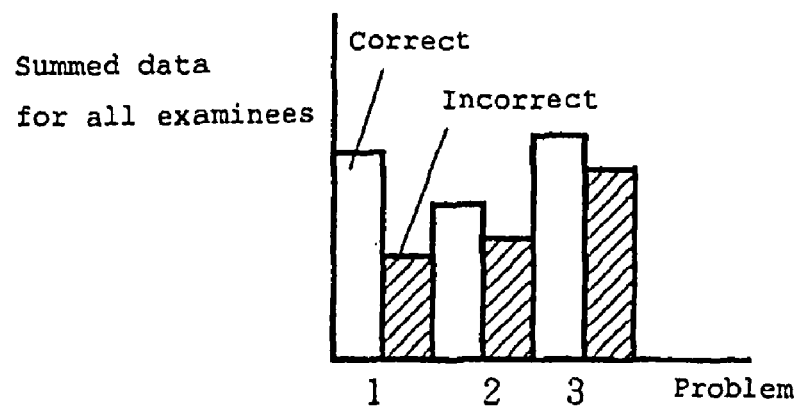
(A)
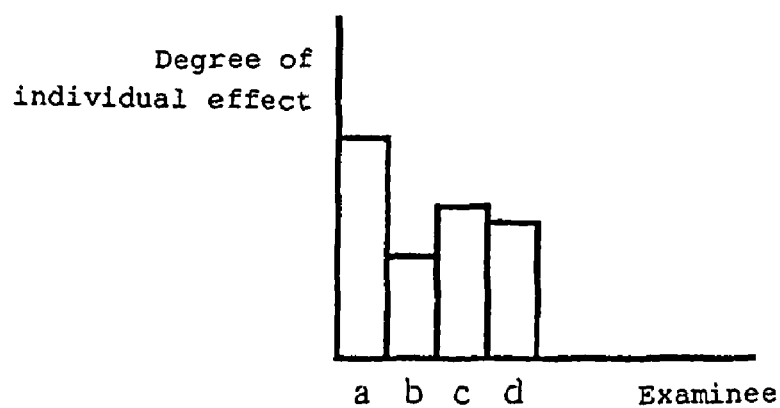
(B)

Figure 87
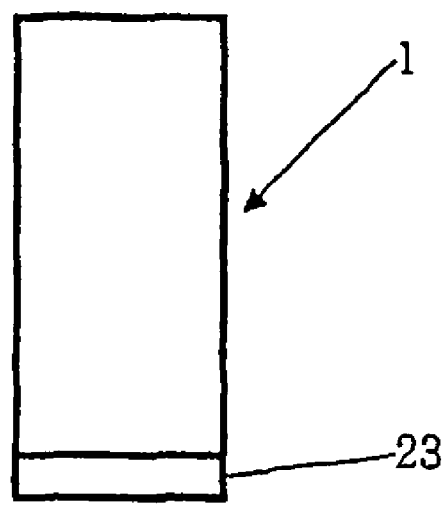
(A)
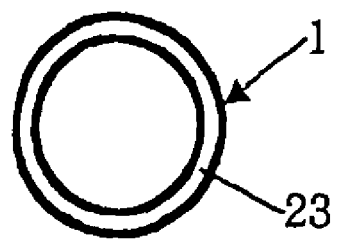
(B)

Figures 90
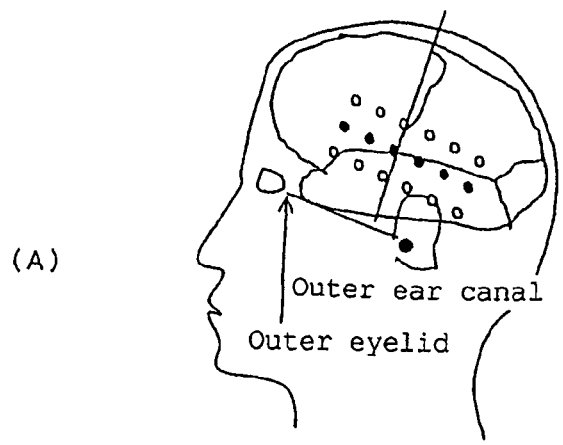
(A)
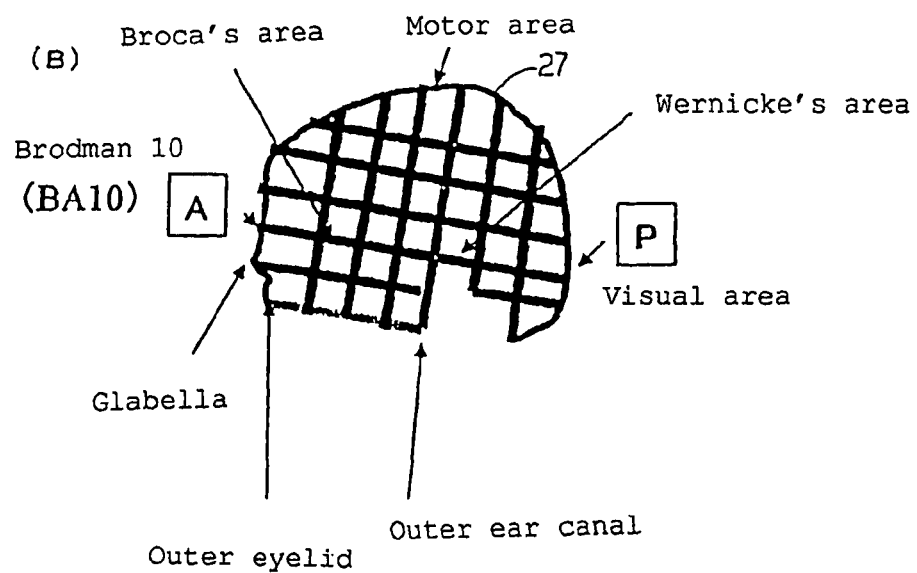
(B)
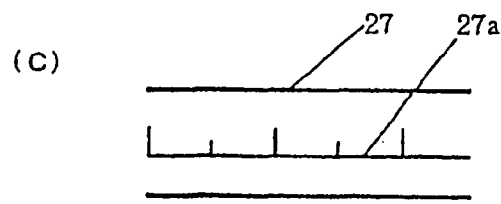
(C)

Figure 91
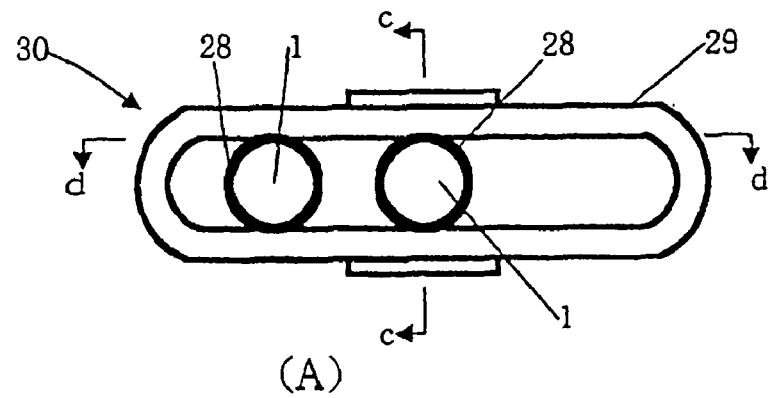
(A)
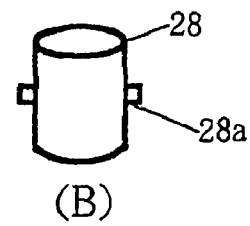
(B)
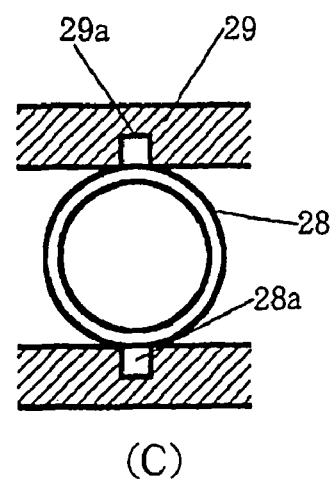
(C)
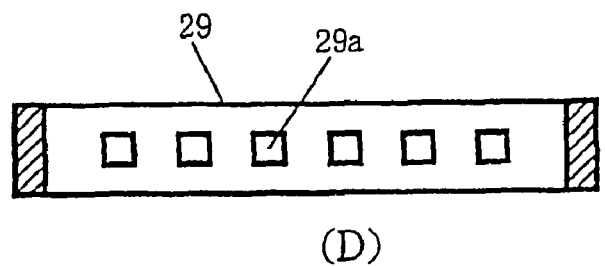
(D)

Figure 93
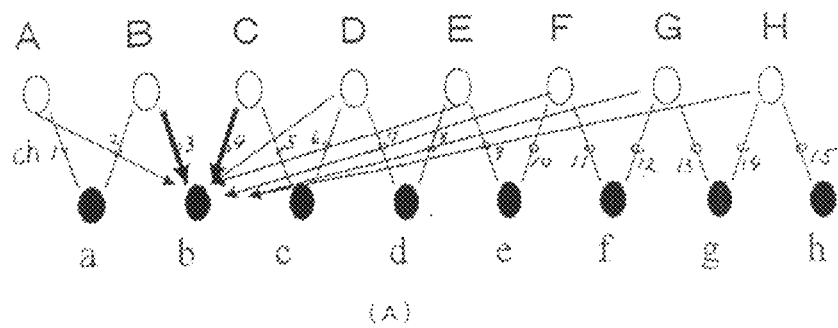
(A)
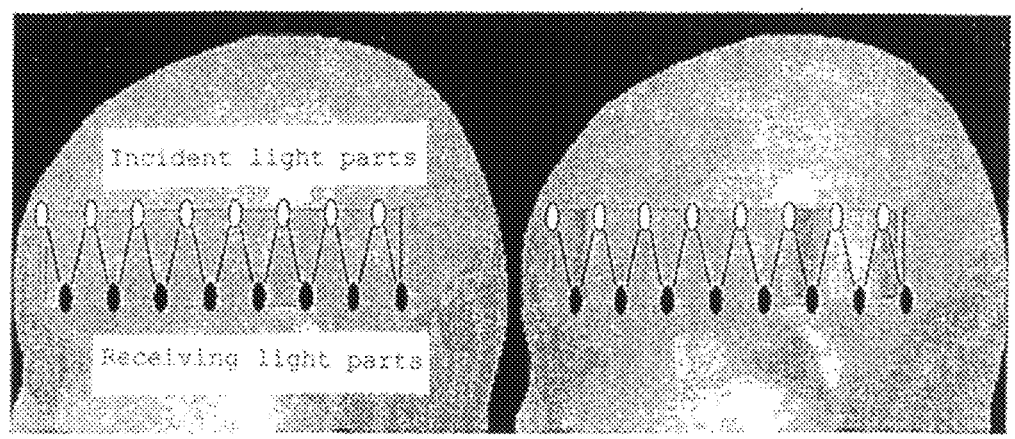
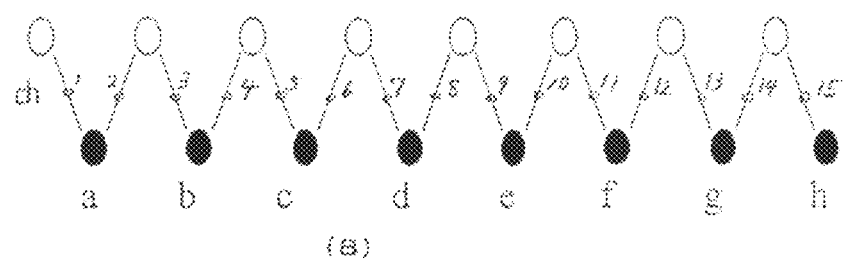
(B)

Figure 94
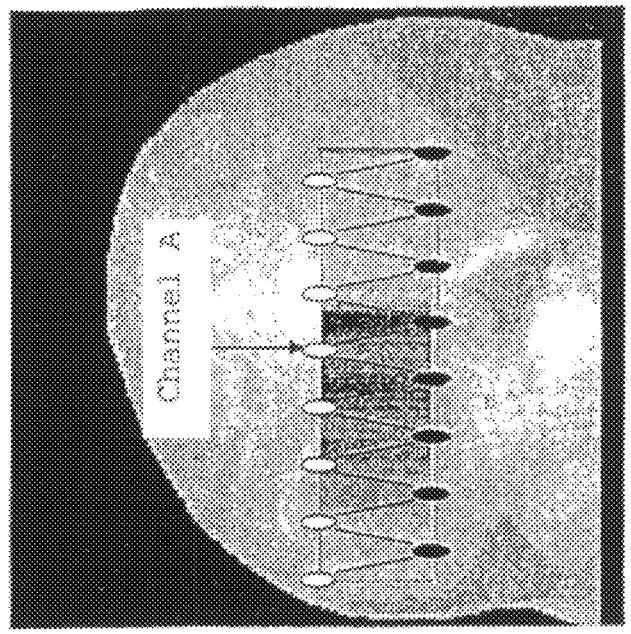
(B)
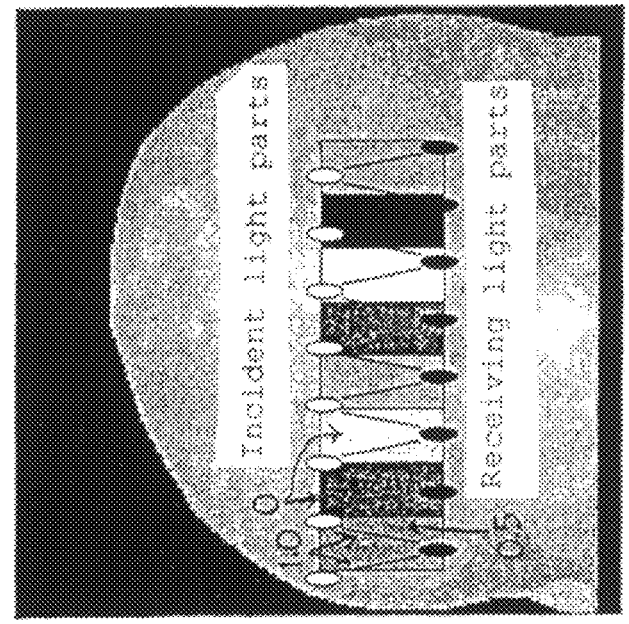
(A)

Figure 95
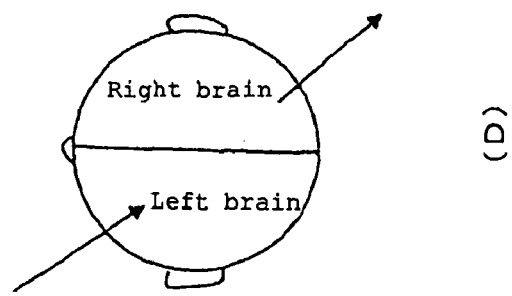
(D)
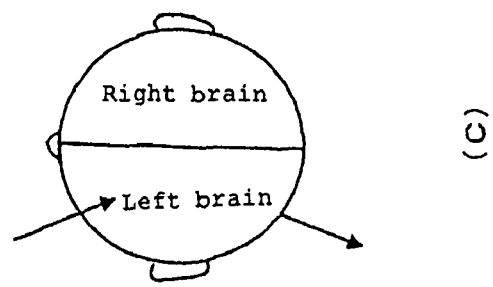
(C)
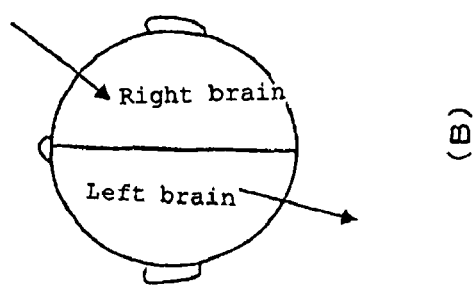
(B)
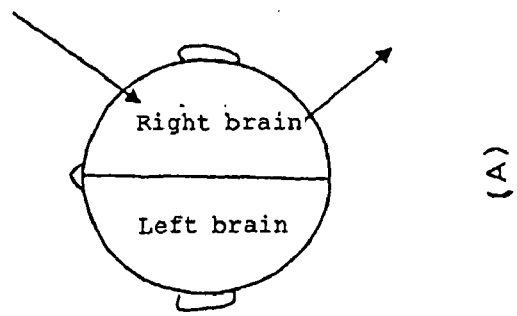
(A)

APPARATUS FOR EVALUATING BIOLOGICAL FUNCTION, A METHOD FOR EVALUATING BIOLOGICAL FUNCTION, A LIVING BODY PROBE, A LIVING BODY PROBE MOUNTING DEVICE, A LIVING BODY PROBE SUPPORT DEVICE AND A LIVING BODY PROBE MOUNTING ACCESSORY

This is a continuation of PCT/JP05/013327 filed Jul. 20, 2005 and published in Japanese.

An apparatus for evaluating biological function, a method for evaluating biological function, a living body probe, a living body probe mounting device, a living body probe support device and a living body probe mounting accessory

TECHNICAL FIELD

The present invention concerns an apparatus for evaluating biological function for the purpose of measuring and evaluating biological function based on transmitted, reflected, scattered or diffused light that is detected from a living body after its interaction with the living body by means of a living body probe, a method for evaluating biological function, a living body probe, a living body probe mounting device, a living body probe support device and a living body probe accessory; and in particular it concerns an apparatus for evaluating biological function and a method for evaluating biological function that utilize near-infrared spectroscopy (NIRs), and a living body probe, a device for mounting a living body probe, a living body probe support device and a living body probe mounting accessory.

BACKGROUND OF THE INVENTION

In recent years, a method was proposed in 1977 by F. F. Jobsis in which weak near-infrared rays (680-1300 nanometers) are irradiated from on the skin of the head through the skull and into the brain to measure changes in concentration of oxygenated hemoglobin (Oxy-Hb, $HbO_2$) and changes in concentration of deoxygenated hemoglobin (Deoxy-Hb, Hb) in the blood at the brain surface (cerebral cortex) just inside the skull.

Since that time, research on the measurement of tissue oxygen concentration by means of this near-infrared spectroscopy (NIRs) method has progressed rapidly.

In general, the near-infrared spectroscopy method has the advantages that metabolism of individual tissue can be measured noninvasively from the surface of the body (noninvasiveness), it can furthermore be implemented by a simple and convenient apparatus (portability), and, in addition, it differs from imaging methods such as PET (positron emission CT), f-MRI (functional magnetic resonance imaging) in that it makes it possible to obtain real-time measurements of changes in tissue metabolism in the brain, muscles and the like over time (temporality); it has thus given rise to expectations of a wide range of application in uses such as brain function monitoring, evaluation of muscle rehabilitation in physical therapy, and exercise physiology.

Jobsis' previous method was an attempt at noninvasive brain oxygen monitoring, and an optical tomography method (optical CT) was devised, in which the brain was cross-sectioned in layers by straight-line light in an attempt to obtain accurate oxygen information from in the depths of the brain, (Shinohara, Y. et al., Optical CT imaging of hemoglobin oxygen-saturation using dual-wavelength time gate technique. Adv Exp Med Biol, 1993. 333: p. 43-6).

However, even if accurate location information could have been measured by the technique of optical CT, by the time light had passed through the skull to the brain surface and into the brain, it was absorbed, and so the method was of no practical use.

Accordingly, in 1991, the present inventor Kato devised and corroborated a new basic principle of NIRS imaging (near-infrared spectroscopy functional imaging) for determining location information by means of the location of a probe on the brain surface and the response to a measurement target.

In addition, the present inventor and his colleagues conducted light stimulus experiments in humans in which the brain was partially irradiated with near-infrared light, which showed, as a result, that localized brain function distribution can be monitored at the bedside, and proved that it is possible to create images of localized brain function using this method and a bedside noninvasive method for detecting local brain function (Sachio Takashima, Toshinori Kato, et al., "NIR Spectroscopy ni yoru kyokusho nouketsuryu hendou no kansatsu", Shinshingaiji (sha) no iryou ryouiku ni kansuru sougouteki kenkyu no houkokusho ["Observation of variation in local brain blood flow by means of near-infrared spectroscopy", in *Comprehensive Research Report Concerning Medical Care for Children (People) with Disabilities* (Japan Ministry of Health and Welfare), p. 179-181 (1992); Kato T, Kamei A, et al., "Human visual cortical function during photic stimulation monitoring by means of near-infrared spectroscopy", *J Cereb Blood Flow Metab.* 13:516-520 (1993).

This basic principle of near-infrared spectroscopy brain functional imaging (NIRS imaging) is currently utilized in, for example, techniques for graphically displaying the functional topography (hemoglobin distribution, i.e., the display of variation in blood volume, reflecting brain activity, like a topographical map) of the brain surface in the frontal region, the occipital region and the like, and in pioneering techniques for obtaining information on brain activity. Subsequent techniques proposed for the graphical display of brain function include, for example, the inventions described in Japan unexamined patent publication nos. 2003-144437, 2003-75331, 2000-237194, H9-135825, 2002-177281 and 2003-10188.

The inventions proposed in these publications concern apparatus for measuring the interior of a living body by irradiating the living body with near-infrared light from a plurality of irradiation sites and detecting light transmitted through the living body at a plurality of detection sites; this is called Optical Topography (registered trademark), and changes in concentration of oxygenated hemoglobin and deoxygenated hemoglobin in the blood are calculated for each measuring point based on light intensity signals measured at a plurality of measuring points and displayed topographically.

It is furthermore utilized in pioneering techniques for obtaining information on brain activity, which occurs as rapidly as electrical activity.

For example, Gratton et al., by means of NIRS imaging, have detected a faint light that varies by means of electrical activity by adding 1-wavelength near-infrared light to a signal (occurring) approximately 100 ms before a brain blood flow response occurs from a stimulus consistent with an electrical response (Gratton G, Fantini S, Corballis P M, et al. Fast and localized event-related optical signals (EROS) in the human occipital cortex: comparisons with the visual evoked potential and fMRI. NeuroImage 6, 168-180, 1997).

Or, a technique has been proposed as a game or apparatus for displaying one's intent, by utilizing changes in cerebral blood flow and outputting them externally (International published patent application no. WO 00/074572 pamphlet, Yamamoto et al.).

Patent reference 1. Japan unexamined patent publication no. 2003-144437 Patent reference 2. Japan unexamined patent publication no. 2003-75331 Patent reference 3. Japan unexamined patent publication no. 2000-237194. Patent reference 4. Japan unexamined patent publication no. H9-135825 Patent reference 5. Japan unexamined patent publication no. 2002-177281 Patent reference 6. Japan unexamined patent publication no. 2003-10188 Patent reference 7. International published patent application no. WO 00/074572 pamphlet

DISCLOSURE OF THE INVENTION

Problems the Invention Attempts to Solve

Previous measurement techniques have had the following problems.

(1) The problems to be resolved by the new basic principle of NIRS imaging (near-infrared spectroscopy functional imaging), in which location information is determined by means of the location of probes on the brain surface and the response of a measurement target, become clear when we compare techniques of determining location information by means of magnetic resonance imaging (MRI) and techniques of determining qualitative information. Namely, NIRS imaging does not form an image by collecting a square matrix (of voxels), as does MRI. Namely, boundaries with adjacent locations are unclear.

Because two probes are utilized, for light incidence and detection, it has been impossible to tell, according to the distance between the two probes, whether or not light reached to the interior of the brain without seeing a response from the brain. Previously, images were displayed in proportion to the size (strength) of this brain response, and the bigger the response was, the better it was considered.

However, the distance from the surface of the skull to the brain tissues is affected by individual differences, site differences, differences according to the size of the cerebral blood vessels and differences in the shape of the gyri and sulci; the brain and skull are not uniform; and in the past, technical attention was not given to this non-uniformity. Namely, the signal-to-noise ratio (S/N) of the optical signals detected by each pair of probes was different, and the size of the range of area measured was also different. In the past, those measurement sites were joined together, like contour lines, and displayed graphically.

(2) In MRI, the nature of the measurement target is determined by a matrix (of voxels) of signal strengths. In NIRS imaging, however, analysis and weighting of a response from the living body at a measurement target becomes an important technique. In the past, this was no more than a technique for independent measurement of oxyhemoglobin, deoxyhemoglobin, total hemoglobin, cytochrome, and reaction patterns of optical signals approximately 100 ms after a stimulus application. A simple signal strength of this kind is directly affected by the S/N ratio, and its measurement sensitivity does not improve. In particular, fluctuation of channels with a bad S/N ratio shows greater changes in signal strength than do channels with a good S/N ratio, and image displays were thus dependent on high noise channels and differed from reality.

In addition, venous signals were likely to be mixed with capillary signals, causing the precision of results to deteriorate markedly. In order to improve the S/N ratio, measures such as addition average and using low-pass filters for smoothing were employed, but in the end, it was impossible to measure just one stimulus application, and only addition average mode measurements or measurements of large, quite slow changes, in units of seconds, were possible.

(3) Previous measuring techniques were based on the widely held physiological concepts that (a) electrical activity occurs simultaneously with a stimulus, and then (b) oxygen metabolism activity and blood flow activity become stronger (occurring after a delay of 2-3 seconds and reaching a peak at 10-15 seconds). Consequently, with a technique for independent measurement of oxyhemoglobin, deoxyhemoglobin, total hemoglobin, cytochrome, and reaction patterns of optical signals approximately 100 ms after a stimulus application, there was no reason for high-speed measurement, and without improvement in the S/N ratio, measurement accuracy would not be improved. Namely, in the past, there were limitations to measuring techniques relying on hemodynamic and metabolic responses of measurement targets.

(4) In addition to NIRS (near-infrared spectroscopy), methods such as EEG (electroencephalograms), MEG (magnetoencephalograms), MRI (magnetic resonance imaging) and PET (positron CT) are also known for measuring brain function. However, with these previous measurement techniques, it was difficult, without addition average, to continuously measure brain responses in milliseconds to the point where network function could be measured.

Because the oxygen partial pressure of the capillaries is approximately equal to that of the tissue, it has been recognized, since times past, that in measuring tissue oxygen concentration, it is extremely important to collect oxygen concentration data from the blood of the capillaries. The near-infrared spectroscopy method, however, takes measurements noninvasively, from the surface of the body, and because changes in the signal are thus the sum of responses occurring in the regions existing on the light path, its quantifiability, i.e., spatial resolution, is considered to be inferior. Data shown in FIG. 1(A) was identified in the past as predominantly capillary data, as is clearly shown in the literature by H. Marc Watzman et al. ("Arterial and venous contributions to near-infrared cerebral oximetry", *Anesthesiology* 2000; 93:947-53) and FIG. 8 of Japan published patent application H9238914, but the present inventor believes that this is inevitably predominantly venous data, by reason of the facts that it was obtained by measuring a site where a vein typically exists on the light path, and the apparatus was configured with wide spacing (approximately 30 mm) between the measurement points.

This is because the capillaries are structured in such a way that application of stimulus is likely to result in a divergence between the variation in the amount of red blood cells and that of the blood serum component. Namely, in the capillaries, the red blood cells and the serum move at different speeds, and changes in the hematocrit or changes in total hemoglobin are therefore more likely to occur there than in the veins; consequently, mirror-image changes in oxygenated hemoglobin and deoxygenated hemoglobin are less likely to occur there than in the veins. Predominantly capillary data is therefore considered necessarily to be that of FIG. 1(B), which shows an asymmetrical mode of change, because of conclusions obtained from the research of the present inventor. If this is the case, then previous measuring apparatus can be said to be configured based on an erroneous theoretical perception.

In addition, even in the rare case when a previous measuring apparatus identifies the data shown in FIG. 1(B) as true predominantly capillary data, it is impossible to tell whether data being collected is predominantly capillary data or predominantly venous data by comparing this data with the predominantly venous data of FIG. 1(A) during the period up until changes occur in the tissue by using a conventional measuring apparatus, which is confined to the output of FIGS. 1(A) and (B), because before the application of stimulus (including both internal stimuli from physiological effects and external stimuli), that is, at rest, before changes occur in the tissue (in the figures, baseline=the period up to approximately 8 seconds), the characteristics of change over time for both predominantly capillary data and predominantly venous data are largely convergent. If we take into account this time lag together with the extremely low probability of collecting predominantly capillary data because of the wide settings of the measurement point intervals (approximately 30 mm), we cannot expect a sufficient contribution to on-site medicine.

In addition, because previous measuring apparatus utilizing near-infrared spectroscopy only measure absolute values and changes in oxygenated hemoglobin and deoxygenated hemoglobin concentration (and even this data is highly inaccurate), and because theories of brain physiology, such as the correlation between these measured data and vasodilatation/vasoconstriction arising in the cerebral blood vessels, and the involvement of the oxygen consumption rate and changes in the hematocrit in the capillaries accompanying changes in total hemoglobin, have not been adequately understood, these apparatus have therefore remained in the realm of monitors for showing changes in concentration of hemoglobin and the like, or simple scientific experimental tools. In addition, even in two-dimensional image displays, when a plurality of sites are measured, the S/N ratio will differ between the sites, so that channels with low S/N ratios are emphasized, and so on, resulting in a distorted image, and so they were not meaningful apparatus capable of evaluating function by means of image displays.

(5) Neuron activity brings a need for oxygen consumption and oxygen supply. In this case, oxygen is thought to be supplied through the glial cells from 7-micron red blood cells in the 5-micron capillaries. The oxygen concentration decreases in the capillaries that supplied the oxygen, and then oxyhemoglobin is supplied from the arterial side. Because it was not previously possible to measure this brain microcirculation, tissue oxygen partial pressure was measured invasively by inserting a needle into the intercellular spaces of the neurons. In actuality, since Roy and Sherrington (Roy C S, Sherrington C S: On the regulation of the blood-supply of the brain. J Physiol 11, 85-108, 1890), cerebral blood-flow responses occurring after neuron activity have focused only on the cerebral blood flow, and during more than 110 years, it was not possible to selectively measure oxygen exchange inside the capillaries.

(6) There was no quantitative method that did not depend on the quantification of hemoglobin.

The present invention is for the purpose of solving the above-stated problems, and first, as the physiological mechanism whereby the blood vessels, namely, the capillaries, provide oxygen to tissue, anywhere in the tissue of the living body, constructs a theory of oxygen exchange rotational motion in the capillaries, in which the phenomenon of oxygen exchange between oxyhemoglobin and deoxyhemoglobin in the red blood cells is considered to be a rotational motion. The present invention takes as its object the provision of an apparatus for evaluating biological function, a method for evaluating biological function, and a living body probe that make it possible to take new physiological indexes related to oxygen exchange metabolism as their measurement target, by placing oxyhemoglobin and deoxyhemoglobin on rectangular coordinates (polar coordinates), from this theory of rotational motion.

Secondly, it takes as its object the provision of an apparatus for evaluating biological function, a method for evaluating biological function, and a living body probe that distinguishes as much as possible between information from the capillaries, which reflects tissue metabolism, and information from outside the tissue (for example, the arteries and veins), and, in order to exclude information corresponding to noise, detects differences in the S/N ratio to identify image distortion, thus providing high speed and accuracy to make it possible to compensate for the low spatial resolution of previous near-infrared spectroscopy methods; this makes it possible to distinguish capillary responses, metabolic responses and the like, while at the same time making it possible to identify oxygen metabolism activity in the capillaries corresponding to behavioral information.

Third, it takes as its object the provision of an apparatus for evaluating biological function, a method for evaluating biological function, and a living body probe that do not simply monitor changes in oxygen concentration and display them graphically, but that make it possible to separate out in detail the volume of the measurement target, namely, the voxel components, and make it possible, by lessening differences in S/N ratio between the voxels, correcting them, or measuring new indexes derived from measured parameters that are not easily affected by S/N ratios, to easily and conveniently distinguish functional data, including location and time information.

Fourth, it takes as its object the provision of a living body probe mounting device, a living body probe support device, and a living body probe mounting accessory for use with the above-mentioned living body probe.

Means for Solution of the Problems

The apparatus for evaluating biological function is an apparatus for evaluating biological function having a plurality of living body probes provided with light-emitting elements for irradiating light to specified sites of a living body and light-receiving elements for receiving and detecting light exiting the living body, a behavioral information measuring part for measuring behavioral information of the aforementioned living body, and an apparatus body for entering light information detected by the aforementioned living body probe and behavioral information measured by the aforementioned behavioral information measuring part and performing calculation, control and memory operations, and utilizing near-infrared spectroscopy to evaluate biological function; and the aforementioned apparatus body is characterized in that it has a controller for calculating, based on the light information from the aforementioned living body probe, a variety of parameters derived from two-dimensional diagrams showing relationships between changes in oxyhemoglobin and changes in deoxyhemoglobin and two-dimensional diagrams showing relationships between absolute amounts of oxyhemoglobin and absolute amounts of deoxyhemoglobin; a behavioral information input part for entering behavioral information measured by means of the aforementioned behavioral information measuring part; and a display part for performing various types of image displays based on various parameters calculated by means of the aforementioned controller and/or the behavioral information entered in the aforementioned behavioral information input part.

The method for evaluating biological function is a method for evaluating biological function in which near-infrared spectroscopy is utilized to evaluate biological function, using an apparatus for evaluating biological function that has a plurality of living body probes provided with light-emitting elements for irradiating light to specified sites of a living body and light-receiving elements for receiving and detecting light exiting the living body, a behavioral information measuring part for measuring behavioral information of the aforementioned living body, and an apparatus body for entering light information detected by means of the aforementioned living body probe and behavioral information measured by means of the aforementioned behavioral information measuring part, and performing calculation, control and memory operations, and utilizes near-infrared spectroscopy to evaluate biological function;

and it is characterized in that it has (1) a step whereby light-emitting elements and light-receiving elements of living body probes are placed on a living body, and (2) a step whereby light from the aforementioned light-emitting elements of the living body probes is irradiated to a living body, and (3) a step whereby, based on light information detected by the aforementioned light-receiving elements of the living body probes, selection or adjustment is made among light-emitting element/light-receiving element combinations in each of the channels formed by the aforementioned living body probes, based on specified criteria, and (4) a step whereby, based on light information detected by the aforementioned living body probes, selection or adjustment is made among combinations of the aforementioned channels, based on specified criteria, and (5) a step whereby baseline data is measured from light information detected by means of the aforementioned living body probes with a living body at rest, and data analysis and data display are performed, and (6) a step whereby task presentation data is measured from light information detected by the aforementioned living body probe when a task is presented to the living body, and data analysis and data display are performed.

The living body probe of the present invention is characterized in that it is used in the aforementioned apparatus for evaluating biological function.

The living body probe mounting device of the present invention is characterized in that the aforementioned living body probes are installed on and retained by a mesh-like stretchable retaining material.

The living body probe support device of the present invention is characterized in that it has retaining rings for holding the aforementioned living body probes, and a ring support frame for movably supporting those retaining rings.

The living body probe mounting accessory of the present invention is a living body probe mounting accessory for aiding in mounting the aforementioned living body probes on the head, and it is characterized in that it is made from a net-like material formed spaced at fixed intervals along lines parallel to the line connecting the outer eyelid and the outer ear canal and the line connecting the outer ear canal and the parietal line, respectively, and measuring marks are displayed on the surface of the aforementioned net-like material.

Effects of the Invention

The present invention has the following excellent effects.

(1) Because two types of selection and adjustment can be performed to reduce variation within and between channels using a variety of parameters (indexes), it becomes possible to evaluate biological function to a high degree of precision.

(2) With conventional techniques, images were displayed with uniform distances between probes, conversely ignoring the shape of the measurement target, but with the present invention, it is possible to judge whether the probe location is really able to properly select a cerebral gyrus. Because of this, even if the channels are mounted somewhat roughly, it is possible to accurately locate or select sites, for example, sites related to brain function, from on the head, and muscle function from the skin surface.

(3) By arranging the living body probes according to the shape and size of the cerebral gyri and sulci, it becomes possible to evaluate biological function with a high degree of precision.

(4) Tissue functional response can be detected even at differences of milliseconds, without relying on peak times of blood response and the like.

(5) Integral values of response times (RT) in units of milliseconds can be utilized to acquire and display images of site information that is dependent on behavioral data, to acquire and display graphically information that is dependent on networks between sites, and so on.

(6) Because the method does not depend on the detection sensitivity of each channel, image display distortion is eliminated.

(7) It can be utilized to extract information in inactive thinking time, and, to measure thinking time between the task presentation period and the implementation period during conversation, writing and the like, independent of artifacts of movement, to evaluate learning effectiveness.

(8) Accurately selected data can be used for signal processing, as a simple and convenient interface with the living body.

Phenomena occurring simultaneously with the behavior period, the stimulus period and the like, which are difficult to observe from fMRI and PET blood flow measurements and from magnetoencephalograms, electroencephalograms and the like, can be observed quantitatively.

(9) It benefits medicine not only as a way of measuring brain function, but also as a way to improve the quality of education/learning and thinking in daily life. For example, it is possible to observe and investigate how oxygen consumption and supply responses can be supported in order to improve the effectiveness of education, prevention of aging, physical therapy, exercise and daily life.

(10) It also becomes possible to evaluate the presence of changes in function or a disability from the surface, with a high degree of precision.

(11) The effect on signals of motion artifacts (a cause of distortion of actual data from the measurement target, by movement of the muscles or the body) can be reduced.

(12) Regions and time periods accompanying blood oxygen exchange that are dependent on oxygen consumption and oxygen supply can be differentiated, rotational energy can be calculated, and a variety of image displays that are dependent on oxygen exchange rate (oxygen exchange angle) and total hemoglobin can be performed.

(13) It becomes possible to evaluate interrelationships of metabolism, blood vessel control and the like between living body tissues.

(14) It becomes possible to improve S/N ratios and take measurements independent of the amount of change, even when the changes in all the hemoglobins that are indexes of oxygen metabolism are weak.

(15) Oxygen metabolism in the capillaries can be measured quantitatively. A quantitative imaging method for oxygen exchange in the capillaries can be realized.

(16) It becomes possible to separate the FORCE effect and the "Watering-the-garden" effect.

It is an apparatus that is capable of judging the strength of tissue oxygen activity by means of differences in FORCE effect.

$$CMRO_2 = a \cdot rCBF$$

is a late phase formula from PET that applies to the blood vessels, and it does not apply for oxygen activity in the capillaries.

Namely, if the late phase is considered to be the oxygen supply time period, this formula does not represent oxygen consumption.

(17) NIRS imaging differentiates the brain functional voxels of two light functional voxels.

Namely, it separates out voxels where oxygen exchange is taking place (FORCE effect) and voxels where oxygen exchange is not taking place (Watering-the-garden effect).

Previously, high oxygen exchange voxels (FORCE effect) and low oxygen exchange voxels (Watering-the-garden effect) were mixed together, but the present invention makes it possible to differentiate them.

(18) Time series pertaining to the passage time through the capillaries for red blood cells can be measured at a plurality of sites.

(19) Oxygen exchange in the capillaries can be selectively measured.

(20) Quantification methods and quantitative imaging methods independent of the quantification of hemoglobin are possible.

(21) By taking into consideration the polar coordinates from two-dimensional diagrams, quadrant shift imaging methods and scalar change imaging methods, utilizing vectors and scalars, are possible.

(22) When blood is utilized in fMRI, PET and the like, errors in functional evaluation arising from intermixed venous components can be identified and avoided in functional imaging.

BRIEF DESCRIPTION OF THE DRAWINGS

FIG. 3. FIG. 3(A) is a perspective view showing a living body probe, and (B) is a bottom view thereof.

FIG. 4(A) is an explanatory drawing showing living body probes arranged on a mounting strip, and (B) is an explanatory drawing showing a mounting strip mounted on the side of the head.

FIG. 5(A) is an explanatory drawing showing a situation in which a pair of living body probes is placed perpendicular to the centerline of a gyrus, between sulci, and (B) is an explanatory drawing showing a situation in which they are placed along the centerline of a gyrus, between sulci.

FIGS. 8(A)-(E) are explanatory drawings showing examples of multilayer probes.

FIG. 9. Cross-sectional views showing (A) a case in which the surface where the living body probes are placed is curved, (B) a case where the surface on which the living body probes are placed is flat, and (C) an example in which a lens support member is established for supporting a lens inside the tip of a living body probe.

FIG. 14. A conceptual explanation of a two-dimensional diagram showing the amplitude of fluctuation at rest: (A) is an example of a small amplitude, and (B) is an example of a large amplitude.

FIG. 16. (A) is a graph showing changes in $ScO_2$ for all the channels, and (B) is a graph explaining the theoretical formula using vectors of OxyHb, DeoxyHb, tHb and $ScO_2$.

FIG. 28. (A) is a graph showing time course changes in tHb, (B) is a graph showing time course changes in the differentials of tHb, and (C) is a two-dimensional diagram of the differentials of tHb and their differentials.

FIG. 30. Graphs showing slopes R that are completely different at rest and during activity for regions displaying different amounts of change in $ScO_2$, but that have a high correlation coefficient.

FIG. 33. (A) is a two-dimensional diagram showing the relationship between behavior time RT and integral values, and (B) is a two-dimensional diagram showing the relationship between integral values measured from a plurality of sites in a desired time period.

FIG. 34 is L-value maps in which identification of learning patterns is extracted in time series from brain site information; (A) is a screen showing cognitive response; (B) is a screen showing thought-associated brain response; and (C) is a screen showing behavior-related brain response.

FIG. 35. A two-dimensional diagram with time as the horizontal axis and integrals as the vertical axis; (A) is the information input period; (B) is the thought period; and (C) is the output period.

FIGS. 47(A)-(C) are drawings explaining arrangements of living body probes utilizing the centerline.

FIG. 51(A) is an explanatory drawing of a view from the back of a human head; (B) is a drawing explaining the intersection of the line joining the left and right outer ear canals and the line joining the glabella and the torus occipitalis.

FIG. 52(A) is an image display, with living body probes arranged in a lattice shape, of K-ratios and L-values from the periphery of the left and right motor areas at a point 22.8 seconds in the midst of lifting a 14 kg dumbbell; and (B) is an image display of k-angles and L-values from the periphery of the left and right motor areas at a point 22.8 seconds in the midst of lifting a 14 kg dumbbell.

FIGS. 82(A) and (B) are graphs showing cumulative summed values for problem response time (RT) at desired sites; (A) is a graph of problems correctly answered by one individual, and (B) is a graph of problems incorrectly answered by one individual.

FIG. 83(A) is a graph showing cumulative summed data for all those taking a test, by problem; (B) is a graph showing the degree of individual effect, by examinee.

FIG. 87(A) is a lateral view showing a modified example of a living body probe, and (B) is a front view thereof.

FIGS. 90(A)-(C) are drawings explaining a living body probe mounting accessory of a working embodiment of the present invention.

FIG. 91(A) is a plan view showing a living body probe support device of a working embodiment of the present invention; (B) is a perspective view showing a retaining ring; (C) is a cross-sectional view along line c-c of (A); and (D) is a cross-sectional view along line d-d of (A).

FIGS. 93(A) and (B) are drawings explaining the independence and interconnectedness of light functional voxels corresponding to a probe arrangement.

FIGS. 94(A) and (B) are drawings explaining the independence and interconnectedness of light functional voxels corresponding to a probe arrangement.

FIGS. 95(A)-(D) are drawings explaining the four thought patterns of the human brain.

EXPLANATION OF THE SYMBOLS

Figure 1:
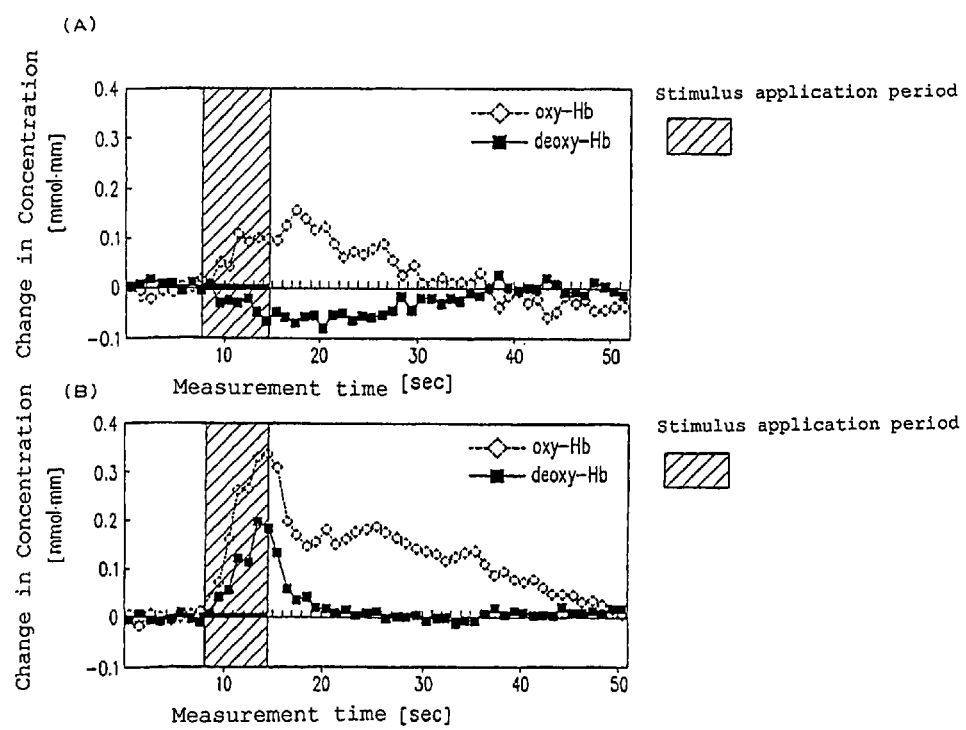
FIG. 1. Characteristic graphs showing changes in hemoglobin concentration over time; (A) shows predominantly venous data and (B) shows predominantly capillary data.

1: Living body probe
1a: Light-emitting element
1b: Light-receiving element
2: Behavioral information measuring part
3: Apparatus body
4: Light intensity adjustor
5: Selector-adjustor
6: Signal amplifier
7: A/D converter
8: Controller
9: Memory
10: Display part
11: Sampling speed adjuster
12: Behavioral information input part
13: Mounting strip
14: Sulcus
15: Gyrus
20: Lens
21: Lens support member
22: Pressure application device
23: Protective cover
24: Soft material
25: Outer ear canal
26: Living body probe mounting device
27: Living body probe mounting accessory
28: Retaining ring
29: Ring support frame
30: Living body probe support device
CL: Centerline

BEST EMBODIMENT FOR CARRYING OUT THE INVENTION

Figure 2:
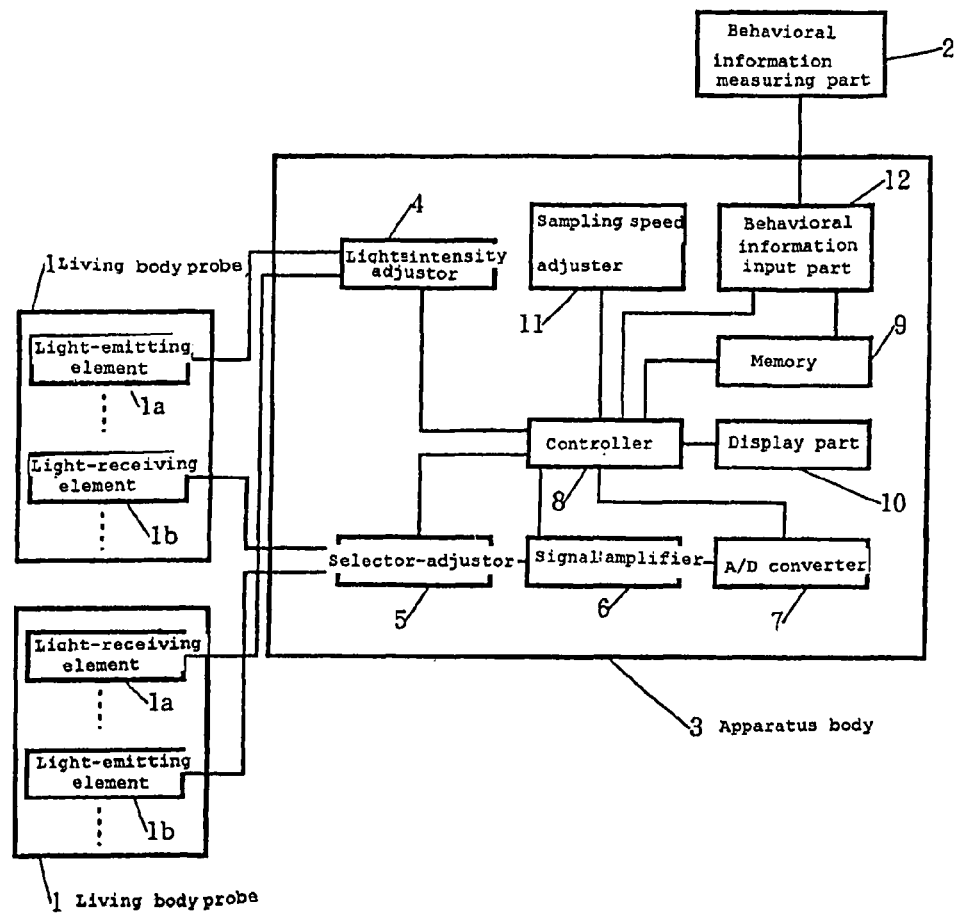
FIG. 2. A block diagram showing the configuration of an apparatus for evaluating biological function of the present working embodiment.

A working embodiment of the present invention is described below with reference to drawings. FIG. 2 shows a block diagram of configuration of an apparatus for evaluating biological function of the present working embodiment.

Overview of the Apparatus for Evaluating Biological Function

The apparatus for evaluating biological function of the working embodiment of the present invention is an apparatus for evaluating biological function utilizing near-infrared spectroscopy, and, as shown in FIG. 2, it has a plurality of living body probes 1 ..., a behavioral information measuring part 2 for measuring behavioral data of the living body, and an apparatus body 3, into which light information detected by living body probes 1 and behavioral data measured by behavioral information measuring part 2 are input, and which performs calculation, control and memory operations.

Each of probes 1 is composed of at least two light-emitting elements (light-emitting diodes) 1a ... for irradiating light to desired measurement sites (tissue) of a living body, and at least two light-receiving elements (photodiodes) 1b ... for receiving light that has been transmitted, reflected, or scattered from the measurement site after the light has interacted with the living body.

The apparatus body 3 is composed of light intensity adjustor 4 for adjusting the amount of light emitted from light-emitting elements 1a ...; selector-adjustor 5 for selectively validating (invalidating) the desired light-receiving elements 1b ... and adjusting overall measurement sensitivity; gain controllable signal amplifier 6 for amplifying signals from light-receiving elements 1b ...; A/D converter 7 for converting output from signal amplifier 6 to numerical values; controller 8 for implementing such things as control of various parts of the apparatus and specified operational processing based on output from A/D converter 7; memory 9 that is used for recording information such as output from A/D converter 7, control data from each part of the apparatus and calculated results; display part 10 for performing displays based on information such as results output from A/D converter 7 and calculated results; and sampling speed adjuster 11 for adjusting the sampling speed for measurement by behavioral information measuring part 2.

In addition, information about behavior such as hearing or seeing is measured by behavioral information measuring part 2, and that measured behavioral information (for example, examiner voice data, subject voice data, trigger signals of all kinds, image signal data of all kinds) is input into behavioral information input part 12 of apparatus body 3 and recorded in memory 9 as simultaneous data Regarding the Living Body Probe FIG. 3(A) is a perspective view showing living body probe 1, and (B) is a bottom view thereof.

With previous near-infrared methods and the like, when signals were detected from a plurality of points on the brain surface, there was no way to immediately know the locations of the speech area, the motor area, the visual area and the like.

With previous methods, in which probes were arranged at equally spaced intervals, for example, one cannot selectively target a gyrus, for example, in the brain, where measurement targets are morphologically complex. If we consider the width of a gyrus, the most precise probe within a range of 10 mm should be selected.

The reason for earlier equally-spaced arrangements was for the purpose of making the size of the measurement regions uniform in order to draw oxyhemoglobin, deoxyhemoglobin and total hemoglobin contour lines. However, this does not reflect the actual meaning of the data, in which the S/N ratio of each channel differs. The amount of exchange in oxygen consumption, the amount of exchange in oxygen supply and the amount of exchange of hemoglobin may be affected by the size of the measurement region, but the oxygen exchange rate (oxygen exchange angle), the oxygen exchange ratio and the like are unrelated to the size of the measurement region. Namely, if the data are unrelated to the size of the measurement area, arranging the probes according to the shape of a gyrus makes it possible to improve the precision of the data, and is thus more appropriate.

Accordingly, as shown in FIGS. 3(A) and (B), in each living body probe 1 of the working embodiment of the present invention, a plurality of light-emitting elements 1a (3, in the drawing) and a plurality of light-receiving elements 1b (3, in the drawing) are arranged parallel to each other no more than 10 mm apart. By this means, from among the combinations of the plurality of light-emitting elements 1a and light-receiving elements 1b within the channels formed by living body probe 1, those with little data variation can be selected. This selection method will be described later.

In addition, because the hair roots are spaced 1 mm apart, the elements are preferably arranged so that the space between them is 1 mm. By this means, it is possible to reduce the attenuation of light intensity from the hair.

Living body probes 1 are disposed, for example, as shown in FIG. 4(A), at suitably spaced intervals on mounting strip 13. In this figure, 5 irradiation-side living body probes are arranged on the upper level and 4 detection-side living body probes are arranged on the lower level, and data can be acquired from 8 channels. Among these combinations between channels, it is also possible to select those with little variation in data values, or to invalidate channels with greater variation, or readjust by changing the placement location. This selection method will be described later.

The space between the living body probes of each level in the horizontal direction is set, for example, at 10 mm; and the space between the living body probes of the upper and lower levels in the diagonal direction is set, for example, at 25 mm.

Mounting strip 13, on which the above-mentioned plurality of living body probes 1 are disposed, is placed, for example, as shown in FIG. 4(B), on the side of a subject's head. In that case, living body probes 1 are preferably disposed taking into consideration the shape and size of the sulci and gyri at each site of the brain of the living body so that they are located on a gyrus, avoiding the sulci. For example, a pair of living body probes 1 may be placed perpendicular to the centerline CL (dotted line) of gyrus 15 between sulci 14 as in FIG. 5(A); or placed along centerline CL of gyrus 15 between sulci 14 as in FIG. 5(B).

As shown in FIG. 5(B), when a probe parallel to the gyrus is defined as having a gyrus-probe angle of zero, then the gyrus-probe angle of FIG. 5(A) is defined as 90 degrees.

Figure 6:
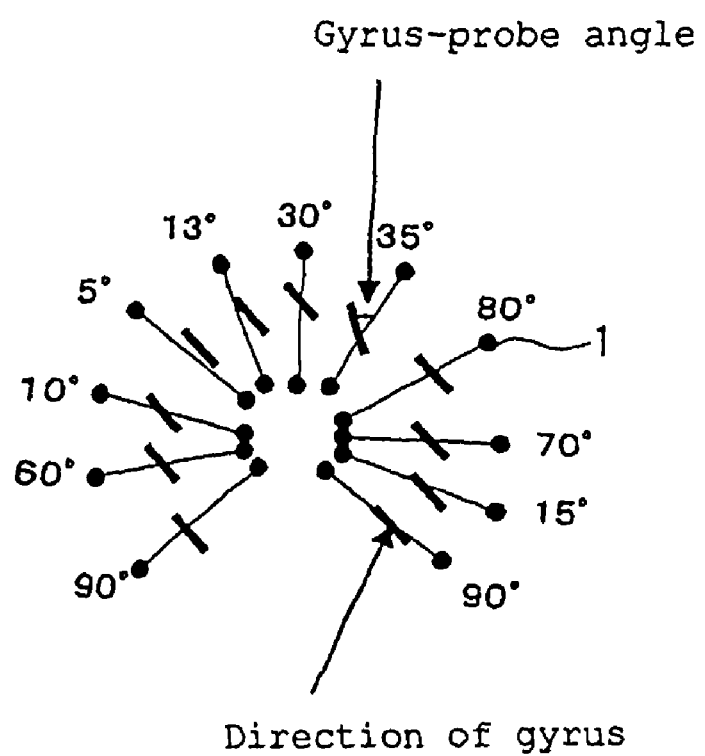
FIG. 6. An explanatory drawing showing an example displayed on a monitor of the angles formed between the direction of living body probes placed in a plurality of sites on the brain surface and the direction of a gyrus (probe angle)

Now, in actuality, the gyri and sulci are folded into the surface of the brain in a complicated way. Accordingly, as shown in FIG. 6, the angle formed between the direction of the arrangement of living body probes 1 placed in a plurality of sites on the brain surface and the direction of the gyrus (the probe angle) may be displayed on the monitor. A site where a display of this kind is particularly useful is the area around the ear, where the gyri and sulci are infolded in a complicated way.

Figure 7:
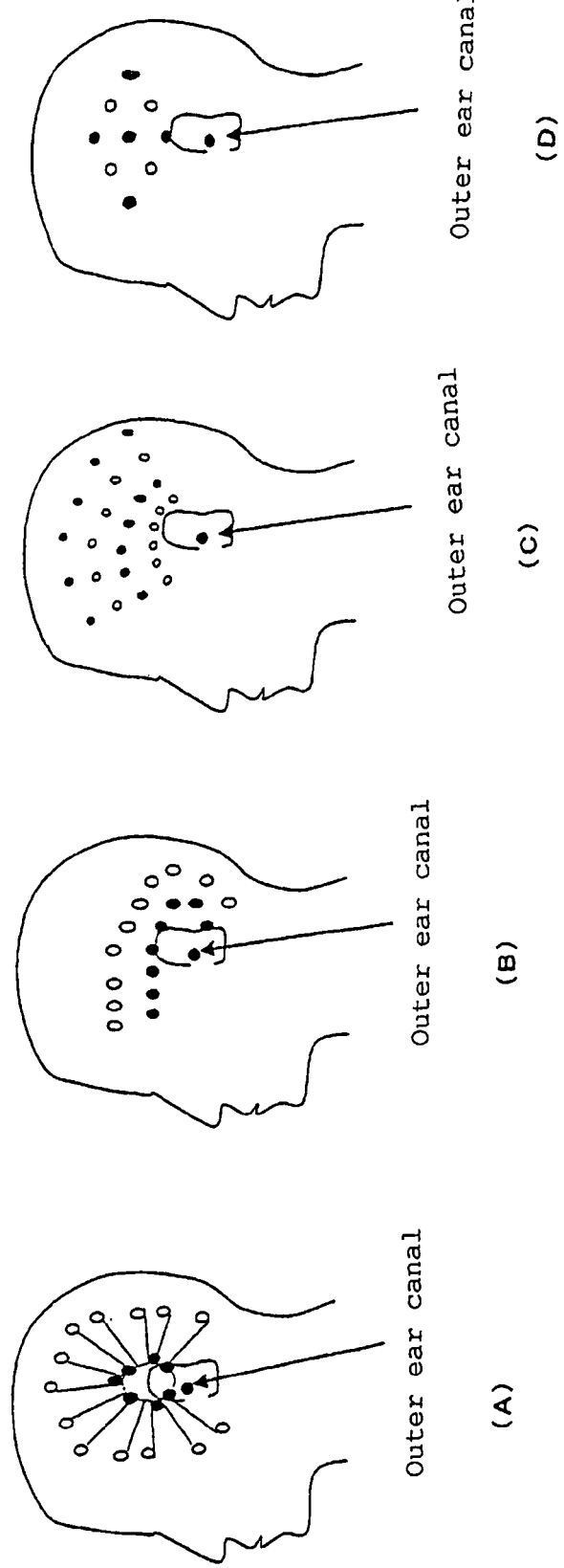
FIGS. 7(A)-(D) are explanatory drawings showing examples of living body probe arrangements.

In addition, for example as shown in FIG. 7, placing living body probes so that they radiate around the ear makes it possible to accurately measure the activity of the auditory cerebral cortex with good precision. In addition, other examples of probe arrangements for effectively measuring the area around the ear include placing them in an eyeglass shape (see FIG. 7(B)), a fan shape (see FIG. 7(C)) and a diamond-shaped combination of diamond shapes (see FIG. 7(D)).

In addition, as shown in FIG. 47(A), taking into consideration the fact that sulci 14 run in the direction of the centerline, light-emitting elements 1a and light-receiving elements 1b of the living body probe may also be arranged in diamond shapes, centered around the frontal lobe side centerline. An arrangement of this kind makes it possible to detect with good precision the right and left superior frontal lobe cortex, running on either side of the venous sinus. Previously, arranging incidence and detection probes on the center line was seen as taboo, because the sinus venous runs in front and back. However, I have found that placing probes on the centerline detects optical signals from the left and right superior frontal gyri of the cerebral hemispheres with good precision. I have found that although light is absorbed by the large venous sinus, by disposing paired probes on the outside, the method of the present invention makes it possible, to the contrary, to selectively detect responses from the capillaries, which are scattered and reflected back.

In addition, whereas the measurement region between measurement points was previously as large as 2.5×2.5 cm, an alignment method of this kind makes it possible to make the measurement area between measurement points K (shown in FIGS. 47(B) and (C)) a 1×2 cm measurement region, making high-resolution functional image displays possible. In addition, it becomes possible to approach a resolution congruent with the width of a human gyrus, 5-10 cm. Furthermore, utilizing the centerline to place the living body probes makes it possible to separate out and detect responses of the left and right frontal lobes, parietal lobes and occipital lobes, which face the arterial and venous sinuses and were difficult to detect previously.

Figure 48:
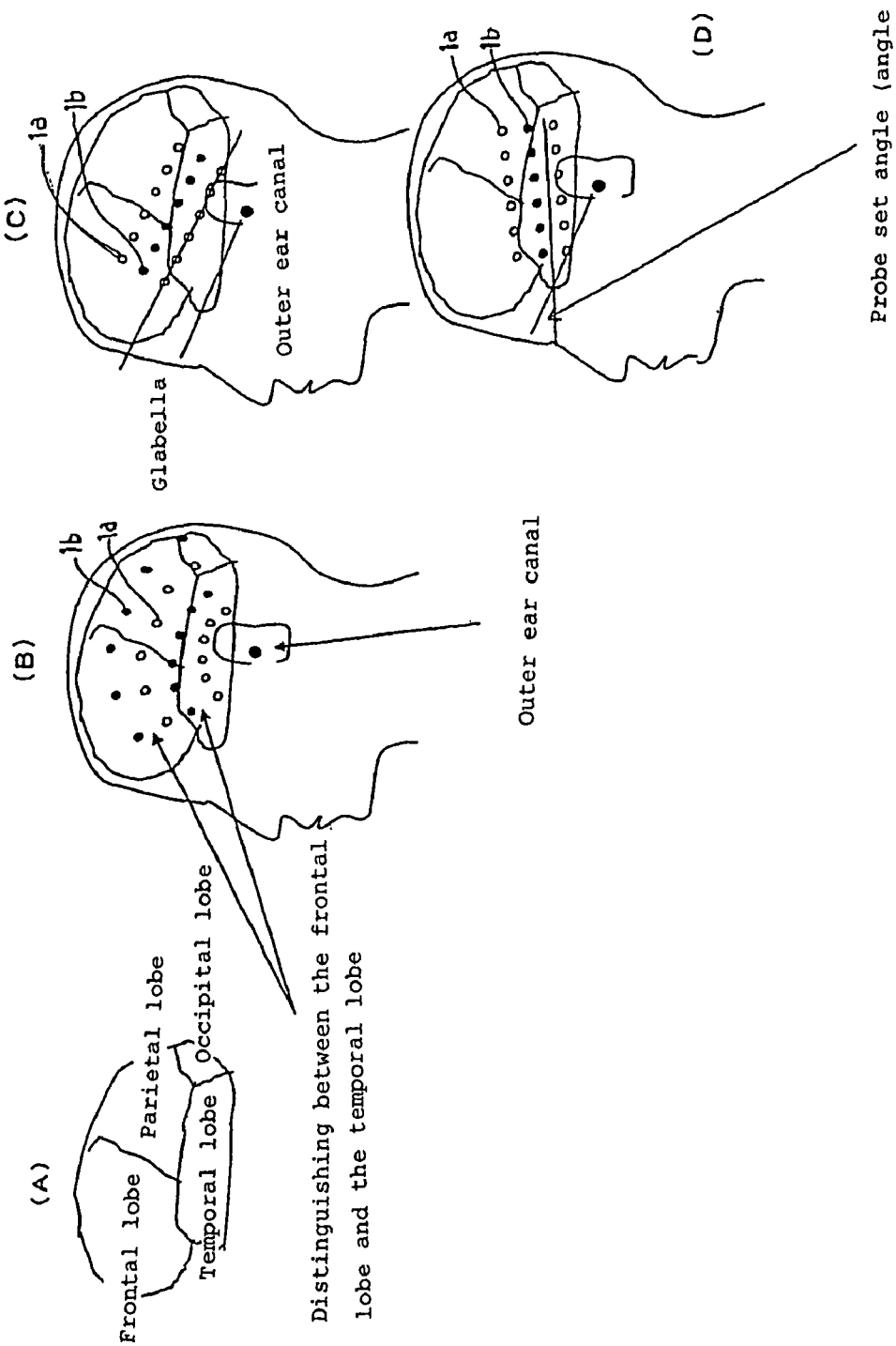
FIG. 48(A) is a drawing explaining the divisions of the cerebrum; (B) is a drawing explaining an example of a fan-shaped probe arrangement; and (C) and (D) are drawings explaining examples of horizontal probe arrangements.

In addition, it is desirable to be able to select a gyrus from on the scalp and measure it. As shown in FIG. 48(A), once the four parts of the cerebrum (frontal, temporal, parietal and occipital lobes) have been differentiated, it becomes possible to further improve gyrus selection.

In particular, the region around the outer ear canal in particular requires differentiating between the four parts. Because the temporal lobe is measured in the regions near the outer ear canal, as shown in FIG. 48(B), the four regions can be easily differentiated positionally with a fan-shaped or radial arrangement, by their distance from the outer ear canal.

In addition, with a horizontal probe arrangement, depending on its slope, it becomes become difficult to differentiate the 4 lobes because the position cannot be determined. Accordingly, for example, a line between the glabella and the outer ear canal can be established, and the angle between this line and the measurement points (the slope of the probe arrangement) defined as the probe setting angle (angle p) to clarify the shape of the head and the measurement points, and by this means, individual and group reproducibility can be maintained. For example, in FIG. 48(C), the probe set angle is zero degrees, and in (B), it is the angle p. This also has the advantage that, by this means, even measurements are taken on different days can be taken from the same site.

Figure 49:
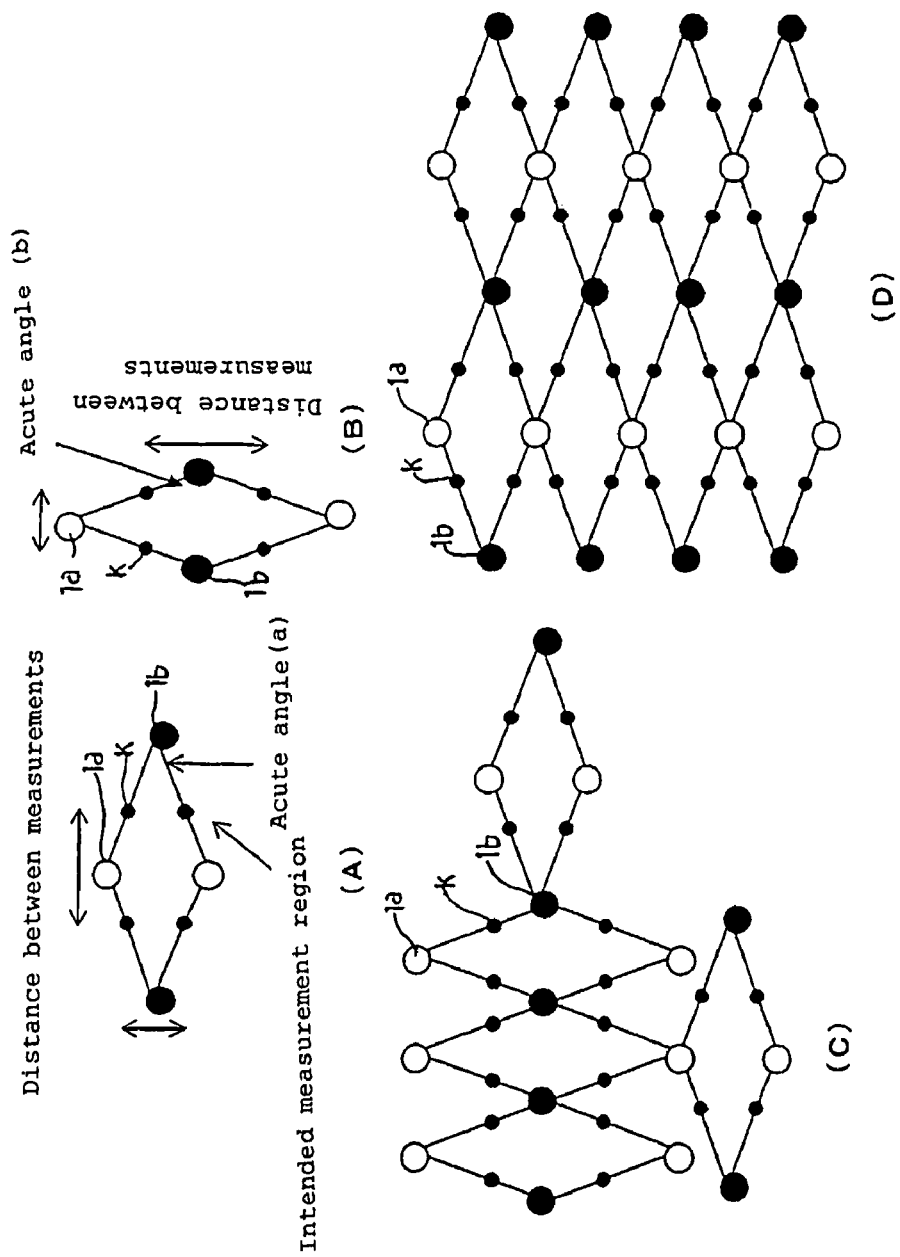
FIGS. 49(A) and (B) are drawings explaining the arrangement of living body probes in diamond-shaped basic shapes; (C) and (D) are drawings explaining examples of living body probes arranged in diamond-shaped applications.

As shown in FIGS. 49(A) and (B), by taking diamond shapes as the basic configuration and changing the angles, the vertical/horizontal distance between measurements can be freely selected by means of a configuration that make it possible to freely select measuring points with (a) as the acute angle or (b) as the acute angle.

Figure 50:
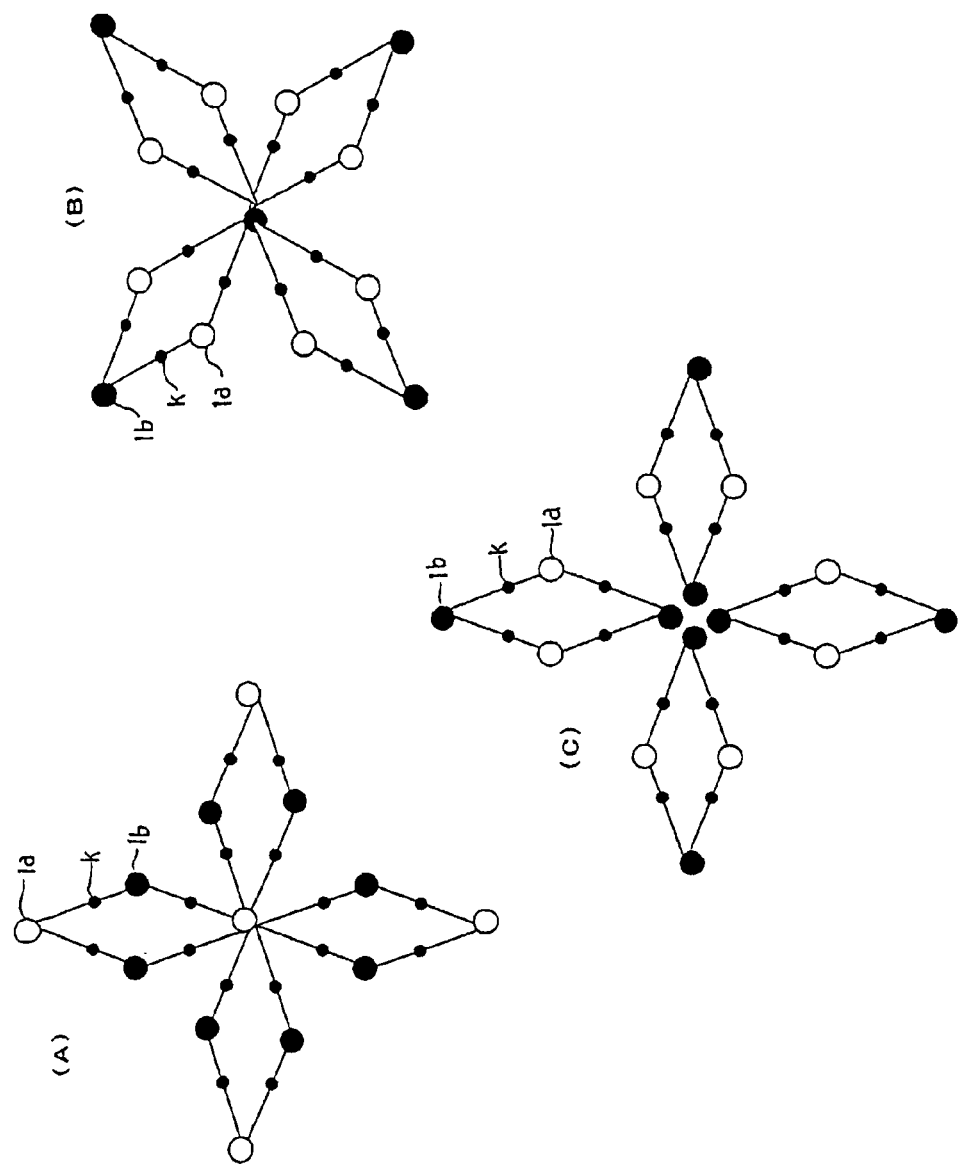
FIGS. 50(A)-(C) are drawings explaining examples of living body probes arranged in radially-shaped applications.

For example, combining basic diamond shapes such as those shown in FIGS. 49(A) and (B) makes it possible to arrange them in diamond-shaped application shapes such as those shown in FIGS. 49(C) and (D), or to arrange them in radially-shaped application shapes such as those shown in FIGS. 50(A)-(C) and so on, suitably selected according to the shape of the brain and the shape of the skull, and according to the objective.

The brain structure, that is, the direction of the sulci, has particular characteristics depending on the site, and by trying out corresponding alignments, it is possible to collect appropriate information from the gyri of the brain (brain tissues). For example, FIG. 51 is a drawing of a human head viewed from the back, but the occipital lobe, which is associated with visual responses, is structured in such a way that the primary visual area in the vicinity of the torus occipitals and the vision association areas wrap around it in a round radial shape, and thus radially-shaped application shapes such as those shown in FIG. 50(A)-(C) are effective arrangement methods. In addition, as shown in FIG. 51(B), by taking the point of intersection p of the line joining the left and right outer ear canal with the line joining the glabella and the torus occipitalis as the center point and applying the radially-shaped application shape shown in FIGS. 50(A) and (B) or the diamond application shape shown in FIG. 49(D), it is easy to know where the measurement points are from on the scalp, and thus possible to know their relationship with the location of cerebral gyri.

The external shape of the tip of living body probe 1 (the part that comes in contact with the measuring site), and the angles of the emission surface of each light-emitting element 1a . . . and the incident surface of the light-receiving surface of each light-receiving element 1b . . . are determined according to such factors as the surface morphology of each site—not only the brain, but also the nails, the palm of the hand, the bottom of the foot, the ear lobe—and the purpose of the probe. In addition, living body probe 1 may also be constructed as a multilayer probe, shaped, for example, like a light bulb, such as that shown in FIG. 8(A), or a geometrically shaped multilayer probe, such as those shown in FIGS. 8(B)-(D). The use of multilayer probes of this kind makes it possible not only to emit and receive light between widely separated probes 1, but because light can be emitted and received at locations close together inside probe 1 (see FIG. 8(E)), switching between far and near probes is possible. These shapes are determined with an endoscopic mode of use in view, such as for the mouth and digestive system, or the respiratory system.

In addition, previous living body probes detected light diffused almost uniformly with respect to the incident point. However, this means that when light from a plurality of light sources is superimposed, in cases where the living body probe 1 placement surface is curved, as shown in FIG. 9(A), the degree of precision of the detection differs from in cases where it is flat, as shown in FIG. 9(B). Consequently, the amount of diffused light with respect to a measurement region was dependent on the shape of the probe placement surface and its degree of curvature. Where the probe placement surface is curved, diffused light tends to accumulate and is easily detected compared to where it is flat, and the two measurement foci are different. For example, in the area around the parietal lobe, the shape of the cranium is in some places a sheer wall, and in some places its curvature changes sharply.

Accordingly, for example, as shown in FIG. 9(C), lens support member 21 for supporting lens 20 may be established inside the tip of living body probe 1, and by constructing that lens support member 21 in such a way that it is movable inside living body probe 1, lens 20 may be changed to the desired angle position. By this means, it becomes possible to make the light incident angle and the light-receiving angle adjustable to a desired angle.

Material of the Living Body Probe

Because previous living body probes and devices for securing them were made of plastic, rubber, or the like covering optical fibers, these were materials which were not likely to be visible in MRI, CT and other images. As a result, even if a subject went into an MRI apparatus wearing an attachment device or wearing a probe and images were taken, it was difficult to tell the positional relationship between the probe and the brain surface. For this reason, a probe might be removed and a different material put in its place for taking MRI images, and there were problems of accuracy, convenience, and difficulty in taking MRI images.

Accordingly, in living body probe 1 of the present invention, instead of materials like metals, which cause artifacts in MRI, a material containing moisture, such as for example, kanten (Agar), may be used as a material in fittings for supporting the probe (seats, caps, etc.). The probe itself may also be made from a material that contains moisture.

Regarding the Controller

For living body probe 1, two types of light-emitting elements 1a . . . are provided, those irradiating light of 730 nm wavelength and those irradiating light of 850 nm wavelength. These are disposed, for example, alternately in the row direction, but when considering other possible patterns, it is important to take into consideration wavelength-dependent attenuation inside the tissue, and dispose them in such a way that the amount of light received can be measured in a balanced way. All the light-emitting elements 1a . . . are connected to light intensity adjuster 4 of the apparatus body 3, and the intensity of the emitted light can be adjusted either overall or individually.

The light-receiving elements 1b . . . , on the other hand, are all connected to signal amplifier 6 through selector-adjuster 5 of the apparatus body 3, and either all or some of the received light signals output from each of light-receiving elements 1b, as selected by selector-adjuster 5, are output to signal amplifier 6, and amplified here. Then, the amplified received light signals are converted to numeric values by A/D converter 7 and output to controller 8. Controller 8, after applying a lowpass filter to the digital data input from A/D converter 7 to eliminate noise, records this processed data (referred to below as "received light intensity") chronologically in memory 9.

Additionally, controller 8 executes the operations described below, based on the received light intensity thus obtained. First, it calculates absorbance at 730 nm wavelength (O.D.$_{730}$) by means of Equation 1, and absorbance at 850 nm wavelength (O.D.$_{850}$) by means of Equation 2, and records the results of these calculations chronologically in memory 9.

$$O.D._{730} = \log_{10}(I_{0\,730}/I_{730}) \qquad \text{(Equation 1)}$$

$$O.D._{850} = \log_{10}(I_{0\,850}/I_{850}) \qquad \text{(Equation 2)}$$

where:
$I_{0\,730}$ is emitted light intensity at 730 nm wavelength
$I_{730}$ is received light intensity at 730 nm wavelength
$I_{0\,850}$ is emitted light intensity at 850 nm wavelength
$I_{850}$ is received light intensity at 850 nm wavelength The relationships expressed by Equations 3 and 4 are known to exist between change in oxygenated hemoglobin concentration, change in deoxygenated hemoglobin concentration, and change in absorbance, from theory known in the art.

$$\Delta O.D._{730} = a_1 \Delta[HbO_2] + a_1' \Delta[Hb] \qquad \text{(Equation 3)}$$

$$\Delta O.D._{850} = a_2 \Delta[HbO_2] + a_2' \Delta[Hb] \qquad \text{(Equation 4)}$$

where:
$\Delta O.D._{730}$ is change in absorbance at 730 nm wavelength
$\Delta O.D._{850}$ is change in absorbance at 850 nm wavelength
$\Delta[HbO_2]$ is change in oxygenated hemoglobin concentration
$\Delta[Hb]$ is change in deoxygenated hemoglobin concentration
$a_1, a_1', a_2, a_2'$ are absorbance coefficients Therefore, solving these simultaneous equations known in the art gives Equations 5 and 6.

$$\Delta[HbO_2] = a[O.D._{730} - (a_1'/a_2')\Delta O.D._{850}] \qquad \text{(Equation 5)}$$

$$\Delta[Hb] = a(a_2/a_2')[(a_1/a_2)\Delta O.D._{850} - O.D._{730}] \qquad \text{(Equation 6)}$$

where:
$a = a_2'/(a_1 a_2' - a_1' a_2) \approx 1$ (1 or a value approaching 1)

Accordingly, after determining the change in absorbance at 730 nm wavelength ($\Delta O.D._{730}$) and the change in absorbance at 850 nm wavelength ($\Delta O.D._{850}$), the change in oxygenated hemoglobin concentration ($\Delta[HbO_2]$) is calculated by means of Equation 5 and the change in deoxygenated hemoglobin concentration ($\Delta[Hb]$) is calculated by means of Equation 6, and the results of these calculations are recorded chronologically in memory 9. Note that the change in total hemoglobin concentration ($\Delta[\text{total Hb}]$) is represented by Equation 7.

$$\Delta[\text{total Hb}] = \Delta[HbO_2] + \Delta[Hb] \qquad \text{(Equation 7)}$$

Now, the situation as regards changes in concentration of oxygenated hemoglobin and deoxygenated hemoglobin in the capillaries induced by stimulus to the tissues shows the 9 patterns of change below, according to the possible combinations of their variation.

(1) $\Delta HbO_2$: increase; $\Delta Hb$: increase
(2) $\Delta HbO_2$: increase; $\Delta Hb$: decrease
(3) $\Delta HbO_2$: increase; $\Delta Hb$: zero
(4) $\Delta HbO_2$: decrease; $\Delta Hb$: increase
(5) $\Delta HbO_2$: decrease; $\Delta Hb$: decrease
(6) $\Delta HbO_2$: decrease; $\Delta Hb$: zero
(7) $\Delta HbO_2$: zero; $\Delta Hb$: increase
(8) $\Delta HbO_2$: zero; $\Delta Hb$: decrease
(9) $\Delta HbO_2$: zero; $\Delta Hb$: zero In actuality, with metabolic activity in the tissues, the patterns above are changing over time according to differences in such factors as stimulus application conditions and the physiological state at rest. $\Delta[Hb]$ and $\Delta[HbO_2]$ vary in the capillaries as hemodynamic and metabolic activities for the purpose of taking oxygen up into the tissue from oxygenated hemoglobin.

Figure 10:
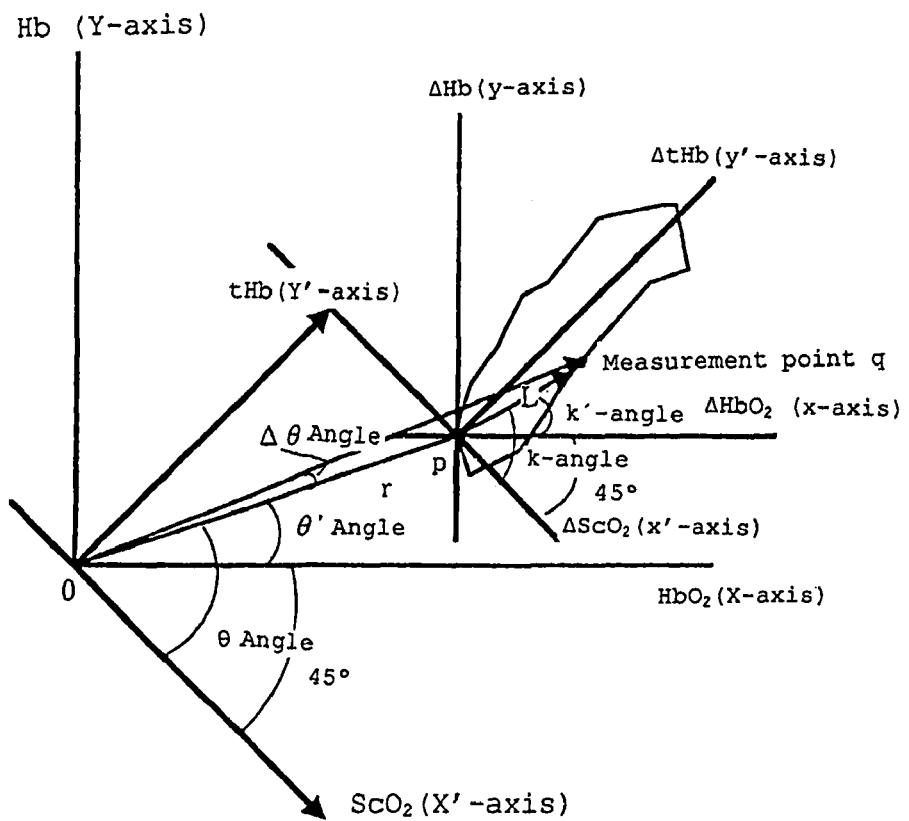
FIG. 10. A two-dimensional diagram showing polar coordinates (rectangular coordinates) with change in oxyhemoglobin $\Delta[HbO_2]$ as the x-axis (horizontal axis) and change in deoxyhemoglobin $\Delta[Hb]$ as the y-axis (vertical axis), and with absolute value of oxyhemoglobin $[HbO_2]$ (concentration: mol/l) as the X-axis (horizontal axis) and absolute value of deoxyhemoglobin $[Hb]$ as the Y-axis (vertical axis).

Accordingly, in the present invention, various parameters, derived based on two-dimensional diagrams obtained by plotting data over time on polar coordinates (rectangular coordinates) with change in oxyhemoglobin $\Delta[HbO_2]$ as the x-axis and change in deoxyhemoglobin $\Delta[Hb]$ as the y-axis, as shown in FIG. 10, are calculated by means of controller 8.

Furthermore, at measurement starting point p(HbO$_2$, Hb), total hemoglobin and oxygen saturation exist in the capillaries. Accordingly, various parameters, derived based on two-dimensional diagrams taking into consideration polar coordinates (rectangular coordinates) with absolute values of oxyhemoglobin [HbO$_2$] (concentration: mol/l) as the X-axis and absolute values of deoxyhemoglobin [Hb] (concentration: mol/l) as the Y-axis, as shown in FIG. 10, are calculated by means of controller 8.

Here, on the polar coordinates formed by the x-axis and the y-axis shown in FIG. 10, the y'-axis established in the +45 degree direction ($\Delta tHb$ axis) shows changes in concentration of total hemoglobin, and the x'-axis established in the −45 degree direction (ΔScO$_2$ axis) shows changes in oxygen saturation in the capillaries. In addition, in the polar coordinate system formed by the X-axis and the Y-axis shown in FIG. 10, the Y'-axis established in the +45 degree direction (tHb axis) shows absolute values of total hemoglobin, and the X'-axis established in the −45 degree direction (ScO$_2$ axis) shows absolute values of oxygen saturation in the capillaries.

FIG. 11(A) is a schematic drawing showing the relationship between a K-ratio diagram and actual neuron activity and capillary oxygen exchange activity. In the microcirculation model of neuron-capillary oxygen exchange of FIG. 11(A), neuron activity results in the need for oxygen consumption and oxygen supply. When this happens, first, when nerve activity occurs (first response), oxygen is supplied from 7-micron red blood cells in an approximately 5-micron capillary, through glial cells. Namely, rapid oxygen consumption is carried out in the capillary (second response). Inside the capillary where oxygen was consumed, the oxygen concentration is reduced, and then, oxyhemoglobin is supplied from the arterial side (third response). Next, an oxygen variation response (active washout flow) occurs in the veins (fourth response). In particular, the change in blood flow occurring in veins, where oxygen exchange with the tissue does not occur, is a "sewage effect", which is a saucer after oxygen exchange activity occurring in the capillary. As the sewage effect is easy to take for the similar with "watering the garden effect", the detection of localized information is more difficult from the venous sewage effect than the local activity in the capillaries, and detection of oxygen consumption is also difficult by means of the sewage effect.

Because it was previously impossible to measure the working of this brain microcirculation, tissue oxygen pressure was measured invasively by sticking a needle into the intercellular spaces of the neurons. It is disclosed about brain blood-flow response occurring after neuron activity in Roy and Sherrington (Roy C S, Sherrington C S: On the regulation of the blood-supply of the brain. J Physiol 11, 85-108, 1890).

Since then, attention has been focused only on blood flow, and for more than 110 years, oxygen exchange inside the capillaries could not be selectively measured. In contrast, with the present invention, it is possible to noninvasively measure the FORCE effect (fast oxygen response in capillary event [oxygen consumption]; second response described previously), which is the oxygen exchange response most closely linked to neuron activity; and the subsequent capillary oxygen supply response (primary watering-the-garden effect; third response described previously).

As shown in FIG. 11(B), at sites where oxygen exchange rate is increasing, oxyhemoglobin tends to decrease due to task load, by means of the FORCE effect. In contrast, as shown in FIG. 11(C), at sites displaying the Watering-the-garden effect, oxyhemoglobin tends to increase.

Peak values are also lower when oxygen exchange rate is increasing than for sites displaying the Watering-the-garden effect.

In this case, measurement by PET, fMRI and the like have erroneously measured greater activity not at FORCE effect sites, where oxygen exchange is increasing, but for the Watering-the-garden effect and the sewage effect.

Namely, with the previous model, in which neuron activity causes a relatively gradual increase in brain blood flow (dogma since 1890), it was imagined that the greater the changes, whether measured by PET, or fMRI, or NIRS, the stronger the neuron activity. However, if we assume that this theory was not necessarily true, and that the stronger the oxygen consumption in the capillaries, which is linked with neuron activity, the stronger the neuron activity, then compared to the increase in oxyhemoglobin and total hemoglobin in the capillaries, linked to the FORCE effect, which depletes oxygen by the transferring it to the nerves, the increase in oxyhemoglobin and total hemoglobin must be greater in the surrounding regions, where oxygen is not exchanged with the nerves, that is to say, the regions where it merely passes through.

In this case, with a gradual response, it is impossible to know what height of increase should be selected. In actuality, with PET and fMRI, there is no reason to select a low response. Namely, By influence of a FORCE effect in PET and fMRI, sites where maximum oxygen consumption has occurred in this way may be masked (hidden) by regions with even greater changes from the Watering-the-garden effect during the time period when oxygen is supplied, and cannot be statistically selected out.

In contrast, with the present invention, it is also possible to measure localized responses that are not masked by the Watering-the-garden effect. The most important concern, for the clinical application of a method for measuring brain function, is misdiagnosis in functional diagnosis. Being able to predict what kinds of misdiagnosis might occur must be sufficiently taken into consideration. In measurement methods utilizing the blood, exclusion of the sewage effect, from venous components, is important. The capillaries perform oxygen exchange, but the role played by the veins is the post-oxygen-exchange sewage effect. A method utilizing this sewage effect itself is fMRI, using T2* weighted imaging. However, from the standpoint of the phenomenon of oxygen exchange, this is, instead, a source of signals causing erroneous diagnoses that must be excluded. Specifically, there are cases in which a considerable supply occurs to low oxygen exchange regions as well. With PET and fMRI, it sometimes happens that regions with low oxygen exchange are measured as having a higher strength than regions with strong oxygen exchange. This leads to misdiagnosis in functional diagnosis. For a medical diagnostic measuring method, this is a fatal flaw. The present invention is also the discovery of an NIRS imaging method that prevents this misdiagnosis.

Now, as shown in FIG. 11(A), the amount of red blood cells (tHb) increasingly fluctuates in a direction of 90 degrees with respect to the capillary wall. Oxygen exchange, on the other hand, occurs with respect to the capillary wall, namely, in a direction 90 degrees from the direction the blood cells are moving. Consequently, the ScO$_2$ vectors, which represent oxygen exchange, and the tHb vector are in a perpendicular relationship. In the same way, the velocity vector of the increase/decrease of red blood cells (tHb), and the ScO$_2$ vector, which represents oxygen exchange, in which oxyhemoglobin changes to deoxyhemoglobin in order to transfer oxygen to the tissues, are also in a perpendicular relationship.

Regarding Various Parameters

Examples of parameters calculated by means of controller 8 include the following:

1) Absolute Oxygen Exchange Ratio (ratio θ')

Absolute amount of deoxyhemoglobin/Absolute amount of oxyhemoglobin

2) Absolute Oxygen Exchange Rate (Angle) (Angle θ)

On a polar coordinates with absolute amount of oxygen saturation as the X'-axis and the absolute amount of total hemoglobin as the Y'-axis, created by rotating rectangular coordinates with absolute amount of oxyhemoglobin as the X-axis and absolute amount of deoxyhemoglobin as the Y-axis 45 degrees to the right around the origin 0, it is the angle formed between the vector from the origin 0 to measurement point q and the aforementioned X'-axis; it can have values of $\pi/4 \leq$ angle $\theta \leq 3\pi/4$.

The absolute oxygen exchange rate (ratio θ') is defined as:

Deoxyhemoglobin/Oxyhemoglobin (ratio θ')=[100−(percent oxygen saturation)]/(percent oxygen saturation)

arctan (ratio θ')=arctan [100−(percent oxygen saturation)]/(percent oxygen saturation)=angle θ' angle θ=angle θ'+45 degrees=arctan (total Hb vector/oxygen saturation vector)

Angle θ is calculated from either of 2 coordinate systems: polar coordinates with deoxyhemoglobin as the X-axis and oxyhemoglobin as the Y-axis, or polar coordinates created by rotating this 45 degrees to the right around the origin 0, with the oxygen exchange vector component as the X'-axis and the total Hb vector amount as the Y'-axis.

3) Calculation of Absolute Oxygen Exchange Velocity: Angular Velocity (ε)

From θ=ε·t, it is equivalent to the differential of θ (Δθ)

ε=Δθ/Δt (units: radians/second)

4) Absolute Oxygen Exchange Angular Acceleration (ε')

The differential of absolute oxygen exchange velocity is further taken to calculate absolute oxygen exchange angular acceleration.

5) Absolute oxygen exchange vorticity u u=2ε (ε absolute oxygen exchange velocity)

From the fact that when the vorticity (u) is high, velocity towards the center is high, it can be judged that a given location is a capillary, and thus predominantly venous data can be excluded.

6) Absolute Oxygen Exchange Amount (r-Value; Scalar)

Distance of a vector from the origin to a measurement point

Note that total Hb vector data for each voxel plotted on the coordinate system can be calculated as r sin θ, and oxygen saturation vector data for each voxel, as r cos θ.

7) Oxygen Exchange Rate [Oxygen Exchange Angle] (k-Angle)

On polar coordinates with change in oxygen saturation as the x'-axis and change in total hemoglobin as the y'-axis, created by rotating rectangular coordinates with change in oxyhemoglobin as the x-axis and change in deoxyhemoglobin as the y-axis 45 degrees to the right around the origin, it is the angle formed between a vector from a desired point, from the standpoint of measurement (the start of measurement may be used as the point of origin), to a measurement point and the aforementioned x'-axis; unlike for the angle θ, any angle can be taken.

Figure 12:
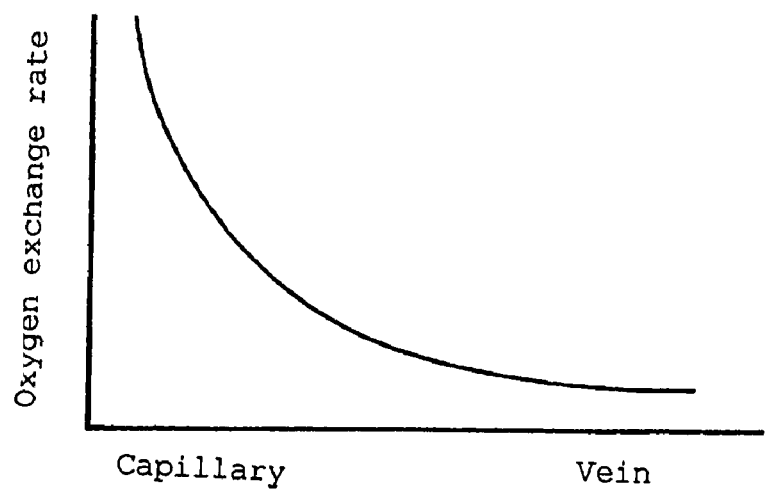
FIG. 12. A graph that shows schematically the relationship between oxygen exchange rate and the capillaries and the veins.

As shown in FIG. 12, the k-angle is high for the capillaries and the k-angle is low for the veins; thus, predominantly capillary data, which has a high k-angle, can be extracted. In addition, handling oxyhemoglobin and deoxyhemoglobin simultaneously causes dependence on S/N to disappear.

Figure 13:
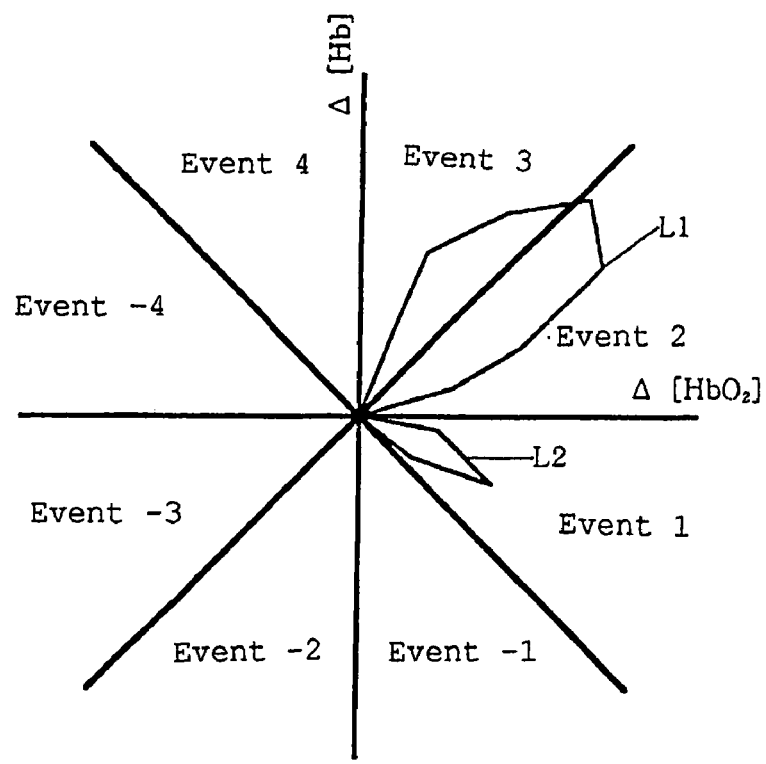
FIG. 13. A conceptual explanation of a two-dimensional diagram showing the various events.

FIG. 13 is a conceptual diagram of a two-dimensional diagram divided into events. With previous measuring methods, it was assumed that when the brain is stimulated, a metabolic response is immediately followed by an increase in blood flow. However, the temporal relationship between the period during which the metabolic response is sustained and the increased-blood-flow response depends on such factors as the type, strength and duration of the stimulus, and it is therefore difficult to distinguish between regions and time periods of predominantly metabolic response and predominantly hemodynamic response.

Accordingly, the k-angle makes it possible to separate predominantly metabolic responses from predominantly hemodynamic responses and display two kinds of images. This is because it independently represents metabolism, in which oxygen is consumed; and if there is no increase in oxyhemoglobin from increased blood flow, there is a shift to event 4, which shows an increase in deoxyhemoglobin and a decrease in oxyhemoglobin.

On the other hand, an increased blood flow response causes a shift to event 1, which shows a decrease in deoxyhemoglobin and an increase in oxyhemoglobin. Consequently, the K-ratio is a predominantly metabolic response in event 4 and event −4, an increased blood flow response in event 1, and a decreased blood flow response in event −1. The increased blood flow response is stronger in event 2 than in event 3. The decreased blood flow response is stronger in event −2 than in event −3.

Thus, a k-angle map is meaningful in 2 ways: as an image showing predominantly metabolism, and as an image showing predominantly hemodynamics.

That is, for the capillaries, because oxygen is consumed, predominantly metabolic responses necessarily occur, and thus events beyond than event 1 (events 2, 3 or 4) are detected (for example, plot L1). However, for the veins, it becomes an image showing predominantly blood flow, and thus events 4 or 3 are unlikely to be detected. Thus, if a response stays in event 1, it can be considered to be either a predominantly venous or a low metabolic response (for example, plot L2).

8) Calculation of Oxygen Exchange Velocity: Angular Velocity (λ)

From k=λ·t, it is equivalent to the differential of k (Δk)

λ=Δk/Δt (units: radians/s)

9) Oxygen Exchange Angular Acceleration (λ')

The differential of oxygen exchange velocity is further taken to calculate oxygen exchange angular acceleration.

10) Oxygen Exchange Vorticity j j=2λ (where λ is oxygen exchange velocity)

11) Oxygen Exchange Ratio (K-Ratio)

Change in deoxyhemoglobin/change in oxyhemoglobin

Even in a resting state, in which no stimulus of any kind is being applied to living body tissue, it becomes possible, based on physiological theory, to immediately judge whether data is predominantly capillary data by evaluating the K-ratio. Namely, because it has been made clear that the K-ratio approaches −1 if it is predominantly capillary data, and the K-ratio moves somewhat away from −1 in a plus direction if it is predominantly venous data, it is possible to judge whether data is predominantly capillary data based on whether the K-ratio is in the vicinity of −1.

12) Amount of Oxygen Exchange (L-Value; Scalar)

Distance of a vector from a desired point, from the standpoint of measurement (the start of measurement may be used as the point of origin), to a measurement point When a specific stimulus is not present, the K-ratio is small, and the amount of oxygen exchange L is small. Because the capillaries are upstream from the veins and the rate of attenuation of the amplitude of fluctuation (SD) from a stimulus is fast, fluctuation can be distinguished. For the same site, the degree of fluctuation can be evaluated by the size of the L-values. For example, in the case of FIG. 14(A), the amplitude of fluctuation at rest is small, showing that the S/N ratio is good; and in the case of FIG. 14(B), the amplitude of fluctuation at rest is large, and showing that the S/N ratio is bad.

In addition, as for veins and capillaries, because noise from the veins is greater and has less periodicity than that of the capillaries, predominantly capillary data can thus be distinguished by means of L-values.

Note that time series data for total Hb change vectors of each voxel plotted on the coordinates can be calculated as L sin θ, and time series data for oxygen saturation change vectors for each voxel, as L cos θ.

13) Hemoglobin Oxygen Exchange Efficiency (E-Ratio)

$$\text{Hemoglobin oxygen exchange efficiency}(E\text{-ratio}) = [\text{oxygen exchange vector}] / [\text{change in hemoglobin vector}] = \cos(k\text{-angle}) / \sin(k\text{-angle}) = 1/\tan(k\text{-angle})$$

Here, when the oxygen exchange vector, cos (k-angle)>0, the hemoglobin oxygen exchange efficiency indicates oxygen consumption efficiency; and when the oxygen exchange vector, cos (k-angle)<0, the hemoglobin oxygen exchange efficiency indicates oxygen supply efficiency.

In addition, when we consider the K-ratio described previously and the E-ratio, from $$(tHb)=[OxyHb]+[DeoxyHb]$$

$$(ScO_2)=[OxyHb]-[DeoxyHb],$$

we derive $$K=[DeoxyHb]/[OxyHb]=(tHb-ScO_2)/(tHb+ScO_2)= (1-E)/(1+E)$$

Figure 15:
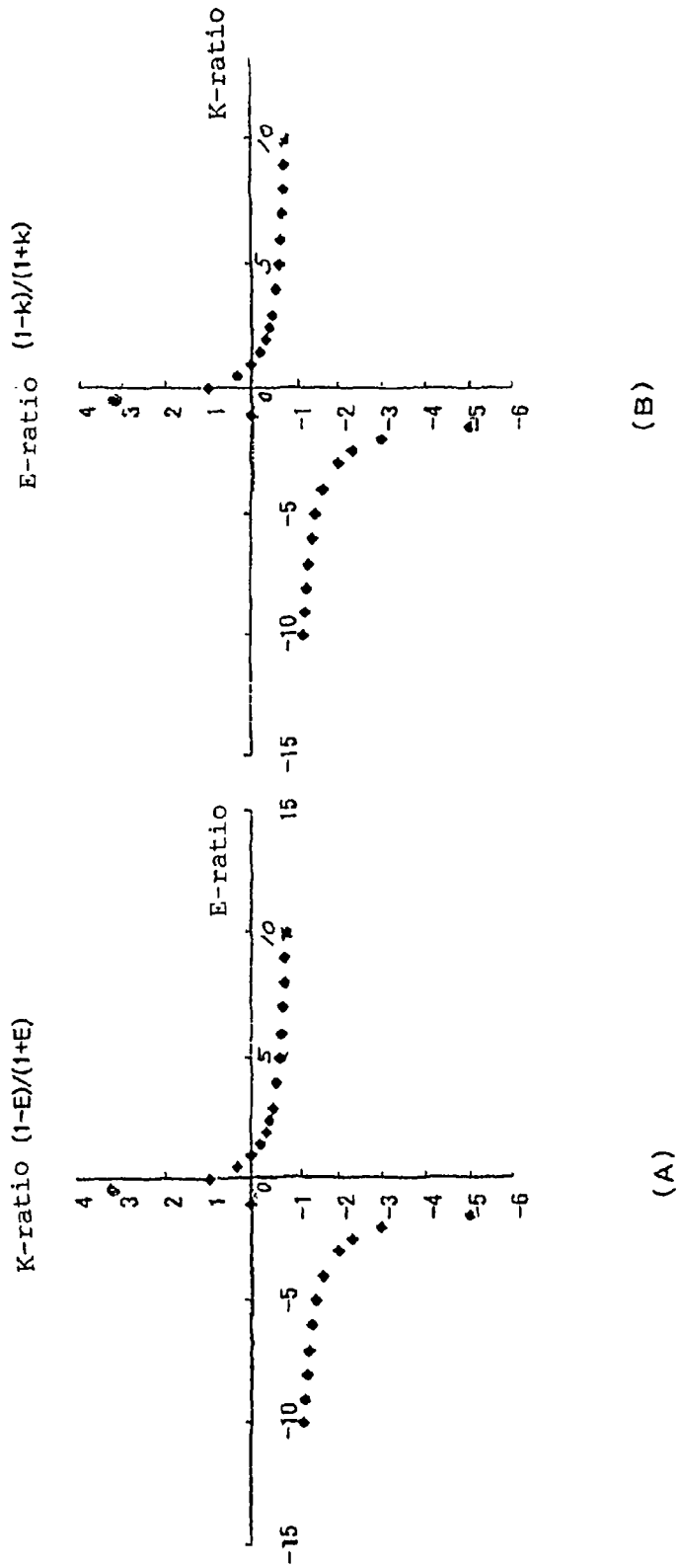
FIG. 15. (A) and (B) are graphs showing relationships between the K-ratio and the E-ratio.
Figure 17:
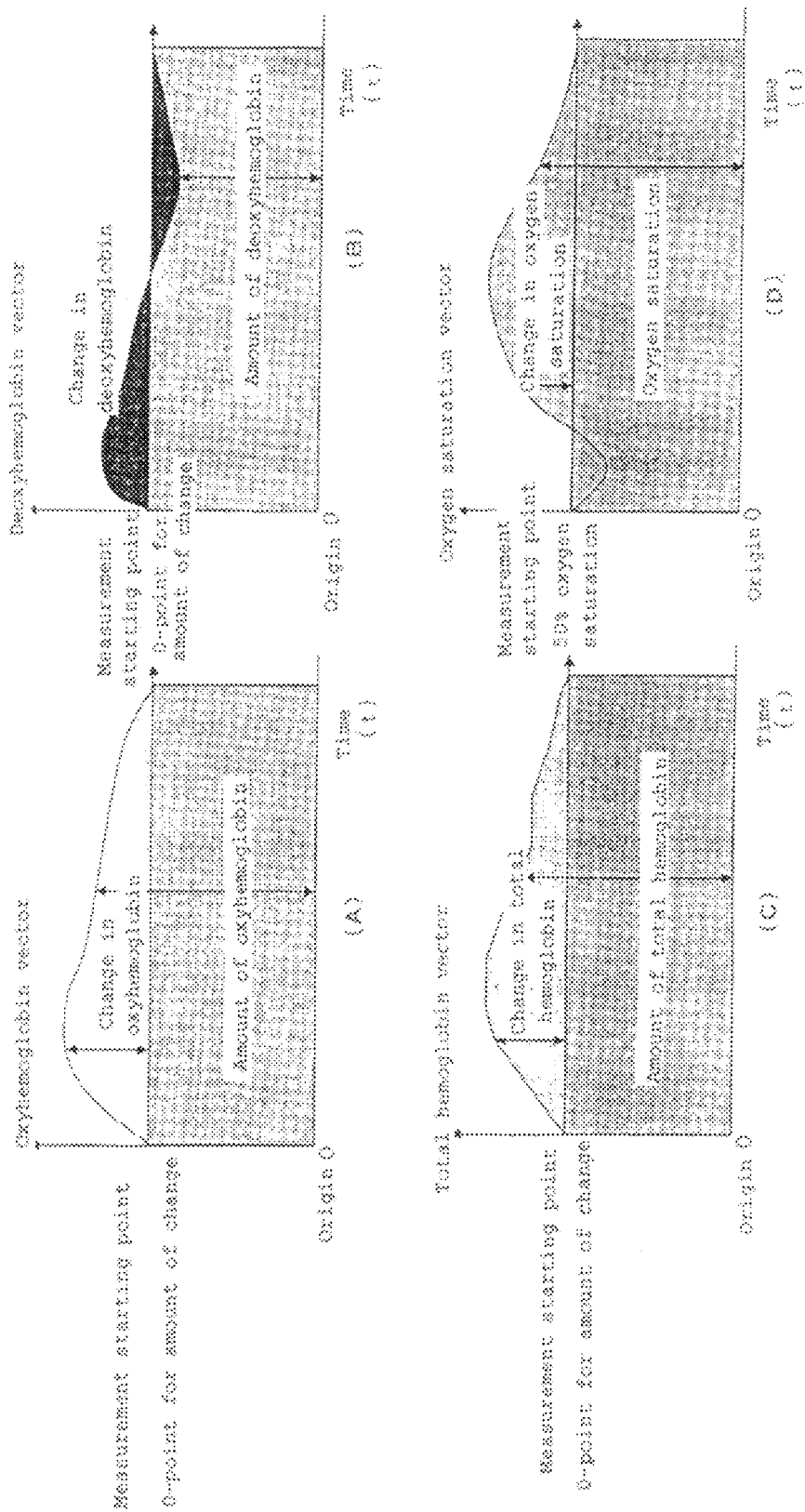
FIG. 17. (A)-(D) are graphs showing changes over time in the four component vectors: oxyhemoglobin, deoxyhemoglobin, total hemoglobin and oxygen saturation.

(see FIG. 15(A)).

In addition, conversely, $$E=(1-k)/(1+k)=ScO_2/tHb=(OxyHb-DeoxyHb)/ (OxyHb+DeoxyHb) \text{ (See FIG. 15(B))}.$$

From the above equation, when k=0, E=1; when k=1, E=0; and when k=−1, E becomes infinitely large. When $ScO_2$=0, E=0; and even if the amount of hemoglobin changes, oxygen exchange does not occur. When tHb=0, E becomes infinitely large, and even if the amount of hemoglobin changes hardly at all, oxygen exchange occurs.

Consequently, when E 0, the E-ratio represents oxygen supply efficiency, and when E<0, the E-ratio represents oxygen consumption efficiency.

14) Y-Values $$Y=[OxyHb]-[DeoxyHb]$$

Here, when Y=0, the change in total hemoglobin (tHb)=0; namely, the force and kinetic energy required to vary the amount (number) of red blood cells are zero.

Thus [Y] becomes an index for distinguishing increases and decreases in $ScO_2$, which is perpendicular to total hemoglobin.

With Y>0, $ScO_2$>0; and with Y<0, $ScO_2$<0.

Consequently, Y=[OxyHb]−[DeoxyHb] conveniently represents relative change in $ScO_2$; for example, as shown in FIG. 16(A), in image display measurements, the lowest value for Y<0 shows the maximum FORCE effect, and the maximum Y>0 shows the maximum Watering-the-garden effect.

Note that FIG. 16(B) is a graph explaining the theoretical formula, using vectors of OxyHb, DeoxyHb, tHb and $ScO_2$.

As shown in FIG. 16(B), if [OxyHb] and [DeoxyHb] are considered to be perpendicular vectors, this leads to $$(tHb)=[OxyHb]+[DeoxyHb]$$

$$(ScO_2)=[OxyHb]-[DeoxyHb],$$

and, in contrast to [OxyHb]+[DeoxyHb], which represents total hemoglobin, [OxyHb]−[DeoxyHb] means the amount of hemoglobin which causes $ScO_2$ to increase or decrease with respect to 50% oxygen saturation.

In addition, the dissociation of tHb and $ScO_2$ is represented by means of [DeoxyHb]. Namely, $$(tHb-ScO_2)=2[DeoxyHb]$$

Here, 1) because in the arteries, [DeoxyHb]=0, the relationship tHb=$ScO_2$=0 applies.

2) Because in the veins, tHb=[OxyHb]+[DeoxyHb]=0, the relationship [DeoxyHb]=−½($ScO_2$)=−[OxyHb] applies.

3) In the capillaries, because oxygen exchange is taking place, [DeoxyHb]=½(tHb−$ScO_2$), and [OxyHb]=½(tHb+$ScO_2$) apply.

Now, the interrelationship described above between oxyhemoglobin and deoxyhemoglobin among the red blood cells in the capillaries is made clear by means of a variety of oxygen exchange indexes.

However, the relationship between the amount of hemoglobin and oxygen exchange indexes has not been made clear. Accordingly, by considering oxygen exchange of the red blood cells in the capillaries to be rotational motion (theory), it is possible to establish a relationship between the amount of hemoglobin and oxygen exchange within the equation of rotational motion.

Figure 11:
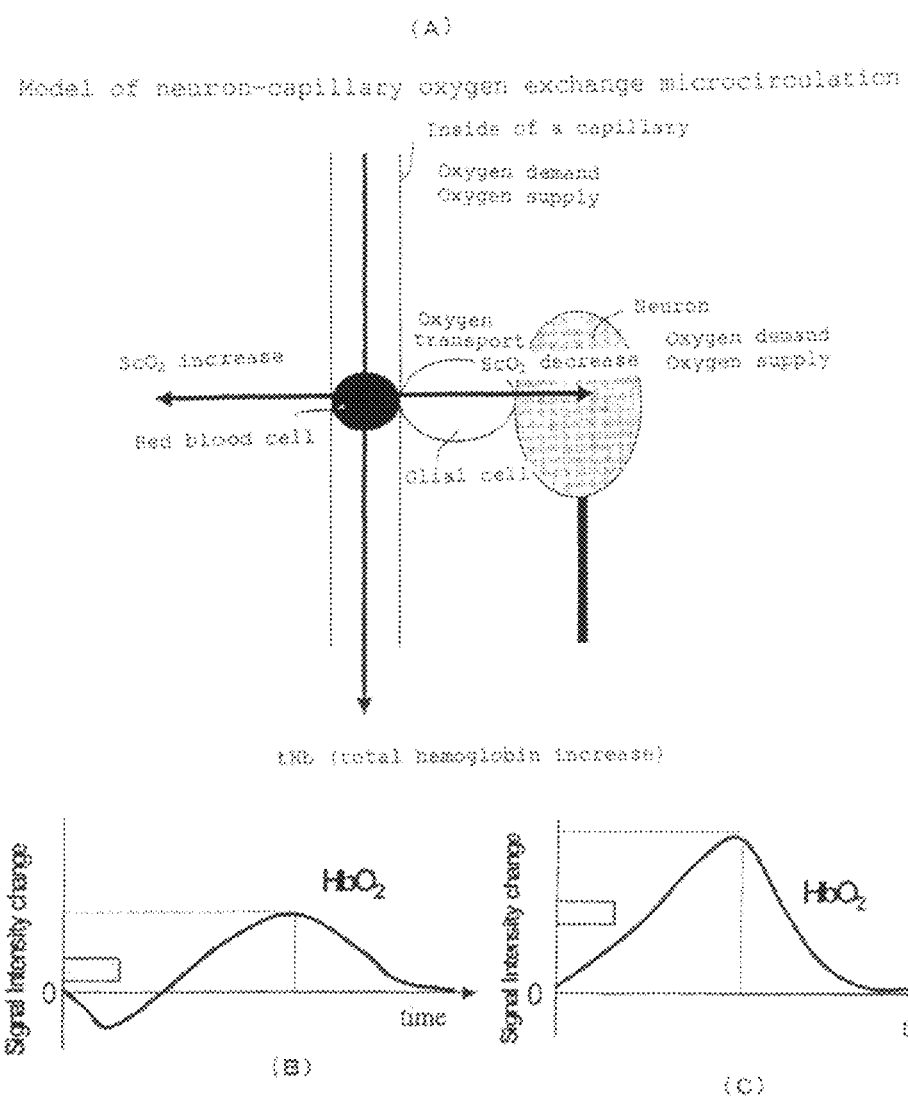
FIG. 11(A) is a schematic drawing showing the relationship between a K-ratio diagram and actual neuronal activity and capillary oxygen exchange activity, and (B) and (C) are graphs showing changes in $HbO_2$ in different regions.

Namely, when the amount (number) of red blood cells increases, oxygen is supplied to the nerve cells from the red blood cells in the capillaries, through the glial cells (see FIG. 11). Because oxygen is required for neuron activity, by measuring oxygen consumption and supply in the capillaries, it is possible to monitor neuron activity. In the past, because oxygen metabolism in the nerve cells and oxygen metabolism of the capillaries could not be measured, it was measured invasively, by inserting needles into the spaces between the nerve cells. However, a capillary oxygen exchange functional imaging measurement method that precisely measures oxygen exchange in the capillaries and is noninvasive now becomes possible.

Accordingly, the present invention makes it possible, by means of time series measurements of changes in absolute amounts and relative changes, to display information in image form, divided into 1) the force and kinetic energy that varies the amount (number) of red blood cells 2) the oxygen exchange rotational energy, which takes variation in the amount (number) of red blood cells as its axis FIG. 17(A)-(D) are graphs showing changes over time in the 4 component vectors: oxyhemoglobin, deoxyhemoglobin, total hemoglobin and oxygen saturation. From FIG. 17, differentials and integrals are calculated, and kinetic energy, force, torque, angular momentum, moment of inertia and the like of the loci of the two-dimensional coordinate axes are calculated and measured.

Namely, if amount of total hemoglobin is taken as mass m, they can be shown as equations using oxygen exchange velocity λ calculated from oxyhemoglobin and deoxyhemoglobin.

15) Force F $$F = m_t \epsilon = F_o + F_d$$

$F_r$: Calculation of momentum $F = m_t \epsilon$ $F_o$=[amount of OxyHb]×[acceleration of change in OxyHb]

$F_d$=[amount of DeoxyHb]×[acceleration of change in DeoxyHb]

16) Rate of Change in Angular Momentum over Time N (Torque)

$$N = r \times F = m_t r \text{ (differential of } \theta) = m_o r \epsilon + m_d r \epsilon$$

17) Angular Momentum $P_t$, $P_o$, $P_d$ of [Amount of DeoxyHb], [Amount of OxyHb] and [Amount of Total Hb] for Each Voxel $$P_t = P_o + P_d$$

$$P_t = m_t r^2 \text{ (differential of } \theta) = m_o r^2 \epsilon + m_d r^2 \epsilon$$

18) Linear Density β (Units: Mass/Length) of Hemoglobin for Each Voxel $$\beta = m_t/r = m_o/r + m_d/r$$

19) Moment of Inertia I $$I_r = [\text{oxygen exchange moment of inertia}]$$
$$= I_o + I_d$$
$$= 1/3[\text{total amount of } Hb]$$
$$[\text{absolute amount of oxygen exchange}]^2$$
$$= 1/3(m_t r^2)$$
$$= I_o + I_d$$
$$= 1/3 m_o/r^2 + 1/3 m_d/r^2$$

20) Rotational Energy Q:

$$Q = \frac{1}{2}(I \epsilon^2)$$

21) Momentum of Total Hemoglobin $P_{tHb}$ $P_{tHb}$=(mass)(velocity)=[total amount of Hb]×[velocity of change in total Hb]

22) Oxygen Exchange Angular Momentum $L_{ScO2}$ $$L_{ScO2} = (\text{mass})(\text{velocity})(\text{arm length}) = [\text{total amount of } Hb] \times [\text{absolute amount of oxygen exchange}] \cdot r \times$$
$$[\text{velocity of change in oxygen saturation}] = [\text{total amount of } Hb] \times$$
$$[\text{absolute amount of oxygen exchange}]^2 \times$$
$$[\text{absolute oxygen exchange angular velocity}]$$
$$[\text{absolute amount of oxygen exchange}]^2 =$$
$$[\text{amount of } OxyHb]^2 + [\text{amount of } DeoxyHb]^2$$

23) Total Hemoglobin Variation Force $F_{tHb}$ $F_{tHb}$=(mass)(acceleration)=[total amount of Hb]×[acceleration of change in total Hb]

24) Oxygen Exchange Torque $N_{ScO2}$ $N_{ScO2}$=[absolute amount of oxygen exchange]×[total amount of Hb]×[acceleration of change in oxygen saturation]

25) Total Hemoglobin Variation Energy $T_{tHb}$ $T_{tHb}=\frac{1}{2}$[total amount of Hb]×[velocity of change in total Hb]$^2$ 26) Oxygen Exchange Rotational Energy $K_{ScO2}$ $K_{ScO2}=\frac{1}{2}$[moment of inertia]×[absolute oxygen exchange angular velocity]$^2$ To map the temporal distribution of vectors of change in capillary oxygen saturation, oxygen exchange angular velocity is calculated by means of the differentials of oxygen exchange rate.

From a map of temporal distribution of the differentials of the capillary oxygen saturation change vectors and a map of temporal distribution of hemoglobin (Hb) change vectors, angular momentum, force F, rate of change in angular momentum over time (torque) N, moment of inertia I and rotational energy Q for each voxel are calculated for DeoxyHb, OxyHb and total Hb.

The meaning of this is that it shows that oxygen exchange index[es from oxyhemoglobin and deoxyhemoglobin, and changes in the amount of hemoglobin are tied together by the equations of rotational energy.

Namely, channels (regions) can be selected by means of the size of the amount of change in kinetic energy.

Below, nine patterns arise in the relationship between changes in the amount of hemoglobin and absolute oxygen exchange angular velocity (or oxygen exchange angular velocity). Energy Q and angular momentum P corresponding to these are as follows:

TABLE 1

| Change in hemoglobin | Absolute oxygen exchange angular velocity (or oxygen exchange angular velocity) | Change in angular momentum P | Change in rotational energy Q |
|---|---|---|---|
| Increase | Increase | Increase | Increase |
| Increase | Decrease | Increase/Decrease | Increase/Decrease |
| Increase | Zero | Increase | Increase |
| Zero | Increase | Increase | Increase |
| Zero | Decrease | Decrease | Decrease |
| Zero | Zero | Zero | Zero |
| Decrease | Increase | Increase/Decrease | Increase/Decrease |
| Decrease | Decrease | Decrease | Decrease |
| Decrease | Zero | Decrease | Decrease |

In this way, the amount of change in rotational energy is determined by the interaction of the values for change in hemoglobin and change in absolute oxygen exchange angular velocity (or oxygen exchange angular velocity), and a spatiotemporal image display of the regions of maximum increase and regions of maximum decrease in rotational energy accompanying oxygen metabolism, and identification of the area of those ranges becomes possible.

27) Moment of Inertia on the Oxygen Saturation—Total Hb Coordinates $$I_{tHb} = [\text{total hemoglobin moment of inertia}]$$
$$= 1/3[\text{total } Hb][\text{total } Hb \text{ vector}]^2$$
$$= 1/3[\text{total } Hb][\text{absolute oxygen exchange}]^2[\sin\theta]^2$$

-continued (because it is thought of as the rotational motion of a kind of pole made of hemoglobin this pole's linear density, $\beta = m_t/r\sin\theta = m_o/r\sin\theta + m_d/r\sin\theta$)

Upon dynamically measuring a locus on two-dimensional coordinates, the two moments of inertia $I_{rHb}$="oxygen exchange moment of inertia", when thinking of it as rotational motion of a kind of pole made of oxyhemoglobin and deoxyhemoglobin from the origin zero, and $I_{tHb}$="total Hb moment of inertia", when thinking of it as rotational movement of a kind of pole made of hemoglobin, are calculated.

When the law of total conservation of energy is applied, the sum of the "rotational energy of a kind of pole made of oxyhemoglobin and deoxyhemoglobin from the origin zero" and the "kinetic energy of mass variation of a kind of pole made of oxyhemoglobin and deoxyhemoglobin", on oxyhemoglobin-deoxyhemoglobin coordinates, can be thought of as divided into "rotational movement of a kind of pole made of Hb" and "kinetic energy of mass variation of a kind of pole made of Hb" on oxygen saturation-total hemoglobin coordinates, created by conversion of the polar coordinates.

Measurement of change in kinetic energy accompanying the phenomenon of oxygen exchange in the capillaries
=[rotational energy of a kind of pole made of oxyhemoglobin and deoxyhemoglobin from the origin zero]+[kinetic energy of mass variation of a kind of pole made of oxyhemoglobin and deoxyhemoglobin]
=[rotational energy of a kind of pole made of Hb]+[kinetic energy of mass variation of a kind of pole made of Hb]

Namely, it can be measured or monitored divided into parallel motion and rotational motion.

Consequently, measurement flowcharts can be described for each of "rotational energy of a kind of pole made of oxyhemoglobin and deoxyhemoglobin from the origin zero", "kinetic energy of mass variation of a kind of pole made of oxyhemoglobin and deoxyhemoglobin", "rotational movement of a kind of pole made of Hb", and "kinetic energy of mass variation of a kind of pole made of Hb".

In addition, the measure values required for the calculation of kinetic energy can be monitored. Furthermore, because these are time series data, it is also possible to display not only absolute amounts, but also the respective amounts of change and amounts of change in energy for each.

Figure 18:
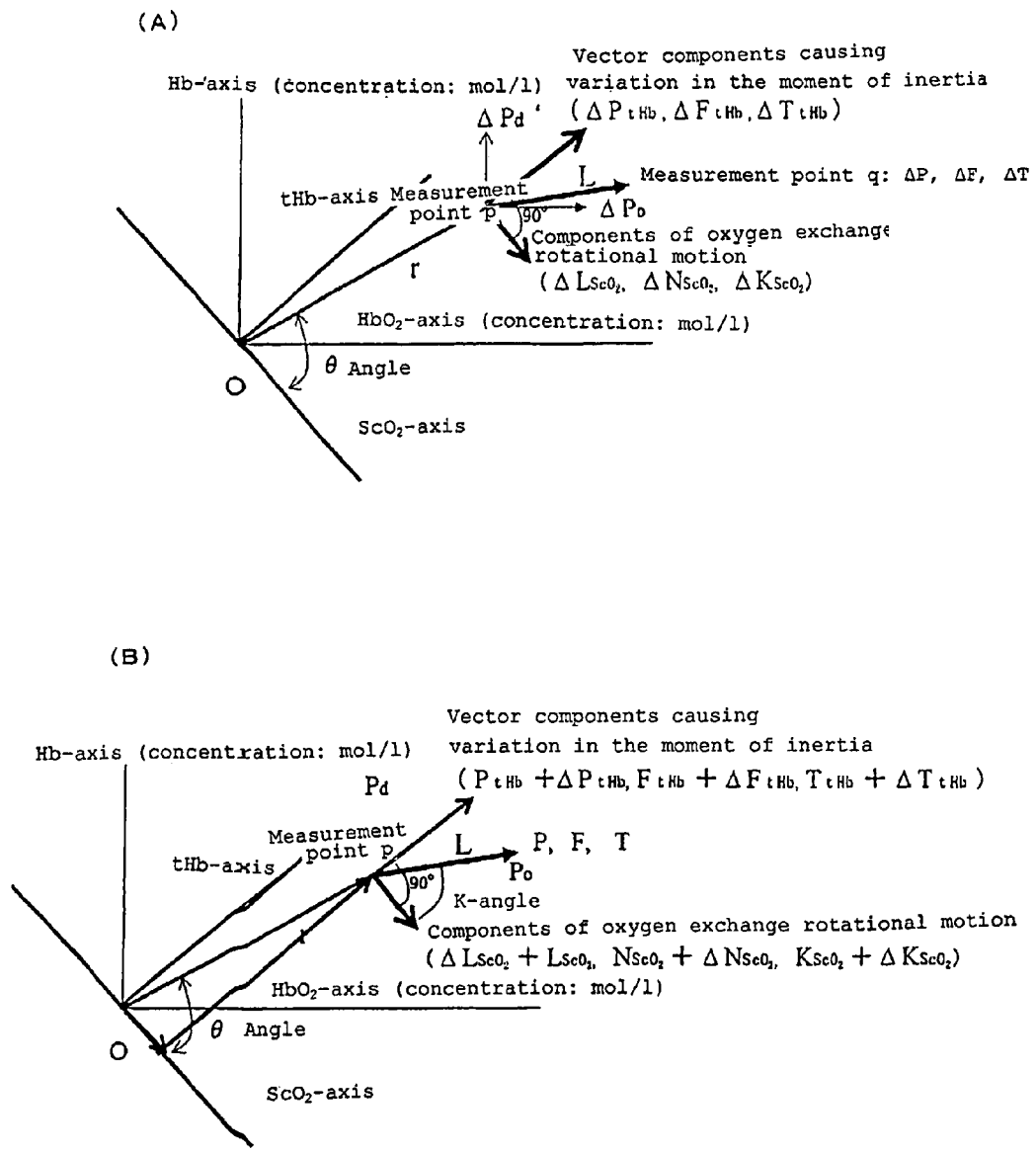
FIG. 18. (A) and (B) are graphs explaining the moment of inertia on two-dimensional diagrams with oxygen saturation as the X-axis and total hemoglobin as the Y-axis; (A) is a graph explaining the amount of change in kinetic energy accompanying the phenomenon of oxygen exchange in the capillaries; and (B) is a graph explaining the absolute kinetic energy accompanying the phenomenon of oxygen exchange in the capillaries.

FIG. 18 shows moment of inertia on two-dimensional diagrams with oxygen saturation as the X-axis and total hemoglobin as the Y-axis. FIG. 18(A) is an explanatory diagram showing the amount of change in kinetic energy accompanying the phenomenon of oxygen exchange in the capillaries; namely, the "change of rotational energy of a kind of pole made of oxyhemoglobin and deoxyhemoglobin from the origin zero" and the "change of kinetic energy of mass variation of a kind of pole made of oxyhemoglobin and deoxyhemoglobin".

Because "change of kinetic energy accompanying the phenomenon of oxygen exchange in the capillaries"="change of rotational energy of a kind of pole made of oxyhemoglobin and deoxyhemoglobin from the origin zero"+"change of kinetic energy of mass variation of a kind of pole made of oxyhemoglobin and deoxyhemoglobin", $$\Delta P = \Delta P_r (= \Delta P_o + \Delta P_d) + \Delta L_r = \Delta P_{tHb} (= \Delta P_o' + \Delta P_d') + \Delta L_{ScO2}$$

$$\Delta F = \Delta F_r (= \Delta F_o + \Delta F_d) + \Delta N_r = \Delta F_{tHb} (= \Delta F_o' + \Delta F_d') + \Delta N_{ScO2}$$

$$\Delta T = \Delta T_r (= \Delta T_o + \Delta T_d) + \Delta K_r = \Delta \Delta T_{tHb} (= \Delta T_o' + \Delta T_d') + \Delta K_{ScO2}$$

FIG. 18(B) is an explanatory diagram showing absolute values for kinetic energy accompanying the phenomenon of oxygen exchange in the capillaries; namely, the "absolute amount of rotational energy of a kind of pole made of oxyhemoglobin and deoxyhemoglobin from the origin zero" and the "absolute amount of kinetic energy of mass variation of a kind of pole made of oxyhemoglobin and deoxyhemoglobin".

Because the "absolute amount of kinetic energy accompanying the phenomenon of oxygen exchange in the capillaries"="absolute amount of rotational energy of a kind of pole made of oxyhemoglobin and deoxyhemoglobin from the origin zero"+"absolute amount of kinetic energy of mass variation of a kind of pole made of oxyhemoglobin and deoxyhemoglobin", $$P + \Delta P = P_{tHb} + \Delta P_{tHb} + \Delta L_{ScO2} + L_{ScO2}$$

$$F + \Delta F = F_{tHb} + \Delta F_{tHb} + N_{ScO2} + \Delta N_{ScO2}$$

$$T + \Delta T = T_{tHb} + \Delta T_{tHb} + K_{ScO2} + \Delta K_{ScO2}$$

Other possible parameters include the following:
28) Calculation of a Sum Total M for All Hb for a Desired Time of Rotational Motion
Calculation of time course data $M = \Sigma m_i$
29) Locus of Movement of the Center of Gravity of Each Voxel
Calculation of center of gravity coordinates $r_G(x,y)$=(oxyhemoglobin coordinate, deoxyhemoglobin coordinate)

Figure 19:
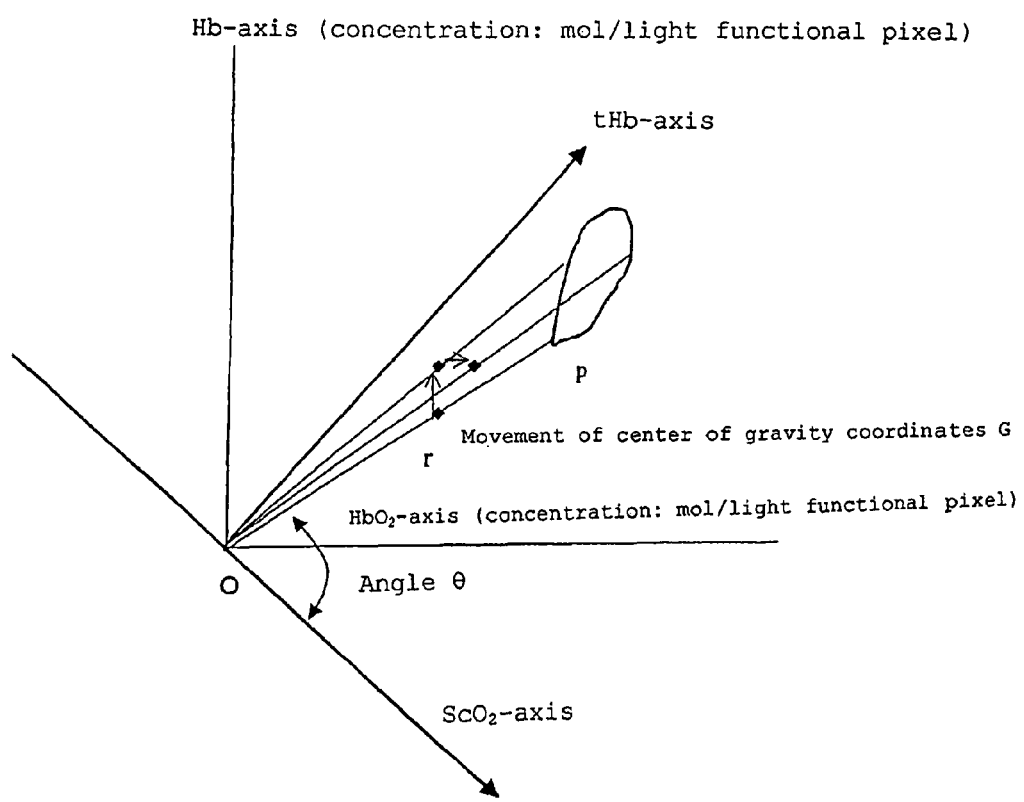
FIG. 19. A conceptual explanation of a two-dimensional diagram showing a shifting locus of centroid coordinates G.
Figure 20:
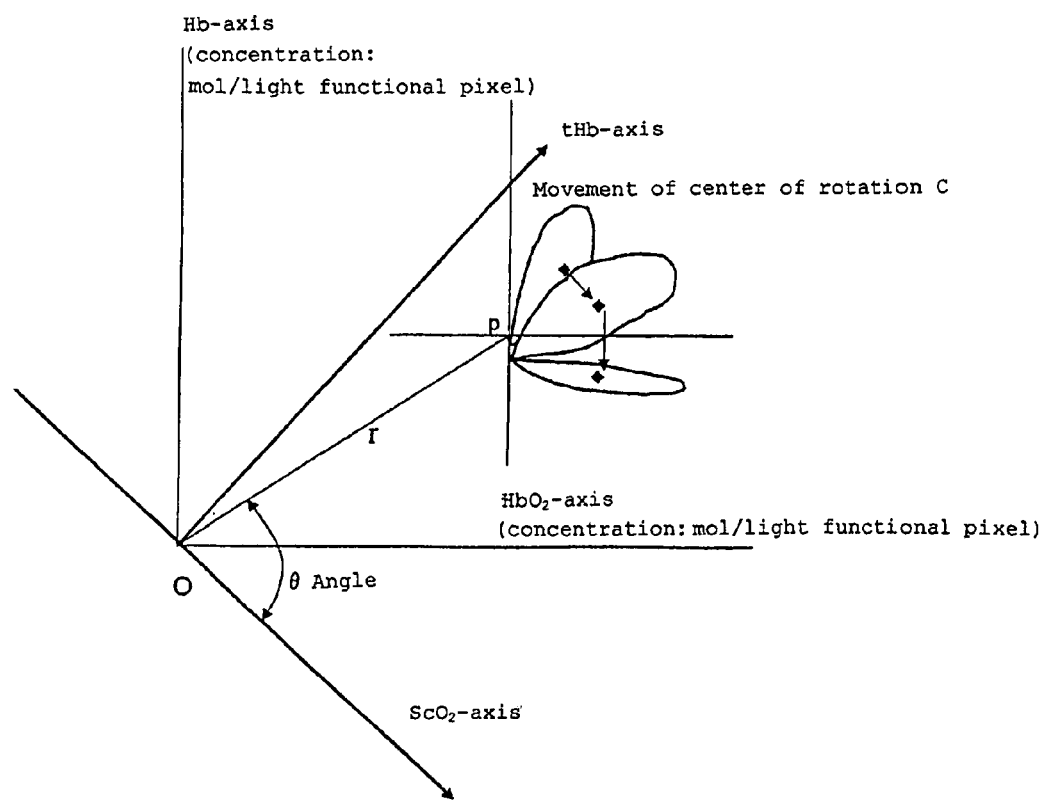
FIG. 20. A conceptual explanation of a two-dimensional diagram showing a shifting locus of center of rotation C.

$r_{Gx} = \int [\text{oxyhemoglobin}] dm$ $r_{Gy} = \int [\text{deoxyhemoglobin}] dm$ As shown in FIG. 19, by taking the locus of movement of the center of gravity G of each voxel, stability of the data at rest can be judged; for example, taking sites with high stability as measurable, and waiting to measure sites with low stability.
30) Locus of Movement of Center of Rotation C of Each Voxel Approximated by calculating maximum values of change of the 4 vector components ($\Delta HbO_2$, $\Delta Hb$, $\Delta ScO_2$ and $\Delta tHb$) from the Hb-HbO$_2$ polar coordinates and the tHb-Sc polar coordinates, and taking the coordinates showing ½ the maximum value of change as the center of rotation C. As shown in FIG. 20, by taking the locus of movement of center C for each voxel, stability of the data can be evaluated; for example, taking sites with high stability as measurable, and waiting to measure sites with low stability.
31) Maximum Trajectory Surface Area of Rotational Motion $\Delta S$ As an approximate formula, $$\Delta S = (\Delta HbO_2) \cdot (\Delta Hb) = (\Delta ScO_2) \cdot (\Delta tHb)$$

Stability of the data can be evaluated by the time course of the maximum trajectory surface area of rotational motion of each voxel; for example, taking sites with high stability as measurable, and waiting to measure sites with low stability.
32) Fluctuation Ratio ($f_i/f_j$)

The total amount of Hb of each functional voxel is measured; the maximum total hemoglobin (tHb$_i$) and the total hemoglobin ratios (tHb$_j$/tHb$_i$) with the other voxels are calculated; the total hemoglobin ratios are ranked; as fluctuation measurements for each functional voxel, the maximum change values of the 4 vector components $\Delta HbO_2$, $\Delta Hb$, $\Delta ScO_2$ and $\Delta tHb$ are calculated from the Hb-$HbO_2$ polar coordinates and tHb-Sc polar coordinates; and ratios $f_i/f_j$ between fluctuation $f_i$ of the maximum total hemoglobin (t$Hb_i$) and the fluctuation of the other voxels $f_j$ are calculated.

Figure 21:
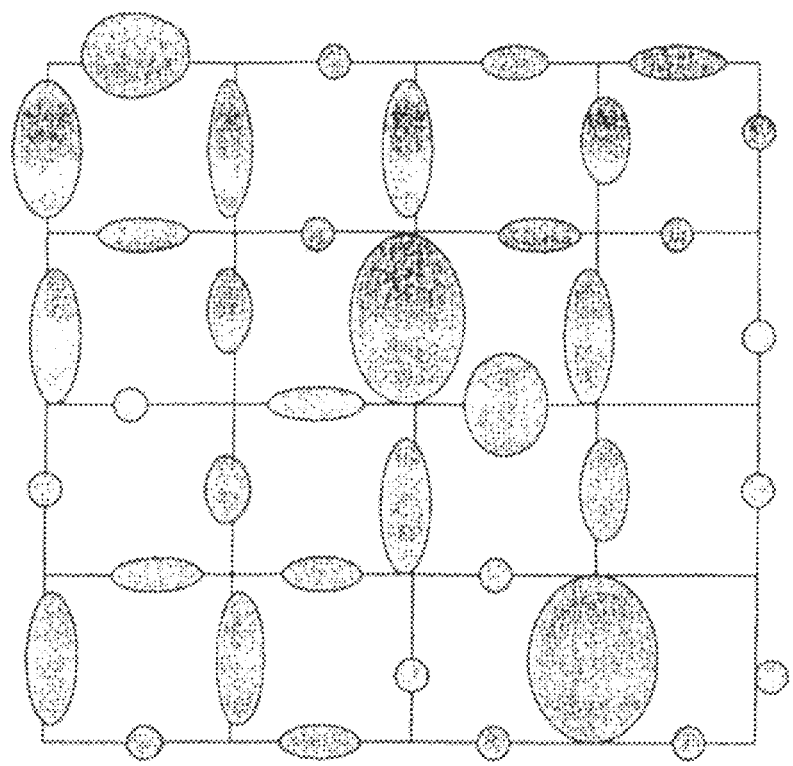
FIG. 21. An explanatory drawing showing the correlation between amplitude of fluctuation and measured voxel size.

From the fluctuation ratio, ratios for the amount (measurement target mass) of total hemoglobin of the measurement targets can be determined. Relative graphs of measured mass and differences in amplitude of fluctuation can be displayed, as shown, for example in FIG. 21 (interpolated display). From this it can be seen which sites have what kind of distortion, and this can also be applied in cases of measuring distortion that is not from noise but that has a pathological origin.

33) Center Trajectory Distance (h-Values)

Center coordinates of an elliptical trajectory in 2 dimensions within a desired time are calculated.

The following are used as 2 approximate equations from 2-coordinate systems.

$$[h^2 = [(\text{maximum } \Delta HbO_2 - \text{minimum } \Delta HbO_2)/2]^2 + [(\text{maximum } \Delta Hb - \text{minimum } \Delta Hb)/2]^2$$

or $$=[(\text{maximum } \Delta tHb - \text{minimum } \Delta tHb)/2]^2 + [(\text{maximum } \Delta ScO_2 - \text{minimum } \Delta ScO_2)/2]^2$$

A desired number of rotations n may also be averaged for the ellipse.

Values for distance h from point p of the center coordinates (measurement start zero point) are measured.

A minimum value for h reflects a channel with little fluctuation. A minimum total value c of the center coordinate distances when rotated n times also reflects a stable channel.

34) Degree of Variation Between Channels (G-Value)

Represents the strength of variation in signal strength between channels. Dispersion is calculated using the following numerical formula.

$$G = 1/n \left\{ \sum_{i=1}^{n} (U_i - U)^2 \right\} \quad \text{Numerical formula 1}$$

Where:
n: number of measurement sites
$U_i$: measured value
U: average of n measured values 35) Scalar Value (S-Value)

$$S^2 = G^2 + L^2$$

Two kinds of selection and adjustment, within channels and between channels, are performed so that scalar S-values on vectors calculated from G-values and L-values are minimized.

36) A complex function that simultaneously handles capillary oxygen saturation (oxygen exchange) vectors and total hemoglobin vectors $$(L * e^{k \cdot angle})$$

The 3-dimensional displays described below—I-spiral, T-spiral, K-spiral and H-spiral—can all be described by means of an oxygen exchange equation using complex functions.

From the use of the "oxygen exchange equation" utilizing the equations of Euler's formula, the locus of the K-spiral in the 3-dimensional diagram is the first time since imaginary numbers appeared in Schrödinger's equation in quantum mechanics that imaginary numbers have come into the description of a life sciences phenomenon, and it shows that oxygen exchange is adjusted according to real-number and imaginary-number factors.

By means of Euler's formulas, amounts with different units (hemoglobin and oxygen exchange) can be represented simultaneously by a complex function.

Euler's formula: $e^{i \cdot k} = \cos k + i \cdot \sin k$ $e^{-i \cdot k} = \cos k - i \cdot \sin k$ Considering the complex function on polar coordinates, $Z$(Gaussian plane)=[change in oxyhemoglobin vector]+$i$·[change in deoxyhemoglobin vector]

=[OxyHb]+$i$·[DeoxyHb]

If this is further rotated 45 degrees, it becomes:

$Z'$(Gaussian plane) = [change in oxygen exchange vector] +

$i$ · [change in hemoglobin vector]

= [$ScO_2$] + $i$ · [$tHb$]

= $L \cdot \cos(k) + L \cdot \sin(k) \cdot i$

= $L[\cos(k) + \sin(k) \cdot i]$

= $L \cdot e^{i*k}$, and if placed in Euler's formula as:

[change in oxyhemoglobin vector]=$L \cdot \cos k = L \cdot (e^{i \cdot k} + e^{-i \cdot k})/2$

[change in deoxyhemoglobin vector]=$L \cdot \sin k = L \cdot (e^{i \cdot k} - e^{-i \cdot k})/2i$ $e^{i \cdot k}$=([change in oxygen exchange vector]+$i$·[change in hemoglobin vector])/$L$ $e^{i \cdot k}$=([change in oxygen exchange vector]-$i$·[change in hemoglobin vector])/$L$, then biological physiological changes, namely hemoglobin and oxygen exchange, which were previously handled separately as different physiological values, are now handled simultaneously, by means of a complex function.

In addition, the following apply:

$L^2$ = [change in oxyhemoglobin vector]$^2$ +

[change in deoxyhemoglobin vector]$^2$

= [$ScO_2^2$]

= [$tHb$]$^2$

= [$oxyhb$]$^2$

= [$DeoxyHb$]$^2$ $2L^2$ = [change in oxyhemoglobin vector]$^2$ +

[change in hemoglobin vector]$^2$ and the following relationships also apply:

[change in oxygen exchange vector] =

$\{ScO_2\}/\sqrt{2} = ([OxyHb] - [DeoxyHb] - [DeoxyHb])\sqrt{2}$

[change in hemoglobin vector] = [$tHb$]$/\sqrt{2}$ = ([$Oxyhb$] + [$Deoxyhb$])$/\sqrt{2}$ To summarize, $$e^{i\cdot k} = ([\text{change in oxygen exchange vector}] + i\cdot[\text{change in hemoglobin vector}])/L$$

$$= [ScO_2]/\sqrt{2} + i\cdot([tHb]/\sqrt{2L})$$

$$= [ScO_2]/\{2([ScO_2]^2 + [tHb]^2)\}^{0.5} + i\cdot[tHb]/\{2([ScO_2]^2 + [tHb]^2)\}^{0.5}$$

$$= ([OxyHb] - [DeoxyHb])/\{2([OxyHb]^2 + [DeoxyHb]^2\}^{0.5} + i\cdot([OxyHb] + [DeoxyHb])/\{2([OxyHb]^2 + \{DeoxyHb]^2)\}^{0.5}$$

$$e^{-i\cdot k} = ([\text{change in oxygen exchange vector}] - i\cdot[\text{change in hemoglobin vector}])/L$$

$$= [ScO_2]/\sqrt{2L} - i\cdot([tHb]/\sqrt{2L})$$

$$= [ScO_2]/\{2([ScO_2]^2 + [tHb]^2)\}^{0.5} + i\cdot[tHb]/\{2([ScO_2]^2 + [tHb]^2)\}^{0.5}$$

$$= ([OxyHb] - [DeoxyHb])/\{2([OxyHb]^2 + [DeoxyHb]^2)\}^{0.5} - i\cdot([OxyHb] + [DeoxyHb])/\{(2([OxyHb]^2 + \{DeoxyHb]^2)\}^{0.5}$$

Because the k-angle and other indexes are all functions of time, they represent K-spirals.

37) Cumulative tHb Change and the Correlation Change Angle, at Rest and During Activity Cumulative tHb change and the correlation change angle, at rest and during activity, are calculated by the following procedure:
1. Data is measured from a plurality of sites.
2. tHb and $ScO_2$ are separated out and calculated.
3. Summed data for tHb and $ScO_2$ from a desired starting point, namely, cumulative change in tHb and cumulative change in $ScO_2$, are determined.
4. $\int_a^t f(t)dt$, taking a=0, and varying time t, is displayed as a graph. f(t) becomes tHb or $ScO_2$.
5. The respective correlation coefficients (slope r) at a given time are determined at rest and during activity. The angle formed by the two slopes r, at rest and during activity, is also determined.
6. For tHb, the angle formed by these two slopes defines the correlation change angle for cumulative tHb change.
7. For $ScO_2$, the angle formed by these two slopes defines the correlation change angle for cumulative $ScO_2$ change.

Figure 22:
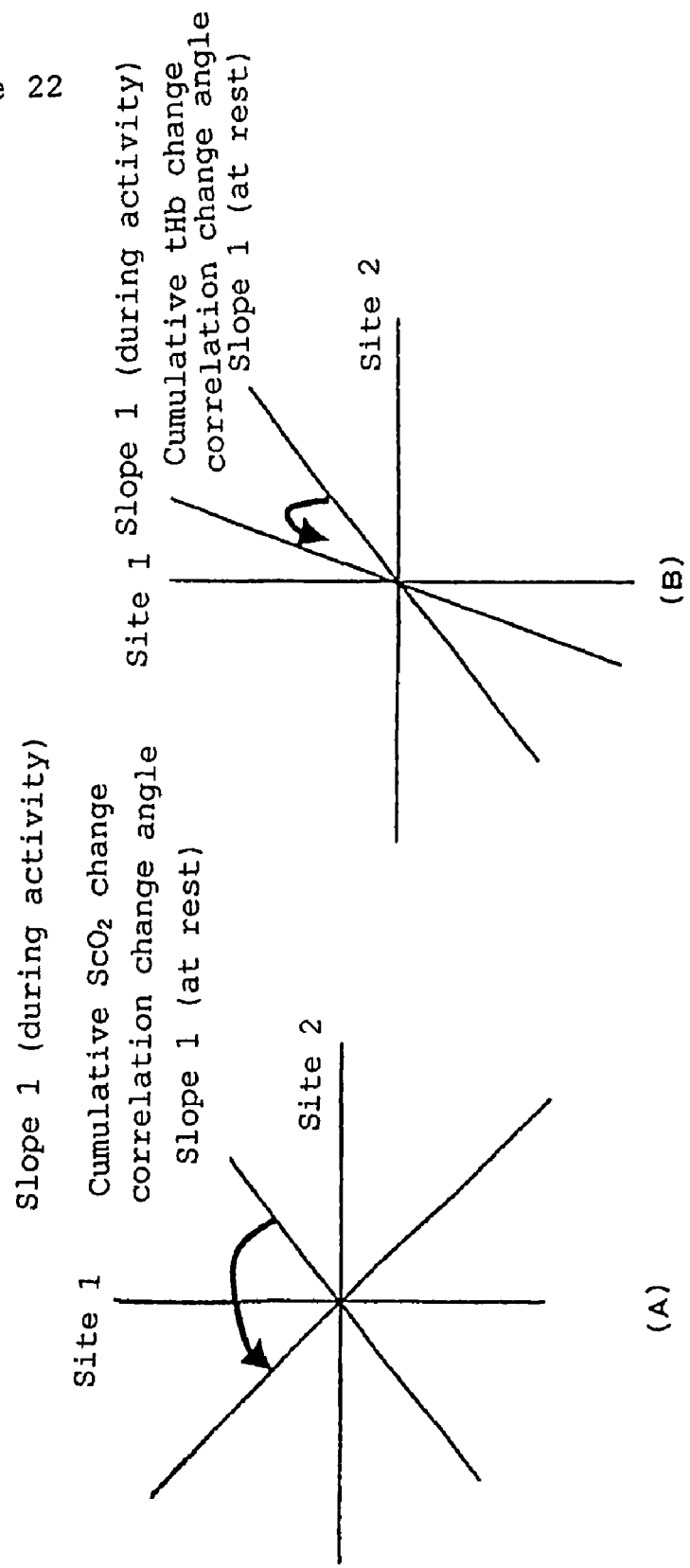
FIG. 22. (A) and (B) are graphs showing the slopes for changes in state between at rest and during activity, for two sites.

Then, as shown in FIGS. 22(A) and (B), the slopes are calculated with a change in state between rest and activity. Because oxygen supply and consumption are exactly opposite, they intersect at right angles.

In the graph of FIG. 22(A), because the two time series data differ to the extent that the changes in correlation of cumulative $ScO_2$ intersect at an angle of approaching 90 degrees, the FORCE effect and the Watering-the-garden effect can be separated.

In FIG. 22(B), the two time series data are differentiated to the extent that the changes in correlation of cumulative tHb change intersect at an angle approaching 90 degrees, but the FORCE effect and the Watering-the-garden effect can be best separated in the initial period of activity.

38) Indexes Pertaining to Capillary Red Blood Cell Circulation Time, etc.

Previously, because there was no means for noninvasively measuring microcirculation in the capillaries, there was no index for measuring the red blood cell capillary circulation time. It was barely possible, using PET and the like, by the rather rough means of the ratio between cerebral blood volume (CBV, ml/100 g) and cerebral blood flow (CBF, ml/100 g/minute) as an index of the reserve circulation capacity, to suggest, from the mean transit time in the blood vessels (MTT=CBV/CBF; in the human brain, approximately 7 seconds), that to the extent that it was slower than 7 seconds, it was a factor in aging and cerebral infarction.

The inverse, CBF/CBV=1/MTT, reflects the perfusion pressure of the brain, and in the early stages of ischemia, this value shows a decrease.

Here, with NIRS imaging, because it is possible to measure total hemoglobin, oxyhemoglobin, deoxyhemoglobin and $ScO_2$ as indexes relevant to the measurement of red blood cell capillary circulation time, 1. Red blood cell capillary circulation time information can be measured through total hemoglobin.
2. Because oxyhemoglobin is carried by the arterial blood, circulation time information pertaining to blood inflow and oxygen consumption can be measured.
3. Because deoxyhemoglobin varies according to the amount of tissue oxygen consumption, circulation time information pertaining to oxygen consumption can be measured.
4. As for $ScO_2$, circulation time information pertaining to oxygen consumption and supply variation can be measured.

Specifically, from change in tHb, we can calculate:
Change in localized capillary red blood cell cumulative transit time $tRTTc = \int_a^t tHb\,dt/tHb$ Change in localized capillary red blood cell transit time $RTTc = tHb/(tHb/t)$ From change in $HbO_2$, we can calculate:
Change in localized capillary oxyhemoglobin cumulative transit time $tHbO_2TTc = \int_a^t \Delta HbO_2\,dt/\Delta HbO_2$ Change in localized capillary oxyhemoglobin transit time $HbO_2TTc = \Delta HbO_2/(HbO_2/t)$ From change in Hb, we can calculate:
Change in localized capillary deoxyhemoglobin cumulative transit time $tHbTTc = \int_a^t Hb\,dt/Hb$ Change in localized capillary deoxyhemoglobin transit time $HbCTc = Hb/(Hb/t)$ From change in $ScO_2$, we can calculate:
Change in localized capillary cumulative oxygen exchange time $tOETc = \int_a^t ScO_2\,dt/ScO_2$ Change in localized capillary oxygen exchange time $OETc = ScO_2/(ScO_2/t)$ From absolute tHb, we can calculate:
Localized capillary red blood cell cumulative transit time $tRTT = \int_a^t tHb\,dt/tHb$ Localized capillary red blood cell transit time $RTT = tHb/(tHb/t)$ From absolute $HbO_2$, we can calculate:
Localized capillary oxyhemoglobin cumulative transit time $tHbO_2TT = \int_a^t HbO_2 dt/HbO_2$ Localized capillary oxyhemoglobin transit time $HbO_2CT = HbO_2/\Delta(HbO_2/t)$ From absolute Hb, we can calculate:
Localized capillary deoxyhemoglobin cumulative transit time $tHbTT = \int_a^t Hb dt/Hb$ Localized capillary deoxyhemoglobin transit time $HbCT = Hb/\Delta(Hb/t)$ From absolute $ScO_2$, we can calculate:
Localized capillary cumulative oxygen exchange time $tOET = \int_a^t ScO_2 dt/ScO_2$ Localized capillary oxygen exchange time $(cOET) = ScO_2/\Delta(ScO_2/t)$ It is also possible to use the inverses of the above as indexes. In actuality, when calculated as the amount of change, for the purpose of avoiding zero and for the purpose of approximating calculation of absolute amounts, $1/(tRTTc+a)$ is used. Here, the value for "a" in seconds is selected as desired (for example, initial speed).

Regarding the Display Part

Display part 10, shown in FIG. 2, performs a variety of kinds of image displays, based on various parameters calculated by means of controller 8 and/or behavioral information entered into behavioral information input part 12 and recorded in memory 9.

Figure 23:
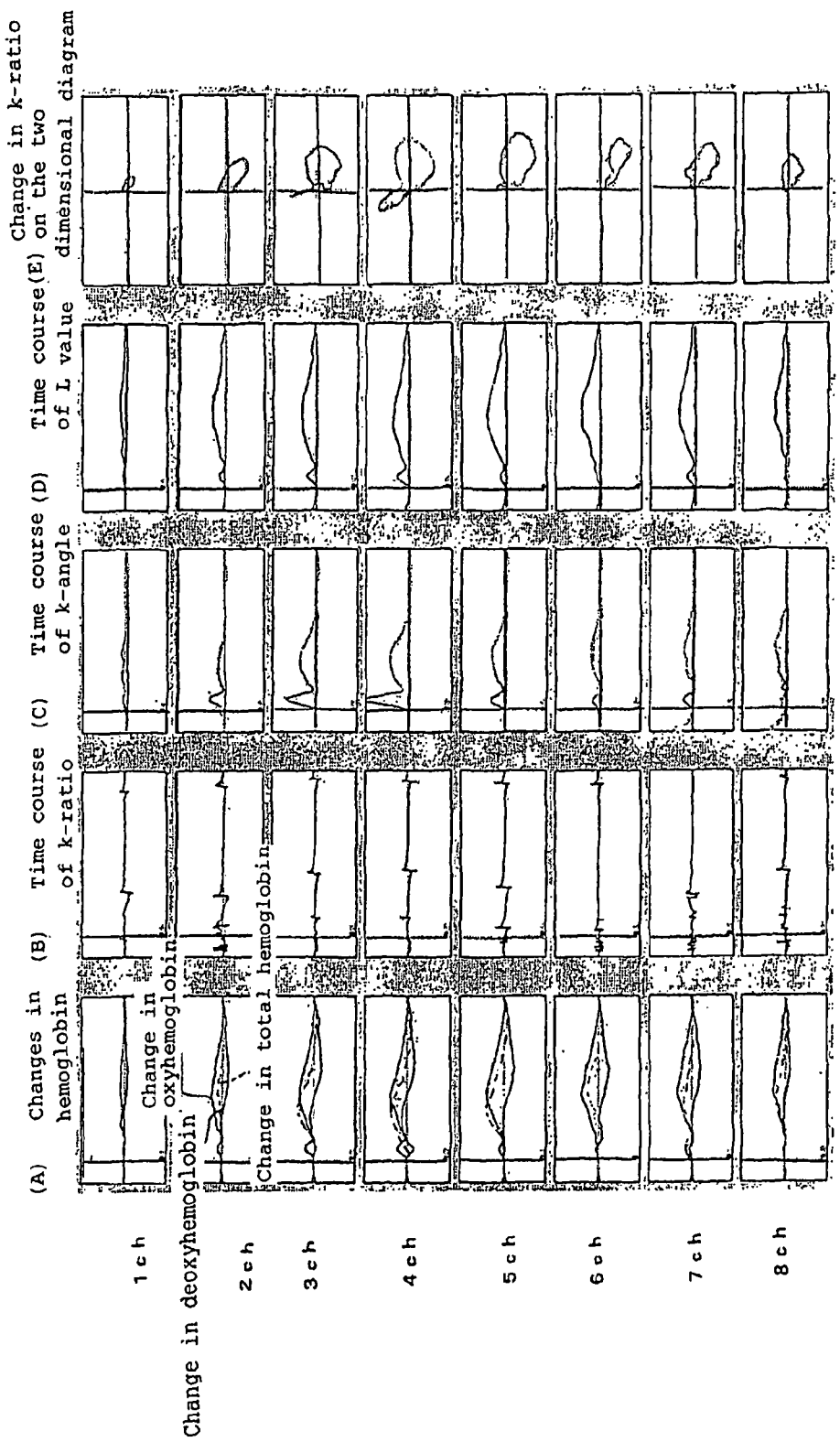
FIG. 23. Graphs showing (A) change in each of the hemoglobins, (B) time course of the K-ratio, (C) time course of the k-angle, (D) time course of the L-value, and (E) two-dimensional changes in the K-ratio.

For example, FIG. 23 shows graphs of measured results for each of 8 channels (ch 1-8) when a subject repeats a word spoken by an examiner. FIG. 23(A) shows the amount of change for each Hb, (B) shows the time course of the K-ratio, C shows the time course of the k-angle (lines divide the events by color), (D) shows the time course of the L-value, and (E) shows two-dimensional changes in the K-ratio. Because the examiner's speaking begins from the vertical lines in FIGS. 23(A)-(E), it can be seen that the K-ratio is changing while the subject is listening to the word spoken by the examiner.

Figure 24:
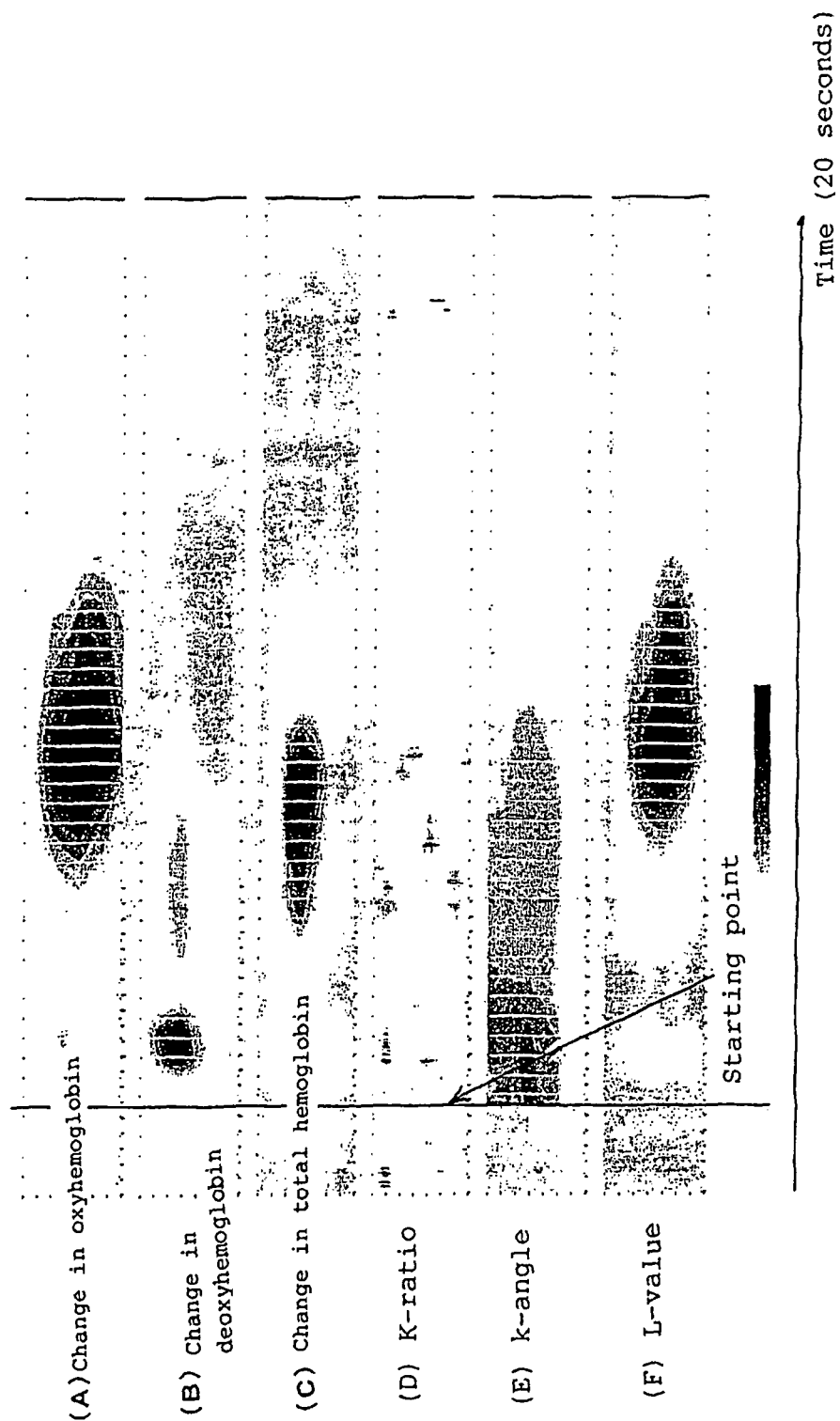
FIG. 24. Explanatory spatiotemporal displays of actual measured data, showing (A) change in oxyhemoglobin, (B) change in deoxyhemoglobin, (C) change in total hemoglobin, (D) K-ratios, (E) k-angles, (F) L-values.

In addition, FIG. 24 shows explanatory spatiotemporal displays of actual measured data; (A) shows oxyhemoglobin; (B), deoxyhemoglobin; (C), total hemoglobin; (D), K-ratios; (E), k-angles; and (F), L-values. Here, the horizontal axis is time, and the vertical axis displays sites from channels 1-8, and increasing and decreasing values are differentiated by color.

From the spatiotemporal display of the k-angle shown in FIG. 24(E), the time course of the sites where oxygen metabolism increased the most, immediately after the stimulus, can be seen.

Figure 25:
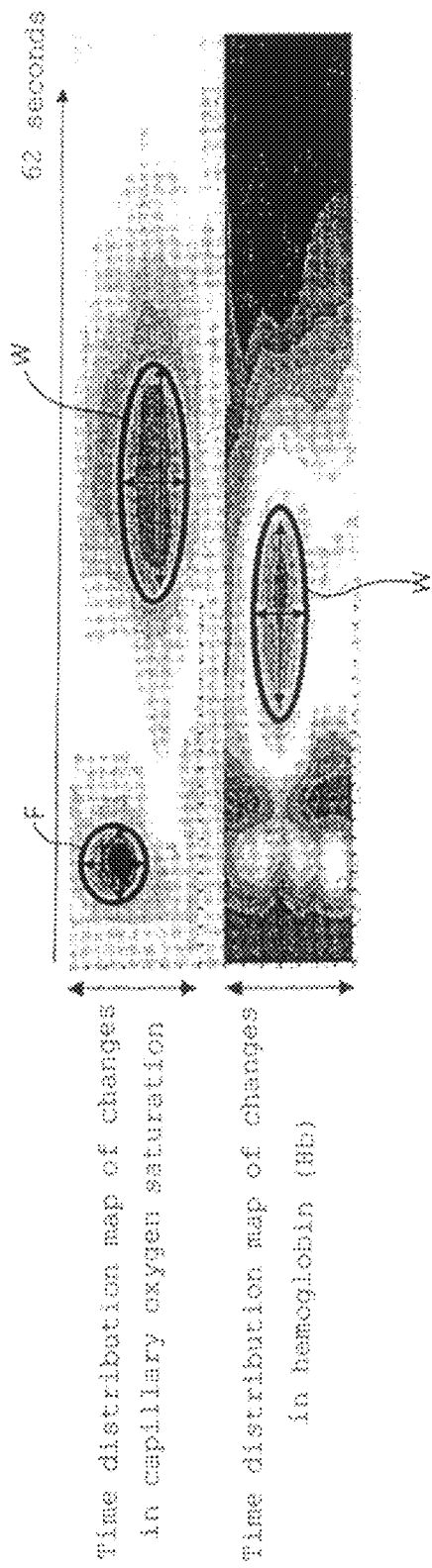
FIG. 25. Graph of time distribution maps of changes in hemoglobin (Hb) and changes in capillary oxygen saturation.

FIG. 25 shows time distribution maps of changes in hemoglobin (Hb) and changes in capillary oxygen saturation. As can be seen from FIG. 25, the 2 distributions are clearly spatially and temporally different. Previously, these 2 elements could not be extracted with a good degree of precision.

With NIRS imaging, it is possible to noninvasively and precisely observe a time series in which low oxygen in the capillaries is succeeded by high oxygenation. By measuring, from site and time distribution maps, the sites and the temporal spread of the FORCE effect (fast oxygen response in capillary event) (F, FIG. 25), it is possible to judge the strength of oxygen consumption. In addition, the fact that widespread changes in oxygen saturation and changes in hemoglobin (Watering-the-garden effect; the phenomenon whereby oxygen is supplied in response to oxygen consumption in a given location and the amount of blood flow also changes in its environs as blood supply) following the FORCE effect are recognized by vascular functional controls can be graphically displayed (W, FIG. 25). Namely, imaging that measures the fast oxygen metabolism response in the capillaries and its relationship to vascular controls is possible. When the Watering-the-garden effect is measured with $T2^*$-fMRI, large signal changes are triggered by veins downstream from the capillaries, and the measurements in units of minutes in PET are convenient for detecting the Watering-the-garden effect; thus it is difficult to differentiate the FORCE effect and the Watering-the-garden effect, as can be done in NIRS imaging.

Time series data for cumulative amounts or cumulative changes for desired regions may also be displayed.

Figure 26:
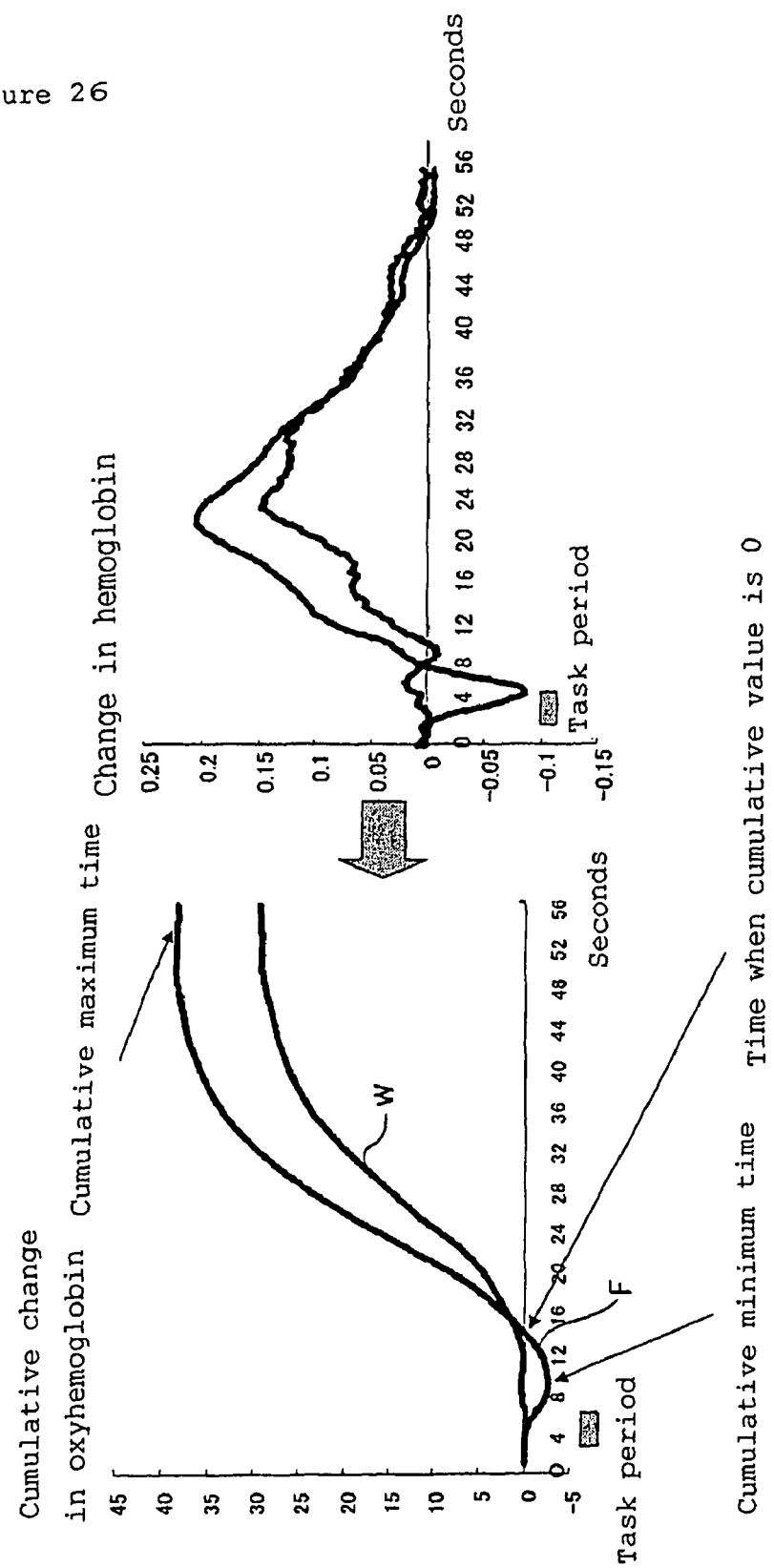
FIG. 26. Graphs displaying cumulative oxyhemoglobin changes based on changes in oxyhemoglobin for two sites.

FIG. 26 shows graphs displaying cumulative oxyhemoglobin changes based on changes in oxyhemoglobin. From the graphs of FIG. 26, it can be seen that the Watering-the-garden effect region W and the FORCE effect region F can be differentiated. If applied to the resting control segment before the task period, a time series data display of cumulative amounts or cumulative changes for a desired region makes it possible to distinguish uniformity and stability of various measurement channels at rest.

Figure 27:
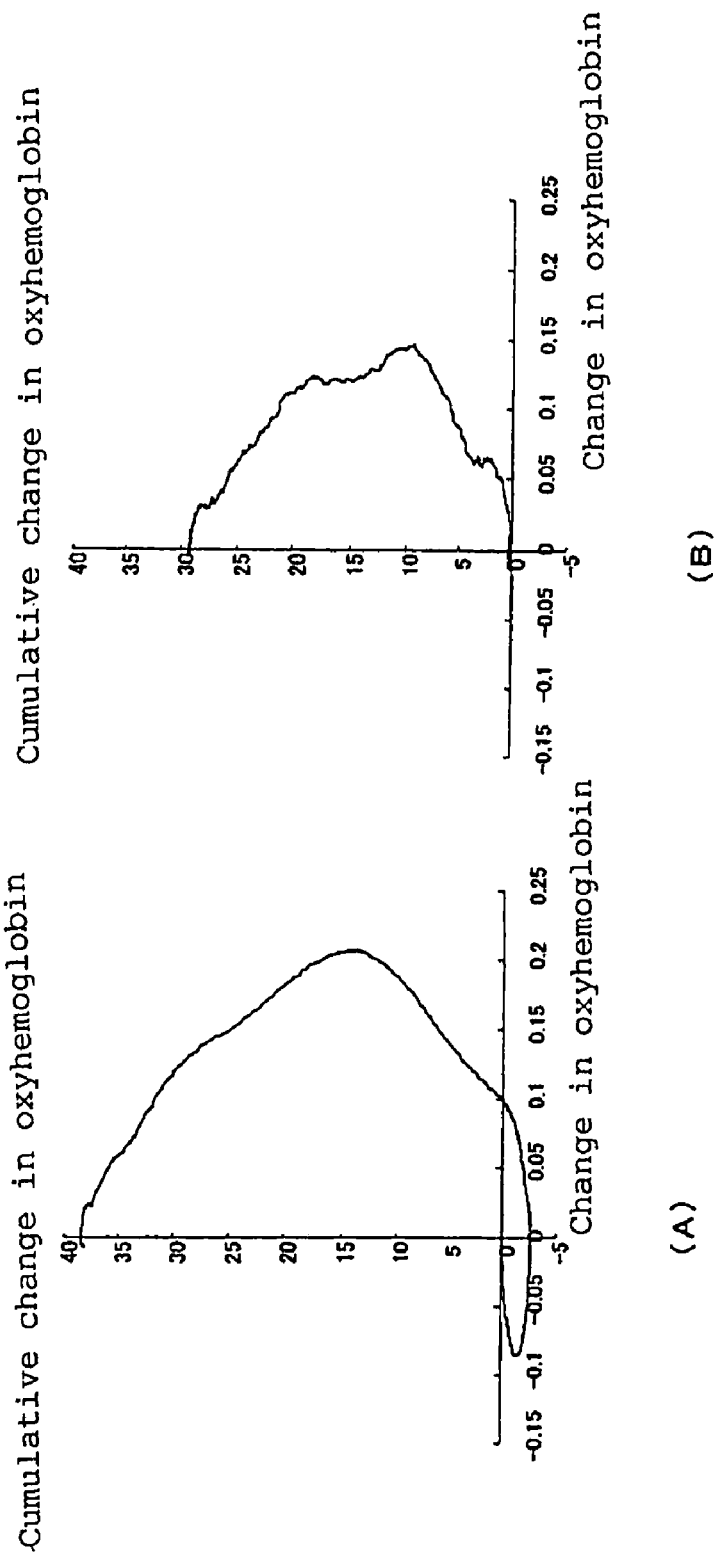
FIG. 27. Shows graphs displaying changes in oxyhemoglobin and cumulative oxyhemoglobin changes, showing (A) a FORCE effect region, and (B) a Watering-the-garden effect region.

FIG. 27 shows graphs displaying changes in oxyhemoglobin and cumulative oxyhemoglobin changes. FIG. 27(A) shows a FORCE effect region, and (B) shows a Watering-the-garden effect region. It can be seen that in the FORCE effect region, as compared to the Watering-the-garden region, the task load causes the oxyhemoglobin to decrease, and then shift to an increase, and the cumulative amount also shifts to a positive direction.

FIG. 28(A) is a graph showing time course changes in tHb, (B) is a graph showing time course changes in the differentials of tHb, (C) is a two-dimensional diagram of the differentials of tHb, and their differentials.

Figure 29:
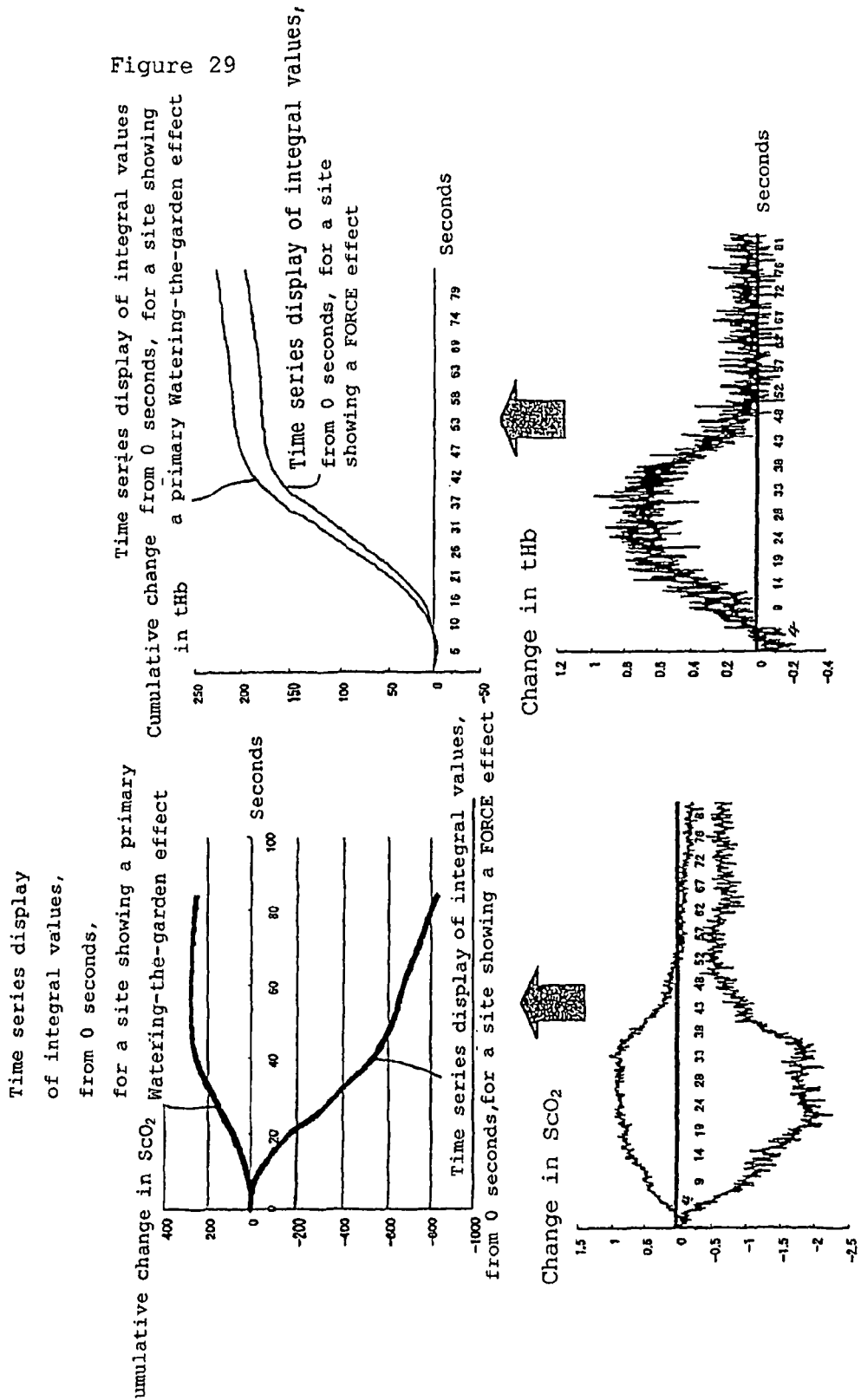
FIG. 29. Graphs displaying time courses of summed data for tHb and $ScO_2$ from a desired starting point, namely, cumulative tHb changes and cumulative $ScO_2$ changes.

Summed tHb and $ScO_2$ data, from a desired starting point, namely, cumulative change in tHb and cumulative change in $ScO_2$, may also be displayed in time series (for example, see FIG. 29).

Furthermore, time series data of integrals for FORCE sites and primary Watering-the-garden sites may be compared and their correlations displayed. For example, in the example in FIG. 30, slopes R at rest and during activity are completely different for regions showing completely different amounts of change in $ScO_2$, but they show a high coefficient of correlation. This proves a precise relationship between the oxygen consumption site and the surrounding oxygen supply sites.

Figure 31:
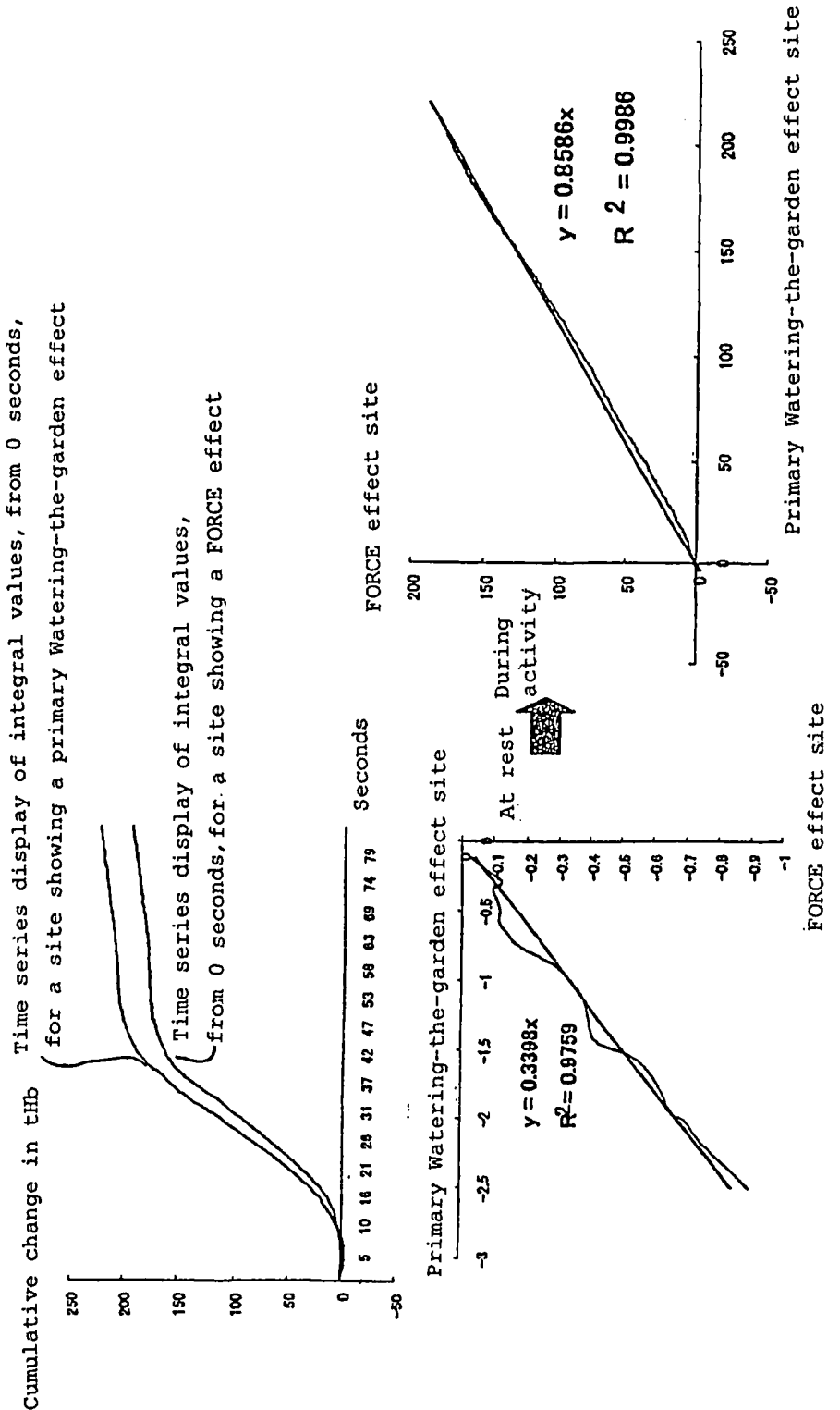
FIG. 31. Graphs showing slopes R that are completely different at rest and during activity for regions displaying different amounts of change in tHb, but that have a high correlation coefficient.

In addition, in the example in FIG. 31, slopes R at rest and during activity are completely different for regions showing completely different amounts of change in tHb, but they show a high coefficient of correlation. This proves a precise relationship between the oxygen consumption sites and the surrounding oxygen supply sites.

Regarding the Method for Evaluating Biological Function

Figure 32:
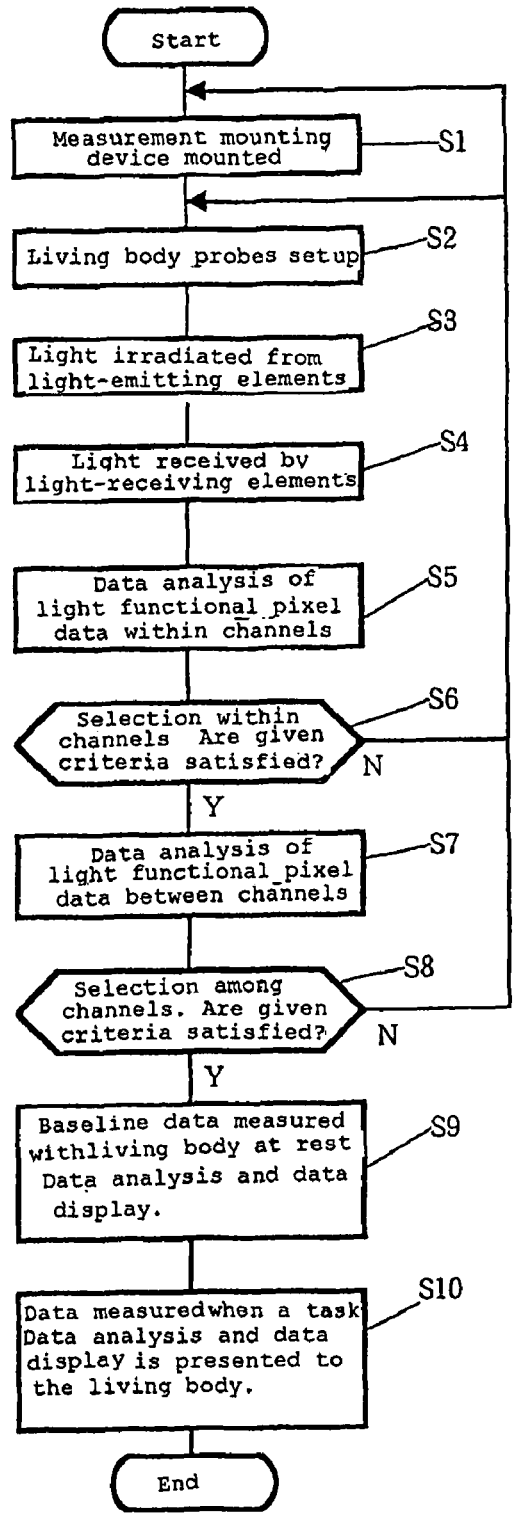
FIG. 32. Flowchart explaining a method for evaluating biological function of a working embodiment of the present invention.

Next, a method for evaluating biological function of a working embodiment of the present invention is explained. FIG. 32 is a flowchart for explaining a method for evaluating biological function of a working embodiment of the present invention.

First, a measurement mounting device furnished with living body probes 1 is mounted on the site of the living body to be measured (step S1).

Next, living body probe light-emitting elements 1a and light-receiving elements 1b are set up (step S2).

Next, while the locations of living body probes 1 are displayed on the monitor, light is emitted from light-emitting elements 1a to irradiate light to the living body (step S3).

Next, light is received by light-receiving elements 1b of living body probes 1 (step S4).

Next, controller 8 of apparatus body 3 analyzes light functional voxel data within the channels of living body probes 1, based on light information detected by living body probes 1 (step S5), and then, based on a variety of parameters, evaluates the need for selecting light-emitting element/light-receiving element combinations within each channel formed by the living body probe for validation/invalidation, or adjusting them (step S6).

In step S6, selection is carried out based on, for example, the parameters that follow. Combinations may be selected using only one parameter, or they may be selected using 2 or more parameters for comprehensive evaluation (setting priorities among the parameters, and so on).

1) K-Ratios

By selecting combinations for which the K-ratio has a value approaching −1, combinations that obtain predominantly capillary data can be selected, and combinations that obtain predominantly venous data can be excluded.

2) L-Values

By selecting combinations for which the L-value is small, combinations that obtain predominantly capillary data with good S/N ratios can be selected, and combinations that obtain predominantly venous data with bad S/N ratios can be excluded.

3) ΔS-Values

By selecting combinations with small ΔS-values, combinations that obtain data with little rotational motion and good S/N ratios can be selected, and combinations that obtain data with large rotational motion and bad S/N ratios can be excluded.

4) h-Values

By selecting combinations with small h-values, combinations that obtain data with little fluctuation and good S/N ratios can be selected, and combinations that obtain data with large fluctuation and bad S/N ratios can be excluded.

Next, controller 8 of apparatus body 3 analyzes light functional voxel data among the channels of living body probes 1, based on light information detected by means of living body probes 1 (step S7), and then, based on a variety of parameters, evaluates the need for selecting combinations among the channels for validation/invalidation, or adjusting them (step S8).

In step S8, selection is carried out based on, for example, the following parameters. Combinations may be selected using only one parameter, or they may be selected using 2 or more parameters for comprehensive evaluation (setting priorities among the parameters, and so on).

1) G-Values

Channels with low G-values are selected and channels with high G-values are deleted or readjusted (the channel is replaced).

2) S-Values

If only G-values are used, there will be cases which all the sites have similar variation, making determination difficult; therefore, S-values are also taken into consideration, and channels with low S-values are selected and channels with high S-values are deleted or readjusted (the channel is replaced).

When the designated criteria are satisfied by selection within and between the channels by means of steps S6 and S8, the controller proceeds to the next step, and in cases when the designated criteria are not satisfied, the data is invalidated or readjusted by changing the position of the measurement mounting device or the living body probe 1 and so on.

Next, baseline data is measured from light information detected by the living body probes with the living body at rest, and data analysis and data display are performed (step S9).

Next, when a task is presented to the living body, task presentation data is measured from light information detected by the living body probes, and data analysis and data display are performed (step S10).

Previous measuring methods only used changes in oxyhemoglobin concentration, changes in deoxyhemoglobin concentration, changes in total hemoglobin concentration and cytochrome, previously known as indexes of blood flow and metabolism and calculated from changes in absorbed light, as shown in FIG. 23(A). However, because hemodynamic and metabolic tissue responses were slow, in units of seconds, it was thought that there was a time lag with actual behavior. In the present method, the signal changes are not necessarily thought of as these indexes; they are thought to be changes corresponding nearly simultaneously, in units of milliseconds, to actual behavior of the measurement target; and measurements that are dependent on response time (RT) are performed.

For response time measurements, response time [RT] is divided into presentation time ($RT_a$), thinking time ($RT_b$), and response time ($RT_c$).

In conventional psychological examinations, a problem was presented and questions answered. Then, those answers were evaluated. On this basis, it was not possible to evaluate thought in the brain during the presentation time, or make a cerebral functional evaluation of the status of thought by the subject during the thinking time.

In contrast, with the present invention, integrals are determined from a variety of parameters corresponding to the respective response times.

Time series data for a variety of parameters (change in oxyhemoglobin, change in deoxyhemoglobin, change in total hemoglobin, amount of oxygen exchange, oxygen saturation vector, hemoglobin vector, etc.) are represented as function of time.

$$\text{Integral of RT segment} = \int_{RT} f(t)dt = \int_a^b f(t)dt$$

The response time RT segment is from a (ms) to b (ms); here, f(t) is a parameter.

Then, for example, as shown in FIG. 33(A), a two-dimensional diagram is displayed from response times RT and the integrals, and its slope, vectors, scalars and the like are determined. By analyzing the integrals of various parameters in the response time RT and its segments from two-dimensional diagrams, behavioral data dependence (RT dependence) in milliseconds can be obtained and evaluated. In FIG. 33(A), if the slope of the two-dimensional diagram approaches minus or plus 45 degrees, it shows a matching response time and tissue response. That is, it becomes possible to perform measurements in which sites are selected that show correlations with a behavior time.

In addition, as shown in FIG. 33(B), if integral values measured from a plurality of sites in a desired time period are continuously plotted in a two-dimensional diagram, and if their slopes approach minus or plus 45 degrees, it shows they are closely associated with each other. That is, within the behavior time, it becomes possible to perform measurements in which sites are selected that are associated with each other.

In addition, RT-dependent channels can be displayed graphically on display part 10. For example, FIG. 34 is L-value maps in which identification of learning patterns is extracted in time series from brain site information; (A) is a screen showing cognitive response; (B) is a screen showing thought-associated brain response; and (C) is a screen showing behavior-related brain response. The horizontal axis is time, the vertical axis is channels, and they are differentiated by color according to the size of the integral values.

In addition, as shown in FIG. 35, data may also be analyzed by two-dimensional diagrams in which the horizontal axis is time and the vertical axis is integral values. FIG. 35(A) is the information input period, (B) is the thought period and (C) is the output period; it can be seen that learning potential is increasing in the thought period.

Figure 36:
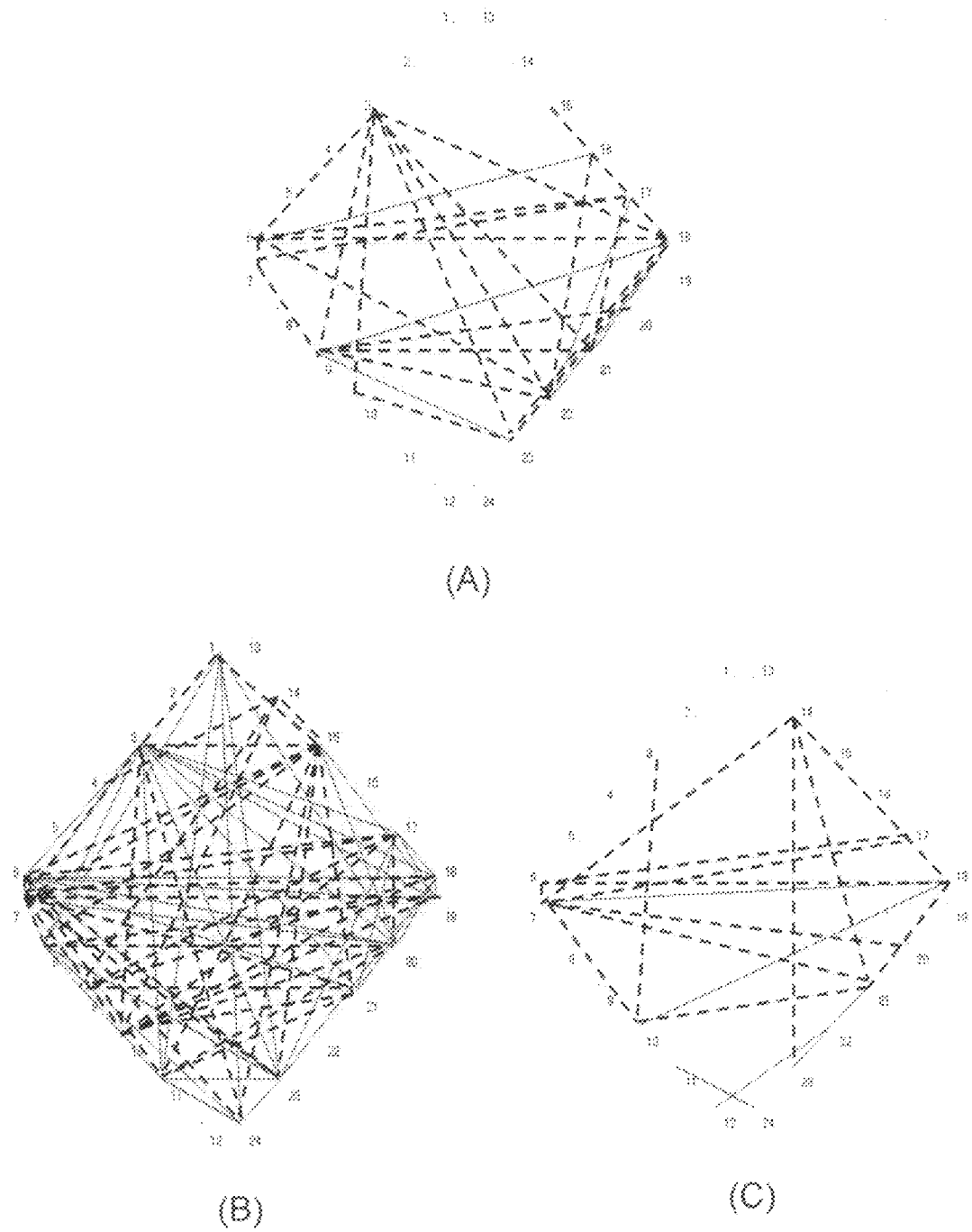
FIG. 36. (A)-(C) are examples of displays in which sites are joined by lines drawn between them to show association between sites during each behavior period.

In addition, as shown in FIGS. 36(A)-(C), within each response time, information may also be displayed so that channels between sites showing correlations are joined by lines, to show association between the sites. Here, the numbers are channel numbers, and changes in total hemoglobin for channels showing a correlation are shown in the data input period (A), the thought period (B), and the output period (C). Data may also be displayed differentiated by color according to the values of the correlation coefficient. It can be seen from FIG. 36(B) that in the thought period, there is a sharp increase in the number of channels with a correlation.

Furthermore, correlation coefficients (c.c.) between response times RT and integral values can be investigated, and sites associated with behavior characteristics can be continuously measured.

Here, correlation coefficient c.c.=Sxy/(SxxSxy)½

Calculation of correlation is carried out at a desired set time (sampling points N). It is determined for n data points, by an index showing the strength of the straight line relationship between 2 measurement points x (response time), y (integral).

Then, sites can be identified for which c.c.>0.6 and c.c.<−0.6 to identify sites dependent on response time.

In addition, correlation coefficients are calculated and investigated using integrals of pairs of sites in the respective RT segments.

Then, sites can be identified for which c.c.>0.6 and c.c.<−0.6 to identify the degree of network interdependence between sites in the response time.

Because these numerical values are not determined by the strength of the signal, they are data with good S/N ratios.

Figure 37:
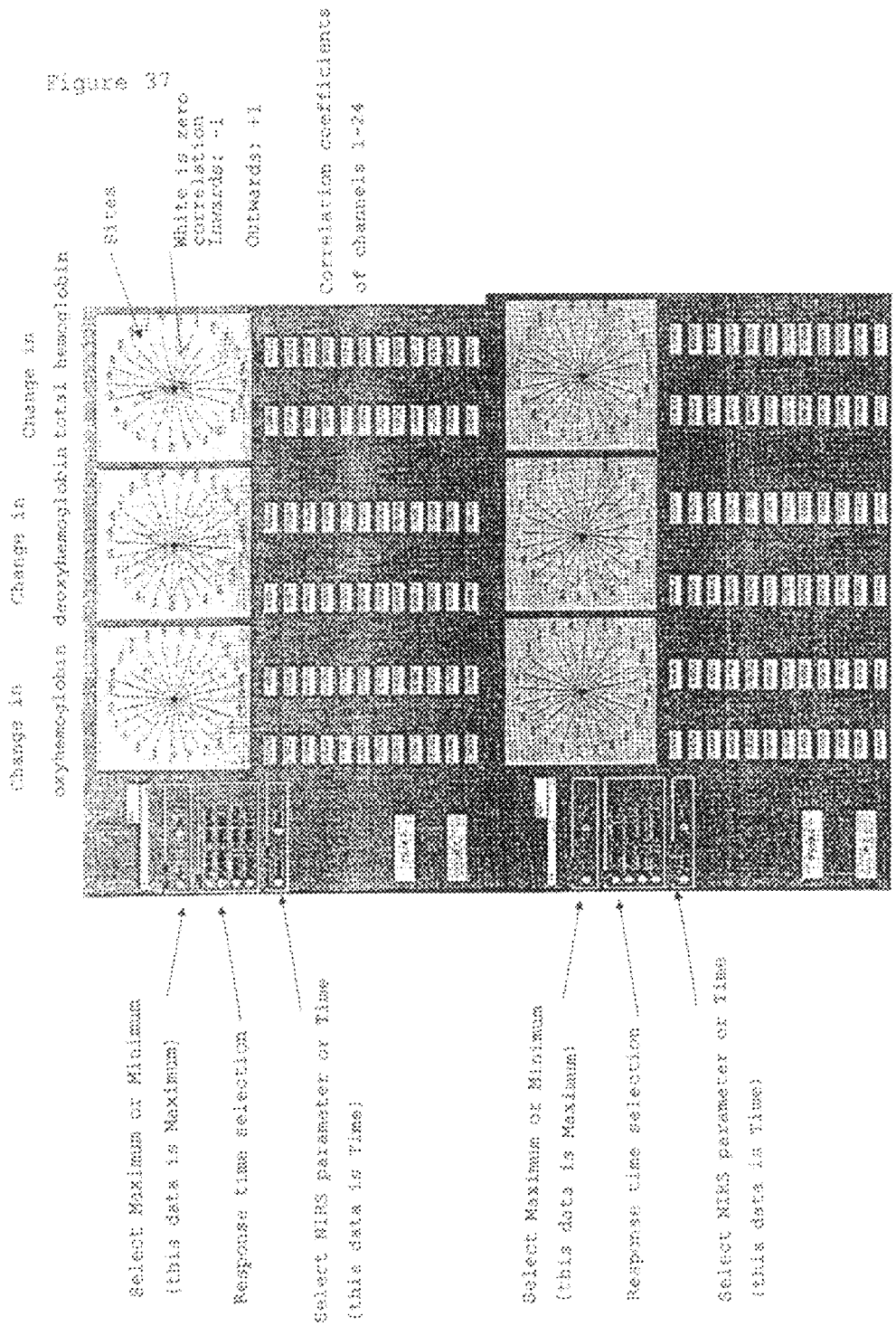
FIG. 37. An explanatory figure showing an example in which variation in target sites in the right brain and the left brain (laterality) is displayed in time series.

In addition, if they are same sites on the left and right, RT segment variation between the left brain and the right brain (laterality) can be determined by means of the slope of diagrams for the same targets, and displayed in time series. As shown in FIG. 37, target site variation (laterality) between the left and right brain may also be displayed in time series.

Figure 38:
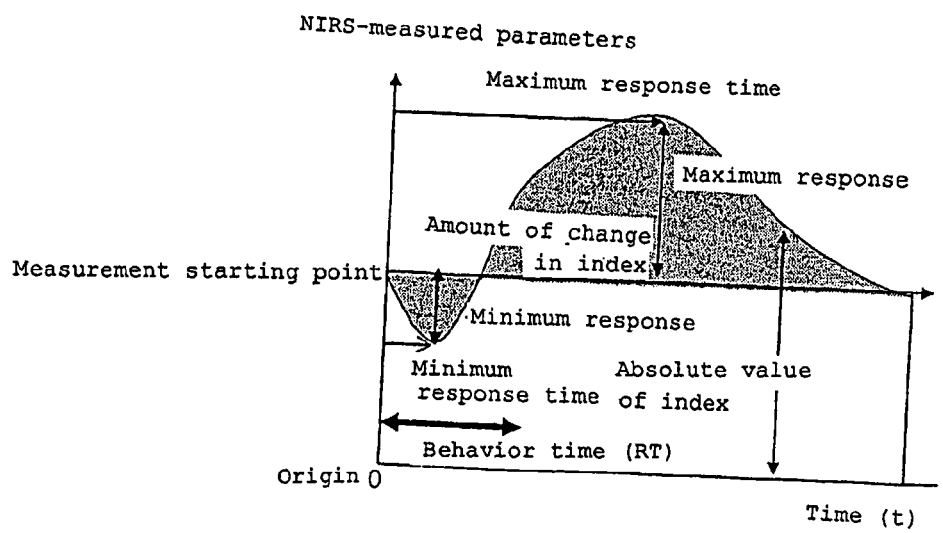
FIG. 38 is a graph explaining the fact that the behavior time RT and maximum and minimum peak times of NIRS-measured parameters do not match.

In addition, as shown in FIG. 38, it frequently occurs with actual measurements that the behavior time RT and the maximum and minimum peak times for NIRS measured parameters do not match. In cases like this, it is possible, by means of a measurement method that takes into consideration a time lag correlation between behavior time RT and NIRS measured parameters, to select channels from among the channels of a plurality of sites, or to emphasize functional differences between sites in the image displays, and so on.

Regarding the Half-Reduction Time

The half-reduction time is the time required for the peak values of indexes concerning oxygen exchange (consumption), oxygen supply and the like to be halved, and consideration of half-reduction times makes it possible to investigate a person's physical condition, person-to-person differences and the like. In addition, because, for example, as explained above, when a K-ratio=1, the E-ratio is infinitely large, by setting half-reduction times, concrete numerical values can be compared between individuals.

Regarding Random Arrangements of Living Body Probes

Figure 39:
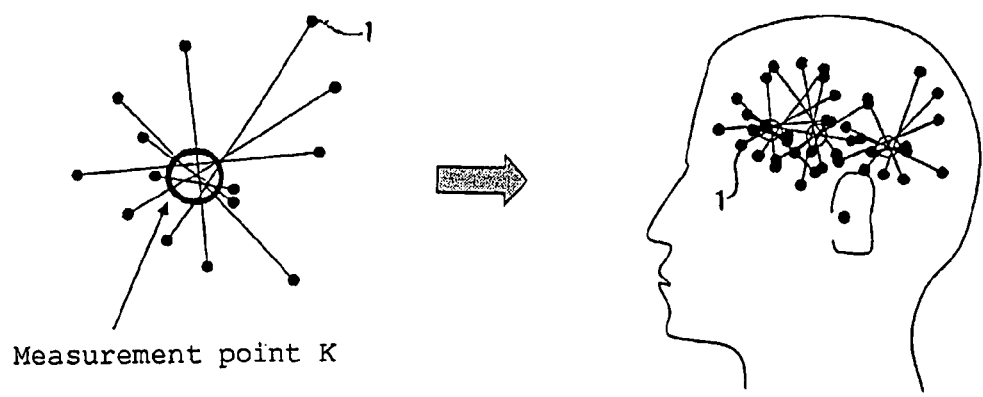
FIG. 39. An explanatory drawing showing an example in which a plurality of living body probes are randomly arranged (spaced) with respect to the measurement point.

As shown in FIG. 39, living body probes may also be placed at a plurality of intervals with respect to measurement point K. Normally, because of the distance and depth to the measurement target, the complicated structure of the target and the like, the appropriate light path length cannot be judged without trying a plurality of measurements, and thus, in actuality, measurements are taken at a plurality of intervals. As shown in FIG. 39, even if living body probes 1 are randomly placed, measurement precision is improved by providing a plurality of measurement values for a measurement region.

Regarding Indexes that are Independent of the Light Path Length

Because highly precise quantification of the amount of hemoglobin by means of accurate measurement of the light paths making up the light functional image is difficult from a measurement standpoint, indexes that are independent of the light path length play an important role as indexes compensating for this, for comparing measured values between individuals, measured values for the same individual, and the like.

Possible examples of these include calculation of:
(1) Correlation of hemoglobin changes during response times
(2) Network share (including left/right differences)
(3) Quadrant shift image displays (both spatiotemporal displays and two-dimensional flat displays)
(4) Task ratios
(5) Learning effectiveness (1) Correlation of Hemoglobin Changes During Response Times First, data for a plurality of subjects n are imported, and time series data for indexes of oxygen exchange rotational motion are calculated for each light functional voxel. Next, average values are calculated for each behavioral response time (RTa, RTb, RTc, . . . ) executed m times, and average values for the maximum value, minimum value, maximum time and minimum time of each of these are calculated by image voxel for m executions, not limited to within the behavioral response time. Next, data for each of n subjects is displayed two-dimensionally, on axes of average values for maximum value, minimum value, maximum time and minimum time, and axes of display and average response time, and the slopes of the graphs (correlation coefficients r) are calculated. Then, behaviors, or thought- or behavior-dependent regions are selected by a criteria, for example, r>0.6, according to response time (RTa, RTb, RTc, . . . ) and each index.

(2) Network Share (Including Left/Right Differences)

First, data is calculated for each of desired segments, dependent on correlated response times between n channels each on the left and right.

Because for an index associated with both sides, the maximum (Max) is n×n, the network share (percent use) for both sides is calculated as

[X/(n×n)]×100%.

X is determined according to display of the desired correlation coefficients r<0.6.

In addition, because an index associated with a same side is a maximum of n×(n−1), the same-side network share (percent use) is calculated as {X/[n×(n−1)]}×100%.

A lateralization index is calculated from the right and left same-side network shares (percent use) (−1 to 1).

Using opposing left and right light functional voxels, it is possible to calculate a Laterality Index=(R−L)/(R+L) from the respective amounts of change in the desired segment.

Figure 40:
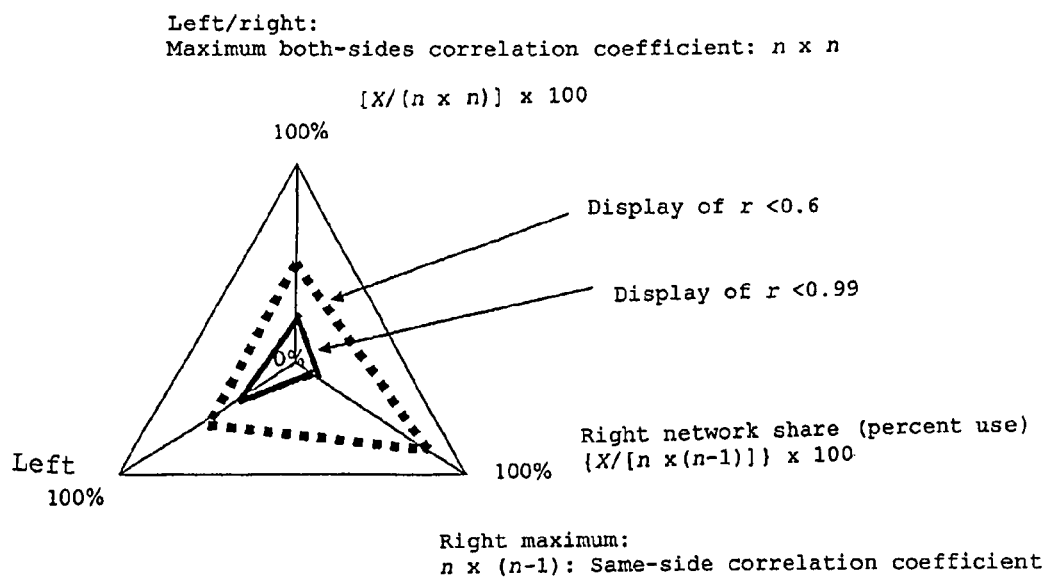
FIG. 40 is an explanatory drawing showing the results when the respective maximum values for left and right network share and both-sides network share are taken as 1.0 (100%); a maximum equilateral triangle is formed from these three points; the area formed by joining those points is taken as the total network share area; and time series data is measured by segment.

Next, as shown in FIG. 40, the respective maximum values for left and right network share and both-sides network share are taken as 1.0 (100%), a maximum equilateral triangle is formed from these 3 points, the area formed by joining those points is taken as the total network share area, and time series data is measured by segment.

The surface area for the desired segment is calculated from the number of right networks, from the time series display of the laterality index. Left/right predominance is determined by the size of the positive/negative for that segment.

In addition, left/right predominance according to the shift from one task to another is detected from time series data in which differentials are taken of the time series display of the laterality index from the number of left/right networks.

(3) Quadrant Shift Image Displays

Figure 41:
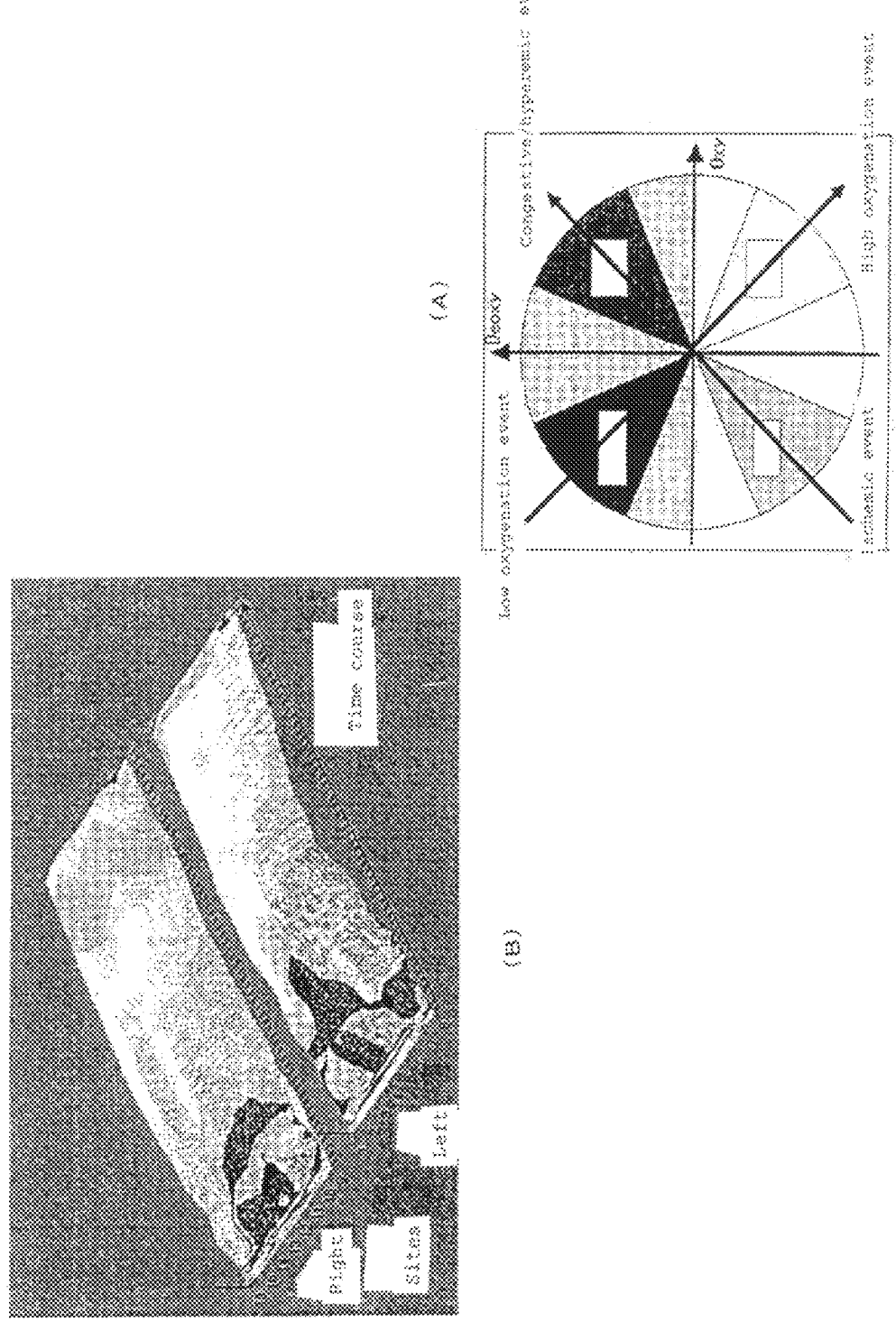
FIG. 41 is explanatory figures showing (A) k-angle quadrants, and (B) an example of a functional image display of quadrants and L-values.

For example, k-angles are calculated, and, as shown in FIG. 41(A), the k-angle quadrants are divided into:
−45°-45°: low oxygenation event
45°-135°: congestive/hyperemic (high circulation) event
135°-225°: high oxygenation event
225°-315°: ischemic (low circulation) event
(They may be color-coded as Well.)

Next, L-values are calculated, and, as shown in FIG. 41(B), a functional image is displayed of quadrants and L-values. If L=0, it becomes a two-dimensional display, and as L-values are added, it becomes a three-dimensional display. By means of a display method of this kind, it is possible to see adjacent regions transitioning while a physiological event changes temporally.

Figure 42:
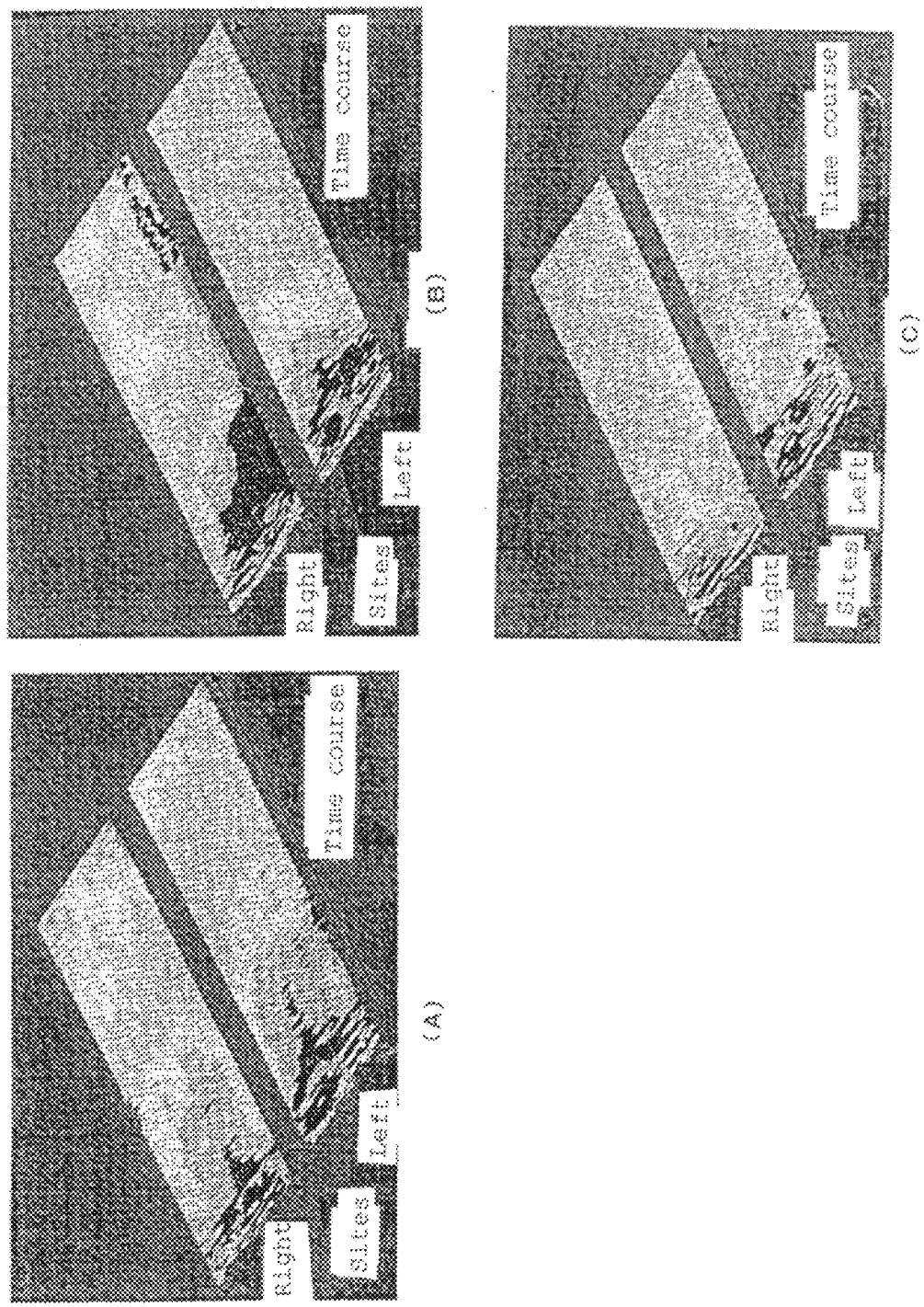
FIG. 42 is explanatory drawings of k-angle quadrant spatiotemporal displays (A) when writing hiragana, (B) when writing kanji, and (C) when the subject does not know the kanji.

For example, K-angle-quadrant spatiotemporal displays are shown in FIG. 42(A) when writing hiragana, (B) when writing kanji, and (C) when a subject does not know how to write a kanji. It can be seen from FIG. 42 that event spatiotemporal information differs according to task. For example, from FIGS. 42(A) and (B), it can be seen that when writing hiragana or kanji, it shifts from a low oxygen state to a congestive/hyperemic state, and then shifts to a high oxygenation event. It can also be seen that when writing kanji, the right brain is working more strongly than the left brain. Furthermore, as shown in FIG. 42(C), when the subject does not know a kanji, it can be seen that it shifts from a low oxygen state to a high oxygenation event, without first shifting to a congestive event.

In addition, FIG. 52(A) is an image display, when living body probes are arranged in a lattice shape, of K-ratios and L-values from the periphery of the left and right motor area at a point 22.8 seconds in the midst of lifting a 14 kg dumbbell; and (B) is an image display of k-angles and L-values from the periphery of the left and right motor area at a point 22.8 seconds in the midst of lifting a 14 kg dumbbell. In the figure, F indicates FORCE effect sites produced in the left primary motor area, and W, a Watering-the-garden effect site.

(4) Task Ratios

The same site is compared by means of task ratios of respective task parameters. Because differences in task ratios differ according to site and time, the magnitude of the difference can be clearly seen, even displayed in image form. Task ratios also differ spatially.

Figure 43:
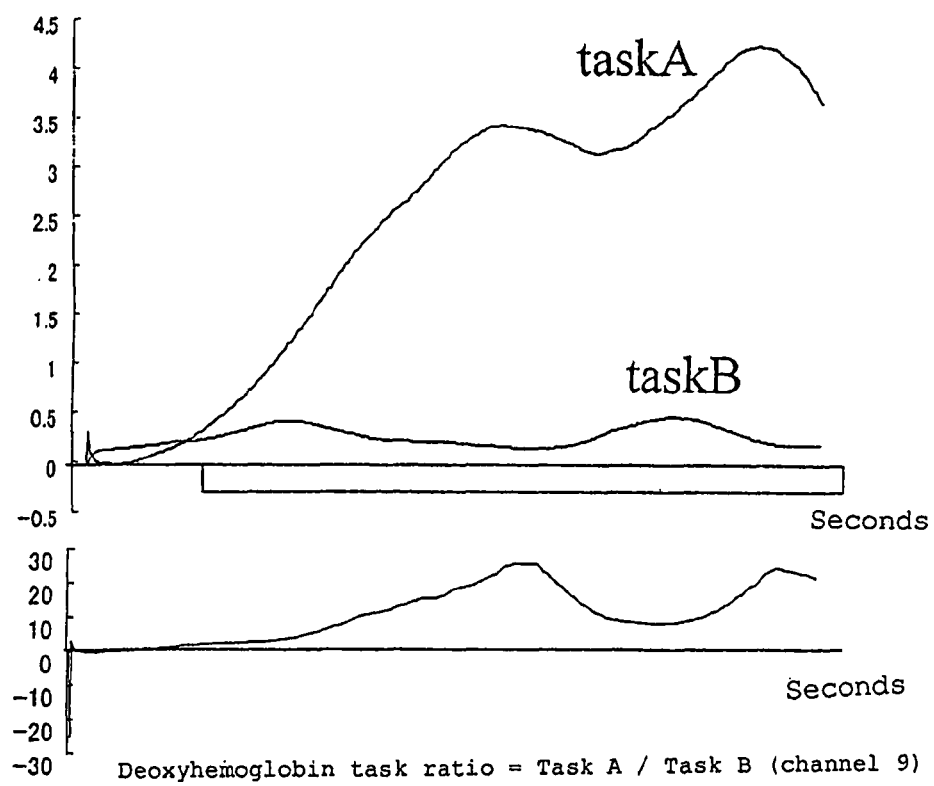
FIG. 43 is graphs showing a case when indexes are compared with respect to the different tasks of lifting 7 kg as task B and lifting 14 kg as task A.

For example, as shown in FIG. 43, when various kinds of indexes are compared with respect to the different tasks of lifting 7 kg as task B and lifting 14 kg as task A, even though task A is only twice the weight of task B, its index of brain metabolism can be seen to reach as much as 30 times that of task B.

(5) Evaluation of Learning Effectiveness

As a means of evaluating learning effectiveness, a region of reduced $ScO_2$, means that a FORCE effect is very clearly produced by learning, showing learning effectiveness. Conversely, when there is no region of reduced $ScO_2$, the Watering-the-garden effect is spread over a wide area, and a FORCE effect cannot be detected, this shows that learning has not been effective.

Displays of Comparisons Between Different Tasks

Figure 44:
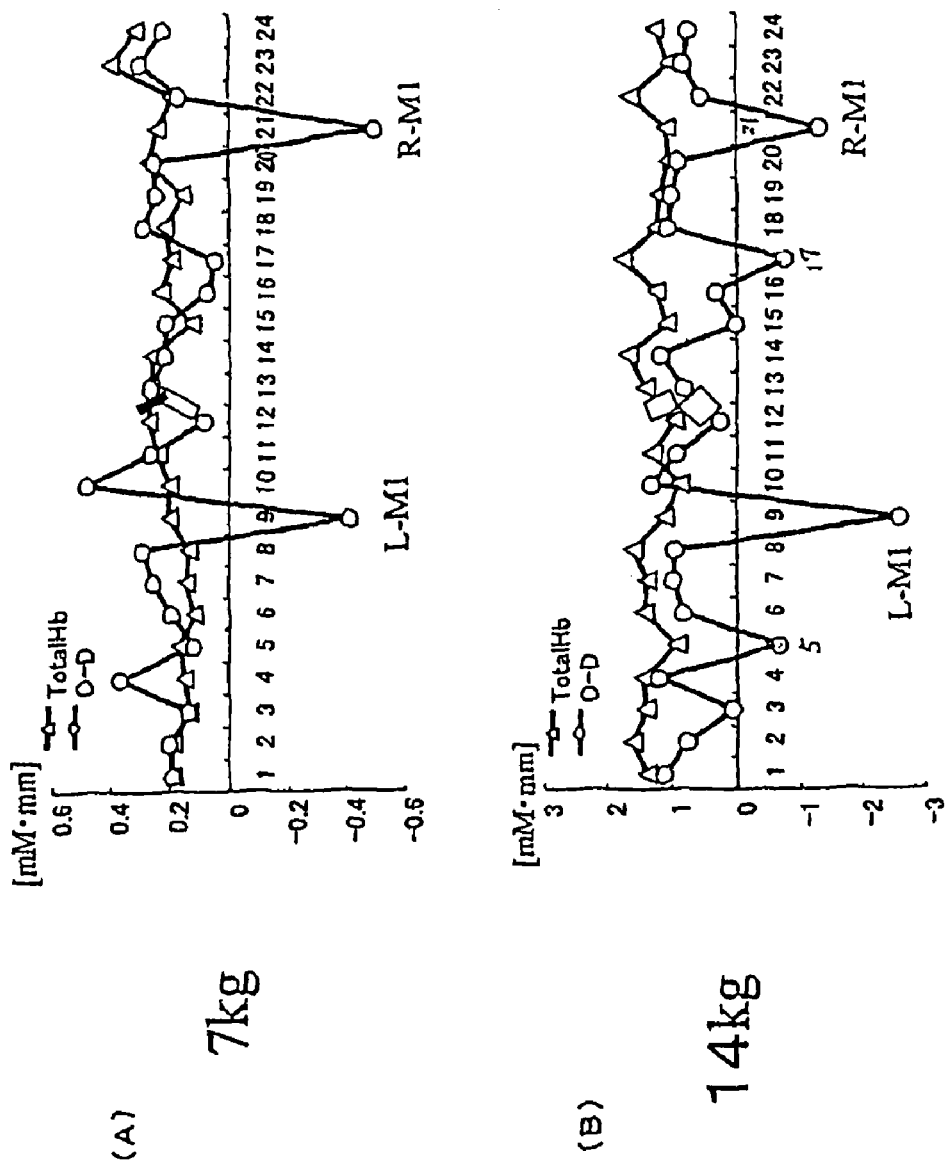
FIGS. 44(A) and (B) are graphs concerning brain data when a subject lifted 7 kg and 14 kg dumbbells for a desired time, when $ScO_2$=(OxyHb−DeoxyHb) and tHb=(OxyHb+DeoxyHb) are displayed in real time.
Figure 45:
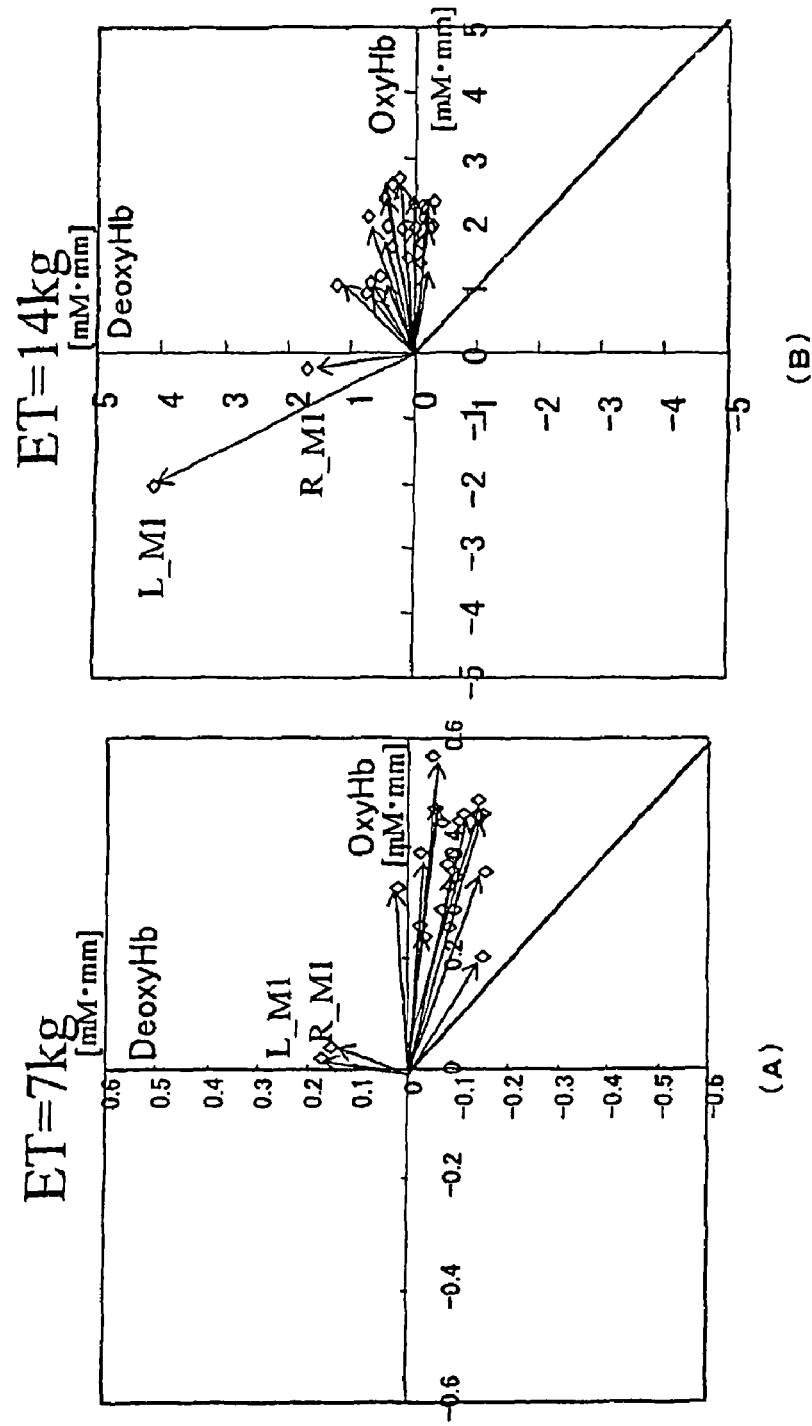
FIGS. 45(A) and (B) are graphs concerning brain data when the subject lifted 7 kg and 14 kg dumbbells for a desired time, when the data are displayed simultaneously in two-dimensional diagrams of OxyHb and DeoxyHb, and the relationships between the respective vectors are displayed.

For example, FIGS. 44(A) and (B) are graphs pertaining to brain data from when a subject lifted 7 kg and 14 kg dumbbells for a desired time, when $[ScO_2]=([OxyHb]-[DeoxyHb])$ and $[tHb]=([OxyHb]+[DeoxyHb])$ are displayed in real time. FIGS. 45(A) and (B) are also graphs pertaining to brain data from when a subject lifted 7 kg and 14 kg dumbbells for a desired time, when the data are displayed simultaneously in two-dimensional diagrams for OxyHb and DeoxyHb, and the relationships between the respective vectors are displayed.

Separation of the FORCE Effect and the Watering-the-Garden Effect

If channels showing a Watering-the-garden effect and little FORCE effect can be selected, blood flow velocity in the capillaries can be calculated from time series data of oxygenated hemoglobin for those channels.

Because of oxygen exchange from the FORCE effect, oxygenated hemoglobin flowing in from the arterial side is reduced, or its velocity is reduced.

From this fact,

The differential of oxygenated hemoglobin of the maximum Watering-the-garden effect represents its inflow velocity for the purpose of oxygen supply.

The differential of oxygenated hemoglobin of the maximum FORCE effect represents its inflow velocity for the purpose of oxygen consumption (may also be negative).

From these facts, (differential of oxygenated hemoglobin of the maximum Watering-the-garden effect)−(differential of oxygenated hemoglobin of the maximum FORCE effect)=oxygen exchange velocity decrease (effect whereby velocity is reduced by oxygen exchange).

The stronger the oxygen exchange, or the FORCE effect, becomes, the more the velocity decreases and the above value increases.

Figure 46:
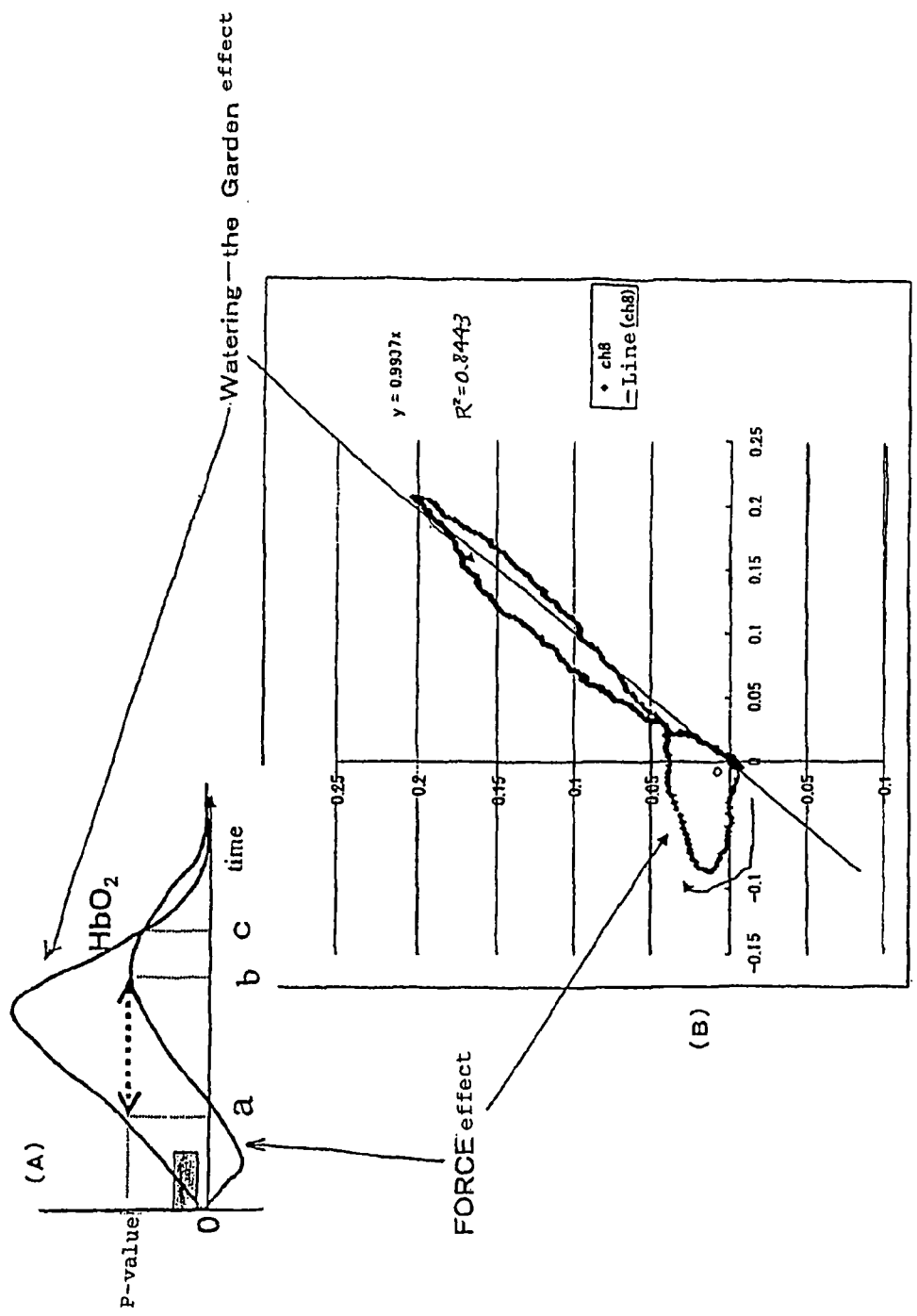
FIG. 46. Graphs explaining the separation of the FORCE effect and the Watering-the-garden effect.

The effect on blood inflow velocity whereby oxygen exchange causes velocity to decrease can also be represented by time (b−a) on the two time series data for determining the maximum value p, as shown in FIG. 46(A). With the passage of time, (b−a), namely, the oxygen exchange velocity decrease time, changes and becomes zero at time c.

By measuring and displaying this time change, the separation of the FORCE effect and the Watering-the-garden effect becomes temporally clear.

In addition, even without differentials, it can be understood that (maximum oxygen exchange effect)=(maximum Watering-the-garden effect)−(maximum FORCE effect).

(oxygen exchange effect)=(Watering-the-garden effect)−(FORCE effect)

By determining the respective values for oxygen exchange velocity decrease, oxygen exchange velocity decrease time, and oxygen exchange effect described above from a plurality of measurement sites, and displaying their image distribution in time series, the center of the FORCE effect can be differentiated from the Watering-the-garden effect and easily determined. Because the amount of oxygen consumption and the amount of oxygen supply tend to diverge both temporally and spatially in the FORCE effect, methods such as the following are also possible.

(1) Differences between channels are calculated and displayed in time series.

Oxygenated hemoglobin is likely to increase rapidly at sites displaying the Watering-the-garden effect. At sites where oxygen exchange rate is increasing, oxygenated hemoglobin is likely to decrease from the task load as a result of the FORCE effect, and thus, by means of (maximum oxygen exchange effect)=(maximum Watering-the-garden effect)−(maximum FORCE effect), sites where there is the most oxygen exchange can be selected from time series differences in oxygenated hemoglobin among a plurality of sites.

(2) The time (segment) of a FORCE effect can be determined by means of time series displays of differences between channels.

The reason is that with the passage of time, the time series of sites where there is the most oxygen exchange also come to resemble the time series of the Watering-the-garden effect.

(3) It is possible to separate the FORCE effect and the Watering-the-garden effect by means of correlation coefficients (similarity) between channels for each desired segment.

In FIG. 46(B), in order to trace time courses between channels, ch7 (on the vertical axis) and ch8 (on the horizontal axis) are displayed by time and their correlation coefficient r is determined. Over a total of approximately 60 seconds, $R^2=0.8444$, showing a high degree of correlation.

However, when the time period is divided into desired segments and their degree of correlation is determined, it can be seen that there is no correlation in the initial period.

By this means, the FORCE effect can be separated out and extracted from the Watering-the-garden effect.

To select channels showing a Watering-the-garden effect and little FORCE effect, all the time courses (oxygenated hemoglobin, deoxygenated hemoglobin, total hemoglobin, etc.) are displayed simultaneously.

When these are furthermore differentiated,
1) Channels showing the sharpest increase in oxyhemoglobin (high velocity channels) can be selected.
2) Channels showing the maximum values for oxyhemoglobin can be selected.

When conditions 1) and 2) are satisfied, that channel can be selected as having the strongest Watering-the-garden effect. This is equivalent to a channel of low oxygen exchange rate.

On the other hand, to select channels showing a FORCE effect, these channels are equivalent to the channels with the greatest decrease in oxyhemoglobin and increase in deoxyhemoglobin, namely, they are equivalent to channels of high oxygen exchange rate.

The present invention is not limited to the working embodiment described above, and a variety of changes are possible within the range of the technical items according to the scope of the patent claims. For example, possible imaging methods include imaging methods that emphasize networks, which emphasize correlations between the channels; imaging methods that emphasize left/right comparisons, which emphasize left/right differences; imaging methods that emphasize behavioral (or thought) response time correlations, emphasizing correlations between behavioral (or thought) response time, and so on.

Display of Three-Dimensional Diagrams

Controller 8 can calculate a variety of parameters derived from three-dimensional diagrams, in which a time axis is added to each of the aforementioned two-dimensional diagrams, and display part 10 can perform three-dimensional displays based on the various parameters calculated by controller 8.

Figure 53:
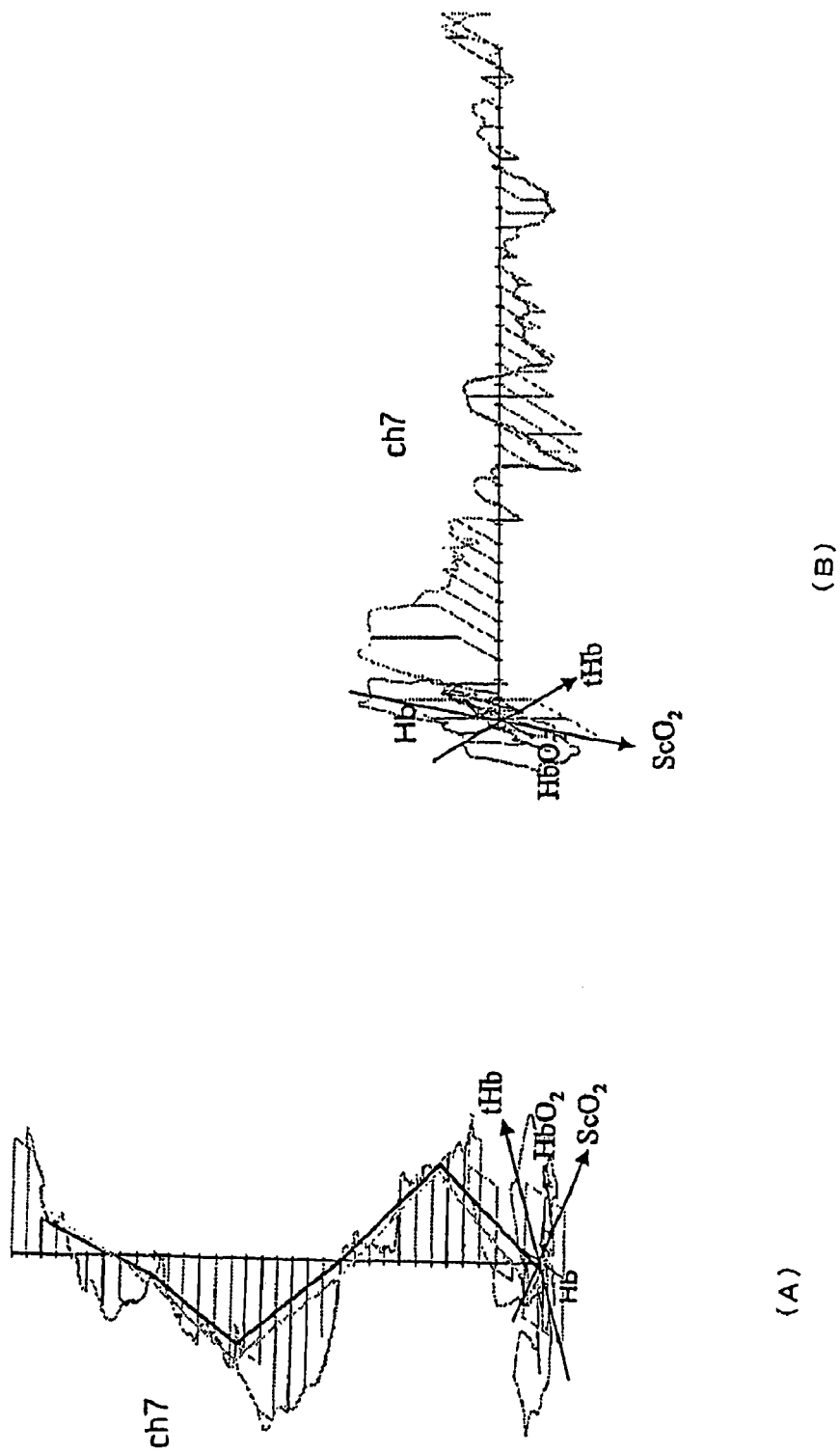
FIG. 53(A) is a graph displaying K-spiral motion vertically, and (B) is a graph displaying it horizontally.

Types of Spiral Motion (1) When a time axis is added to a two-dimensional diagram of $HbO_2$ (oxyhemoglobin) and Hb (deoxyhemoglobin), and to the two-dimensional diagram in which this is rotated 45 degrees to show the relationship between changes in oxygen saturation ($ScO_2$) and changes in total hemoglobin concentration (tHb), and a locus is joined of task onset points or task completion points for each channel, a spiral-shaped motion (referred to below as a K-spiral motion) is displayed. FIG. 53(A) is a graph displaying a K-spiral motion vertically, and (B) is a graph displaying it horizontally.

(2) When a time axis is added to a two-dimensional diagram of cumulative $HbO_2$ (oxyhemoglobin) and cumulative Hb (deoxyhemoglobin), and to the two-dimensional diagram in which this is rotated 45 degrees to show the relationship between changes in cumulative oxygen saturation ($ScO_2$) and changes in cumulative total hemoglobin concentration (tHb), and a locus is joined of task onset points or task completion points for each channel, a spiral-shaped motion (referred to below as a T-spiral motion) is displayed.

(3) When a time axis is added to a two-dimensional diagram of differentials of $HbO_2$ (oxyhemoglobin) and differentials of Hb (deoxyhemoglobin), and to the two-dimensional diagram in which this is rotated 45 degrees to show the relationship between differentials of changes in oxygen saturation ($ScO_2$) and differentials of changes in total hemoglobin concentration (tHb), and a locus is joined of task onset points or task completion points for each channel, a spiral-shaped motion (referred to below as H-spiral motion) is displayed.

(4) When a time axis is added to a two-dimensional diagram of the differentials of the differentials of $HbO_2$ (oxygenated hemoglobin) and differentials of the differentials of Hb (deoxygenated hemoglobin), and to the two-dimensional diagram in which this is rotated 45 degrees to show the relationship between differentials of the differentials of changes in oxygen saturation ($ScO_2$) and differentials of the differentials of changes in total hemoglobin concentration (tHb), and a locus is joined of task onset points or task completion points for each channel, a spiral-shaped motion (referred to below as I-spiral motion) is displayed.

Various Parameters of Each Spiral Motion
(1) Various Kinds of K-Spiral Motion Parameters
  1) Amount of Oxygen Exchange (L-Value)

$(L)^2=(ScO_2)^2+(tHb)^2$

2) Oxygen Exchange Rate (Oxygen Exchange Angle) (k-Angle)
  3) M-Value $(M)^2=(\text{time from measurement start})^2+(L)^2$ (2) Various Kinds of T-Spiral Motion Parameters
  1) Cumulative Amount of Oxygen Exchange (R-Value)

$(R)^2=(\text{cumulative } L)^2=(\text{cumulative } ScO_2)^2+(\text{cumulative tHb})^2$ 2) Cumulative Oxygen Exchange Rate (T-Angle)
3) Y-Value $(Y)^2 =$ (time from measurement start)$^2 +$(cumulative $L)^2$ 4) Acute Angle Between Time Axis and Cumulative M-Values (Y-Value) (Y-Angle)

(3) Various Kinds of H-Spiral Motion Parameters

1) Amount of Oxygen Exchange Velocity (E-Value)

$(E)^2 =$ (differential of $L)^2 =$ (differential of $ScO_2)^2 +$(differential of $tHb)^2$ 2) Oxygen Exchange Velocity (H-Angle)

$H$-angle=Arctan [(differential of $ScO_2$)/(differential of $tHb$)]=Arctan ($H$-ratio)

$H$-ratio=(differential of $ScO_2$)/(differential of $tHb$)= ratio of oxygen exchange velocity for velocity of total hemoglobin 3) O-Value $(O)^2 =$ (differential of time axis from measurement start)$^2 +$(differential of $L)^2$ 4) Acute Angle Between Time Axis and O-Value (O-Angle)

(4) Various I-Spiral Motion Parameters

1) Amount of Oxygen Exchange Acceleration (I-Value)

$(I)^2 =$ (differential of differential of $L)^2 =$ (differential of differential of $ScO_2)^2 +$(differential of differential of $tHb)^2$ 2) Oxygen Exchange Acceleration (I-Angle)

$I$-angle=Arctan [(differential of differential of $ScO_2$)/(differential of differential of $tHb$)]=Arctan ($I$-ratio)

$I$-ratio=(differential of differential of $ScO_2$)/(differential of differential of $tHb$)=ratio of oxygen exchange acceleration for acceleration of total hemoglobin 3) C-Value $(C)^2 =$ (differential of time axis from measurement start)$^2 +$(differential of differential of $L)^2$ 4) Acute Angle Between Time Axis and C-Value (Angle C)

Criteria for Evaluation of Each of the Spiral Motion Three-Dimensional Displays

Figure 54:
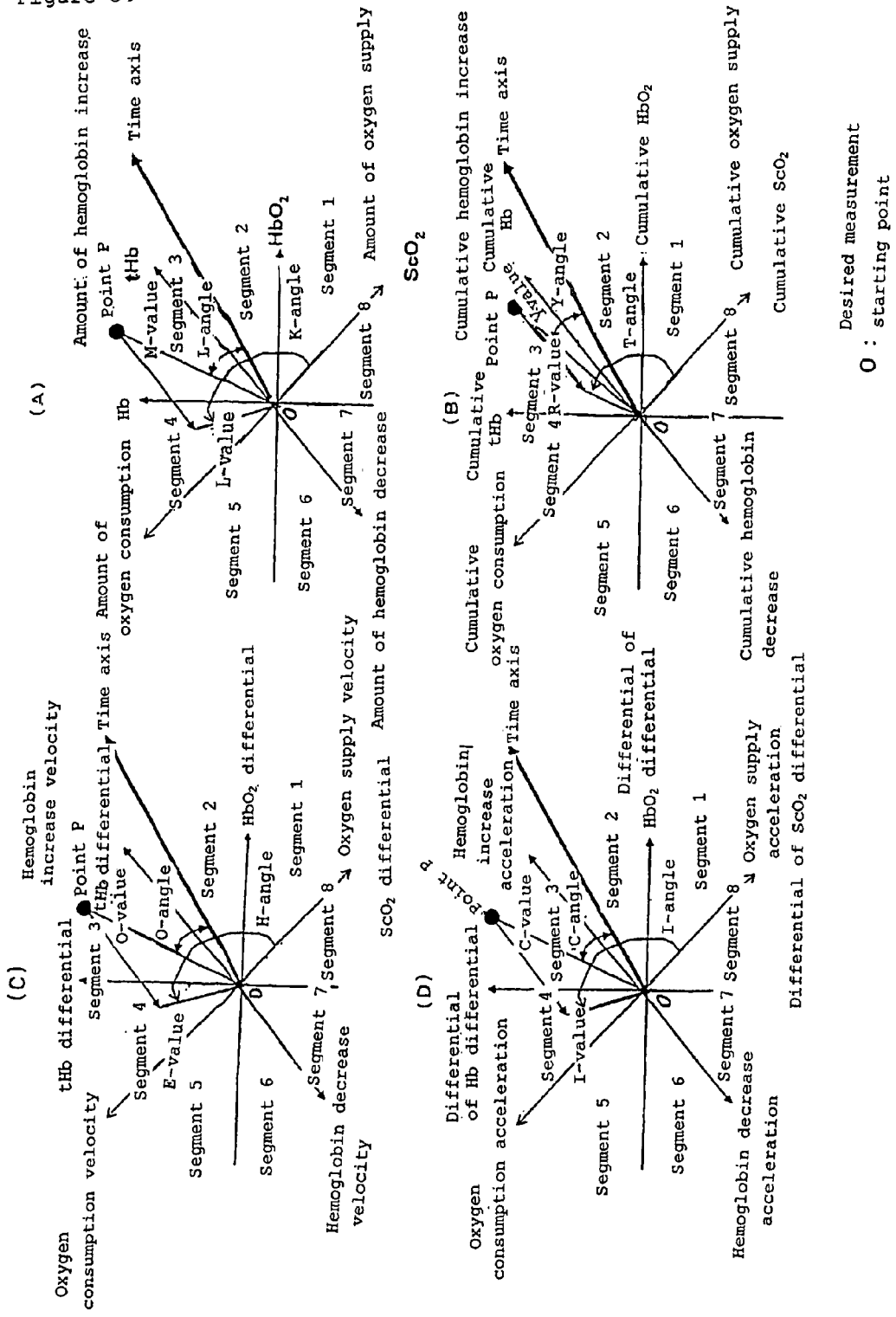
FIG. 54(A) is a diagram explaining K-spiral motion three-dimensional display evaluation criteria, (B) is a diagram explaining T-spiral motion three-dimensional display evaluation criteria, (C) is a diagram explaining H-spiral motion three-dimensional display evaluation criteria, and (D) is a diagram explaining I-spiral motion three-dimensional display evaluation criteria.
Figure 55:
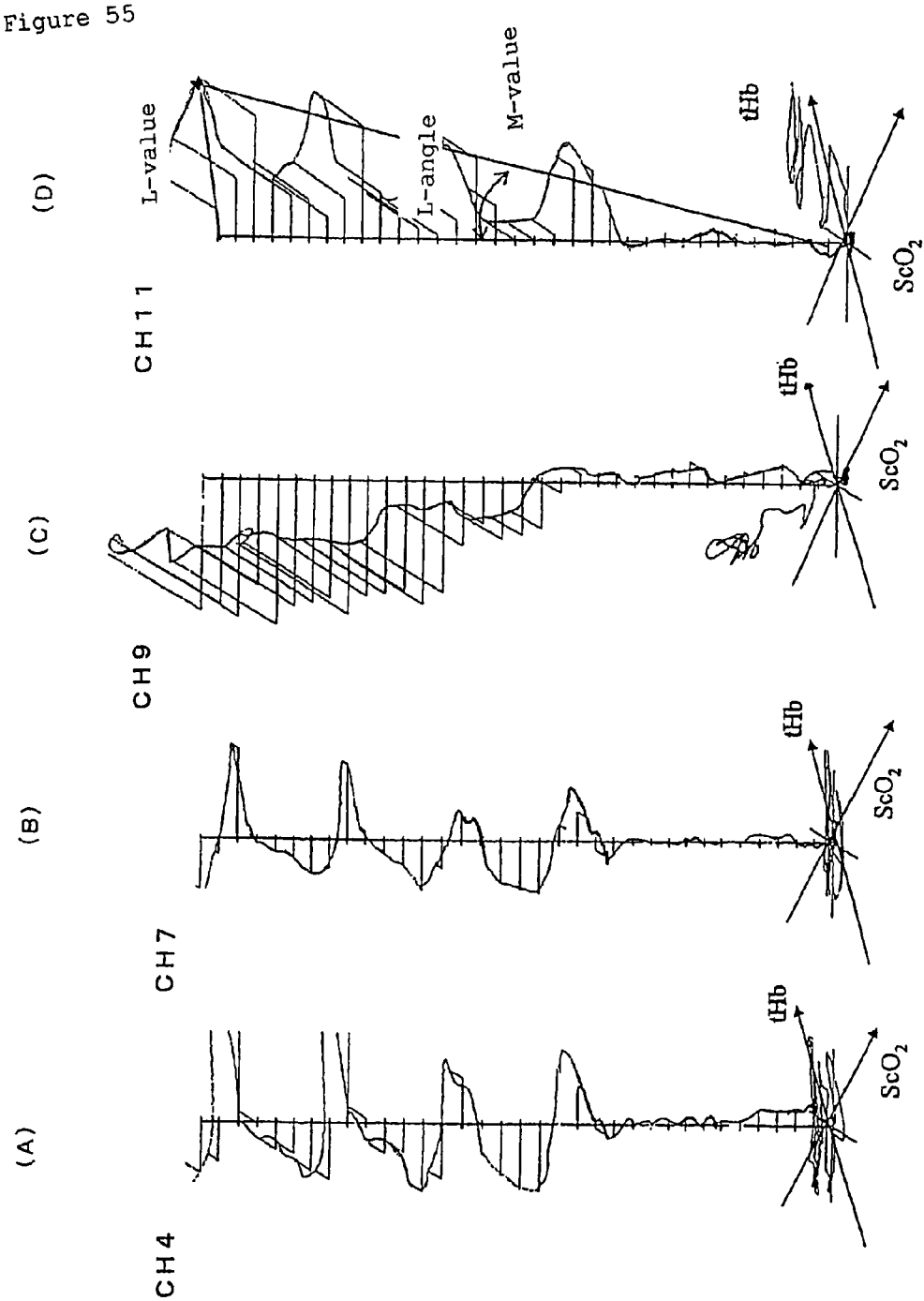
FIGS. 55(A)-(D) are three-dimensional diagrams showing the K-spiral motion of channels 4, 7, 9 and 11; they are examples in which lines are entered for Hb and $HbO_2$.
Figure 56:
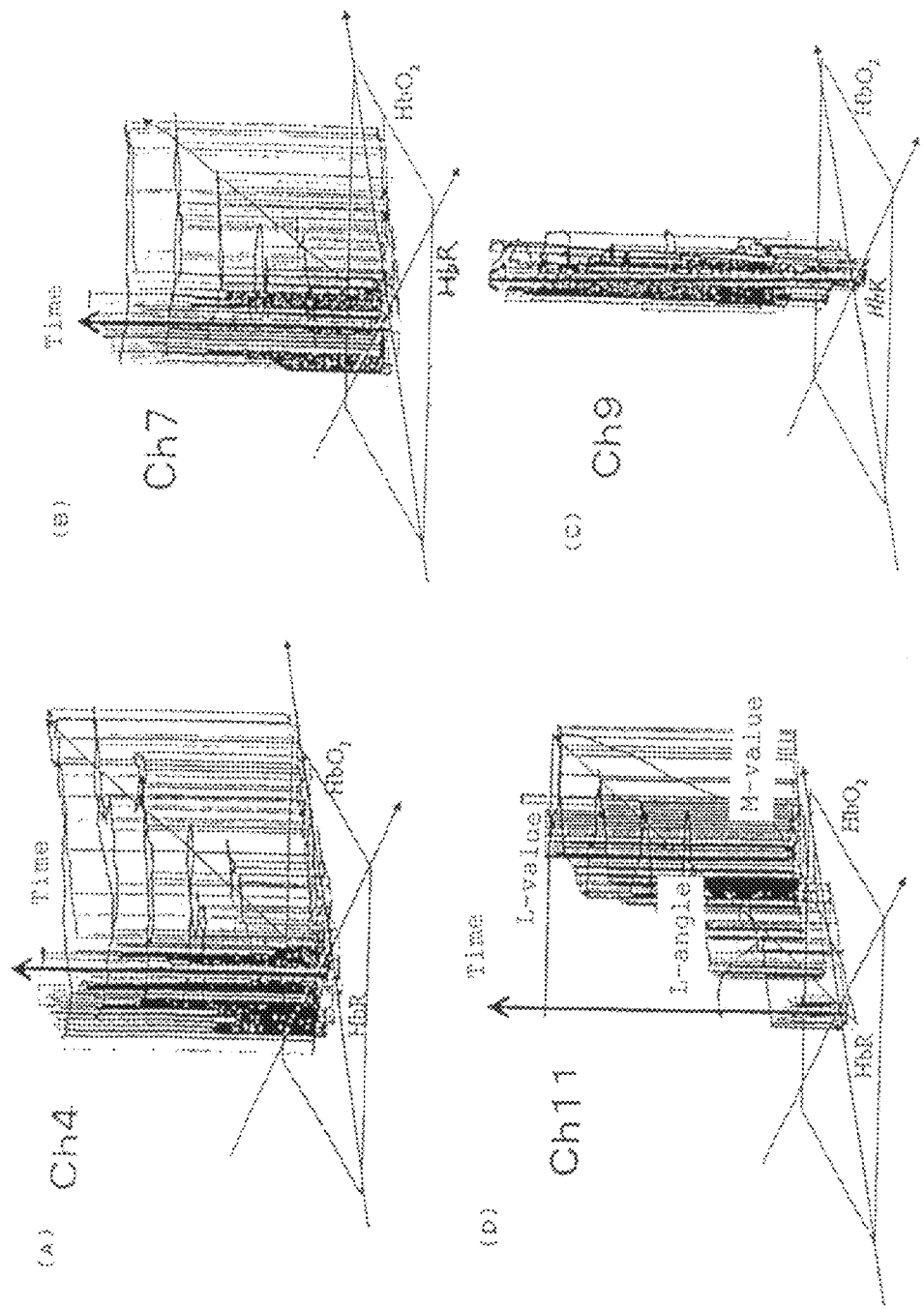
FIGS. 56(A)-(D) are three-dimensional diagrams showing the K-spiral motion of channels 4, 7, 9 and 11; they are examples in which vertical lines are entered along the time axis.

FIG. 54(A) is a diagram explaining K-spiral motion three-dimensional display evaluation criteria, (B) is a diagram explaining T-spiral motion three-dimensional display evaluation criteria, (C) is a diagram explaining H-spiral motion three-dimensional display evaluation criteria, and (D) is a diagram explaining I-spiral motion three-dimensional display evaluation criteria.

Here, segments 1-4 are events in which tHb increases (blood supply increases), segments 5-9 are events in which tHb decreases (blood supply decreases), segments 3-6 are events in which $ScO_2$ decreases (low oxygen state), and segments 1, 2, 7 and 8 are events in which $ScO_2$ increases (high oxygen state).

When a three-dimensional display is created, it becomes an evaluation index for learning effectiveness, recovery of motion, or the like, by indicating the event towards which it tends over time.

In addition, regarding the extent of oxygen exchange, in the case of segments 1 and 2, it shows the extent of high oxygenation from congestion. In the case of segments 7 and 8, it shows the extent of high oxygenation from ischemia. In the case of segments 5 and 6, it shows the extent of low oxygenation from ischemia, and the extent of decrease in tissue oxygen consumption. In the case of segments 3 and 4, it shows the extent of low oxygenation from congestion, and the extent of increase in tissue oxygen consumption.

Specific Examples of Three-Dimensional Displays

FIGS. 55(A)-(D) are three-dimensional diagrams showing K-spiral motions of channels 4, 7, 9 and 11; they are examples in which lines are entered for Hb and $HbO_2$.

FIGS. 56(A)-(D) are three-dimensional diagrams showing K-spiral motions of channels 4, 7, 9 and 11; they are examples in which vertical lines are entered along the time axis.

According to these three-dimensional diagrams, it can be seen that at channel 4, the phase shifts into segments 3, 4 and 5; at channel 7, it shifts into segment 2; at channel 9, it shifts into segment 4; and at channel 11, it shifts into segment 3.

In this way, the respective quadrant shift properties differ at each channel, making it possible to judge that the characteristics added to the brain are different.

Effects that can be Obtained from Three-Dimensional Diagrams and their Various Parameters Three-dimensional diagrams and their various parameters have the following kinds of effects:

1) They can be divided into two situations with respect to the time axis: clockwise revolution and counterclockwise revolution.

Different oxygen exchange states can be distinguished by differentiating between clockwise revolution, as an excitatory response to a task, and counterclockwise rotation, as a suppressive response to a task.

2) The state during rest can be measured, and if the oxygen exchange function is constant, the spiral is infinitely parallel to the time axis. At this time, the I-, O-, L- and Y-angles infinitely approach zero. In the same way, the I-, E-, L- and R-values are near zero. Or, there is no change in any of the values or angles.

3) Conversely, if the I-, O-, L- and Y-angles, or the I-, E-, L- and R-values move away from the time axis and increase in size, this shows that oxygen exchange activity is becoming more active. In this case, the 8 segments into which the diagram is divided, from event 1 through event 8, represent the properties and the state of oxygen exchange activity.

4) Of the 8 segments, the segment is determined for the T-spiral by the ratio between the cumulative amount of oxygen consumption/supply and the cumulative amount of hemoglobin increase/decrease.

For the K-spiral, the segment is determined by the ratio between the amount of oxygen consumption/supply and the amount of hemoglobin increase/decrease.

For the H-spiral, the segment is determined by the ratio between the velocity of oxygen consumption/supply and the velocity of hemoglobin increase/decrease.

For the I-spiral, the segment is determined by the ratio between the acceleration of oxygen consumption/supply and the acceleration of hemoglobin increase/decrease.

5) The more the spiral moves away from the time axis of the three-dimensional display, the greater the reduction in the reserve capacity of cerebral oxygen exchange function it shows.

For determining the reserve capacity of cerebral oxygen exchange function, using the K-spiral and the T-spiral is most effective. When the oxygen exchange function has been working with respect to a task load, a return to the measurement starting point is taken as the reserve capacity, and judged to be normal.

The K-spiral is effective in determining the reserve capacity of cerebral oxygen exchange function for each trial of a task.

The T-spiral is effective in cases when continuous trials, overall load or the like are evaluated.

6) Efficiency of the reserve capacity of cerebral oxygen exchange function is judged by a quick return. The I-spiral and the H-spiral are used for this purpose. Efficiency is judged by how fast they return to the axis of the measurement starting point.

7) Segments 4 and 5 in particular are directions in which reserve capacity disappears with respect to low oxygen, and a spiral moving into these segments without recovering shows a need to consider treatment, so that it will move toward the oxygen supply segments 8 and 1.

8) Conversely, if there is no movement into segments 4 and 5 even when studying, this can be understood to mean that oxygen consumption is not taking place because the appropriate neural activity is not being obtained in the brain, and new ways to support learning need to be devised. Segments 6 and 7 in particular are directions in which reserve capacity disappears with respect to hemoglobin, and a spiral moving into these segments without recovering shows a need to consider treatment so that it will move towards the blood supply segments 2 and 3.

9) If, with physical therapy, the quadrant continues in segments 6 and 7, or quadrant 5, without shifting to segments 2 and 3, there is a problem with brain oxygen supply, and it is necessary to seek the advice of a physician, and the subject must stop the exercise and rest.

Regarding Reserve Capacity of Cerebral Oxygen Exchange Function (Residual Function of Cerebral Oxygen Exchange Function)

Previously, to evaluate brain circulation reserve capacity, changes in blood flow distribution arising from the vascular dilation response to the carbon dioxide load were compared to the situation before a load was applied.

However, the disadvantage of this method of examination is that it looked not at the vascular response at the capillary level, but at the response of the arterioles, which do not perform the oxygen exchange that is the response to a carbon dioxide load. With this method, it was not possible to judge the degree of functional reserve capacity with respect to the working of the brain. In addition, the response to carbon dioxide was measured for the whole brain, and not for localized selective function.

A possible solution to this problem is to measure reserve capacity of cerebral oxygen exchange function by means of the slope of the L-angle and segment shifts of the K-spiral.

Here, the L-angle represents degree of oxygen exchange functional reserve, and the greater it is, the less reserve capacity there is judged to be. In addition, reserve oxygen exchange time, or OET, is defined, and the reserve oxygen exchange time up to a desired L-angle, for example 45 degrees, is compared to normal, and the shorter it is, the less the reserve capacity is judged to be. In addition, it can be judged that the more the L-angle moves towards the deoxyhemoglobin axis, the less the reserve capacity; and it can be judged that the more the L-angle moves towards the oxyhemoglobin axis, the greater the reserve capacity.

Figure 57:
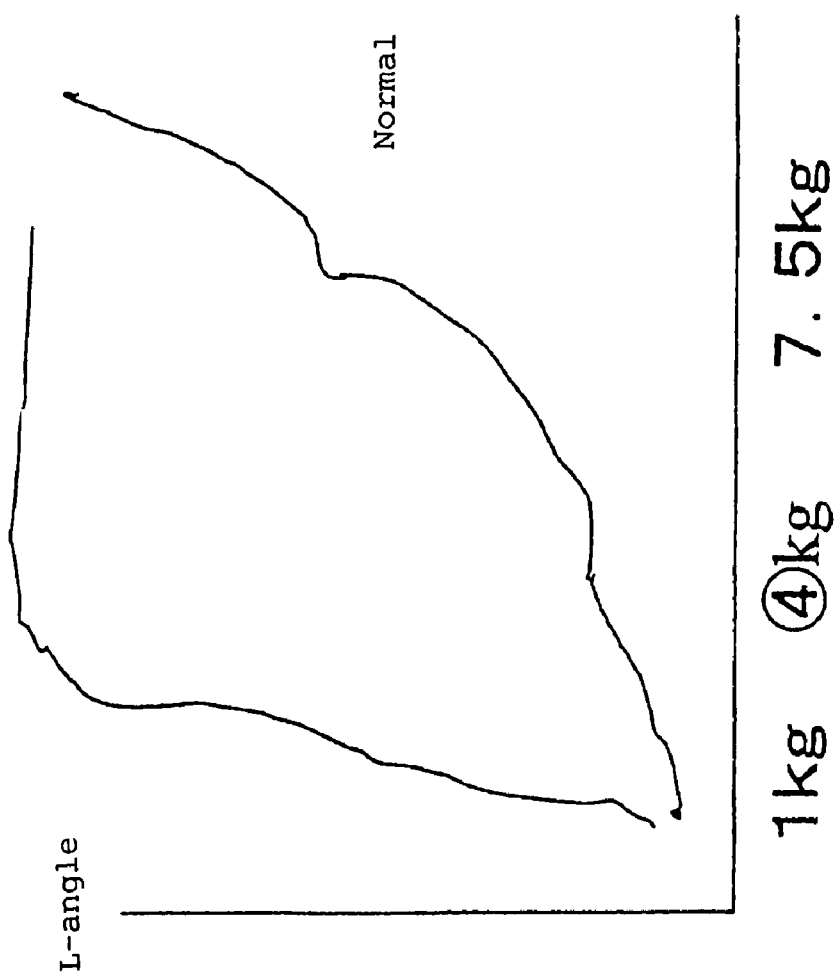
FIG. 57 is a graph showing changes in the L-angle when a subject lifted dumbbells in the order of 1 kg, 4 kg and 7.5 kg.

FIG. 57 is a graph showing changes in the L-angle when a subject lifted dumbbells in the order of 1 kg, 4 kg and 7.5 kg. As shown in FIG. 57, when the L-angle is increasing sharply, reserve oxygen exchange function capacity decreases sharply, showing that oxygen exchange in the cerebral blood vessels is in an abnormal state. When the L-angle is increasing gradually, there is surplus reserve oxygen exchange functional capacity, showing that oxygen exchange in the cerebral blood vessels is in a normal state.

Regarding a Qualitative K-Ratio

A qualitative K-ratio is defined according to the following formula:

Qualitative $K$-ratio=(change in the predominantly deoxyhemoglobin wavelength absorption coefficient)/(change in the predominantly oxyhemoglobin wavelength absorption coefficient)

By means of a method of calculating a qualitative K-ratio using wavelengths directly, changes similar to the oxygen exchange rate can be measured qualitatively from its slope (Arctan [K-ratio].

Figure 58:
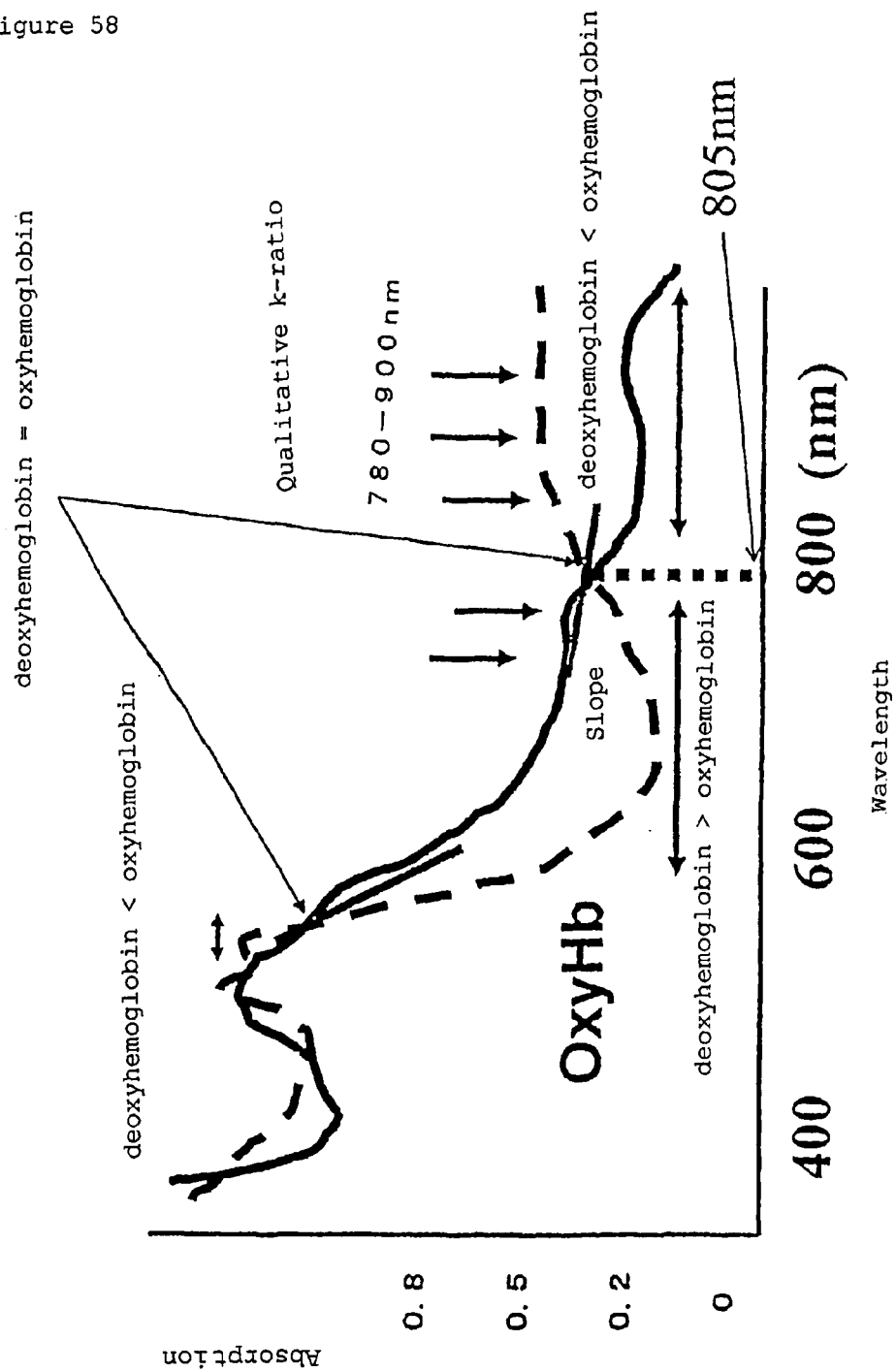
FIG. 58 is a graph showing the relationship between wavelength and absorbance.

FIG. 58 is a graph showing the relationship between wavelength and absorbance. In FIG. 58,
(1) When deoxyhemoglobin<oxyhemoglobin, the slope of the qualitative K-ratio rises (to the right) at rest ($\geq 50\%$ oxygenation), and during oxygen exchange activity, it becomes a counterclockwise change (high oxygenation).
(2) When deoxyhemoglobin>oxyhemoglobin, the slope of the qualitative K-ratio rises to the right at rest ($\geq 50\%$ oxygenation), and during oxygen exchange activity, it becomes a clockwise change (low oxygenation).

Figure 59:
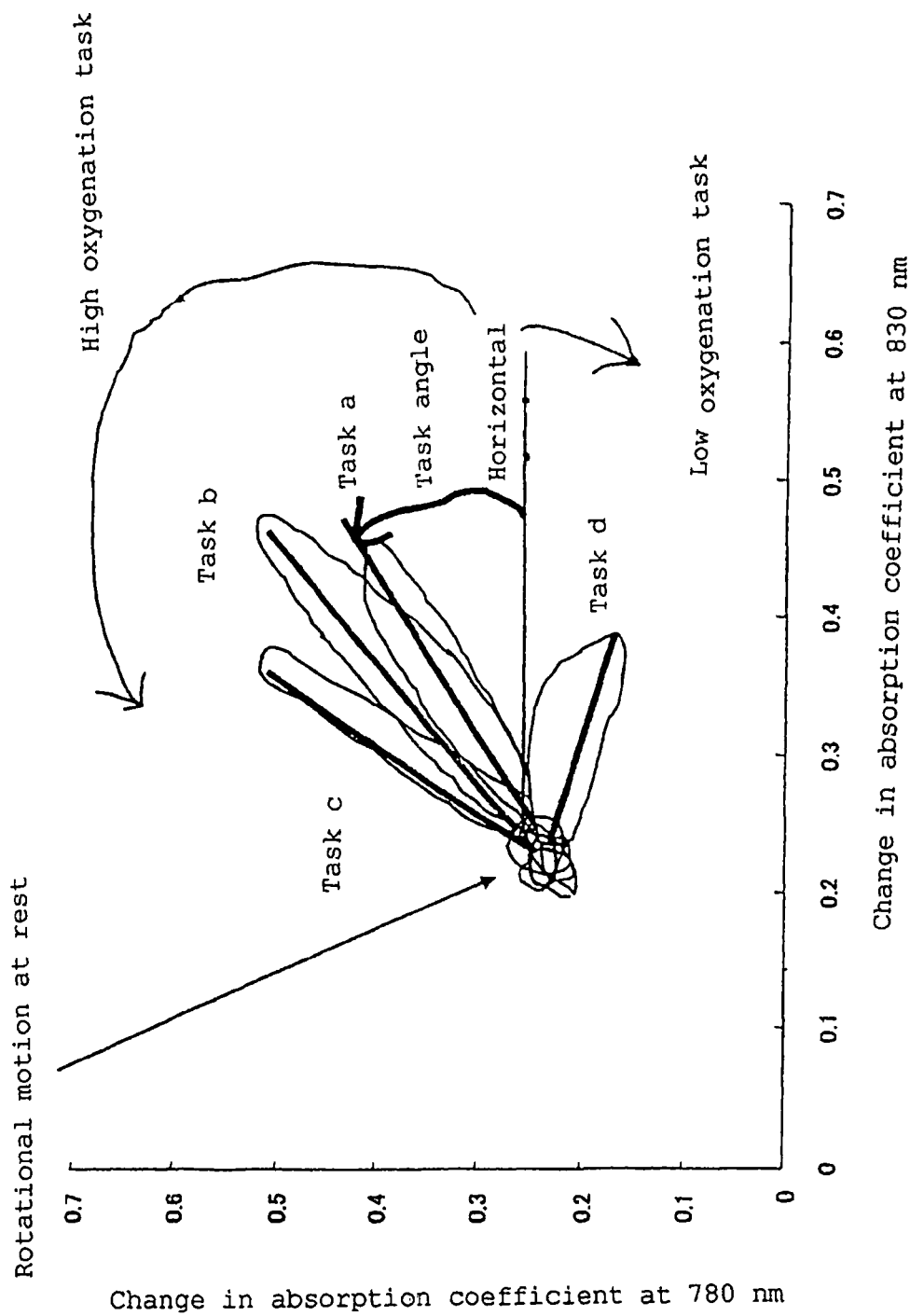
FIG. 59 is a graph of changes in absorption coefficient at 830 nm and changes in absorption coefficient at 780 nm plotted in two dimensions by task.

FIG. 59 is a graph of changes in absorption coefficient at 830 nm and changes in absorption coefficient at 780 nm plotted in two dimensions by task. Task angles, differing by task, are measured. When the task causes the task angle to change in a clockwise direction, it shows low oxygenation; when the task causes the task angle to change in a counterclockwise direction, it shows high oxygenation.

Figure 60:
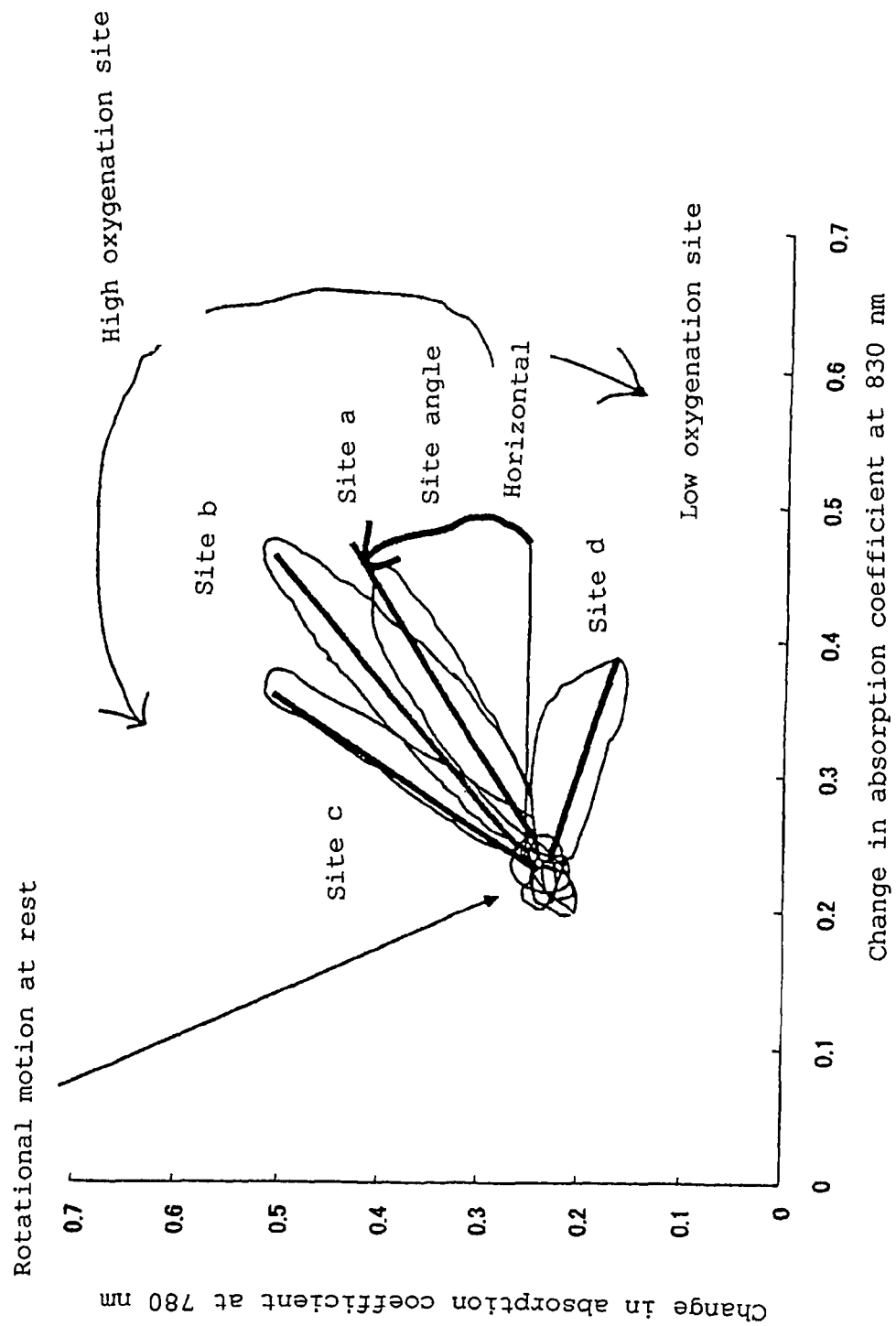
FIG. 60 is a graph of changes in absorption coefficient at 830 nm and changes in absorption coefficient at 780 nm plotted in two dimensions by site.

FIG. 60 is a graph of changes in absorption coefficient at 830 nm and changes in absorption coefficient at 780 nm plotted in two dimensions by site. Site angles, differing by site, are measured. When the site causes the site angle to change in a clockwise direction, it shows low oxygenation; when the site causes the site angle to change in a counterclockwise direction, it shows high oxygenation.

Image Displays Monitoring Light Path Length Variation

Previously, a potential problem with measuring at a plurality of points was differences in light path lengths for each point, and thus there was a problem with equivalent valuations. Conversely, however, disparities in light path length can be thought to represent differences in the state of the tissue of the measurement target.

Accordingly, although it was previously believed that there were no changes in light path length (path length; PL), variation in PL is displayed graphically. By this means, once PL has been calculated in each of the time periods, during the FORCE effect, the Watering-the-garden effect and the sewage effect, the changing nature of PL can be utilized to extract the time period of the FORCE effect. Because the light path length PL differs according to the extent of scattering, monitoring PL makes it possible to measure the extent of the involvement of capillary signals and venous signals.

However, because the Modified Beer-Lambert (MBL) method determines $\Delta HbO_2 \cdot p_1$ and $\Delta Hb \cdot p_1$, in the NIRS measuring method, absolute values for $\Delta HbO_2$ and $\Delta Hb$ are calculated not by the MBL method, but by using methods such as time-resolved spectroscopy (TRS) and phase-resolved spectroscopy (PRS), and inserting them into one of the equations below, thus making it possible to monitor PL.

$$\Delta O.D._{730} = a_1 \Delta[HbO_2] \cdot p1 + a_1' \Delta[Hb] \cdot p1 \quad \text{(Equation 8)}$$

$$O.D._{830} = a_2 \Delta[HbO_2] \cdot p1 + a_2' \Delta[Hb] \cdot p1 \quad \text{(Equation 9)}$$

$$O.D._{850} = a_3 \Delta[HbO_2] \cdot p1 + a_3' \Delta[Hb] \cdot p1 \quad \text{(Equation 10)}$$

In this case, by the MBL method, $p_1$ can be determined by 1 wavelength.

Figure 61:
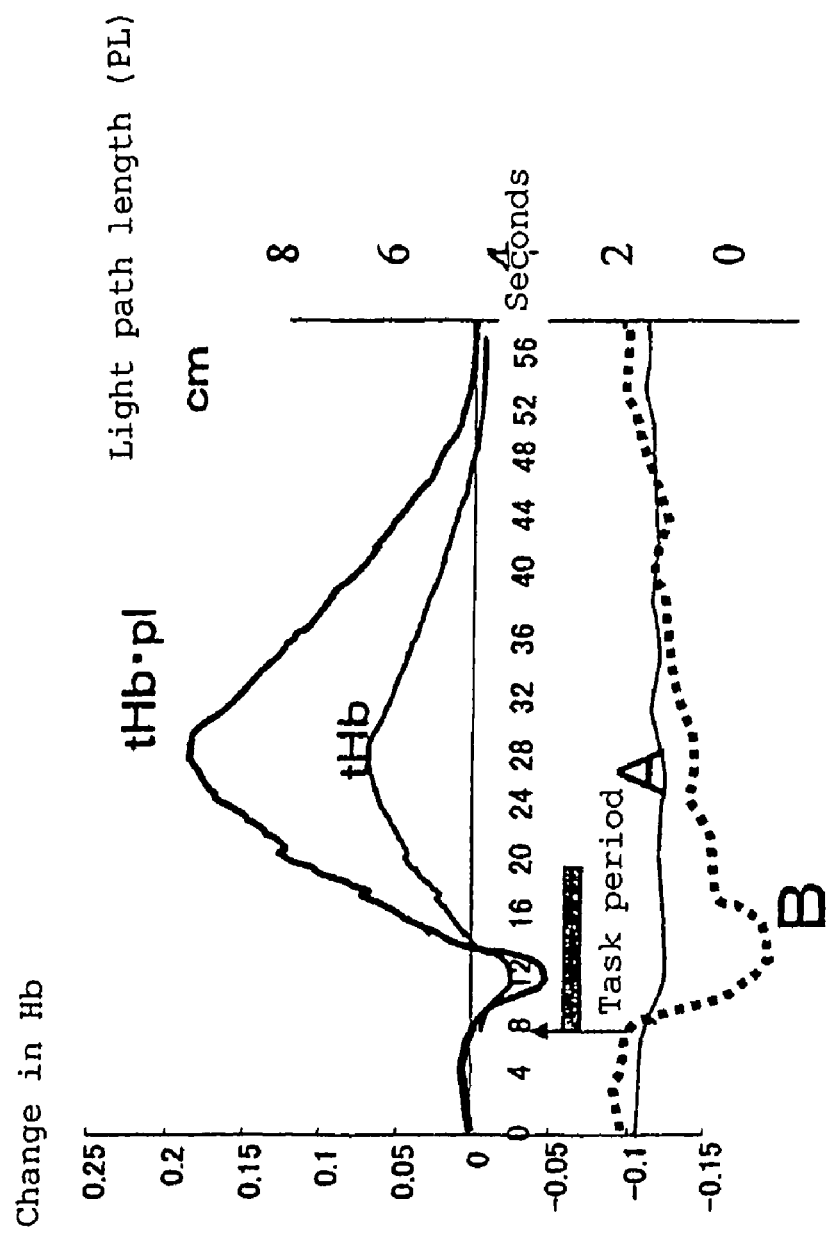
FIG. 61 is a graph showing time series changes in light path length (PL) when a task is presented.

Or, by the MBL method, $\Delta[HbO_2] \cdot p_1$ and $a_1' \Delta[Hb] \cdot p_1$ can be determined and $\Delta[HbO_2]$ and $\Delta[Hb]$ measured directly by TRS and PRS, to monitor PL and changes in PL. FIG. 61 is a graph showing time series changes in light path length (PL) when a task is presented. Site B, where changes in PL are large when a task is presented, can be judged to be a site where there are many veins.

Figure 62:
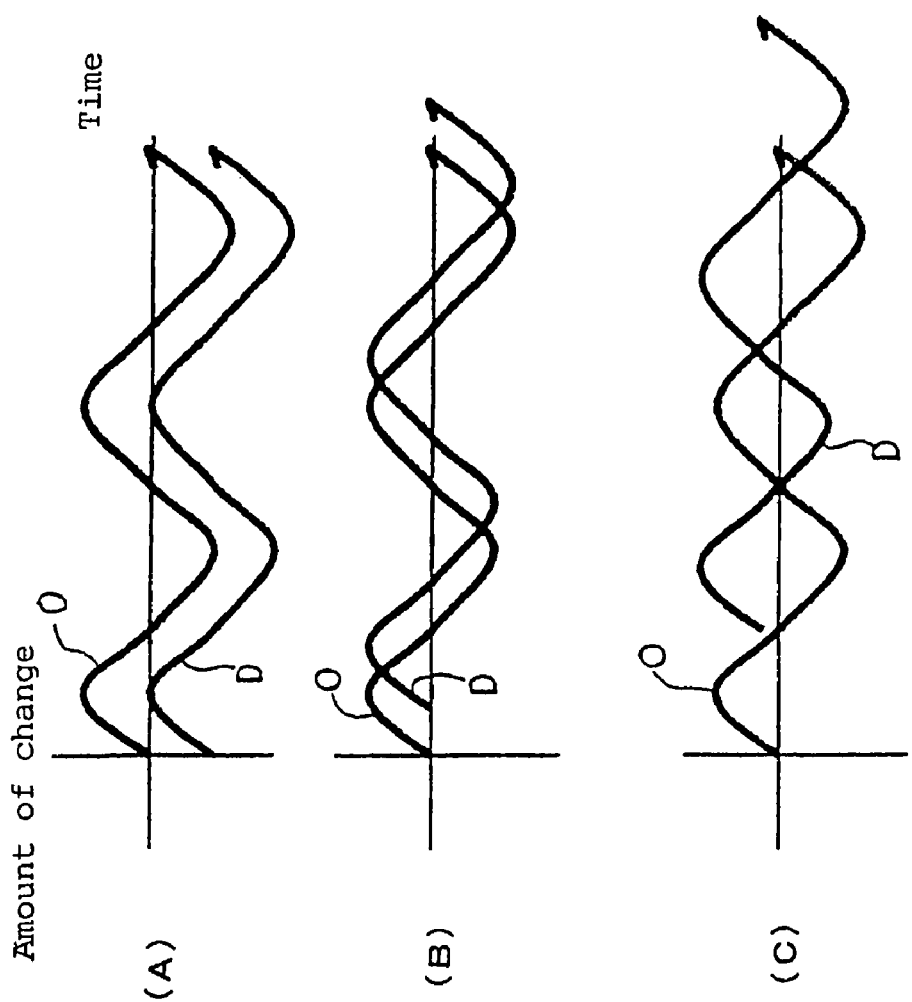
FIG. 62 shows waveforms for oxyhemoglobin (O) and deoxyhemoglobin (D); (A) shows a phase difference of 0 degrees; (B), a phase difference of 90 degrees; and (C), a phase difference of 180 degrees.

A Method for Measuring Oxyhemoglobin and Deoxyhemoglobin Waveform Phase Differences FIG. 62 shows waveforms for oxyhemoglobin (O) and deoxyhemoglobin (D); (A) shows a phase difference of 0 degrees; (B), a phase difference of 90 degrees; and (C), a phase difference of 180 degrees. When the oxyhemoglobin and deoxyhemoglobin waveform phase changes, the oxygen exchange state changes.

Namely, because oxygen exchange rate (k-angle) is directly related to the phase difference between O and D, this phase difference can be measured from two-dimensional and three-dimensional coordinates and the k-angle.

Figure 63:
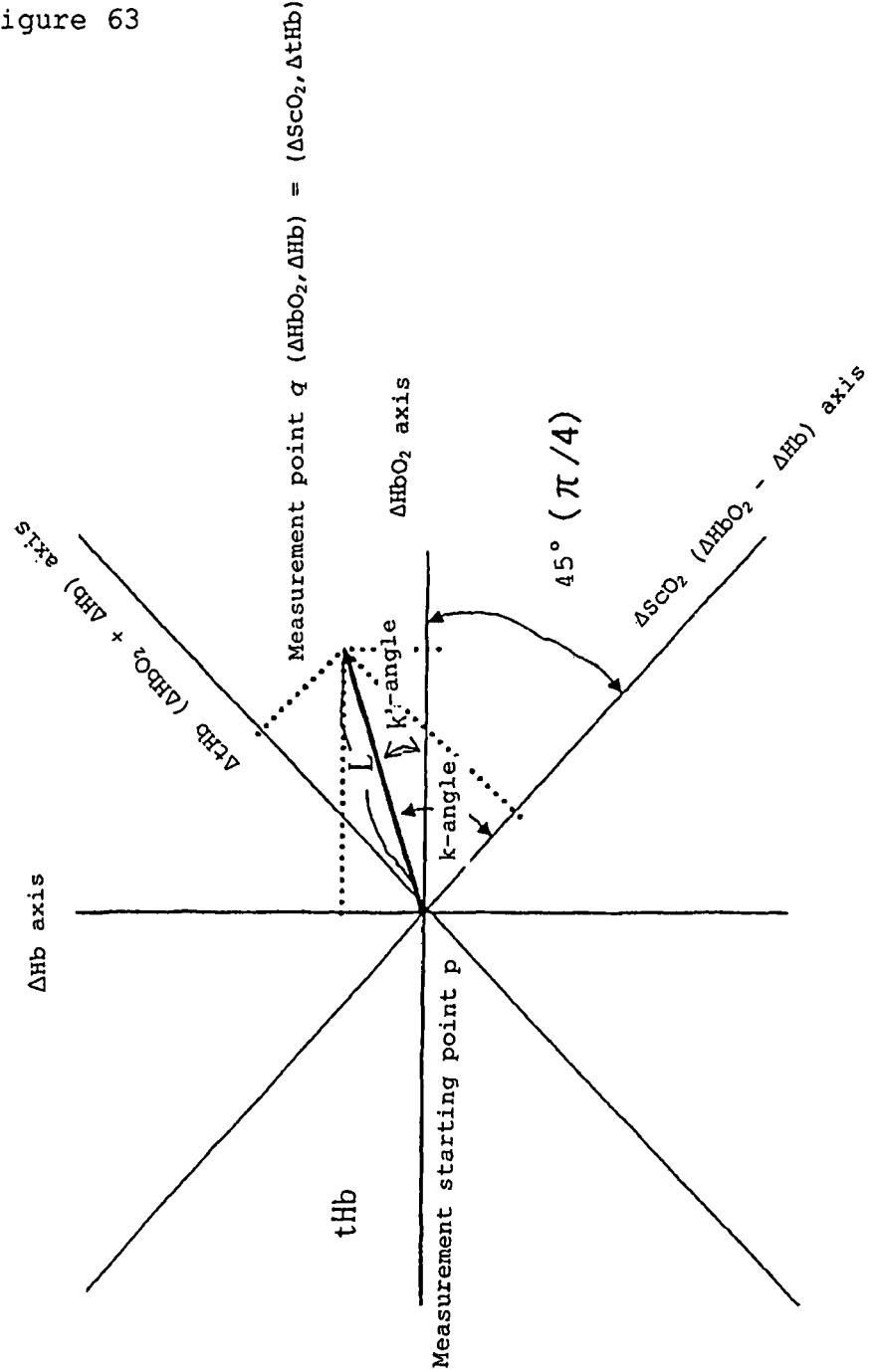
FIG. 63 is a graph explaining the oxygen exchange phase difference angle.

FIG. 63 is a graph explaining the oxygen exchange phase difference angle. Phase differences between the four indexes utilizing oxygen exchange rate (k-angle), $\Delta HbO_2$, $\Delta Hb$, $\Delta tHb$ ($\Delta HbO_2+Hb$) and $\Delta ScO_2$ ($\Delta HbO_2-\Delta Hb$), are defined as the oxygen exchange phase difference angle from two-dimensional or three-dimensional coordinates and determined.

Measurement point q ($\Delta HbO_2, \Delta Hb$) on the 2 rectangular coordinates of the $HbO_2$ axis and the Hb axis is also converted to coordinates formed from the $\Delta tHb$ ($\Delta HbO_2+\Delta Hb$) axis and the $\Delta ScO_2$ ($\Delta HbO_2-\Delta Hb$) axis by means of oxygen exchange rate (k-angle) and the scalar L.

On the $HbO_2$–Hb coordinates, measurement point q is described as $q(\Delta HbO_2, \Delta Hb) = (L \cos k', L \sin k') = (L \sin(\pi/2 - k'), L \sin k')$ On the $ScO_2$–tHb coordinates,
measurement point q is described as $q(\Delta ScO_2, \Delta tHb) = (L \cos k, L \sin k) = (L \sin(\pi/2 - k), L \sin k)$ From the above, using trigonometric functions, because the coordinates of measurement point q are defined by L and k, the four indexes, $\Delta HbO_2$, $\Delta Hb$, $\Delta tHb$ ($\Delta HbO_2+\Delta Hb$) and $\Delta ScO_2$ ($\Delta HbO_2-\Delta Hb$), can thus be converted to sine curves.

When defined as $\Delta HbO_2$ phase=$k_o$, $\Delta Hb$ phase=$k_d$, $\Delta ScO_2$ phase=$k_s$, $\Delta tHb$ phase=$k_t$, they can be written as follows:
$\Delta HbO_2$ and $\Delta Hb$ oxygen exchange phase difference angle $k_o - k_d = (\pi/2 - k') - k' = \pi/2 - 2k' = \pi - 2k$ $\Delta ScO_2$ and $\Delta tHb$ oxygen exchange phase difference angle $k_s - k_t = (\pi/2 - k) - k = \pi/2 - 2k$ $\Delta HbO_2$ and $\Delta tHb$ oxygen exchange phase difference angle $k_o - k_t$ $= (\pi/2 - k') - k = (\pi/2 - k') - (k' + \pi/4)$ $= \pi/4 - 2k'$ $= (\pi/2 - (k - \pi/4)) - k = 3\pi/4 - 2k$ $\Delta HbO_2$ and $\Delta ScO_2$ oxygen exchange phase difference angle $k_o - k_s = (\pi/2 - k') - (\pi/2 - k) = (\pi/2 - k) = -k' + k = \pi/4$ (becomes a constant)

$\Delta Hb$ and $\Delta tHb$ oxygen exchange phase difference angle $k_d - k_t = k' - k = -\pi/4$ (becomes a constant)

$\Delta Hb$ and $\Delta ScO_2$ oxygen exchange phase difference angle $k_d - k_s$ $= k' - (\pi/2 - k) = k' + k - \pi/2$ $= k' + (k' + \pi/4) - \pi/2 = 2k' - \pi/4$ $= 2(k - \pi/4) - \pi/4 = 2k - 3\pi/4$ Each of the oxygen exchange phase difference angles is calculated using the k-angle or the k'-angle. The oxygen exchange rate k-angle is a function of time, varying with time; from the fact that it shows the extent of oxygen exchange, it is effective in distinguishing the FORCE effect and the Watering-the-garden effect, and it makes it possible to measure how much phase change is received by the various indexes corresponding to a load task or stimulus. Namely, from two-dimensional and three-dimensional coordinate displays, an oxygen exchange phase modulation measurement method and a phase difference imaging method, utilizing oxygen exchange rate, were able to invent.

Figure 64:
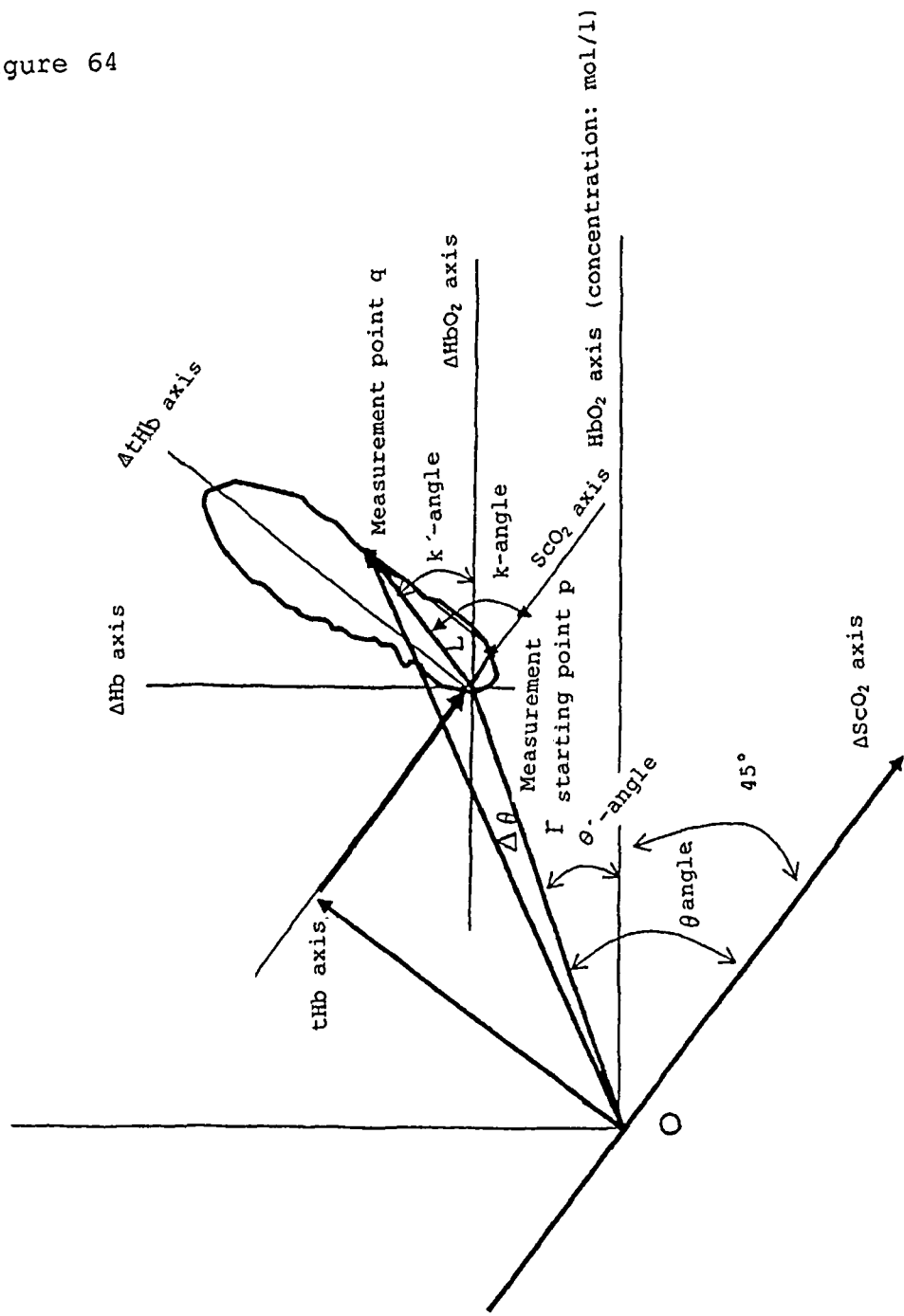
FIG. 64 is a graph explaining the absolute oxygen exchange phase difference angle.

FIG. 64 is a graph explaining the absolute oxygen exchange phase difference angle.

Phase differences among the four indexes, $\Delta HbO_2$, $\Delta Hb$, $\Delta tHb$ ($\Delta HbO_2+\Delta Hb$) and $\Delta ScO_2$ ($\Delta HbO_2-\Delta Hb$), which utilize absolute oxygen exchange rate (angle θ) from two-dimensional or three-dimensional coordinates, are defined as the absolute oxygen exchange phase difference angle and determined.

By means of absolute oxygen exchange rate (angle θ) and the scalar r, measurement point p ($HbO_2$, Hb) on the 2 rectangular coordinates $HbO_2$ and Hb, is also converted to coordinates formed by the tHb ($HbO_2+Hb$) axis and the $ScO_2$ ($HbO_2-Hb$) axis.

On the $HbO_2$–Hb coordinates, it can be written as:

measurement point $p$ ($HbO_2$, Hb) = ($L \cos θ', L \sin θ'$) = ($L \sin(\pi/2 - θ'), L \sin θ'$)

On the $ScO_2$-tHb axes, it can be written as:

measurement point $p$ ($ScO_2$, tHb) = ($L \cos θ, L \sin θ$) = ($L \sin(\pi/2 - θ), L \sin θ$)

From the above, using trigonometric functions, because the coordinates of measuring point p are defined by r and θ, the four indexes, $\Delta HbO_2$, $\Delta Hb$, $\Delta tHb$ ($\Delta HbO_2+\Delta Hb$) and $\Delta ScO_2$ ($\Delta HbO_2-\Delta Hb$) can be converted to sine curves.

When defined as $HbO_2$ phase=$θ_o$, Hb phase=$θ_d$, $ScO_2$ phase=$θ_s$, tHb phase=$θ_t$, they can be written as follows:

$HbO_2$ and Hb oxygen exchange phase difference angle $θ_o - θ_d = (\pi/2 - θ') - θ' = \pi/2 - 2θ' = \pi - 2θ$ $ScO_2$ and tHb oxygen exchange phase difference angle $θ_s - θ_t = (\pi/2 - θ) - θ = \pi/2 - 2θ$ $HbO_2$ and tHb oxygen exchange phase difference angle $θ_o - θ_t$ $= (\pi/2 - θ') - θ = (\pi/2 - θ') - (θ + \pi/4)$ $= \pi/4 - 2θ'$ $= (\pi/2 - (θ - \pi/4)) - θ = 3\pi/4 - 2θ$ $HbO_2$ and $ScO_2$ oxygen exchange phase difference angle $θ_o - θ_s = (\pi/2 - θ') - (\pi/2 - θ) = -θ' + θ = \pi/4$ (becomes a constant)

Hb and tHb oxygen exchange phase difference angle $θ_d - θ_t = θ' - θ = -\pi/4$ (becomes a constant)

Hb and ScO$_2$ oxygen exchange phase difference angle
$\theta_d - \theta_s$ $= \theta' - (\pi/2 - \theta) = \theta' + \theta - \pi/2 = \theta' + (\theta' + \pi/4) - \pi/2$ $= 2\theta' - \pi/4$ $= 2(\theta - \pi/4) - \pi/4 = 2\theta - 3\pi/4$ Each of the oxygen exchange phase difference angles is calculated using angle θ or angle θ'. The absolute oxygen exchange angle θ is a function of time, varying with time; from the fact that it shows the extent of oxygen exchange, it is effective in distinguishing between the FORCE effect and the Watering-the-garden effect, and it makes it possible to measure how much phase change is received by the various indexes corresponding to a load task or stimulus. Namely, from two-dimensional and three-dimensional coordinate displays, an absolute oxygen exchange phase modulation measurement method and a phase difference imaging method, utilizing absolute oxygen exchange rate, were able to invent in the same way as the k-angle.

A Method for Detecting and Displaying Time Series Changes at Rest, FORCE Effect, Watering-the-Garden Effect and Sewage Effect, by Means of Fluctuation Problems with the new basic principle of NIRS imaging (near-infrared spectroscopy brain functional imaging), in which location information is determined by means of the probe position on the brain surface and the response of the measurement target, become clear when it is compared with techniques for determining location information and techniques for determining the characteristic information by means of magnetic resonance imaging (MRI). NIRS imaging does not collect a rectangular matrix (voxels) to form an image, as MRI does. Namely, adjacent locations and their boundaries are not clear.

In addition, because 2 probes are utilized, for light incidence and detection, whether or not light reaches into the brain cannot be determined according to the 2 probe distances without seeing a brain response.

In addition, image displays were previously performed based on the belief that the greater the size (strength) of this brain response, the better the response. However, responses are not uniform: the distance from the surface of the skull to the brain tissue is affected by individual differences, site differences, differences according to the size of the cerebral blood vessels and differences in the shape of the gyri and sulci; the brain and skull are not uniform. Previously, technical attention was not given to this non-uniformity. Namely, the signal-to-noise ratio (S/N) of optical signals detected by each pair of probes was different, and the size of the range of area measured was also different In addition, previously, those measurement sites were joined together, like contour lines, and displayed graphically. The fluctuation of channels with bad S/N ratios in particular shows greater changes in signal strength than channels with good S/N ratios, and image displays were thus dependent on channels with large amounts of noise and differed from reality. Accordingly, a method of correction based on fluctuation of light functional voxels can be conceived. This method makes it possible to obtain images that do not depend on the light path length.

Figure 65:
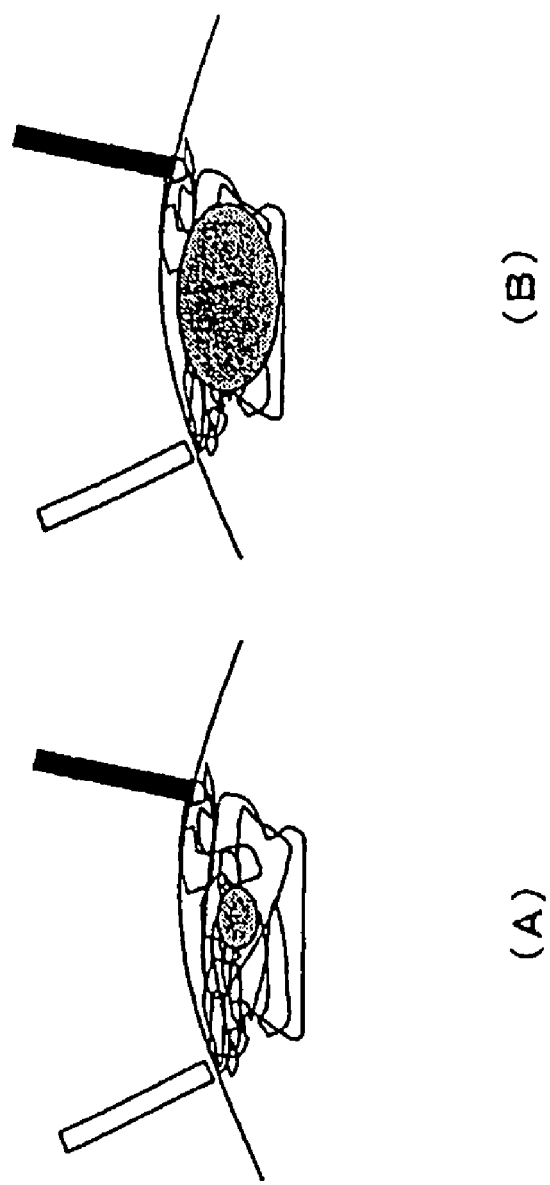
FIGS. 65(A) and (B) are explanatory drawings showing the relationships between total hemoglobin and fluctuation for different measurement targets.

FIGS. 65(A) and (B) are explanatory drawings showing the relationship between total hemoglobin and fluctuation for different measurement targets.

Because the measurement target mass, namely, total hemoglobin, is greater in FIG. 65(B) than in FIG. 65(A), fluctuation becomes less in the total hemoglobin time series data. If the respective fluctuations are taken as $f_i$ and $f_j$, their relationships with total hemoglobin are tHb$_i$ and tHb$_j$, and can be shown by the functions below.

$f_i = a(1/(\text{tHb}_i)^{0.5})$, where a is a coefficient of proportion $f_j = b(1/(\text{tHb}_j)^{0.5})$, where b is a coefficient of proportion Fluctuation ratio $f_i/f_j = a/b \times (\text{tHb}_j/\text{tHb}_i)^{0.5}$ For the same region, a=b, and thus the fluctuation ratio $f_i/f_j$ is represented as $(\text{tHb}_j/\text{tHb}_i)^{0.5}$ Because total Hb=(oxygenated Hb)+(deoxygenated Hb), fluctuation $f_i$ and $f_j$ are determined by the variation coefficient for the change in total hemoglobin (a).

This is determined by:

Variation coefficient σ=[standard deviation]/[average change in total Hb]

Consequently, from the fluctuation ratio, the total hemoglobin ratio of a measurement target can be determined.

tHb$_j$/tHb$_i = (f_i/f_j)^2$

Thus it can be determined from the approximate formula for total hemoglobin ratio and fluctuation ratio for a plurality of measurement regions. Near-infrared spectroscopy is both a quantitative measurement method and method for measuring amounts of change, but image correction between channels is possible even if quantitative measurement is not performed.

Namely, if, from the fact that where there are many capillaries there is less fluctuation and where there are few capillaries there is more fluctuation, voxels with high fluctuation are excluded and only voxels with low fluctuation are selected, then good measurements can be performed.

In addition, it is also possible to separate out FORCE segments from the size of and changes in fluctuation.

Figure 66:
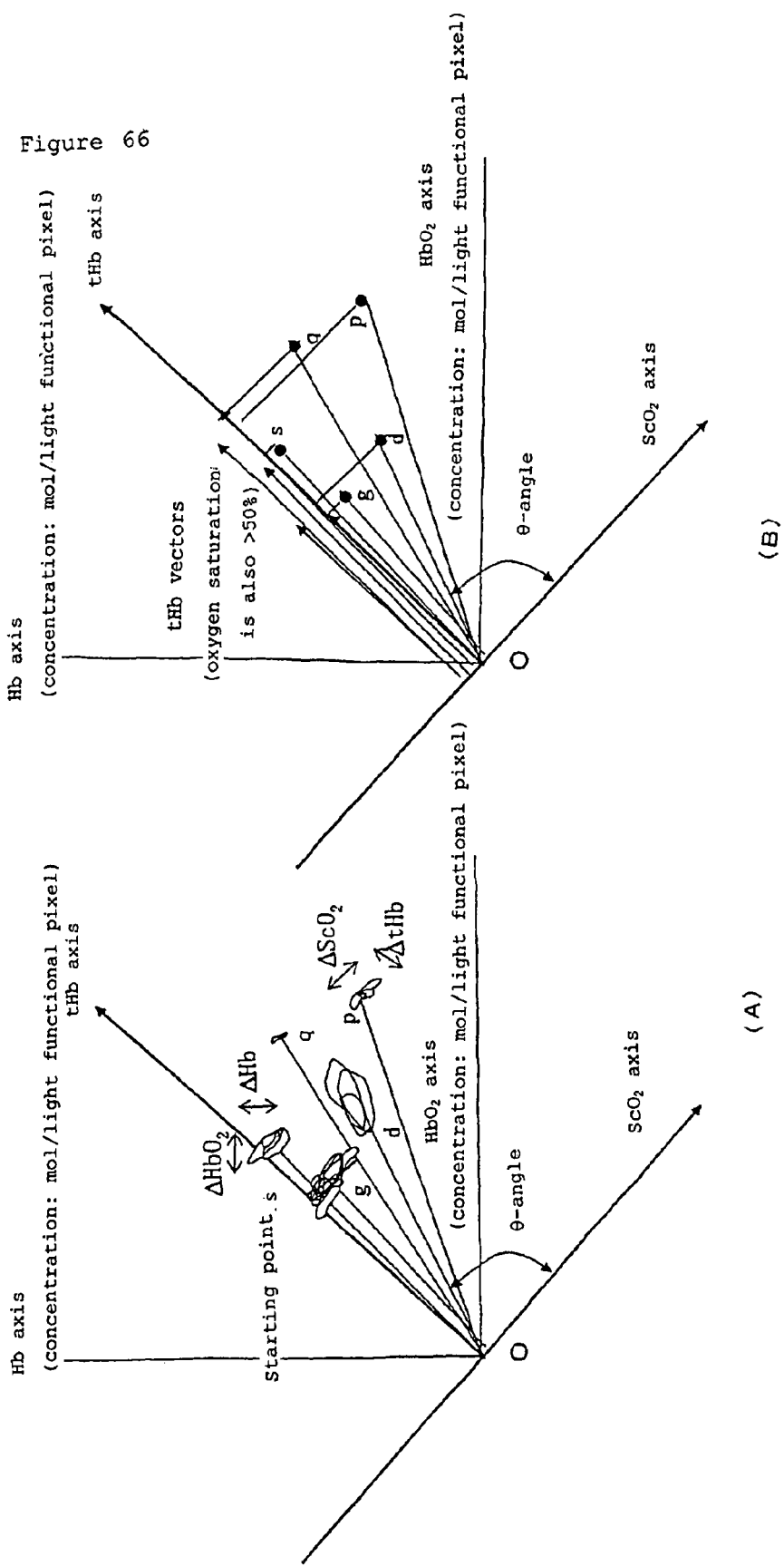
FIG. 66(A) is a graph displaying fluctuation for a plurality of measurement regions on polar coordinates, and (B) is a graph displaying vectors.

FIG. 66(A) is a graph displaying the fluctuation of a plurality of measurement regions on polar coordinates, and (B) is a graph displaying vectors.

Fluctuation of a plurality of measurement points at rest are each displayed by a rotational motion. In reality, because measurement targets are not uniform, their light path lengths will differ, and the S/N ratio will differ for each light functional voxel because of factors such as the mixture of capillary components and venous components, and the amount of hemoglobin measured. Once the rotational motion of this fluctuation has been measured as accurately as possible and understood, it becomes possible to obtain more precise measurements.

This fluctuation can be calculated from the four vector components (ΔHbO$_2$, ΔHb, ΔScO$_2$ and ΔtHb) from the Hb and HbO$_2$ polar coordinates and the tHb and ScO$_2$ polar coordinates. In a situation where this rotational motion is small and the center of gravity of the rotational motion tends not to vary by means of fluctuation, the S/N ratio is judged to be good.

In addition, even if the oxygen saturation differs at a plurality of sites, fluctuation can be estimated by vector correction of the total hemoglobin, to evaluate fluctuation that is independent of the amount of Hb measured.

From the size of fluctuation e, the facts that (a) when it is not inversely proportional to the mass, (b) there is an admixed venous component, and (c) activity is not stabilized, can be understood in turn, to improve the precision.

Figure 67:
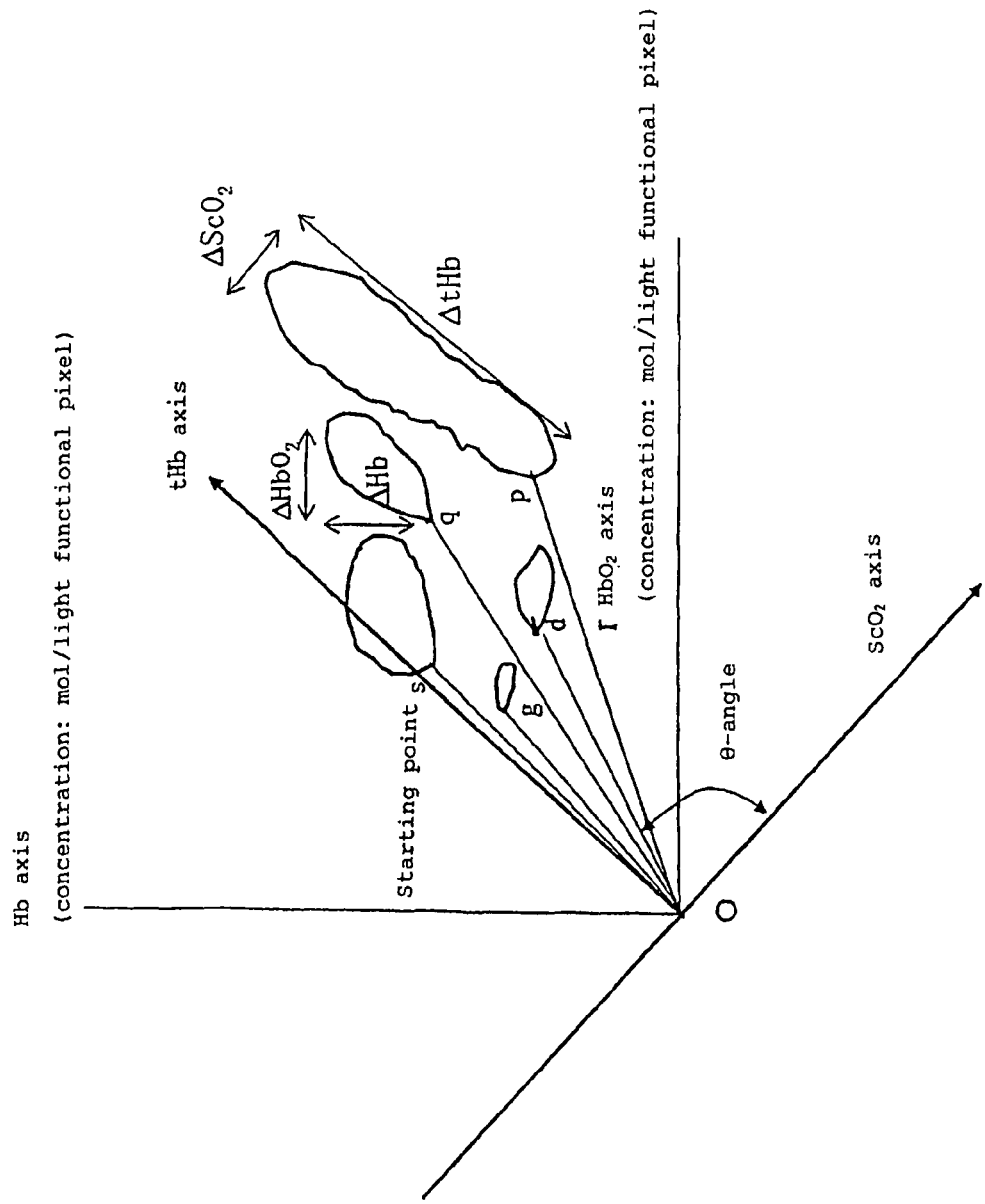
FIG. 67 is a graph displaying oxygen exchange rotational motion of a plurality of measurement regions on polar coordinates.

FIG. 67 is a graph displaying oxygen exchange rotational motion of a plurality of measurement regions on polar coordinates. The rotational motion from oxygen exchange of a plurality of points from a measurement starting point is displayed for each point. Because the measurement targets are non-uniform, the light path lengths are different, and thus even if the measurement probes are arranged at equal intervals, the amounts of hemoglobin measured will differ for each light functional voxel. Consequently, from differences in scalars and angles of deviation on the polar coordinates, the values for hemoglobin oxygen exchange variation L-value, oxygen exchange rate k-angle, absolute oxygen exchange variation r, and absolute oxygen exchange rate θe-angle will differ. In addition, for measured amounts, concentration as mol/light functional voxel will be more accurate than concentration as mol/l.

Mapping Cerebral Pulse Wave Measurement Distribution

Regarding "brain waves", arteriosclerosis and the like have been conventionally diagnosed from fingertip pulse waves. However, cerebral pulse waves are not being measured in the brain. Brain waves are a delayed vascular response to the blood pressure, with the same period as the heartbeat.

In the brain, using NIRS, the cerebral pulse wave can be measured for different sites by addition based on heartbeat synchronicity and respiratory synchronicity.

Measurement of cerebral pulse waves has the following effects.

1) This noninvasive measurement of cerebral pulse waves makes it possible to evaluate localized brain condition without the addition of a task.

It is possible to noninvasively diagnose vascular abnormalities of the major left and right anterior cerebral arteries, middle cerebral arteries and vertebral-basilar arteries.

2) Even if a task is added, evaluation of brain condition can be performed from a time series moving distribution map image.

3) Because the effect of respiration and the heartbeat differs according to venous and capillary components, it is possible to select only the most stable capillary regions where they have little effect.

The following 2 addition methods are possible:

1) A method whereby respiration and the heartbeat are actually monitored separately, and put timings together by data from the monitoring and add it for synchronization.

2) A method whereby, from among measurements from a plurality of channels for total hemoglobin, oxygenated Hb, deoxygenated Hb and (oxygenated Hb−deoxygenated Hb), the heartbeat period and respiratory cycle are selected from among optionally selected channels where the heartbeat and respiratory cycle have the most effect and added it for synchronization.

Figure 68:
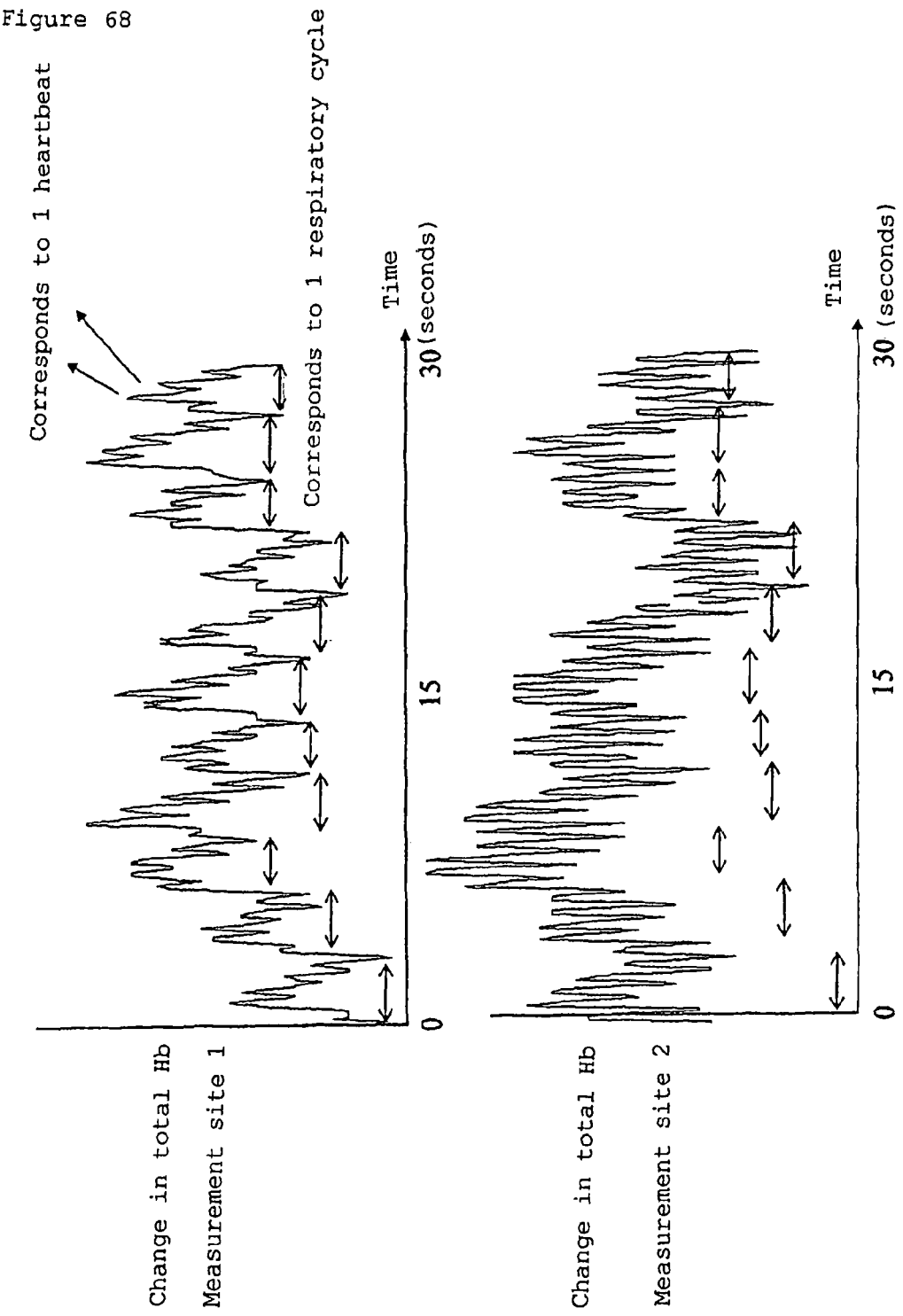
FIG. 68 is graphs showing changes in total hemoglobin at measuring sites 1 and 2.

The graphs of FIG. 68 show changes in total hemoglobin at measuring sites 1 and 2. As shown in FIG. 68, the involvement of the respiratory cycle and the heartbeat period in the signal strength differs according to the measurement site, but the respiratory cycle and the heartbeat period can be easily extracted from the time series of total hemoglobin change.

Figure 69:
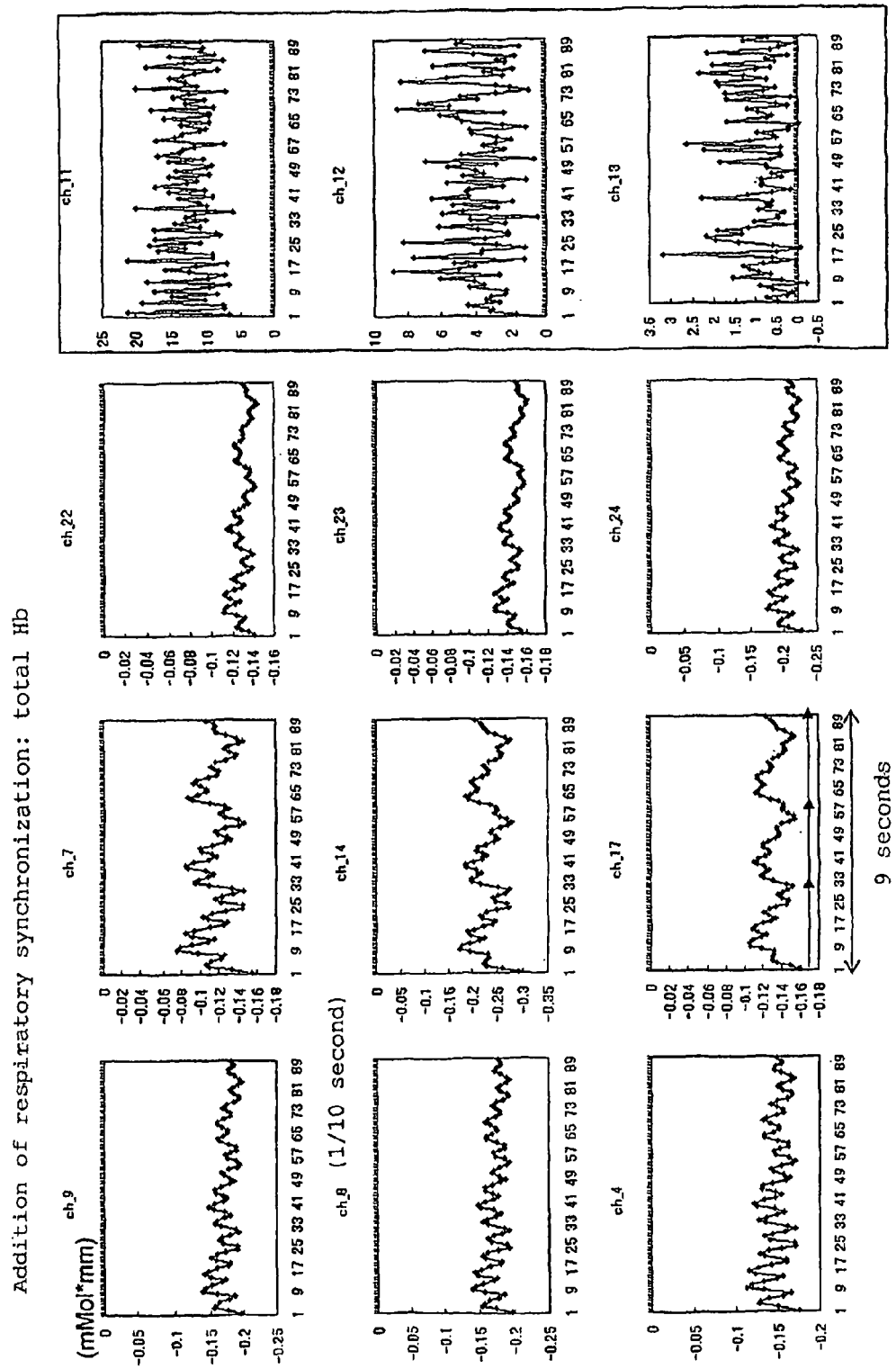
FIG. 69 shows a graph every each channel which added time series data of a change of total Hb which synchronized to respiratory cycle.

FIG. 69 shows a graph every each channel which added time series data of a change of total Hb which synchronized to respiratory cycle.

Note that channels where they were not synchronized are excluded as unsuitable measurements.

Figure 70:
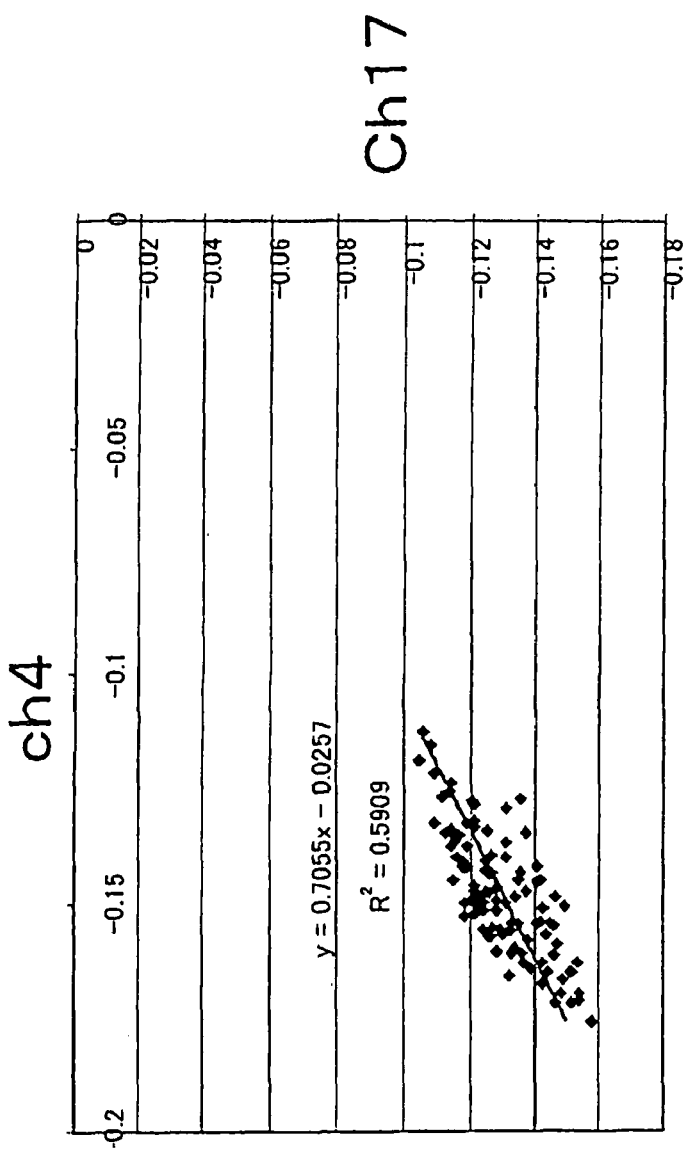
FIG. 70 is a graph showing time-series correlations for channel 4 and channel 17.

FIG. 70 is a graph showing time-series correlations for channel 4 and channel 17. The degree of involvement of respiratory frequency is measured from correlations between the channel that most reflects the breathing frequency and the other channels. If this is mapped, it becomes a map of the involvement of respiratory frequency in the brain. For heartbeat frequency, the degree of the involvement of heartbeat frequency is measured in the same way, and if this is mapped, it becomes a map of the involvement of heartbeat frequency in the brain.

Figure 71:
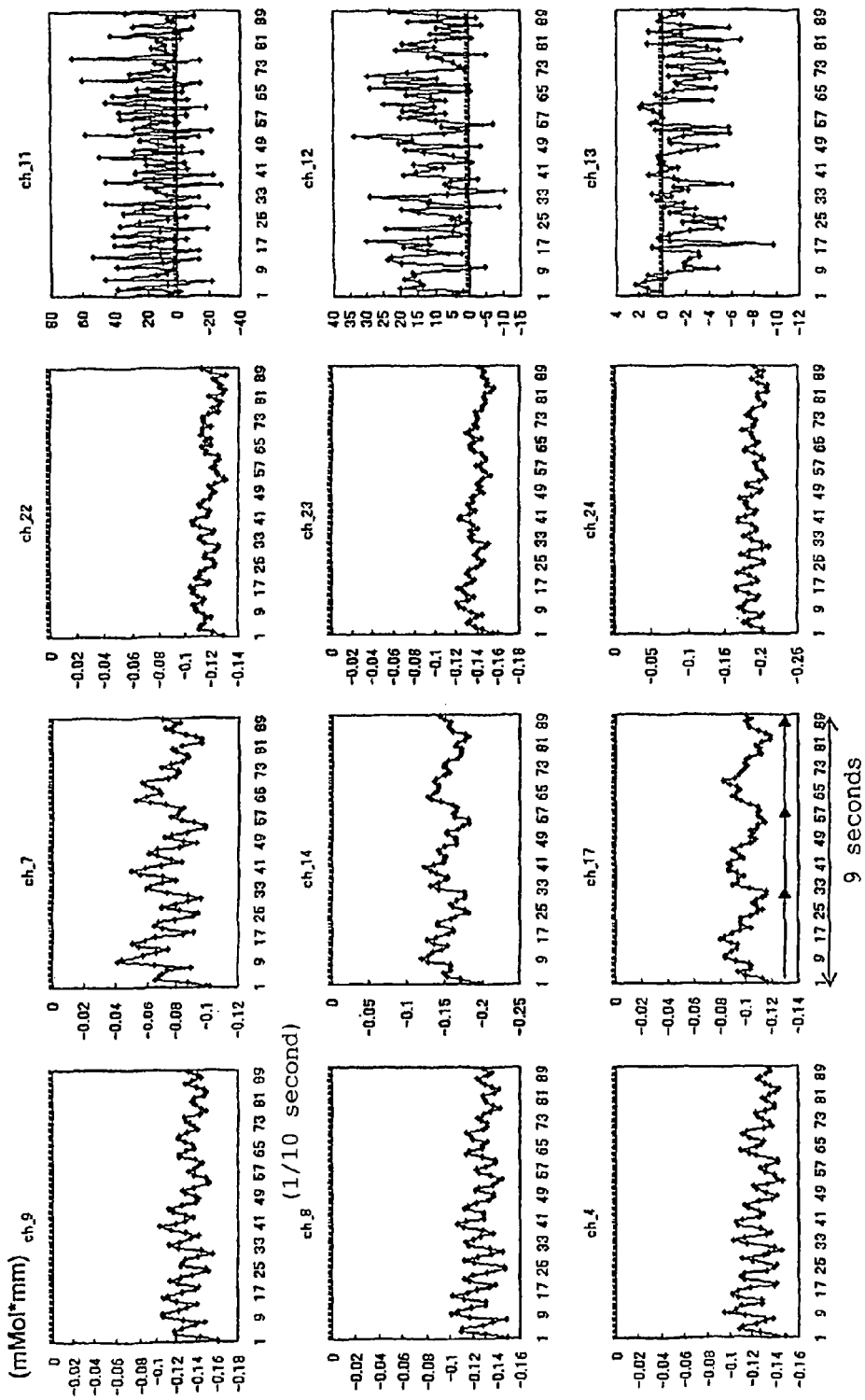
FIG. 71 is shows a graph every each channel which added time series data of a change of $HbO_2$ which synchronized to respiratory cycle.

FIG. 71 is shows a graph every each channel which added time series data of a change of $HbO_2$ which synchronized to respiratory cycle.

Figure 72:
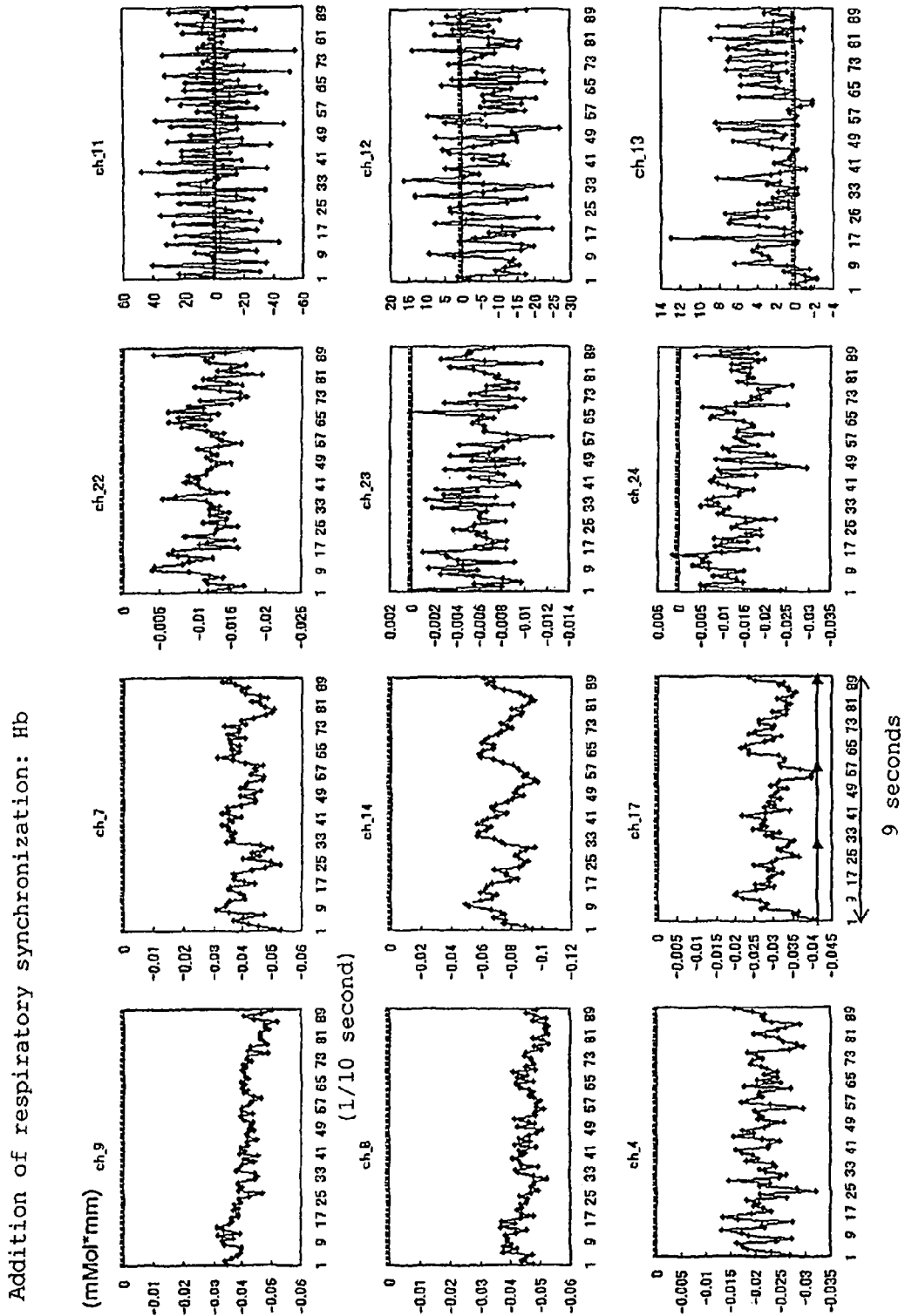
FIG. 72 is shows a graph every each channel which added time series data of a change of Hb which synchronized to respiratory cycle.

FIG. 72 is shows a graph every each channel which added time series data of a change of Hb which synchronized to respiratory cycle.

Figure 73:
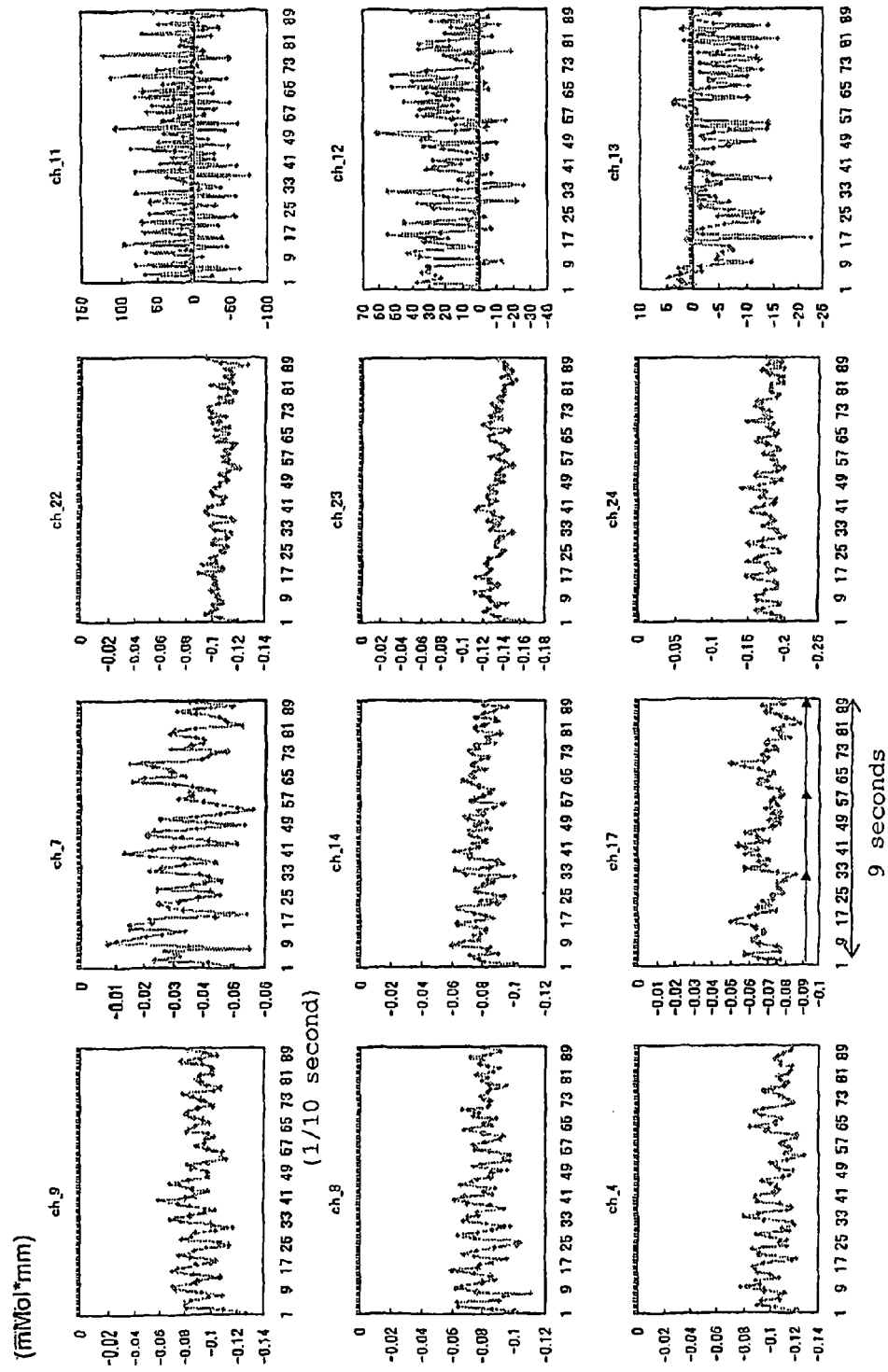
FIG. 73 shows a graph every each channel which added time series data of a change of ($[HbO_2]-[Hb]$) which synchronized to respiratory cycle.

FIG. 73 shows a graph every each channel which added time series data of a change of ($[HbO_2]$-$[Hb]$) which synchronized to respiratory cycle.

Figure 74:
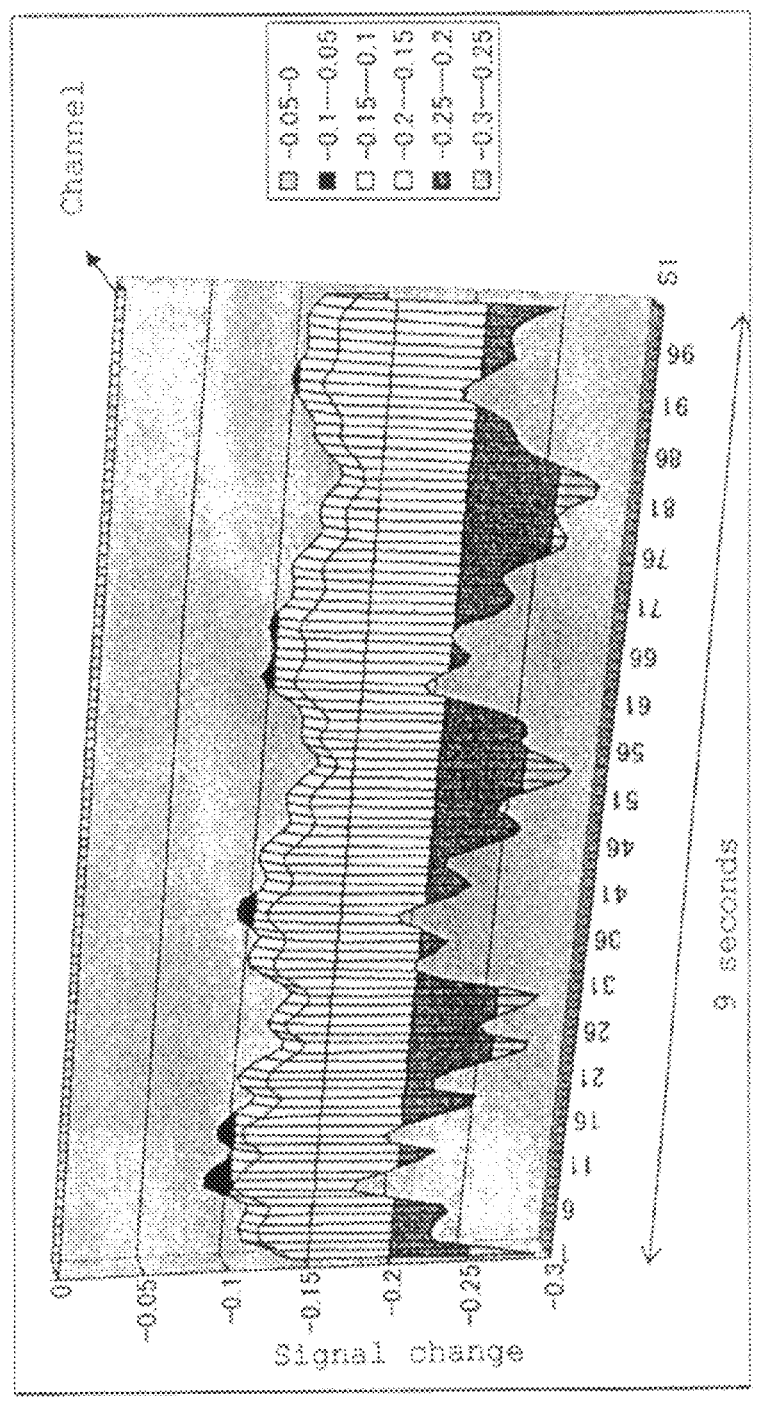
FIG. 74 is a graph in which heartbeat and respiratory cycle variation are spatiotemporally displayed for each channel.

FIG. 74 is a graph in which heartbeat and respiratory cycle variation are spatiotemporally displayed for each of various channel. Heartbeat and respiratory variation can be visually differentiated according to the size (range) of the variation for each. Because the involvement of heartbeat and respiration differs in this way according to factors such as site, time and laterality, these properties are utilized to differentiate them from task load response while displaying them graphically. Auto-correlations and inter-correlations of respiration and heartbeat utilizing time series showing the FORCE effect make it possible to effectively extract the FORCE effect in very small signals.

Figure 75:
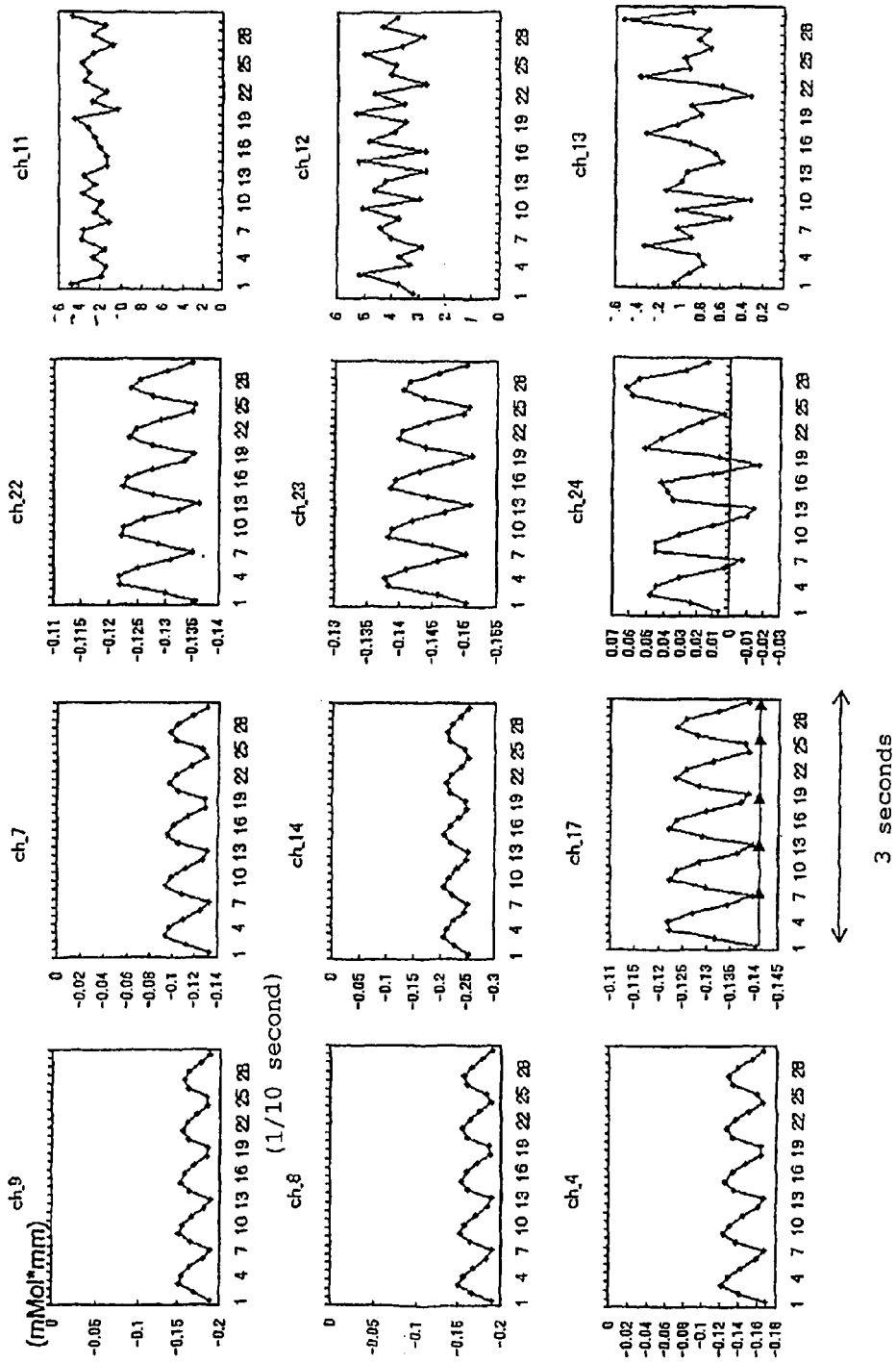
FIG. 75 shows a graph every each channel which added time series data of a change of total Hb which synchronized to heartbeat.

FIG. 75 shows a graph every each channel which added time series data of a change of total Hb which synchronized to heartbeat.

Figure 76:
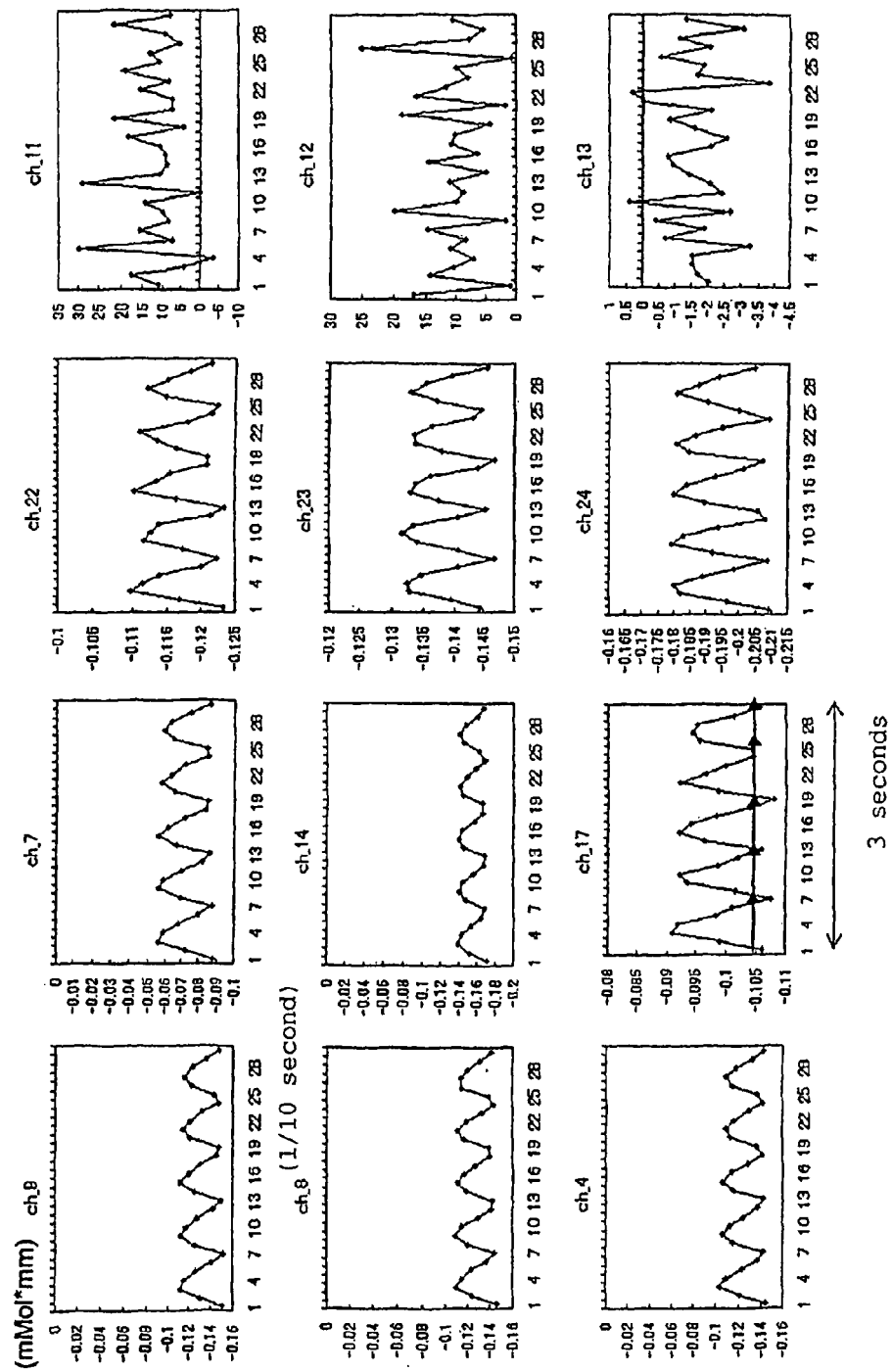
FIG. 76 shows a graph every each channel which added time series data of a change of $HbO_2$ which synchronized to heartbeat.

FIG. 76 shows a graph every each channel which added time series data of a change of $HbO_2$ which synchronized to heartbeat.

Figure 77:
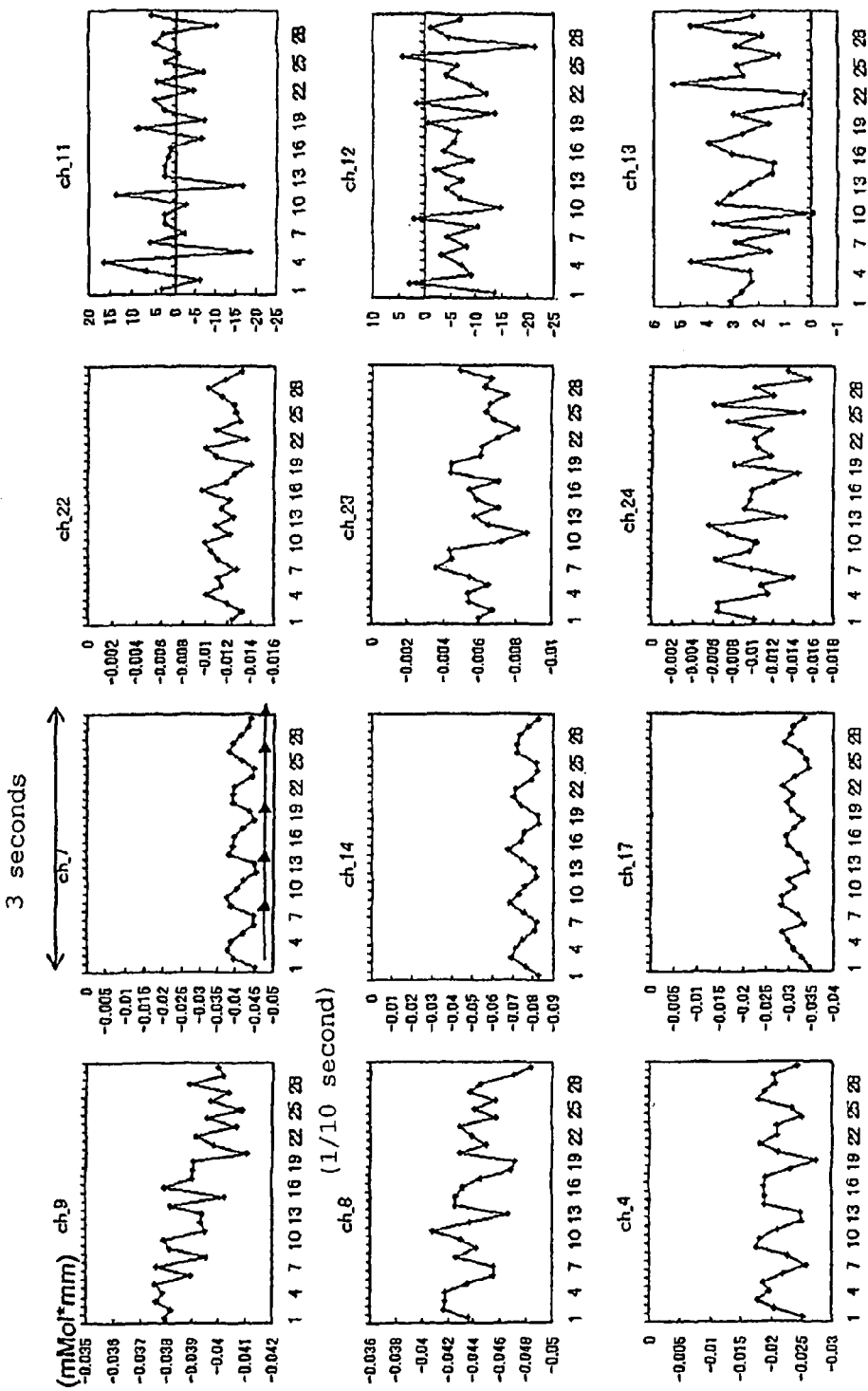
FIG. 77 shows a graph every each channel which added time series data of a change of Hb which synchronized to heartbeat.

FIG. 77 shows a graph every each channel which added time series data of a change of Hb which synchronized to heartbeat.

Figure 78:
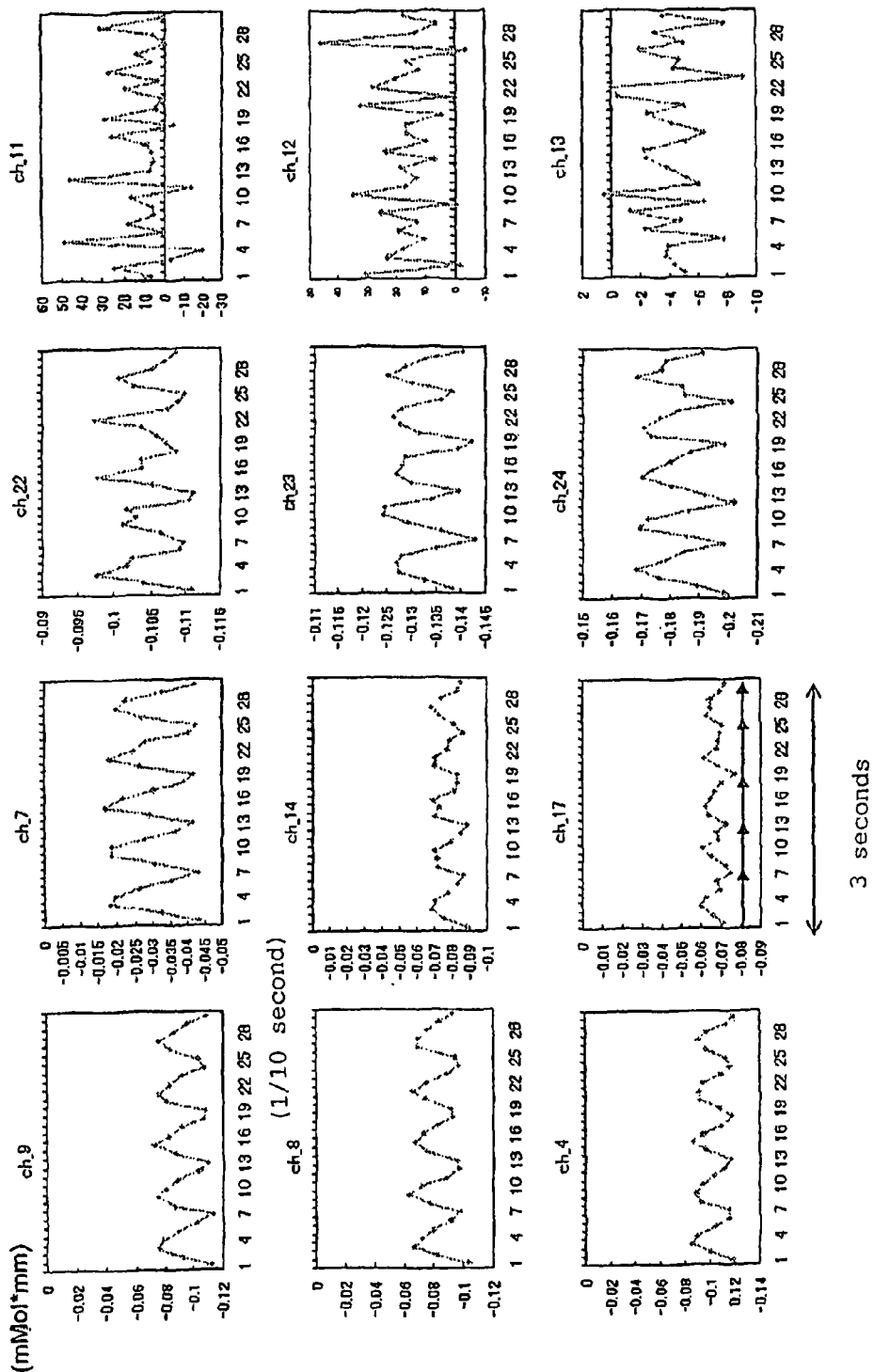
FIG. 78 shows a graph every each channel which added time series data of a change of ($[HbO_2]-[Hb]$) which synchronized to heartbeat.

FIG. 78 shows a graph every each channel which added time series data of a change of ($[HbO_2]$–$[Hb]$) which synchronized to heartbeat.

Figure 79:
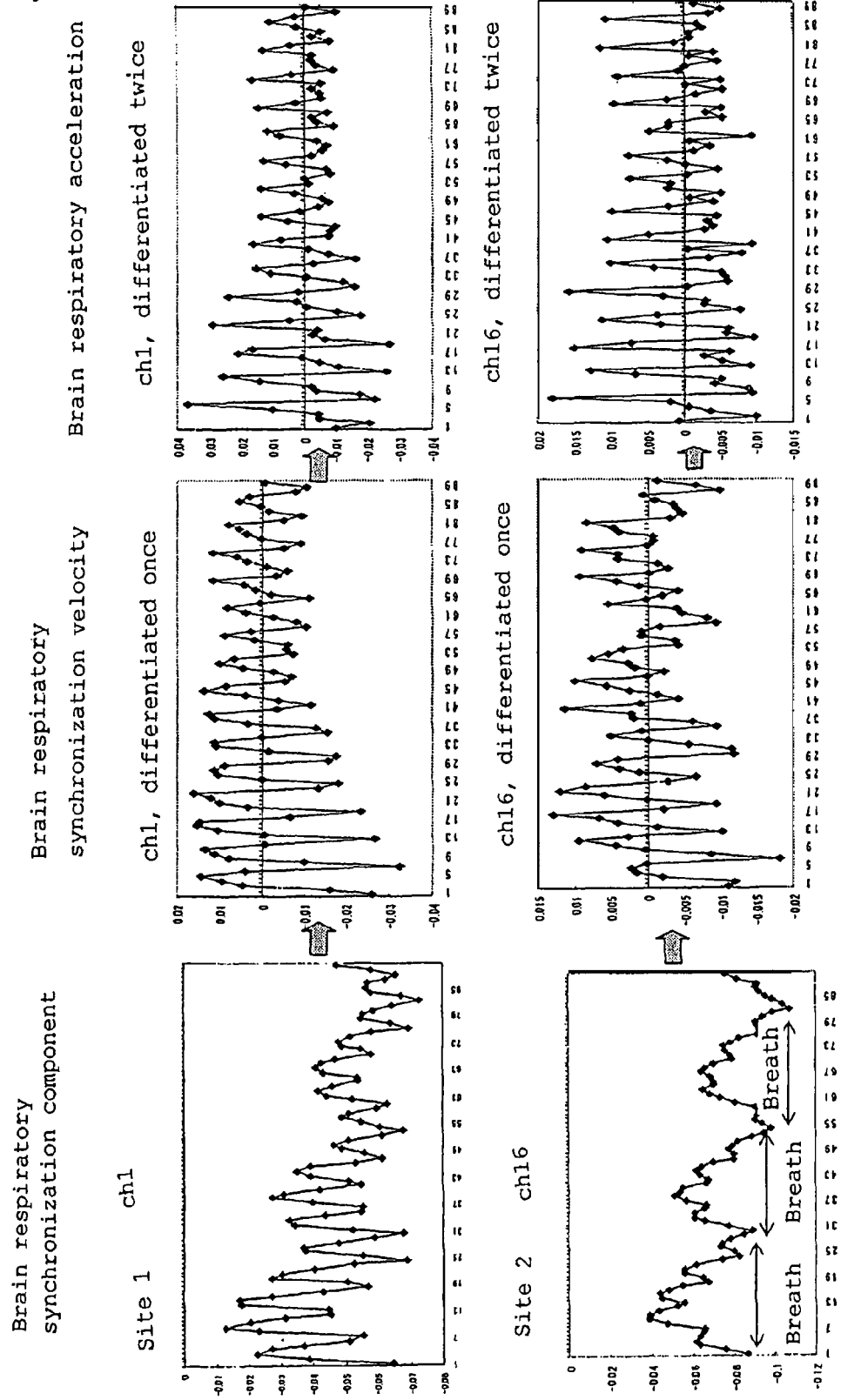
FIG. 79 is graphs showing the brain respiratory synchronization component for site 1 and site 2; their differentials, brain respiratory synchronization velocity; and their further differentials, brain respiratory acceleration.

The graphs of FIG. 79 show the brain respiratory-synchronization components for site 1 and site 2; their differentials, brain respiratory-synchronization velocity; and their further differentials, brain respiratory acceleration.

Figure 80:
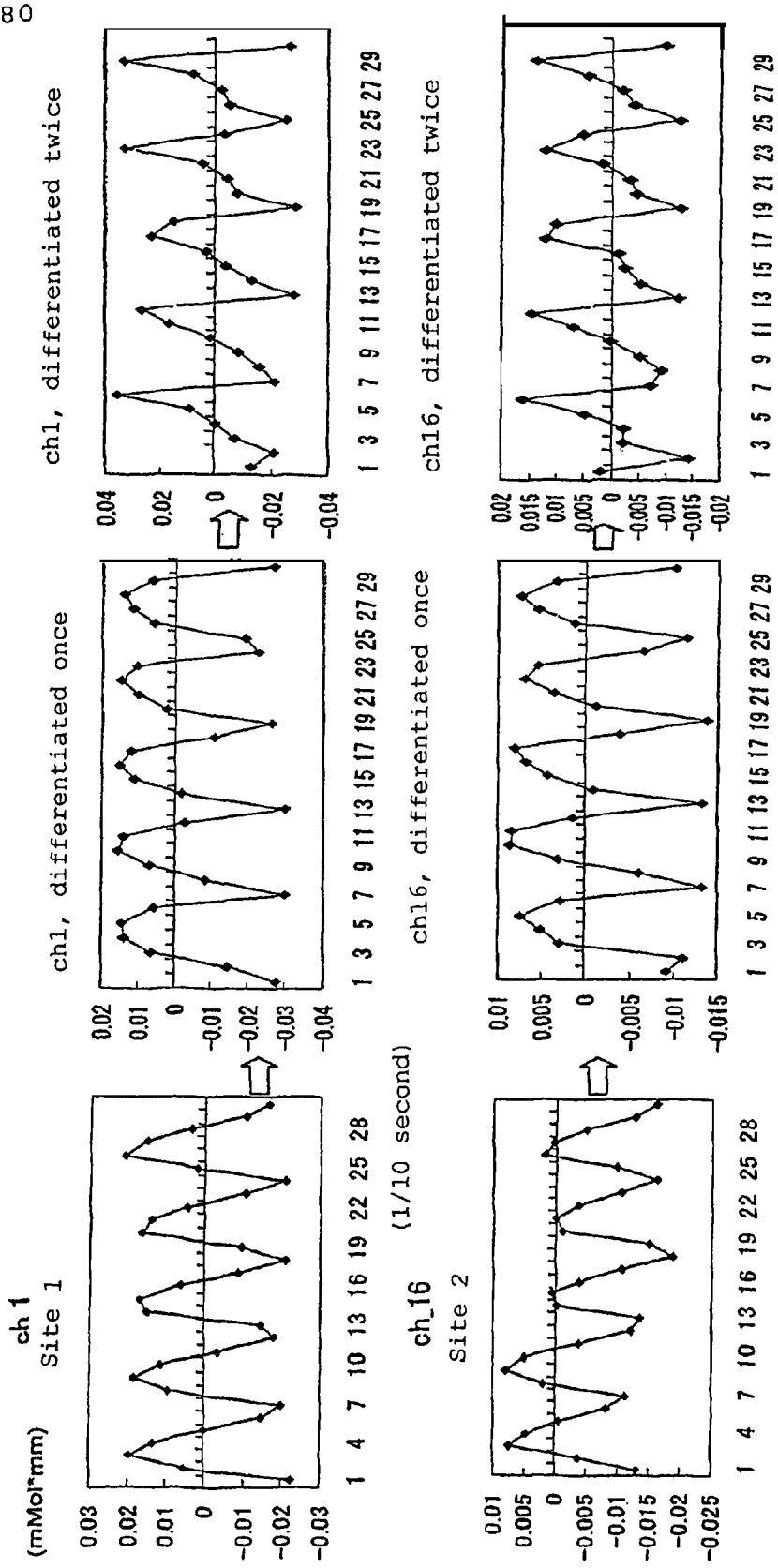
FIG. 80 is graphs showing the brain heartbeat synchronization component for site 1 and site 2; their differentials, brain heartbeat synchronization velocity; and their further differentials, brain heartbeat acceleration.

The graphs of FIG. 80 show the brain heartbeat-synchronization components for site 1 and site 2; their differentials, brain heartbeat-synchronization velocity; and their further differentials, brain heartbeat acceleration.

Figure 81:
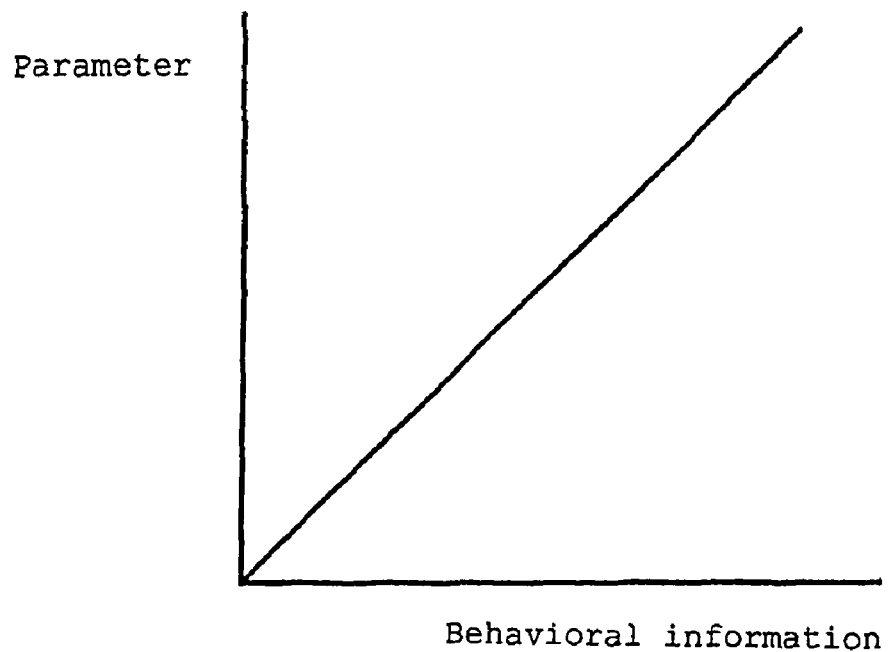
FIG. 81 is a two-dimensional diagram showing the correlation between behavioral information (the meaning of written characters, the length of a line, scores, etc.) and various parameters (integral values, amounts of change) during the same time period.

FIG. 81 is a two-dimensional diagram showing the correlation between behavioral information (the meaning of written characters, the length of a line, scores, etc.) and various parameters (integral values, amounts of change) during the same time period. By analyzing correlations of this kind, for example, it is possible to judge whether a task is understood or not, in a case, for example, where the response time is the same but the task is different (for example, when a subject is made to listen to the different words "touzainanboku" [the cardinal points of the compass, all directions] and "kokontouzal" [all times and places, all ages and countries]; these are both 4-character kanji compounds containing 2 of the same characters).

Procedure for Evaluating the Degree of Effect in the Brain of a Series of Problems Presented in a Test First, M problems are presented to N people, and (a) the percentage of correct answers for each problem and (b) the percentage of correct answers for each person taking the test are calculated. Next, the degree of brain oxygen consumption and oxygen supply corresponding to the percentage of correct answers for each problem (change in oxyhemoglobin, change in deoxyhemoglobin, and the sum and difference of these changes) are measured and added together.

FIGS. 82(A) and (B) are graphs showing cumulative summed values for problem response time (RT) at desired sites; (A) is a graph of problems correctly answered by one individual, and (B) is a graph of problems incorrectly answered for one individual.

Next, as a procedure in a program for percentage of correct answers and data processing, oxygen exchange rate (k-angle) for all correct answers or the greatest percentage of correct answers is taken as the standard and the other data is arranged in order.

Next, average time series data and the time course of the standard deviation from the average are calculated, and the oxygen exchange times and supply times are ranked.

Next, from the time series for all correct or incorrect answers, the oxygen exchange consumption and supply times and amounts are measured.

And, by the following formula, the degree of effect in the brain for each individual, and the oxygen exchange efficiency in the brain for each problem are calculated.

Individual brain effect=(cumulative summed data for problems answered correctly)+(cumulative summed data for problems answered incorrectly)

Brain oxygen exchange efficiency for each problem= (respective cumulative summed problem response times [RT])/[RT]

From the results calculated above, it can be determined whether an individual is responding as efficiently as possible by investigating the fact that even if all problems are answered correctly, oxygen loads on the brain are different.

In addition, even when all the problems are answered incorrectly, it can be determined whether a subject was not thinking at all, or was thinking, but unable to answer.

FIG. 83(A) is a graph showing cumulative summed data for all those taking the test, by problem. By means of cumulative summed data for each problem, it is possible to rank the degree of effect of each problem in the brain.

FIG. 83(B) is a graph showing the degree of individual effect, by problem. When the degree of individual effect is divided by the response time, smaller values can be said to show high brain efficiency. In this case, for problems with incorrect answers, it can be said that the smallest value is best.

Methods to Measure Hardness and Stenosis of the Brain Vessels

By mounting living body probes of the present invention on the brain vessel areas and simultaneously monitoring the heartbeat, it is possible to investigate correlations, peak values, velocity and acceleration to determine in which brain blood vessels, left or right, a delayed response occurs, and to use differences in transmission time to distinguish between the normal and the abnormal.

Figure 84:
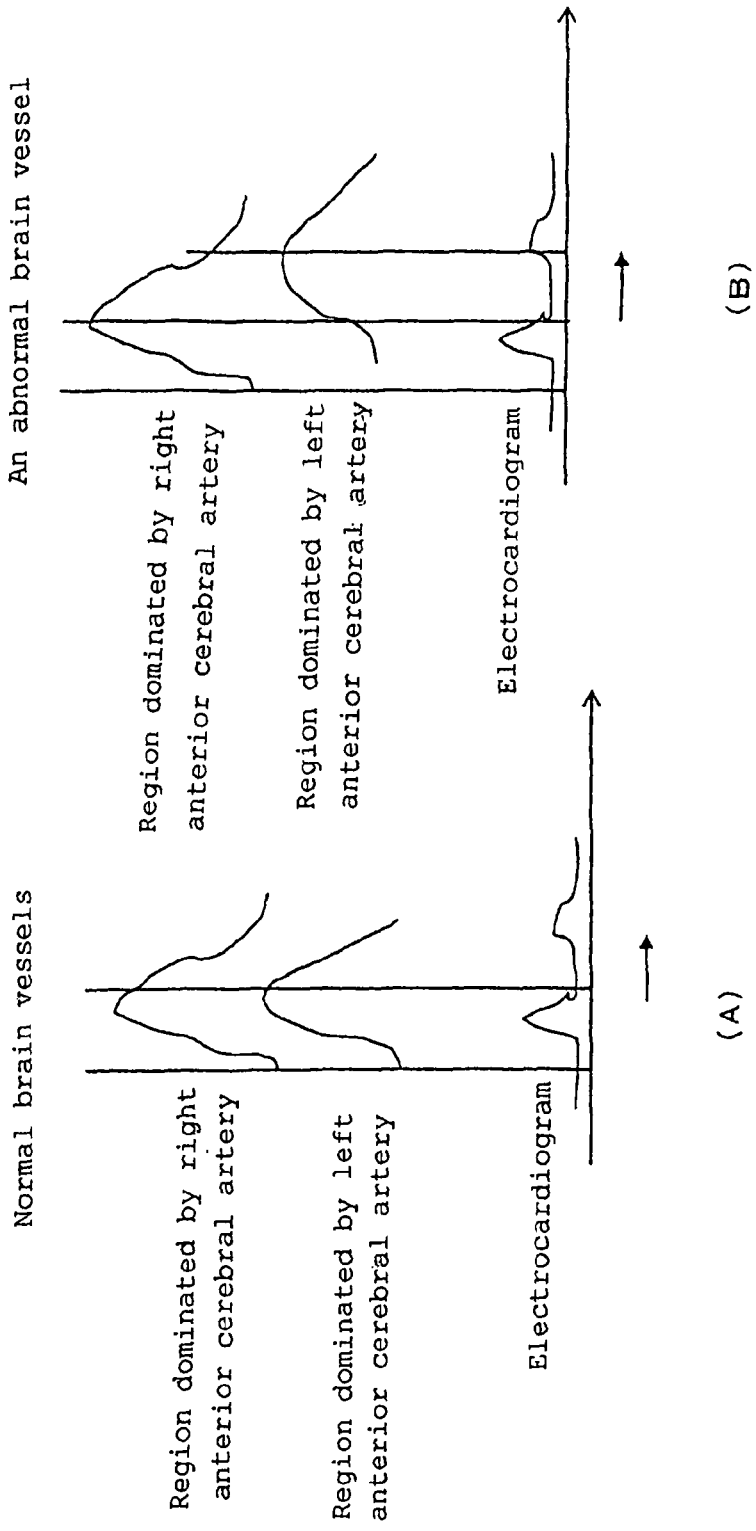
FIG. 84(A) is a graph showing the relationship between the electrocardiogram and changes in parameters of regions dominated by the left and right anterior cerebral arteries in the case of normal brain vessels, and (B) is a graph showing the relationship between the electrocardiogram and changes in parameters of regions dominated by the left and right anterior cerebral arteries in the case of an abnormal brain vessel.

FIG. 84(A) is a graph showing the relationship between the electrocardiogram and changes in parameters of the regions dominated by the left and right anterior cerebral arteries in a case of normal brain vessels, and (B) is a graph showing the relationship between the electrocardiogram and changes in parameters of the regions dominated by the left and right anterior cerebral arteries in a case of an abnormal brain vessel. In the case of normal brain vessels, there is little difference between the right and left brain pulse waves (see FIG. 84 [A]), and in the case of an abnormal brain vessel, there is a big difference between the right and left brain pulse waves (see FIG. 84 [B]). In addition, it can be seen that the left cerebral artery has a low peak value, and thus it is a hardened blood vessel (see FIG. 84 [B].

Determining Comfort/Discomfort by Means of Brain Response

When eyeglasses strength or dentures are adjusted, they are conventionally adjusted according to a person's own report of comfort or discomfort.

Figure 85:
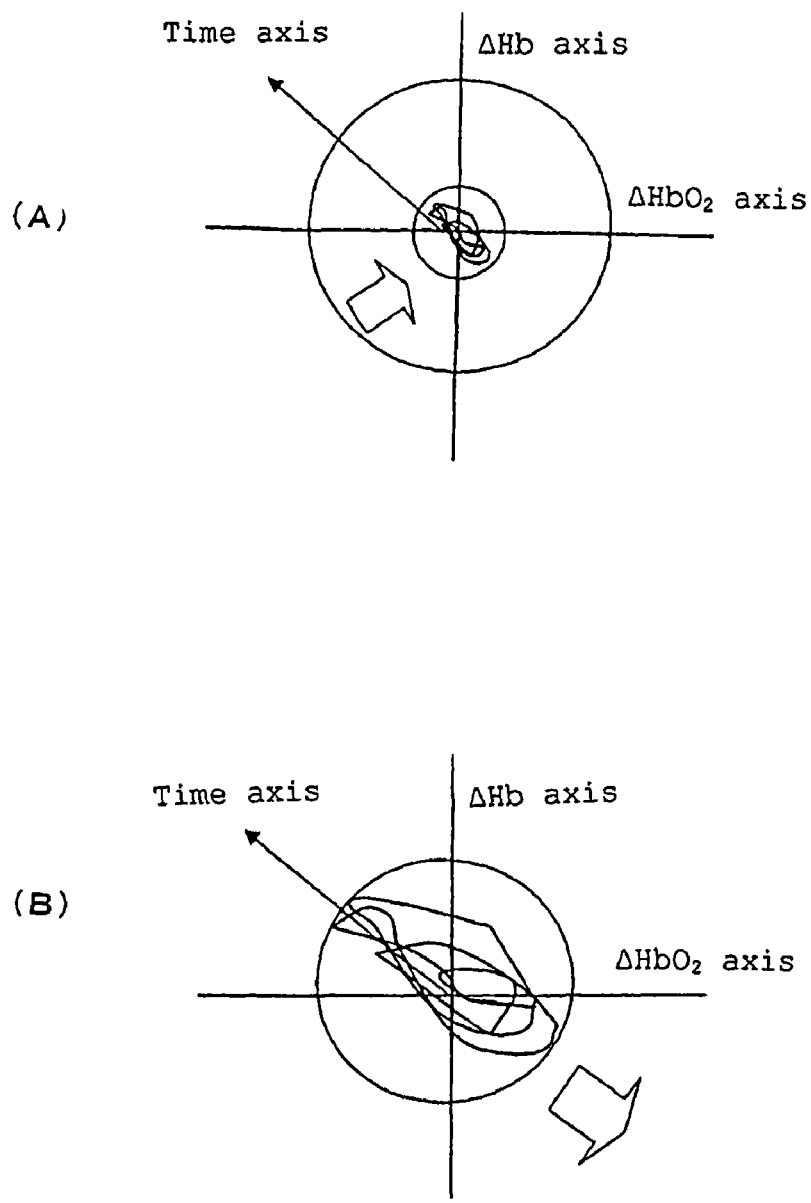
FIG. 85(A) shows a case in which the spread of L-values is small; and (B), a case in which the spread of L-values is large.

If an apparatus for evaluating biological function of a working embodiment of the present invention is used, it is possible for parameters concerning brain oxygen exchange function from the frontal lobe of the brain when eyeglasses or dentures are mounted on the human body to be calculated by means of controller 8, and moreover for the comfort and discomfort of the human body to be determined and mapped on display part 10, and by this means the degree of comfort can be determined without relying on the wearer's own report. For example, if the spread of L-values is small, as shown in FIG. 85(A), the subject can be judged to be comfortable, and if the spread of the L-values is large, as shown in (B), the subject can be judged to be uncomfortable.

Figure 86:
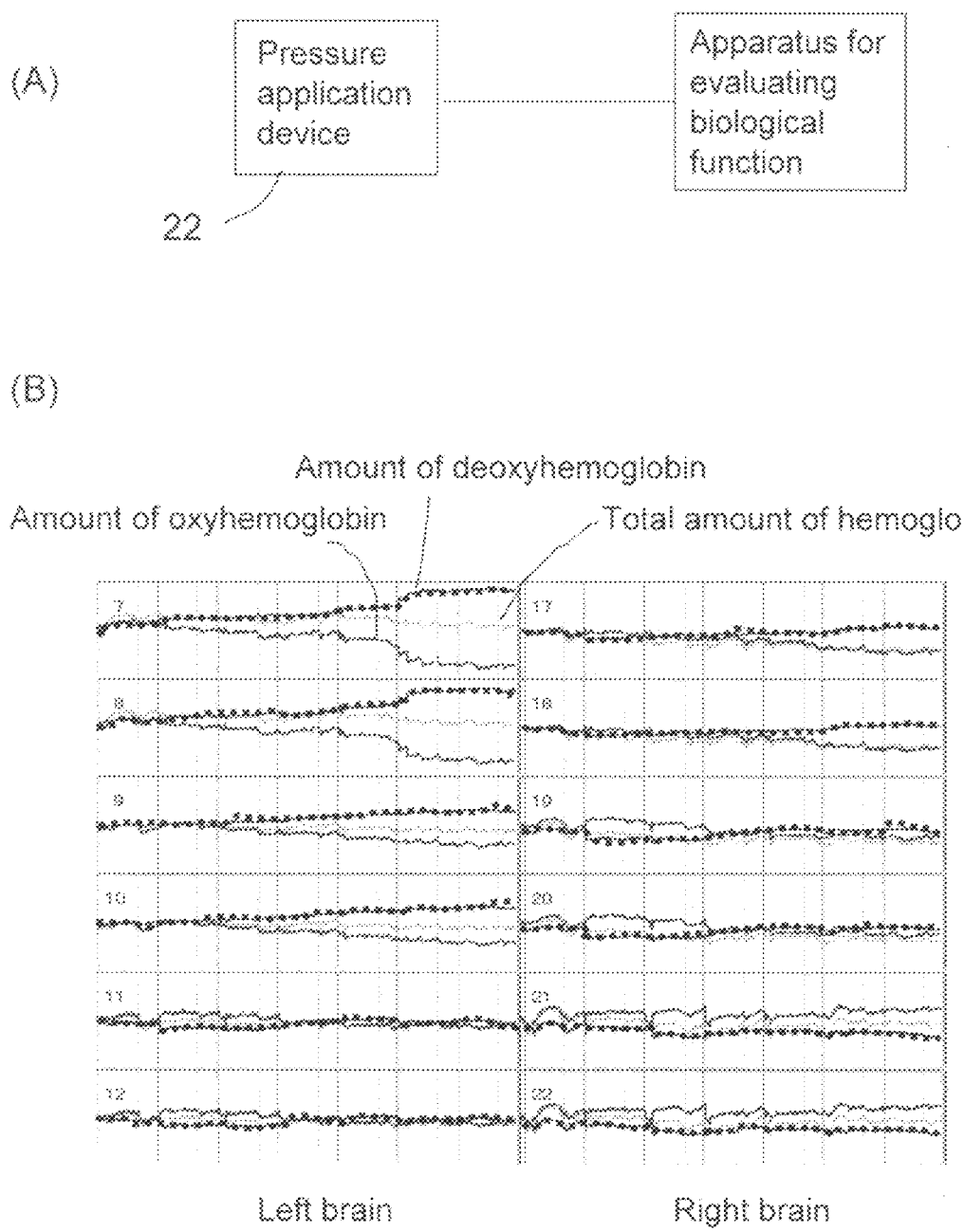
FIG. 86(A) is a block diagram showing an example in which an apparatus for evaluating biological function of a working embodiment of the present invention is connected with a pressure application device for applying stimulus (pressure) to the brain.
FIG. 86(B) is a graph showing the results of measuring changes in each kind of Hb for each of a number of channels (the numbers show the channel numbers), when pressure is applied to the right arm by means of a pressure application device.

An Apparatus for Evaluating Biological Function with a Device for Applying Pressure Attached As shown in FIG. 86(A), an apparatus for evaluating biological function of a working embodiment of the present invention may be configured so that it is connected to a pressure application device 22 for applying stimulus (pressure) to the brain. An example of a pressure application device 22 is one in which a manchette, similar to a blood pressure monitor, is wrapped around the arm to apply pressure.

By pressing on the muscles of the arm with a pressure application device, a low oxygenation state can be created in the brain on the side opposite the arm. Namely, compression controls overwhelming it from a peripheral nerve and displays presence and degree of a FORCE effect to occur in a brain and can judge a function of a brain blood vessel state.

For example, FIG. 86(B) is a graph showing the results of measuring changes in the various hemoglobins for each of a number of channels (the numbers show the channel numbers) when pressure is applied to the right arm by means of a pressure application device. It can be seen, as shown in figure (B), that low oxygenation is produced in the left brain.

Modified Examples of a Living Body Probe

FIG. 87(A) is a lateral view showing a modified example of a living body probe, and (B) is a front view thereof. As shown in FIGS. 87(A) and (B), protective cover 23, made a soft material such as a silicone gel may be installed on the tip of living body probe 1. By means of this protective cover 23, it is possible to prevent hurting or scratching the skin when living body probe 1 comes in contact with the skin of the scalp or the like.

A measuring Technique for the Inferior Temporal Gyrus

With previous measuring techniques, it was difficult to measure the inferior temporal gyri, which are associated with memory and the like, from on the skin of the head.

Figure 88:
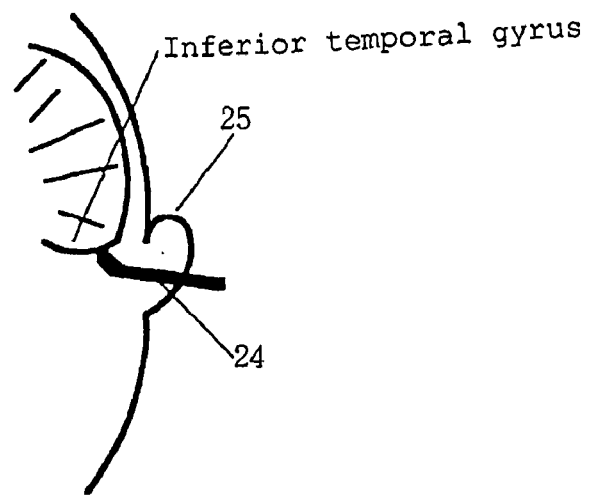
FIG. 88 is a drawing explaining a measuring technique for the inferior temporal gyrus.

Accordingly, as shown in FIG. 88, the tip of living body probe 1 may be formed into a soft material 24, like an earplug, inserted from the outer ear canal, and the inferior temporal gyrus measured in a situation where no light leaks in.

Living Body Probe Mounting Device

Figure 89:
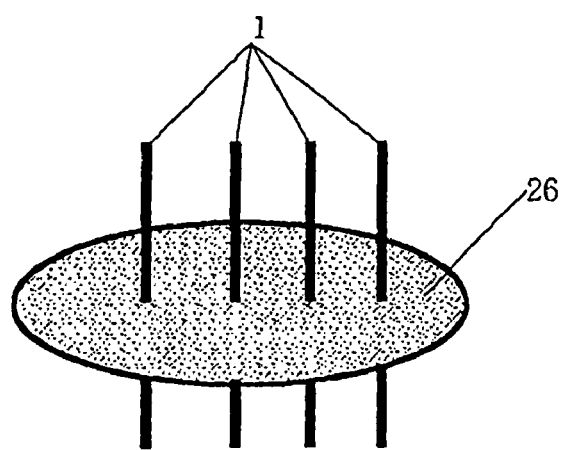
FIG. 89 is a perspective view showing a living body probe mounting device 26 of a working embodiment of the present invention.

FIG. 89 is a perspective view showing a living body probe mounting device 26 of a working embodiment of the present invention.

As shown in FIG. 89, this living body probe mounting device 26 is a device in which living body probes 1 are installed and supported on stretchable support material 26a, made of mesh-like fabric or the like, and it is mounted on the place to be measured on the head or the like. By using this living body probe mounting device 26, living body probes 1 can be kept from moving around, and noise arising from the incidence of outside light can be prevented.

In order to prevent the incidence of outside light, black fabric or the like is preferably used for the protective material, and the device is preferably made in mesh form in order to provide good ventilation.

Living Body Probe Mounting Accessory

With previous measurement methods using near-infrared and the like, when signals were detected from a plurality of sites on the brain surface, there was no way to quickly know the location of the language area, the motor area, the visual area and the like. Accordingly, it is convenient to use living body probe mounting accessory 27, which makes it possible to easily obtain location information for brain measurement target sites of the language area, the motor area, the vision area and the like, based on distance from the location of the ear.

This living body probe mounting accessory 27, as shown in FIGS. 90(A) and (B), is made from a net-like material formed at fixed intervals along lines parallel to the line connecting the outer eyelid and the outer ear canal and the line connecting the outer ear canal and the parietal line, respectively. As shown in FIG. 90(C), measuring marks 27a (in units of 1 cm, for example,) are displayed on the surface of the net-like material.

From the fact that the AC-PC line (AC: anterior commissure; PC: posterior commissure) in the brain is normally parallel to the outer eyelid—outer ear canal line on the scalp, an outer ear canal—parietal line is formed perpendicular to the outer eyelid—outer ear canal line. By this means, because position on the scalp corresponds to the AC-PC line used in brain imaging, the use of the living body probe mounting accessory 27 of the present invention, by determining the position of the outer eyelid—outer ear canal line and the outer ear canal—parietal line, makes it possible to easily identify the location of structures inside the brain from on the scalp. In addition, because scale markings 27a are displayed on the surface of the net material, it is possible to easily identify the location of structures in the brain from on the scalp. In addition, because markings 27a are displayed on the surface of the net material, it is possible to easily know the appropriate positions for living body probes 1.

For example, if one wants to measure Wernicke's area, living body probes 1 should be positioned in locations 4-5 cm from the outer ear canal. In addition, names of measurement target sites may be displayed on the net material surface with labels or the like.

Living Body Probe Support Device

FIG. 91(A) is a plan view showing a living body probe support device of a working embodiment of the present invention; (B) is a perspective view showing a retaining ring; (C) is a cross-sectional view along line c-c of (A); and (D) is a cross-sectional view along line d-d of (A).

As shown in FIGS. 91(A)-(D), inside the living body probe support device 30 of a working embodiment of the present invention there are retaining rings 28 for holding living body probes 1, and a ring support frame 29 that is roughly oval-shaped in plan view, for supporting retaining rings 28 moveably in the longitudinal direction (direction of the arrow). On the inside of support frame 29 are formed a plurality of indentations 29a at fixed intervals along the lengthwise direction, into which protrusions 28a on the outside of retaining rings 28 can be latched. To make it possible to move retaining rings 28, ring support frame 29 is formed of a material that can be deformed slightly outwards.

This living body probe support device 30 makes it possible to move a retaining ring 28, supporting living body probe 1, within ring support frame 29 in the lengthwise direction, and to secure it at the desired position, and thus makes minute adjustment of the set position of living body probe 1 possible.

Figure 92:
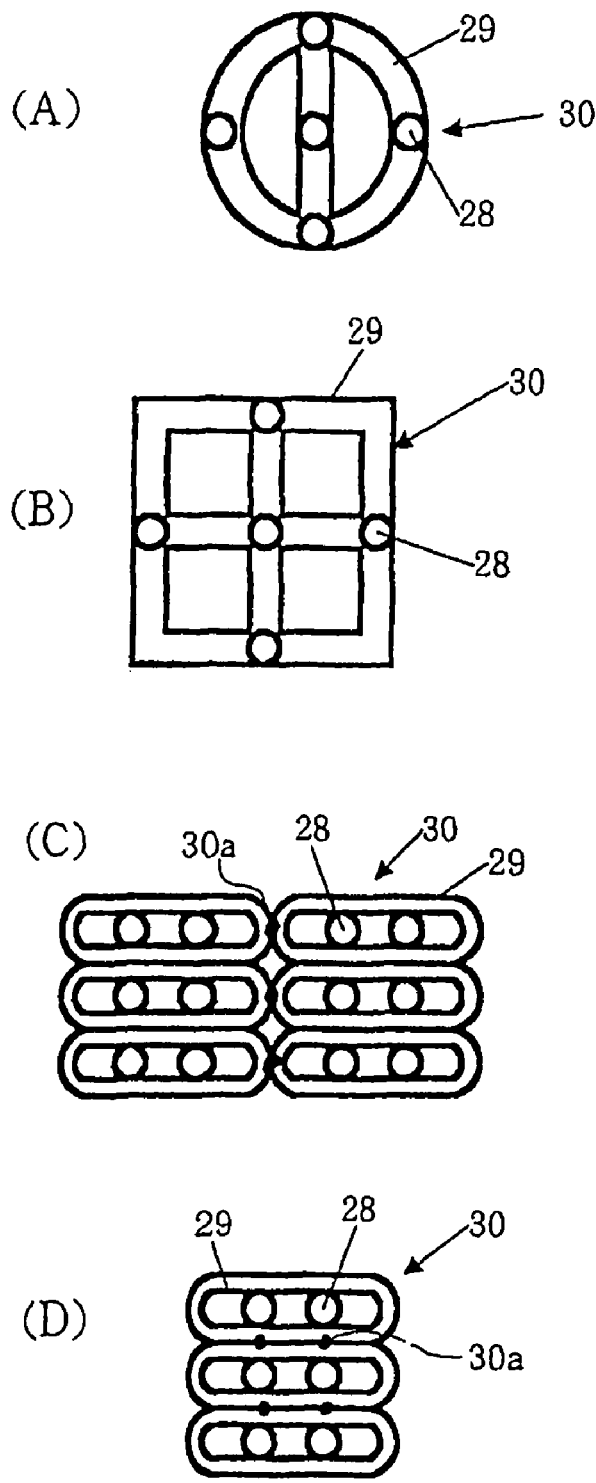
FIGS. 92(A)-(D) are plan views showing modified examples of living body probe support devices.

Ring support frame 29 may also be formed, for example, as shown in FIG. 92(A), as a circular frame and a straight line frame, or the like; or a plurality of living body probe support devices 30 may be secured by connecting part 30a, as shown in FIG. 92(B).

Independence and Interconnectedness of Light Functional Voxels Corresponding to the Probe Arrangement The principle of the light functional imaging method discovered by the present inventor Kato et al. is a fundamental method whereby light functional voxels of different regions (sites) are detected by means of 2 probes for light incidence and light reception.

The following methods are used in conventional techniques:

1) Simultaneous light irradiation methods, in which a plurality of pairs of probes, for light incidence and reception, are placed on the scalp, and a light functional voxel is sampled for each pair.

2) Phased light irradiation methods, utilizing phase differences to separate closely adjacent light functional voxels, by irradiating and receiving different phase light.

3) Time difference irradiation methods, in which light is received from different light incidence times, to separate closely adjacent light functional voxels.

However, conventional techniques have problems of the following kinds:

1) With simultaneous light irradiation methods, without phase polarization or time-difference irradiation, the functional response components of closely adjacent light functional voxels are mixed together and it is difficult to separate the two voxels.

2) However, a greater number of light-emitting elements must be provided in order to carry out phase polarization and time-difference irradiation, and this has the disadvantage that in order to measure a plurality of regions, the apparatus becomes larger.

3) Furthermore, with time difference irradiation methods, producing a time difference, causes differences between the sampling times for the light functional voxels, and this imposes limitations on the measurement of oxygen exchange function, which proceeds simultaneously with electrical activity, which occurs in milliseconds.

Accordingly, as a means for resolving the above problems, the present invention suppresses the size of the apparatus, and implements measurement of a plurality of points and high-speed measurement by introducing probe arrangements, mathematical analysis, and a method f for displaying the independence and interconnectedness of desired light functional voxels into the simultaneous light irradiation method.

In the case of simultaneous light irradiation, as shown in FIG. 93(A), light receiving area b, for example, receives not only light components from the closest incidence B and C, but also, theoretically, light from A, D, E, F, G and H.

Accordingly, it is important, for understanding the characteristic properties of light functional voxels, to display the theoretical independence and interconnectedness between probes corresponding to the probe arrangement and irradiation method in the probe arrangement and simultaneous light irradiation method, or even in the phased light irradiation method and the time-difference irradiation method; to measure the actual measured independence and interconnectedness; and to measure and display the difference between the theoretical values and the measured values.

In addition, by this means, the apparatus can be made more compact by minimizing the number of light emitters for incident light and separating voxels by the light receiving parts.

For example, in FIG. 93(B), it can be seen from the above that as many light functional voxels are separated out as there are light receiving parts.

It can furthermore be seen that ch1 and ch2, or ch3 and ch4, etc., are actually separated.

In addition, as an image display of the theoretical separation precision of light functional voxels, complete independence (0% interconnectedness) may be displayed as 0, complete non-independence (100% interconnectedness) as 1, and between 0 and 1 as 0.5; and upon measurement, correlations r (from −1 to +1) of the time series of a desired segment for desired channel A may be displayed in a color-coded display (a moving image is possible), as shown in FIG. 94. FIG. 94(A) shows an image display of the theoretical separation precision from the probe arrangement and light irradiation method, and (B), an example of a time series display of time series correlations between desired segments of the desired channel A upon measurement.

In addition, if the correlations from the time-difference or phase-difference irradiation methods A are compared with those of the simultaneous irradiation method B, and the difference between them ([measured value A]−[measured value B]) approaches zero, this can be judged to show an increase in functional independence (the effect from simultaneous irradiation is minimal), and if the difference approaches 1 or −1, it can be judged to show an increase in functional interconnectedness (the effect from simultaneous irradiation is large).

Measurement of the Four Thought Patterns

FIG. 95 shows drawings explaining the four thought patterns of the human brain: (A) shows a right-brain input, right-brain output thought type; (B), a right-brain input, left-brain output thought type; (C), a left-brain input, left-brain output thought type; and (D), a left-brain input, right-brain output thought type.

The working of the human brain can be divided into four types. From the strength of the FORCE effect, left/right brain can be determined during information collection, to determine predominance at time of input. In the same way, left/right brain can be determined during information output, to determine predominance at time of output.

The FORCE effect is determined from the amount of oxygen consumption during input or output, namely, increases in deoxyhemoglobin, decreases in oxyhemoglobin and decreases in (oxyhemoglobin-deoxyhemoglobin), and cumulative summed values are used.

The invention claimed is:

1. An apparatus for evaluating biological function comprising:
 a plurality of living body probes provided with light-emitting elements for irradiating light to specified sites of a living body and light-receiving elements for receiving and detecting light exiting the living body;
 an apparatus body for entering light information detected by said living body probe and behavioral information of said living body measured in response to said living body being given a task to perform, and performing calculation, control and memory operations, and utilizing near-infrared spectroscopy to evaluate biological function, said apparatus body comprising:
  a controller for calculating, based on light information from said living body probe, a variety of parameters derived from two-dimensional diagrams, wherein each diagram shows at least one of:
   the relationship between amounts of change in oxyhemoglobin and amounts of change in deoxyhemoglobin is inclined 45 degrees to show the relationship between amounts of change in oxygen saturation and amounts of change in total hemoglobin concentration, and
   the relationship between absolute amounts of oxyhemoglobin and absolute amounts of deoxyhemoglobin is inclined 45 degrees to show the relationship between absolute oxygen saturation and absolute total hemoglobin concentration;
  a behavioral information input part for entering behavioral information of said living body measured in response to said living body being given a task to perform; and
  a display part for performing various types of image displays based on various parameters calculated by means of said controller and/or behavioral information entered in said behavioral information input part.

2. The apparatus for evaluating biological function according to claim 1, wherein said controller calculates a variety of parameters derived from three-dimensional diagrams, in which a time axis is added to said two-dimensional diagrams, and said display part performs three-dimensional displays based on the variety of parameters calculated by said controller.

3. The apparatus for evaluating biological function according to claim 1, wherein said controller calculates a variety of parameters establishing a relationship between hemoglobin and oxygen exchange in a formula of rotational motion or wave dynamics, by considering oxygen exchange in the hemodynamics as rotational motion or wave motion.

4. The apparatus for evaluating biological function according to claim 1, wherein said controller calculates integral values, corresponding to a behavior time, for light information detected by the living body probes, and, based on the calculated integral values, acquires living body site information that is dependent on said behavior time and/or information on network interdependence between sites of the living body; and said display part displays the living body site information.

5. The apparatus for evaluating biological function according to claim 1, wherein said controller calculates a qualitative K-ratio, calculated by a formula (change in the absorption coefficient of the wavelength of predominantly deoxyhemoglobin)/(change in the absorption coefficient of the wavelength of predominantly oxyhemoglobin), and its slope.

6. The apparatus for evaluating biological function according to claim 1, wherein said controller calculates the length of the light path of light irradiated from one of the light-emitting elements of the living body probe until it is received by one of the light-receiving elements.

7. The apparatus for evaluating biological function according to claim 1, wherein said controller measures the phase difference between changes in oxyhemoglobin and changes in deoxyhemoglobin.

8. The apparatus for evaluating biological function according to claim 1, wherein the light-emitting elements and the light-receiving elements form channels each comprising a plurality of voxels, and wherein said controller detects fluctuation for each voxel.

9. The apparatus for evaluating biological function according to claim 1, wherein said controller calculates respiratory synchronization, synchronous with a respiratory cycle of the living body, and/or heartbeat synchronization, synchronous with a heartbeat period of the living body.

10. The apparatus for evaluating biological function according to claim 1, wherein the living body is that of a person to whom a series of problems are presented, wherein the specified sites are in the brain of the person, and wherein said controller calculates the extent of oxygen consumption and oxygen supply of the brain corresponding to the percentage of correct answers of each problem, by cumulative addition.

11. The apparatus for evaluating biological function according to claim 1, wherein said controller has a means for determining comfort and discomfort of the living body based on specified criteria.

12. The apparatus for evaluating biological function according to claim 1, wherein said controller has a means for determining a type of left/right thought pattern of the brain of the living body based on specified criteria.

13. The apparatus for evaluating biological function according to claim 1, wherein said display part displays sites or regions showing an oxygen consumption response and an oxygen supply response in the capillaries of the living body.

14. The apparatus for evaluating biological function according to claim 1, wherein the light-emitting elements and the light-receiving elements form channels each comprising a plurality of voxels, and wherein said display part displays independence and interconnectedness between the voxels of each channel.

15. The apparatus for evaluating biological function according to claim 1, wherein said apparatus body has a selector-adjuster for determining the need to select for validation/invalidation or adjust said living body probes, based on said parameters, and for adjusting a measurement sensitivity of said light-receiving elements.

16. The apparatus for evaluating biological function according to claim 1, wherein said apparatus body has a sampling speed adjuster for adjusting a sampling speed of measurements made in response to said living body being given a task to perform.

17. The apparatus for evaluating biological function according to claim 15, wherein said living body probes are provided with a plurality of light-emitting elements and a plurality of light-receiving elements, and said selector-adjuster determines the need to select for validation/invalidation or adjust the light-emitting element/light-receiving element combinations within each channel formed by the living body probe, based on said parameters; and determines the need to select for validation/invalidation or adjust combinations between said channels, based on said parameters.

18. The apparatus for evaluating biological function according to claim 1, wherein said living body probes are placed in such a way that they are positioned on a gyrus of the brain of the living body, avoiding the sulci of the brain, by taking into consideration the shape and size of sulci and gyri at each site of the brain of the living body.

19. The apparatus for evaluating biological function according to claim 18, wherein said living body probes are placed at roughly right angles to the centerline of a gyrus between sulci.

20. The apparatus for evaluating biological function according to claim 18, wherein said living body probes are placed along the centerline of a gyrus between sulci.

21. The apparatus for evaluating biological function according to claim 1, wherein said display part displays the angle formed by the direction of living body probes placed at a plurality of sites of the brain surface and the direction of a gyrus of the brain of the living body.

22. The apparatus for evaluating biological function according to claim 1, wherein the apparatus is connected to a pressure application device for applying stimulus to the brain.

23. A method for evaluating biological function in which near-infrared spectroscopy is utilized to evaluate biological function, using the apparatus according to claim 1, said method comprising the steps of:
(1) placing said light-emitting elements and said light-receiving elements of the living body probes on a living body;
(2) irradiating light from said light-emitting elements of the living body probes to the living body;
(3) based on light information detected by means of said light-receiving elements of the living body probes, making a selection or adjustment among light-emitting element/light-receiving element combinations within each of the channels formed by said living body probes, based on specified criteria;
(4) based on light information detected by means of said living body probes, making a selection or adjustment among combinations among said channels, based on specified criteria;
(5) measuring baseline data from light information detected by said living body probes with the living body at rest, and performing data analysis using the controller and data display using the display part; and
(6) measuring task presentation data from light information detected by said living body probes at the time when a task is presented to the living body, and performing data analysis using the controller and data display using the display part.

24. The apparatus for evaluating biological function according to claim 1, wherein said living body probes are made of a material containing, at least, moisture.

25. The apparatus for evaluating biological function according to claim 1, wherein said living body probes are supported by a material containing, at least, moisture.

26. The apparatus for evaluating biological function according to claim 1, wherein the living body probes have a protective cover made of a soft material installed on the tips thereof.

27. The apparatus for evaluating biological function according to claim 1, further comprising a living body probe mounting device formed by a mesh-like stretchable retaining material, wherein said living body probes are installed on and retained by the mesh-like stretchable retaining material.

28. The apparatus for evaluating biological function according to claim 1, further comprising a living body probe support device including retaining rings for holding said living body probes, and a ring support frame for movably supporting those retaining rings.

29. The apparatus for evaluating biological function according to claim 1, further comprising a living body probe mounting accessory for aiding in mounting said living body probes on the head of the living body, wherein the living body probe mounting accessory is made from a net-like material formed spaced at fixed intervals along lines parallel to a line connecting the outer eyelid of the head and the outer ear canal of the head and the line connecting the outer ear canal and the parietal line of the head, respectively, and the surface of said net-like material has measuring marks displayed thereon.

* * * * *